US012268869B2

(12) United States Patent
Pawsey et al.

(10) Patent No.: US 12,268,869 B2
(45) Date of Patent: *Apr. 8, 2025

(54) ADVANCED ELECTRODE ARRAY INSERTION

(71) Applicant: Cochlear Limited, Macquarie University (AU)

(72) Inventors: Nicholas Charles Pawsey, Macquarie University (AU); Frank Risi, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 209 days.

This patent is subject to a terminal disclaimer.

(21) Appl. No.: 17/706,321

(22) Filed: Mar. 28, 2022

(65) Prior Publication Data

US 2022/0339434 A1    Oct. 27, 2022

Related U.S. Application Data

(63) Continuation of application No. 15/241,745, filed on Aug. 19, 2016, now Pat. No. 11,285,314.

(51) Int. Cl.
*A61N 1/05* (2006.01)
*A61B 34/30* (2016.01)
(Continued)

(52) U.S. Cl.
CPC ............ *A61N 1/0541* (2013.01); *A61B 34/30* (2016.02); *A61N 1/36036* (2017.08);
(Continued)

(58) Field of Classification Search
CPC ......... A61B 34/30; A61B 34/35; A61B 34/37; A61B 34/70; A61B 34/71; A61B 17/3468; A61B 34/72; A61B 2034/301; A61B 2034/302; A61B 2034/303; A61B 2034/304; A61N 1/0541; A61N 1/36036; A61N 1/36038; B25J 9/1694
See application file for complete search history.

(56) References Cited

U.S. PATENT DOCUMENTS

| 4,423,732 A | 1/1984 | Tarjan et al. |
| 4,522,209 A | 6/1985 | Patrick et al. |

(Continued)

FOREIGN PATENT DOCUMENTS

| EP | 1959856 B1 | 4/2013 |
| GB | 2358934 B | 11/2003 |
| KR | 20130089549 A | 8/2013 |

OTHER PUBLICATIONS

International Search Report and Written Opinion for PCT/IB2017/055001, mailed Dec. 13, 2017.
(Continued)

*Primary Examiner* — Kathleen S Holwerda
(74) *Attorney, Agent, or Firm* — Pilloff Passino & Cosenza LLP; Martin J. Cosenza

(57) ABSTRACT

An apparatus including an actuator and an electrode array support, wherein the apparatus is configured to insert an electrode array into a cochlea via controlled actuation of the actuator, wherein the controlled actuation is at least partially based on data that is at least partially based on electrical characteristics associated with the recipient.

29 Claims, 111 Drawing Sheets

(51) Int. Cl.
*A61N 1/36* (2006.01)
*B25J 9/16* (2006.01)
*A61B 34/00* (2016.01)

(52) U.S. Cl.
CPC ........ *A61N 1/36038* (2017.08); *B25J 9/1694* (2013.01); *A61B 2034/742* (2016.02); *A61N 1/36031* (2017.08)

(56) References Cited

U.S. PATENT DOCUMENTS

| | | | |
|---|---|---|---|
| 5,237,991 | A | 8/1993 | Baker, Jr. et al. |
| 5,443,493 | A | 8/1995 | Byers et al. |
| 5,579,919 | A | 12/1996 | Gilman et al. |
| 5,772,575 | A | 6/1998 | Lesinski et al. |
| 5,957,958 | A | 9/1999 | Schulman et al. |
| 5,997,466 | A | 12/1999 | Adams et al. |
| 5,999,856 | A | 12/1999 | Kennedy |
| 6,116,413 | A | 9/2000 | Tabor et al. |
| 6,321,125 | B1 | 11/2001 | Kuzma |
| 6,368,267 | B1 | 4/2002 | Lenhardt |
| 6,629,922 | B1 | 10/2003 | Puria et al. |
| 6,968,238 | B1 | 11/2005 | Kuzma |
| 7,063,708 | B2 | 6/2006 | Gibson et al. |
| 7,137,946 | B2 | 11/2006 | Waldmann |
| 7,766,905 | B2 | 8/2010 | Paterson et al. |
| 7,949,412 | B1 | 5/2011 | Harrison et al. |
| 8,010,210 | B2 | 8/2011 | Rau et al. |
| 8,086,319 | B2 | 12/2011 | van Dijk |
| 8,249,724 | B2 | 8/2012 | Risi et al. |
| 8,594,799 | B2 | 11/2013 | Haller et al. |
| 9,072,468 | B2 | 7/2015 | Buchman et al. |
| 11,285,314 | B2 * | 3/2022 | Pawsey .................. B25J 9/1694 |
| 2001/0023347 | A1 | 9/2001 | Sharkey et al. |
| 2001/0027297 | A1 | 10/2001 | Ito |
| 2002/0045862 | A1 | 4/2002 | Briscoe et al. |
| 2002/0188252 | A1 | 12/2002 | Bardy |
| 2003/0055377 | A1 | 3/2003 | Sirhan et al. |
| 2004/0220651 | A1 | 11/2004 | Kuzma |
| 2005/0020873 | A1 | 1/2005 | Berrang et al. |
| 2005/0131272 | A1 | 6/2005 | Waldmann |
| 2006/0271128 | A1 | 11/2006 | Keuninckx |
| 2006/0276749 | A1 | 12/2006 | Selmon et al. |
| 2006/0287690 | A1 | 12/2006 | Bouchataoui et al. |
| 2007/0106360 | A1 | 5/2007 | Gibson et al. |
| 2007/0225787 | A1 | 9/2007 | Simaan et al. |
| 2007/0282396 | A1 | 12/2007 | Overstreet et al. |
| 2008/0234793 | A1 | 9/2008 | Gibson |
| 2009/0054908 | A1 * | 2/2009 | Zand ..................... A61B 34/30 600/300 |
| 2010/0114288 | A1 * | 5/2010 | Haller ................... A61B 34/76 607/137 |
| 2011/0022145 | A1 | 1/2011 | Beerling et al. |
| 2011/0066160 | A1 * | 3/2011 | Simaan .................... A61N 1/05 606/129 |
| 2011/0152602 | A1 | 6/2011 | Perkins et al. |
| 2011/0295053 | A1 | 12/2011 | Ball |
| 2011/0319974 | A1 | 12/2011 | Thenuwara et al. |
| 2012/0136197 | A1 | 5/2012 | Van Gerwen |
| 2012/0172893 | A1 | 7/2012 | Taylor et al. |
| 2012/0220818 | A1 | 8/2012 | Grasso |
| 2013/0165737 | A1 | 6/2013 | Van den Heuvel |
| 2013/0225912 | A1 | 8/2013 | Leigh |
| 2014/0052148 | A1 | 2/2014 | Vancaillie et al. |
| 2014/0066951 | A1 | 3/2014 | Llinas et al. |
| 2014/0350640 | A1 * | 11/2014 | Patrick ................. A61N 1/0541 607/57 |
| 2015/0049888 | A1 | 2/2015 | Johnston et al. |
| 2015/0057714 | A1 | 2/2015 | Litvak et al. |
| 2015/0105794 | A1 | 4/2015 | Dhanasingh et al. |
| 2015/0237452 | A1 | 8/2015 | Vanpoucke |
| 2015/0314122 | A1 * | 11/2015 | Kabot ..................... A61N 1/08 607/137 |
| 2015/0341731 | A1 | 11/2015 | Polak |
| 2016/0059014 | A1 | 3/2016 | Johnston et al. |
| 2016/0059015 | A1 | 3/2016 | Risi et al. |
| 2017/0080211 | A1 | 3/2017 | Walling et al. |
| 2017/0180889 | A1 | 6/2017 | Walraevens et al. |
| 2017/0347209 | A1 | 11/2017 | Heasman et al. |
| 2017/0367733 | A1 | 12/2017 | Murphy et al. |
| 2018/0050196 | A1 | 2/2018 | Pawsey et al. |
| 2018/0304069 | A1 | 10/2018 | Koka et al. |

OTHER PUBLICATIONS

Stenfelt et al., "Fluid volume displacement at the oval and round windows with air and bone conduction stimulation," Journal of the Acoustical Society of America, Feb. 2004, pp. 797-812, vol. 115, No. 2, ResearchGate.

* cited by examiner

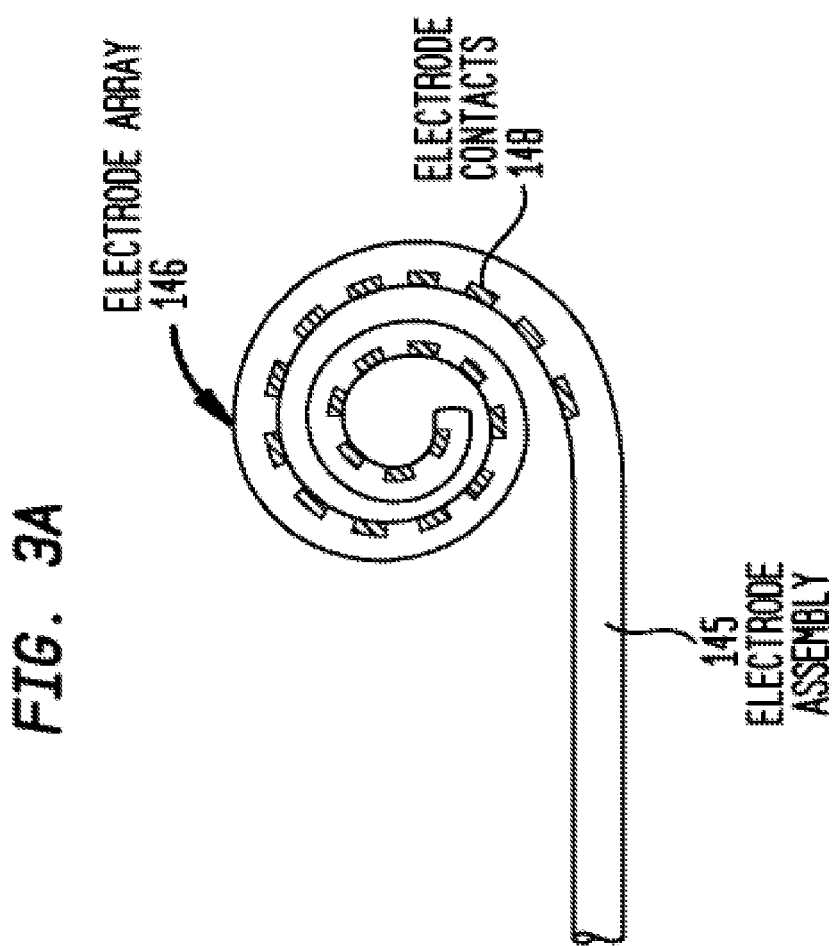

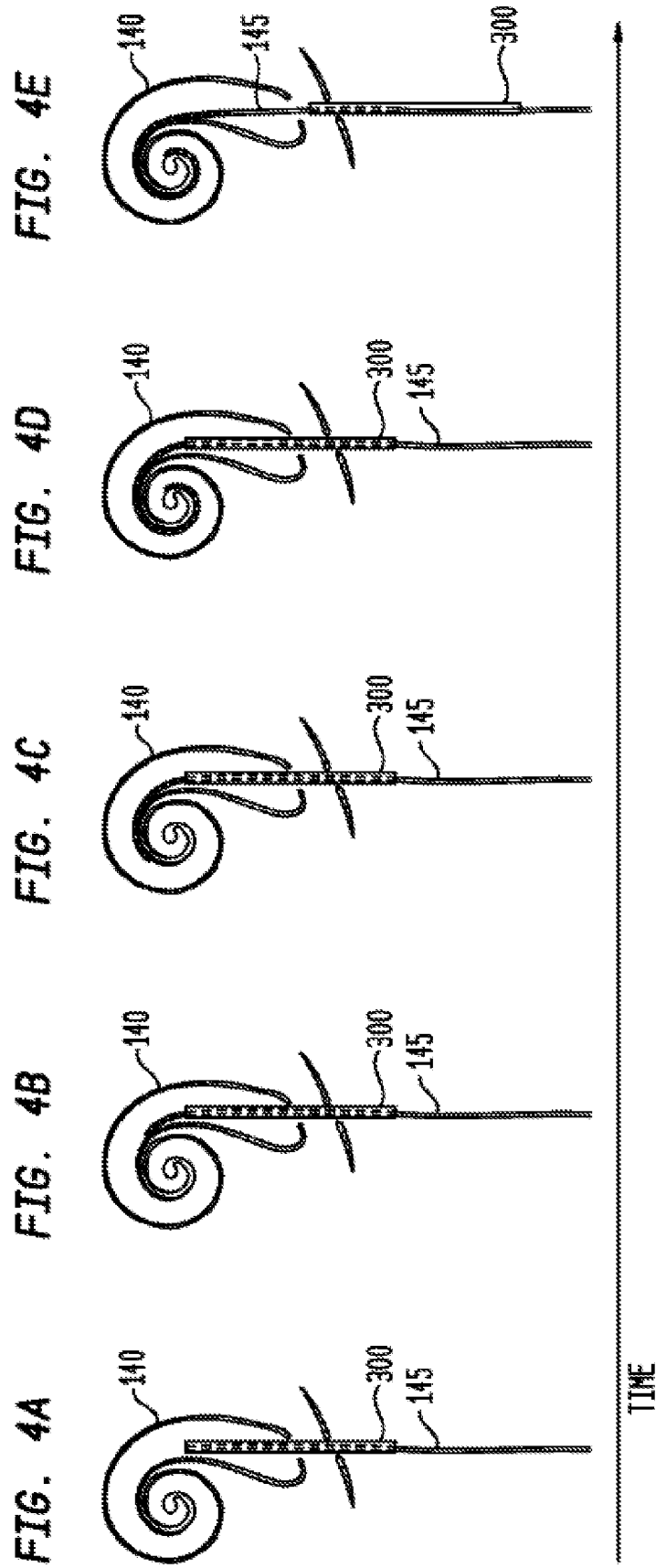

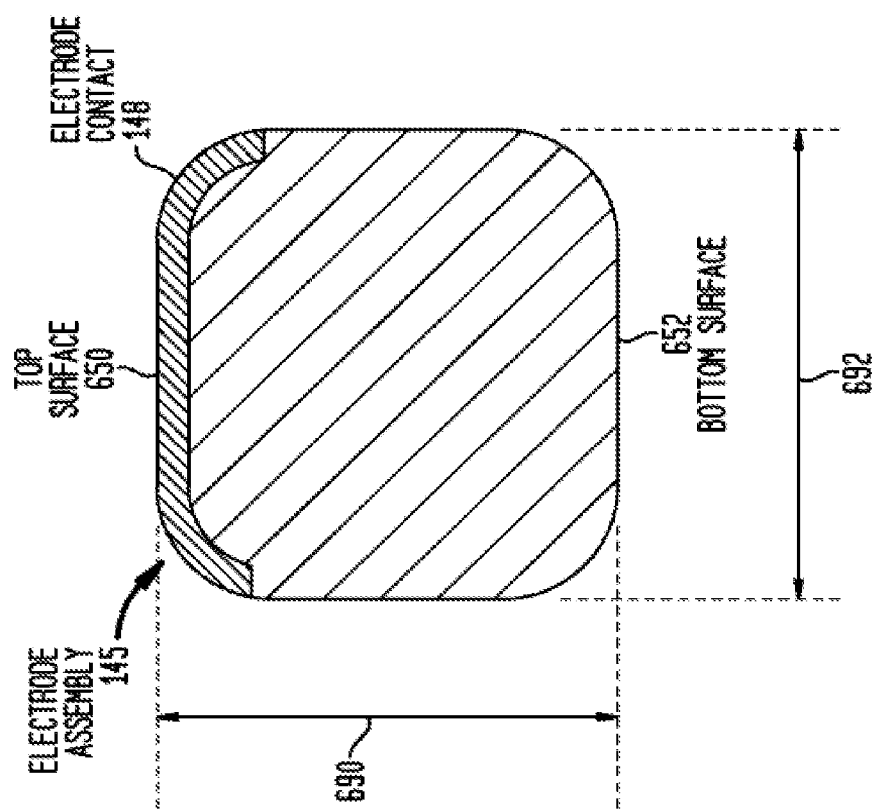

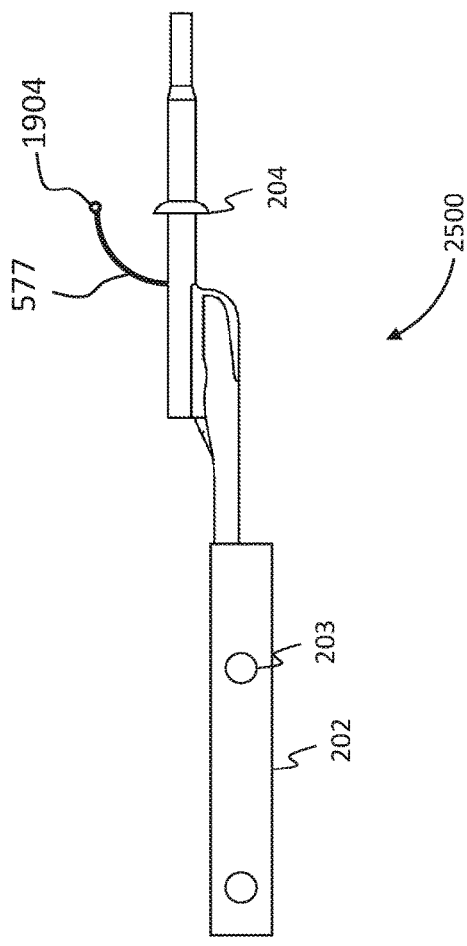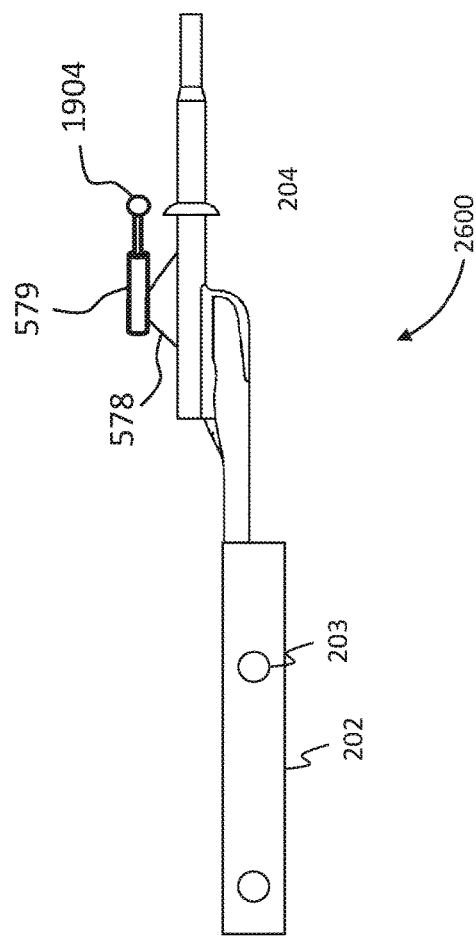

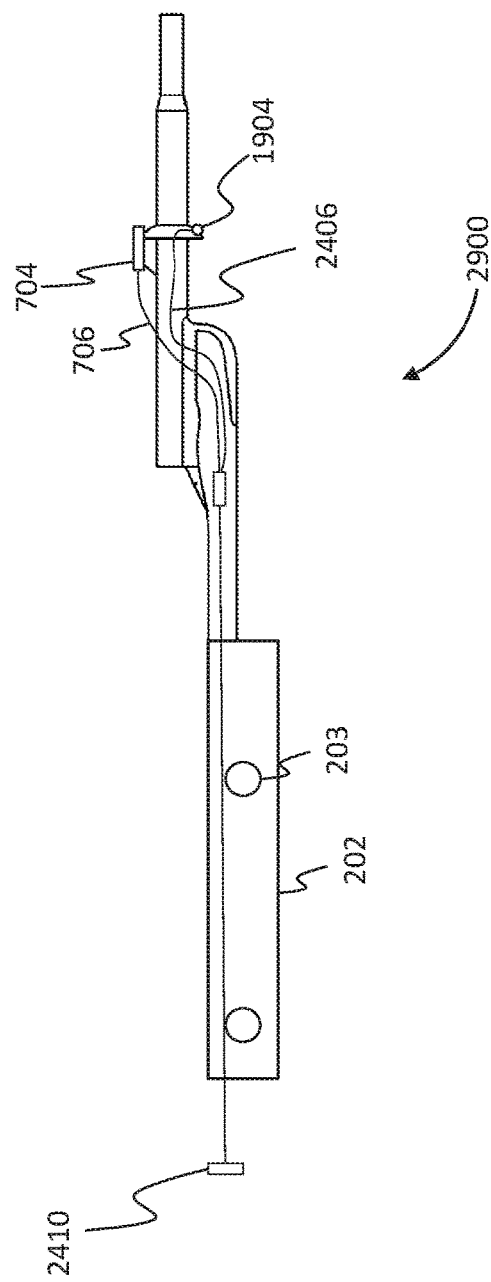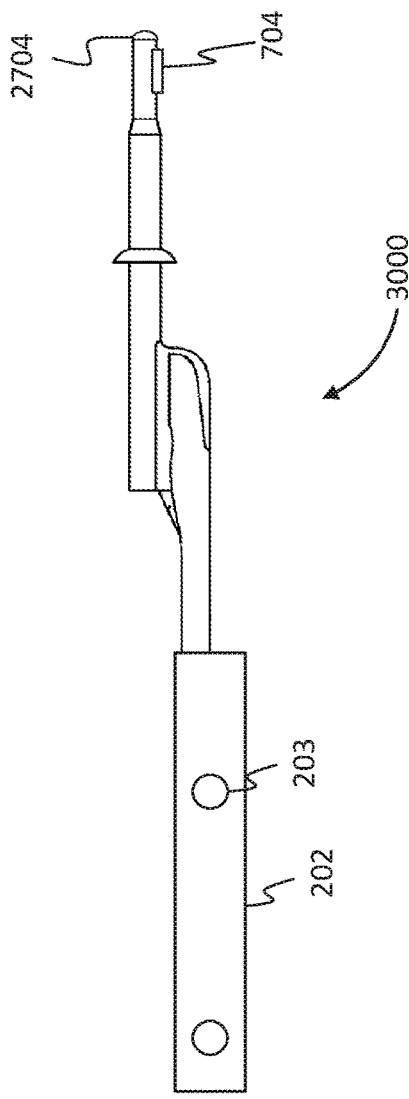

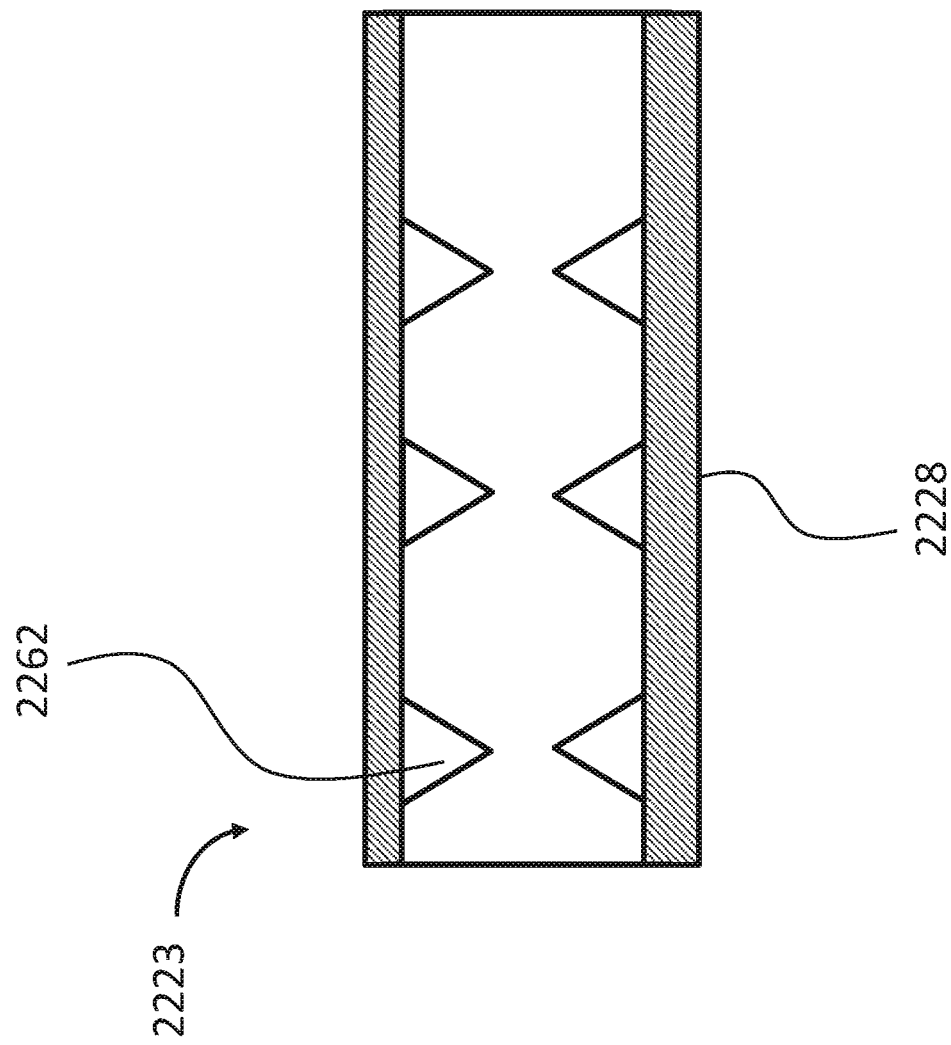

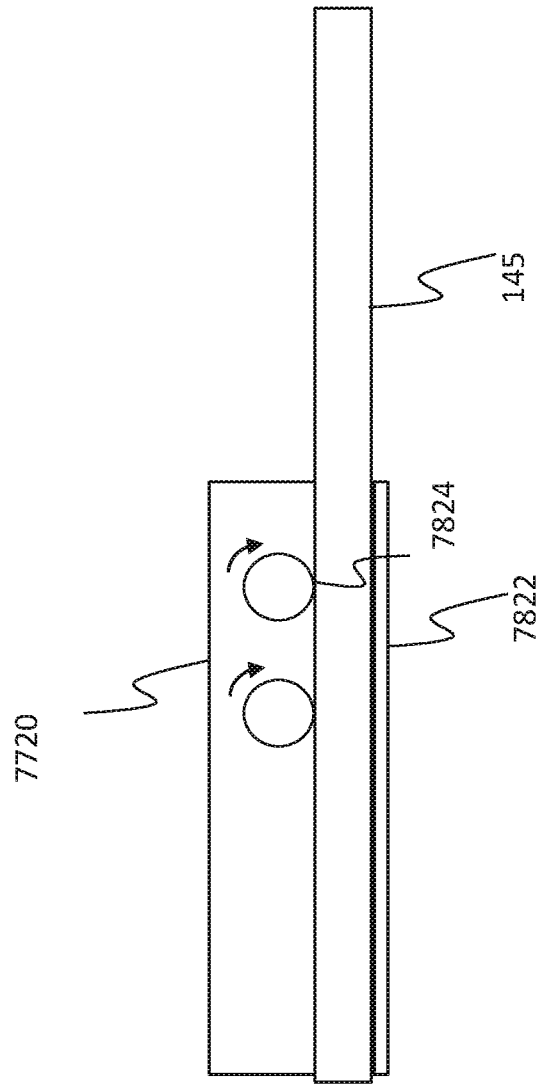

8131
8143

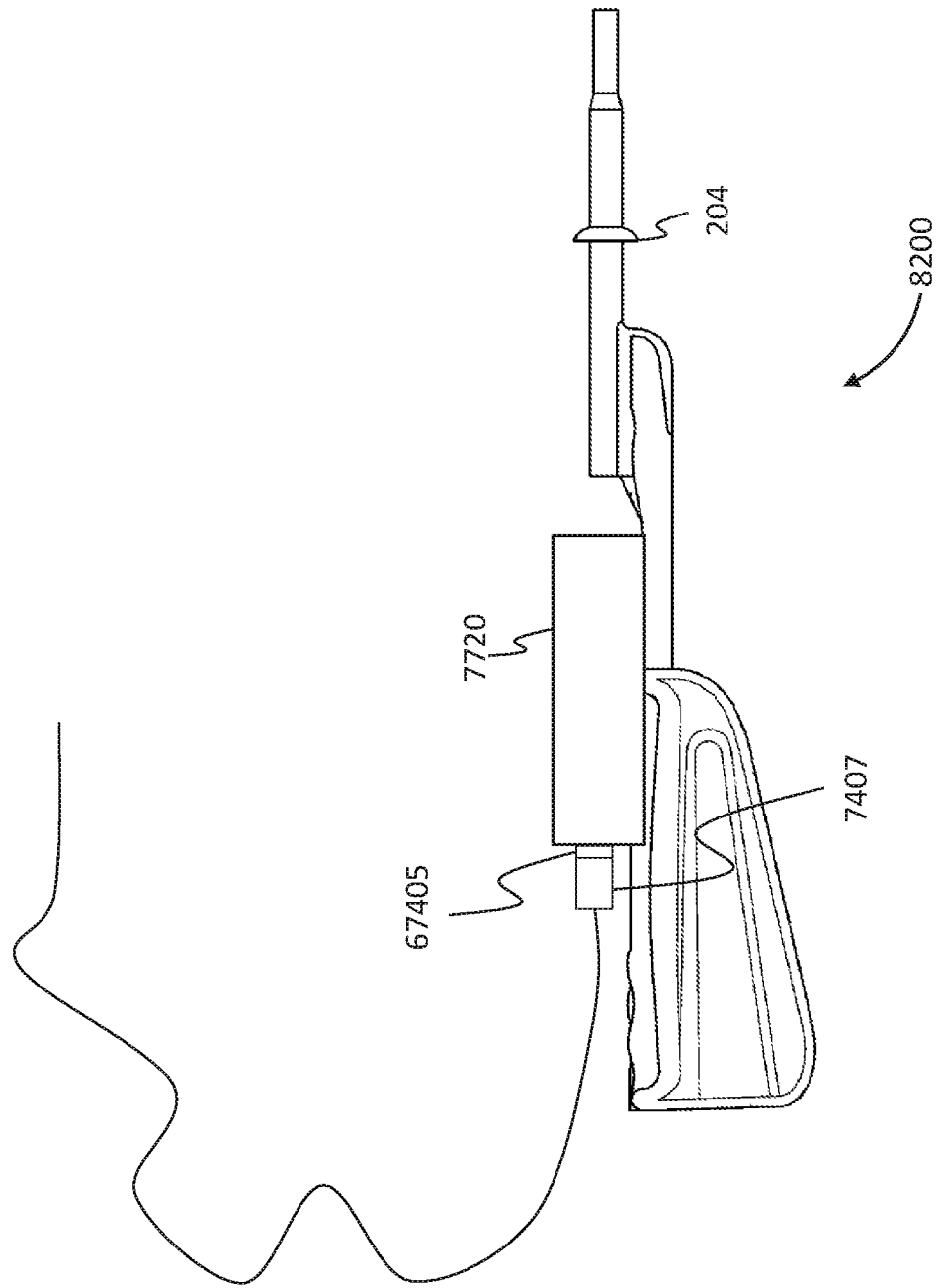

ADVANCED ELECTRODE ARRAY INSERTION

CROSS REFERENCE TO RELATED APPLICATIONS

The present application is a Continuation application of U.S. patent application Ser. No. 15/241,745, filed Aug. 19, 2016, naming Nicholas Charles PAWSEY as an inventor, the entire contents of that application being hereby incorporated by reference herein in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

It is noted that in at least some instances, there is utilitarian value to fitting a hearing prosthesis to a particular recipient. In some examples of some fitting regimes, there are methods which entail a clinician or some other professional presenting sounds to a recipient of the hearing prosthesis such that the hearing prosthesis evokes a hearing percept. Information can be obtained from the recipient regarding the character of the resulting hearing percept. Based on this information, the clinician can adjust or otherwise establish settings of the hearing prosthesis such that the hearing prosthesis operates according to these settings during normal use.

It is also noted that the electrode array of the cochlear implant generally shows utilitarian results if it is inserted in a cochlea.

SUMMARY

In accordance with an exemplary embodiment, there is an apparatus, comprising an actuator and electrode array support, wherein the apparatus is configured to insert an electrode array into a cochlea via controlled actuation of the actuator, wherein the controlled actuation is at least partially based on data that is at least partially based on electrical characteristics associated with the recipient.

In accordance with an exemplary embodiment, there is a system, comprising a robotic assembly configured to move an electrode array relative to the cochlea, and a control unit configured to receive data based on electrical phenomenon inside the recipient and control the robotic assembly based at least in part on the received data.

In accordance with another exemplary embodiment, there is a method, comprising advancing at least a first portion of an electrode array into a cochlea of a recipient during a first temporal period at least partially assisted by activation of an actuator that moves the electrode array monitoring an electrical phenomenon within the recipient at least one of during the first temporal period or during a second temporal period subsequent to the first temporal period, and controlling the actuator based on the action of monitoring.

In accordance with another exemplary embodiment, there is a method, comprising inserting an electrode array into a cochlea of a recipient utilizing a robotic apparatus by controlling the robotic apparatus at least partially based on electrical phenomenon associated with the recipient.

BRIEF DESCRIPTION OF THE DRAWINGS

Embodiments are described below with reference to the attached drawings, in which:

FIGS. 3A and 3B are side and perspective views of an electrode assembly extended out of an embodiment of an insertion sheath of the insertion guide illustrated in FIG. 2;

FIGS. 4A-4E are simplified side views depicting the position and orientation of a cochlear implant electrode assembly insertion guide tube relative to the cochlea at each of a series of successive moments during an exemplary implantation of the electrode assembly into the cochlea;

FIG. 6C is a cross-sectional view of a conventional electrode assembly;

FIGS. 19-27 depict side views of exemplary embodiments of exemplary electrode array insertion guides;

FIGS. 29-35 depict side views of exemplary embodiments of exemplary electrode array insertion guides;

FIGS. 51A-51C depict exemplary conductive apparatus is that can be utilized to test for open circuit according to some exemplary embodiments;

FIGS. 78-80 and 99 depict exemplary details of the actuator assembly of FIG. 77;

FIG. 82 depicts an exemplary embodiment of a insertion tool that can be handheld by a surgeon utilizing the actuator assembly to advance and/or retract the electrode array;

DETAILED DESCRIPTION

Figure 1:
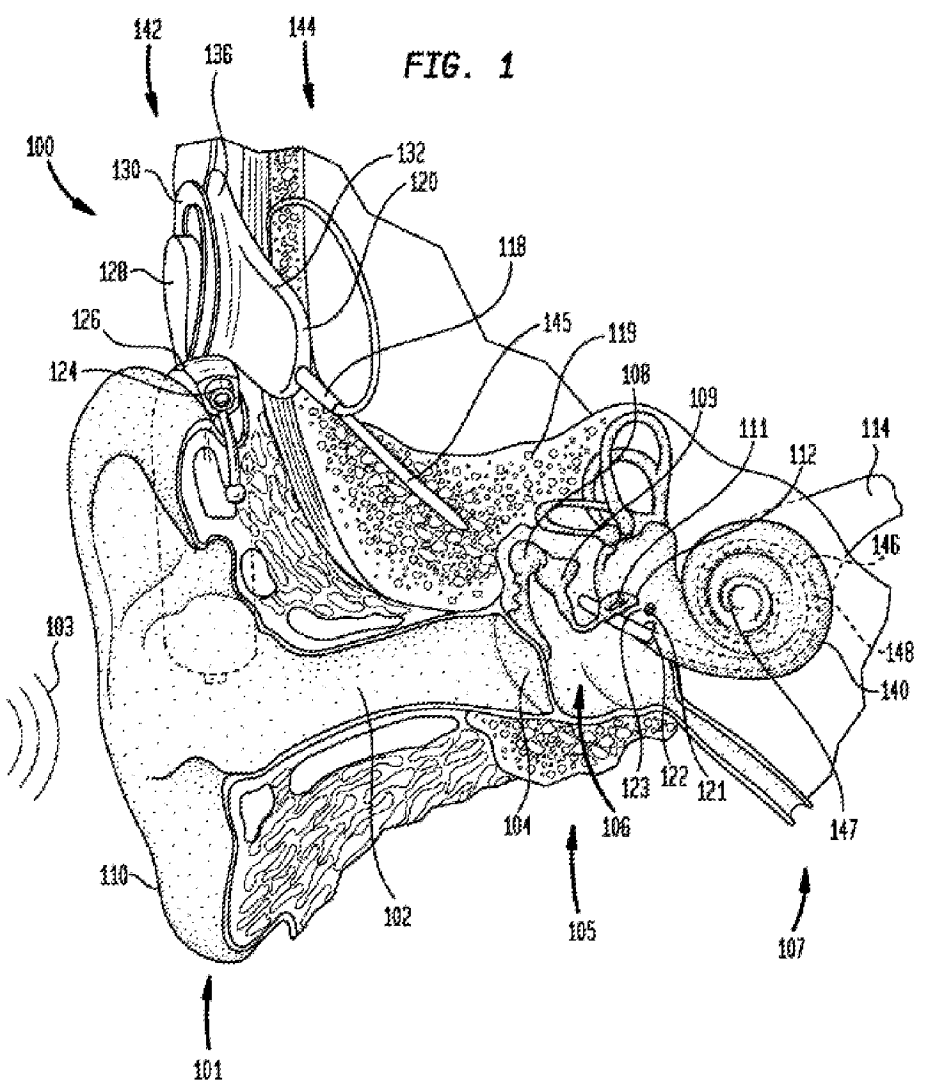
FIG. 1 is a perspective view of an exemplary hearing prosthesis in which at least some of the teachings detailed herein are applicable.

FIG. 1 is a perspective view of an exemplary cochlear implant 100 implanted in a recipient having an outer ear 101, a middle ear 105, and an inner ear 107. In a fully functional ear, outer ear 101 comprises an auricle 110 and an ear canal 102. Acoustic pressure or sound waves 103 are collected by auricle 110 and channeled into and through ear canal 102. Disposed across the distal end of ear canal 102 is a tympanic membrane 104 that vibrates in response to sound waves 103. This vibration is coupled to oval window or fenestra ovalis 112 through the three bones of the middle ear 105, collectively referred to as the ossicles 106, and comprising the malleus 108, the incus 109, and the stapes 111. Ossicles 106 filter and amplify the vibrations delivered by tympanic membrane 104, causing oval window 112 to articulate, or vibrate. This vibration sets up waves of fluid motion of the perilymph within cochlea 140. Such fluid motion, in turn, activates hair cells (not shown) inside the cochlea which in turn causes nerve impulses to be generated which are transferred through spiral ganglion cells (not shown) and auditory nerve 114 to the brain (also not shown) where they are perceived as sound.

The exemplary cochlear implant illustrated in FIG. 1 is a partially implanted stimulating medical device. Specifically, cochlear implant 100 comprises external components 142 attached to the body of the recipient, and internal or implantable components 144 implanted in the recipient. External components 142 typically comprise one or more sound input elements for detecting sound, such as microphone 124, a sound processor (not shown), and a power source (not shown). Collectively, these components are housed in a behind-the-ear (BTE) device 126 in the example depicted in FIG. 1. External components 142 also include a transmitter unit 128 comprising an external coil 130 of a transcutaneous energy transfer (TET) system. Sound processor 126 processes the output of microphone 124 and generates encoded stimulation data signals which are provided to external coil 130.

Internal components 144 comprise an internal receiver unit 132 including a coil 136 of the TET system, a stimulator unit 120, and an elongate stimulating lead assembly 118. Internal receiver unit 132 and stimulator unit 120 are hermetically sealed within a biocompatible housing commonly referred to as a stimulator/receiver unit. Internal coil 136 of receiver unit 132 receives power and stimulation data from external coil 130. Stimulating lead assembly 118 has a proximal end connected to stimulator unit 120, and extends through mastoid bone 119. Lead assembly 118 has a distal region, referred to as electrode assembly 145, a portion of which is implanted in cochlea 140.

Electrode assembly 145 can be inserted into cochlea 140 via a cochleostomy 122, or through round window 121, oval window 112, promontory 123, or an opening in an apical turn 147 of cochlea 140. Integrated in electrode assembly 145 is an array 146 of longitudinally-aligned and distally extending electrode contacts 148 for stimulating the cochlea by delivering electrical, optical, or some other form of energy. Stimulator unit 120 generates stimulation signals each of which is delivered by a specific electrode contact 148 to cochlea 140, thereby stimulating auditory nerve 114.

Figure 2:
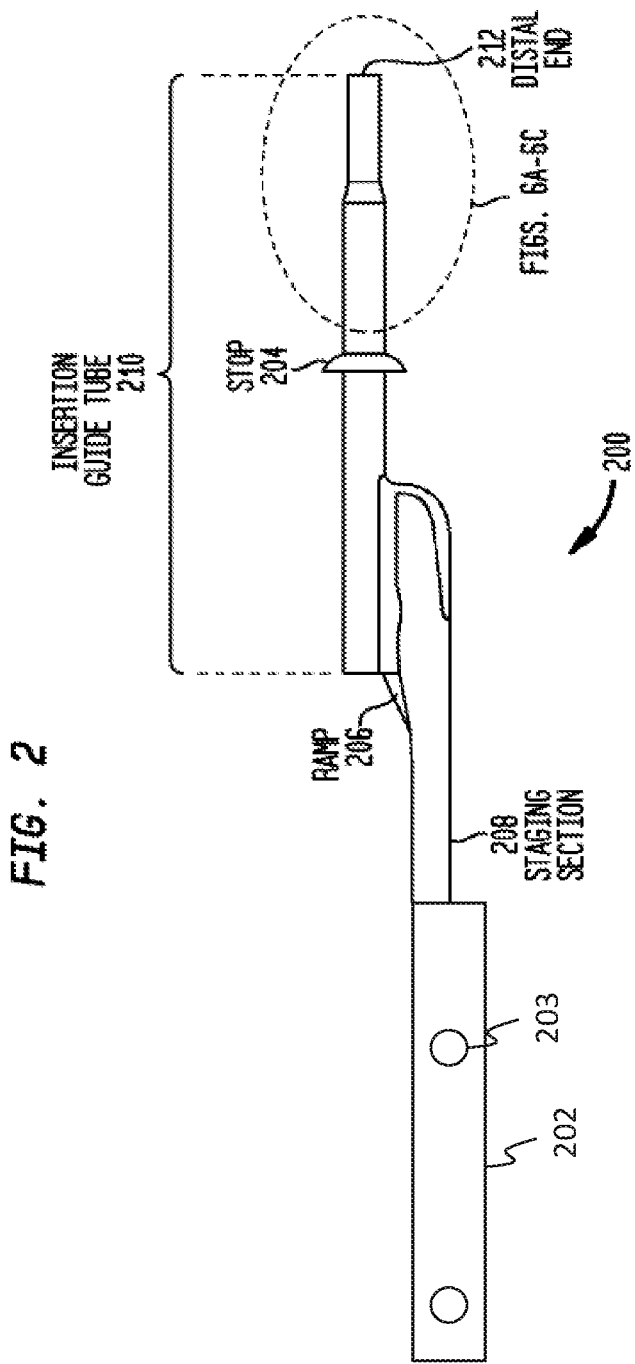
FIG. 2 is a side view of an embodiment of an insertion guide for implanting a cochlear implant electrode assembly such as the electrode assembly illustrated in FIG. 1.

Electrode assembly 145 may be inserted into cochlea 140 with the use of an insertion guide. FIG. 2 is a side view of an embodiment of an insertion guide for implanting an elongate electrode assembly generally represented by electrode assembly 145 into a mammalian cochlea, represented by cochlea 140. The illustrative insertion guide, referred to herein as insertion guide 200, includes an elongate insertion guide tube 210 configured to be inserted into cochlea 140 and having a distal end 212 from which an electrode assembly is deployed. Insertion guide tube 210 has a radially-extending stop 204 that may be utilized to determine or otherwise control the depth to which insertion guide tube 210 is inserted into cochlea 140.

Insertion guide tube 210 is mounted on a distal region of an elongate staging section 208 on which the electrode assembly is positioned prior to implantation. A robotic arm adapter 202 is mounted to a proximal end of staging section 208 to facilitate attachment of the guide to a robot, which adapter includes through holes 203 through which bolts can be passed so as to bolt the guide 200 to a robotic arm, as will be detailed below. During use, electrode assembly 145 is advanced from staging section 208 to insertion guide tube 210 via ramp 206. After insertion guide tube 210 is inserted to the appropriate depth in cochlea 140, electrode assembly 145 is advanced through the guide tube to exit distal end 212 as described further below.

Figure 3B:
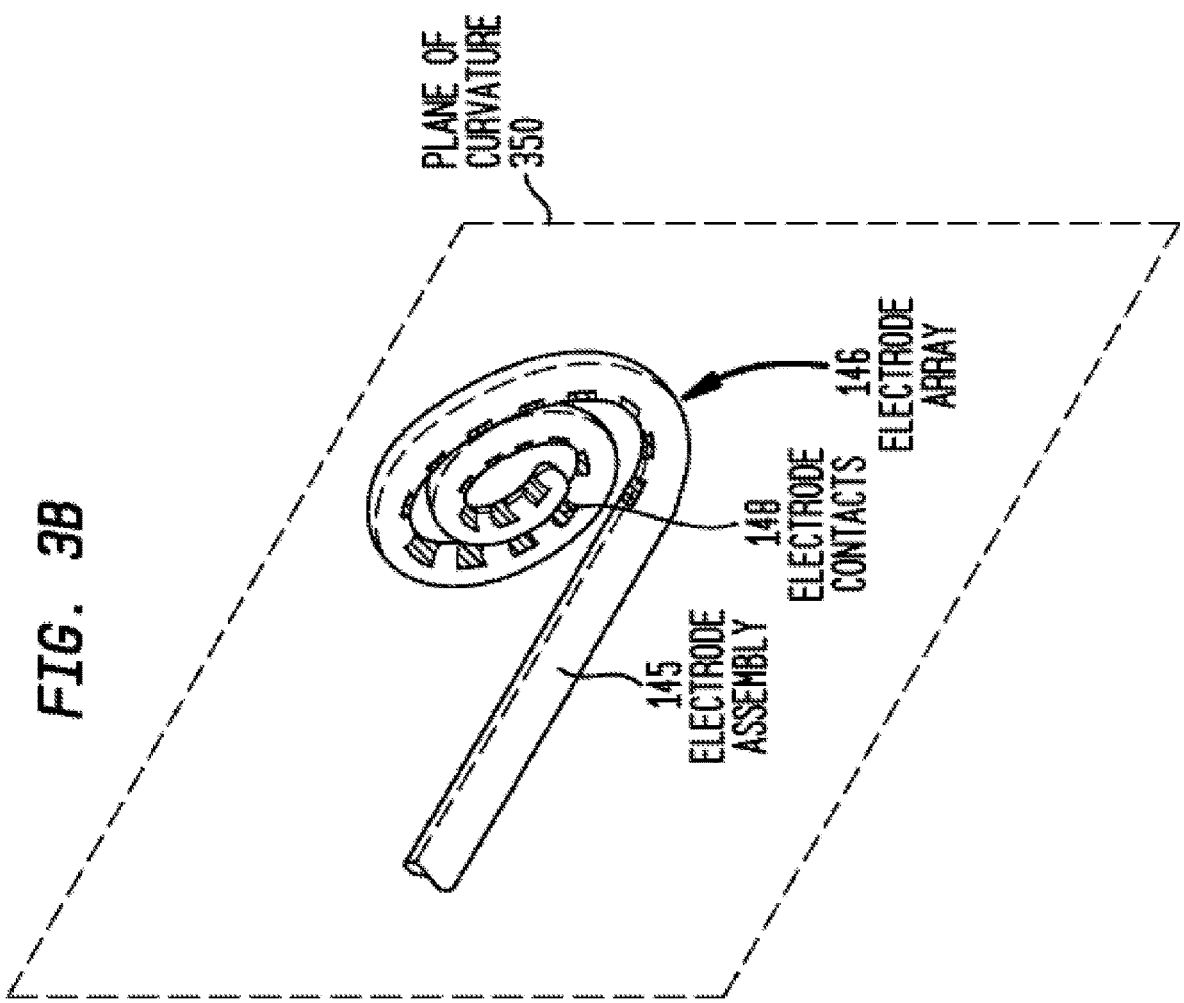

FIGS. 3A and 3B are side and perspective views, respectively, of representative electrode assembly 145. As noted, electrode assembly 145 comprises an electrode array 146 of electrode contacts 148. Electrode assembly 145 is configured to place electrode contacts 148 in close proximity to the ganglion cells in the modiolus. Such an electrode assembly, commonly referred to as a perimodiolar electrode assembly, is manufactured in a curved configuration as depicted in FIGS. 3A and 3B. When free of the restraint of a stylet or insertion guide tube, electrode assembly 145 takes on a curved configuration due to it being manufactured with a bias to curve, so that it is able to conform to the curved interior of cochlea 140. As shown in FIG. 3B, when not in cochlea 140, electrode assembly 145 generally resides in a plane 350 as it returns to its curved configuration. That said, it is noted that embodiments of the insertion guides detailed herein and/or variations thereof can be applicable to a so-called straight electrode array, which electrode array does not curl after being free of a stylet or insertion guide tube etc., but instead remains straight FIGS. 4A-4E are a series of side-views showing consecutive exemplary events that occur in an exemplary implantation of electrode assembly 145 into cochlea 140. Initially, electrode assembly 145 and insertion guide tube 310 are assembled. For example, electrode assembly 145 is inserted (slidingly or otherwise) into a lumen of insertion guide tube 300. The combined arrangement is then inserted to a predetermined depth into cochlea 140, as illustrated in FIG. 4A. Typically, such an introduction to cochlea 140 is achieved via cochleostomy 122 (FIG. 1) or through round window 121 or oval window 112. In the exemplary implantation shown in FIG. 4A, the combined arrangement of electrode assembly 145 and insertion guide tube 300 is inserted to approximately the first turn of cochlea 140.

As shown in FIG. 4A, the combined arrangement of insertion guide tube 300 and electrode assembly 145 is substantially straight. This is due in part to the rigidity of insertion guide tube 300 relative to the bias force applied to the interior wall of the guide tube by pre-curved electrode assembly 145. This prevents insertion guide tube 300 from bending or curving in response to forces applied by electrode assembly 145, thus enabling the electrode assembly to be held straight, as will be detailed below.

As noted, electrode assembly 145 is biased to curl and will do so in the absence of forces applied thereto to maintain the straightness. That is, electrode assembly 145 has a memory that causes it to adopt a curved configuration in the absence of external forces. As a result, when electrode assembly 145 is retained in a straight orientation in guide tube 300, the guide tube prevents the electrode assembly from returning to its pre-curved configuration. This induces stress in electrode assembly 145. Pre-curved electrode assembly 145 will tend to twist in insertion guide tube 300 to reduce the induced stress. In the embodiment configured to be implanted in scala tympani of the cochlea, electrode assembly 145 is pre-curved to have a radius of curvature that approximates the curvature of medial side of the scala tympani of the cochlea. Such embodiments of the electrode assembly are referred to as a perimodiolar electrode assembly, and this position within cochlea 140 is commonly referred to as the perimodiolar position. In some embodiments, placing electrode contacts in the perimodiolar position provides utility with respect to the specificity of electrical stimulation, and can reduce the requisite current levels thereby reducing power consumption.

As shown in FIGS. 4B-4D, electrode assembly 145 may be continually advanced through insertion guide tube 300 while the insertion sheath is maintained in a substantially stationary position. This causes the distal end of electrode assembly 145 to extend from the distal end of insertion guide tube 300. As it does so, the illustrative embodiment of electrode assembly 145 bends or curves to attain a perimodiolar position, as shown in FIGS. 4B-4D, owing to its bias (memory) to curve. Once electrode assembly 145 is located at the desired depth in the scala tympani, insertion guide tube 300 is removed from cochlea 140 while electrode assembly 145 is maintained in a stationary position. This is illustrated in FIG. 4E.

Conventional insertion guide tubes typically have a lumen dimensioned to allow the entire tapered electrode assembly to travel through the guide tube. Because the guide tube is able to receive the relatively larger proximal region of the electrode assembly, there will be a gap between the relatively smaller distal region of the electrode assembly and the guide tube lumen wall. Such a gap allows the distal region of the electrode assembly to curve slightly until the assembly can no longer curve due to the lumen wall.

Returning to FIGS. 3A-3B, perimodiolar electrode assembly 145 is pre-curved in a direction that results in electrode contacts 148 being located on the interior of the curved assembly, as this causes the electrode contacts to face the modiolus when the electrode assembly is implanted in or adjacent to cochlea 140. Insertion guide tube 500 retains electrode assembly 145 in a substantially straight configuration, thereby preventing the assembly from taking on the configuration shown in FIG. 3B. The inability of electrode assembly 145 to curve to accommodate the bias force induces stress in the assembly. Pre-curved electrode assembly 145 will tend to twist while exiting insertion guide tube 510 to reduce this stress. With the distal end of the electrode assembly curved to abut the lumen wall, the assembly twists proximally.

Figure 5A:
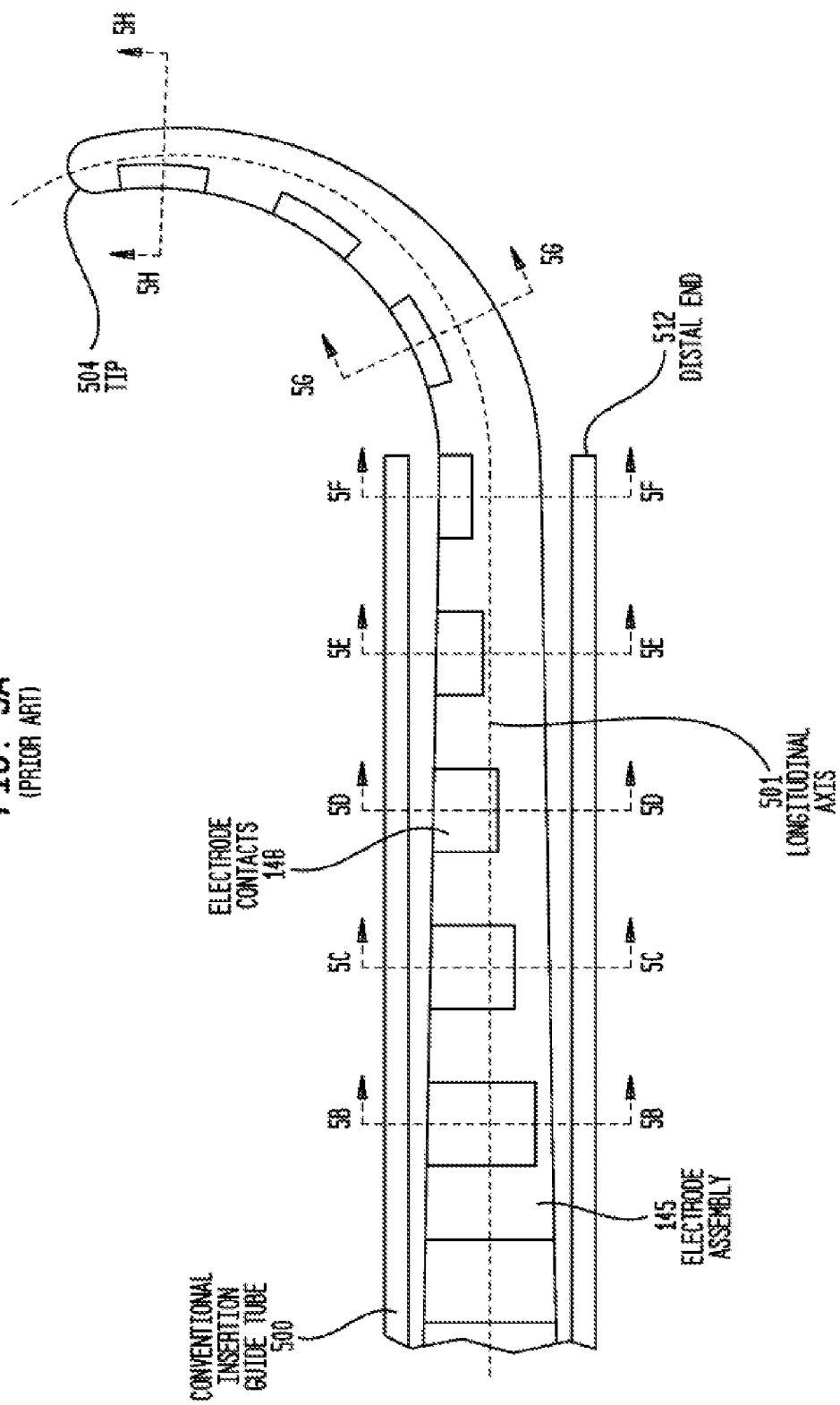
FIG. 5A is a side view of a perimodiolar electrode assembly partially extended out of a conventional insertion guide tube showing how the assembly may twist while in the guide tube.
Figure 5E:
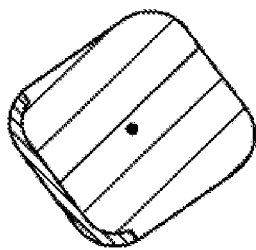
FIGS. 5B-5I are cross-sectional views of the electrode assembly illustrated in FIG. 5A.
Figure 5D:
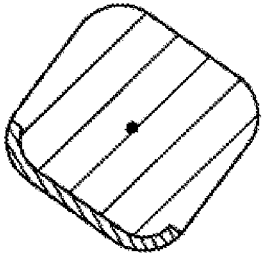
Figure 5C:
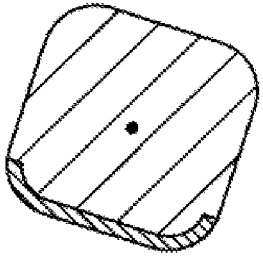
Figure 5B:
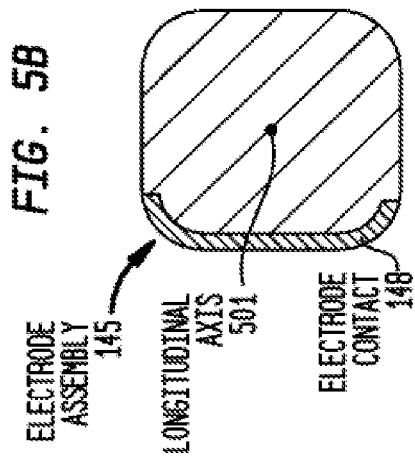
Figure 5I:
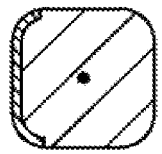
Figure 5H:
Figure 5G:
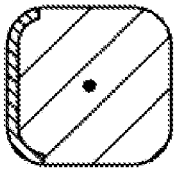
Figure 5F:
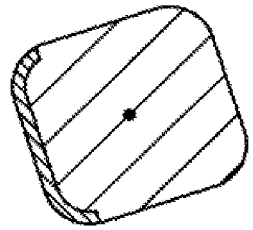

This is illustrated in FIGS. 5A-5I. FIG. 5A is a side view of perimodiolar electrode assembly 145 partially extended out of a conventional insertion guide tube 500, showing how the assembly may twist while in the guide tube. FIGS. 5B-5F are cross-sectional views taken through respective sections 5B-5B, 5C-5C, 5D-5D, 5E-5E, and 5F-5F of electrode assembly 145 in FIG. 5A.

As shown in FIGS. 5A-5F, the portion of electrode assembly 145 in insertion guide tube 510 is twisted about its longitudinal axis, resulting in electrode contacts 148 in the twisted region to have a different radial position relative to insertion guide tube 510. As shown in FIGS. 5A and 5G-I, as electrode assembly 145 exists insertion guide tube 500, the assembly is free to curve in accordance with its bias force. However, the orientation of electrode contacts in the deployed region of the assembly is adversely affected by the twisted region of the assembly remaining in guide tube 510.

Accordingly, some embodiments detailed herein and/or variations thereof are directed towards an insertion guide having an insertion guide tube that maintains a perimodiolar or other pre-curved electrode assembly in a substantially straight configuration while preventing the electrode assembly from twisting in response to stresses induced by the bias force which urges the assembly to return to its pre-curved configuration. This generally ensures that when the electrode assembly is deployed from the distal end of the insertion guide tube, the electrode assembly and insertion guide tube have a known relative orientation.

Figure 6A:
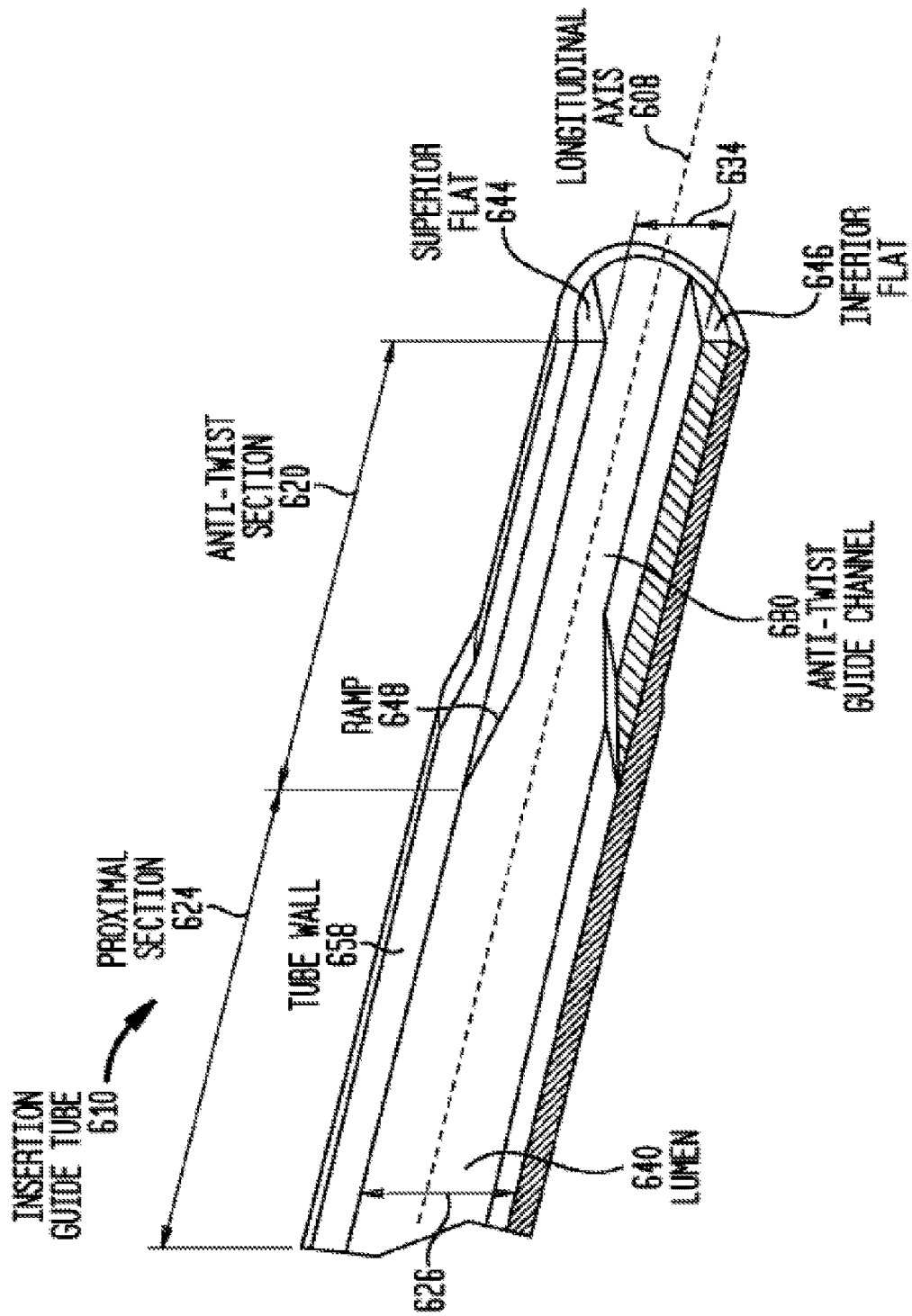
FIG. 6A is a cross-sectional view of an embodiment of the insertion guide tube.
Figure 6B:
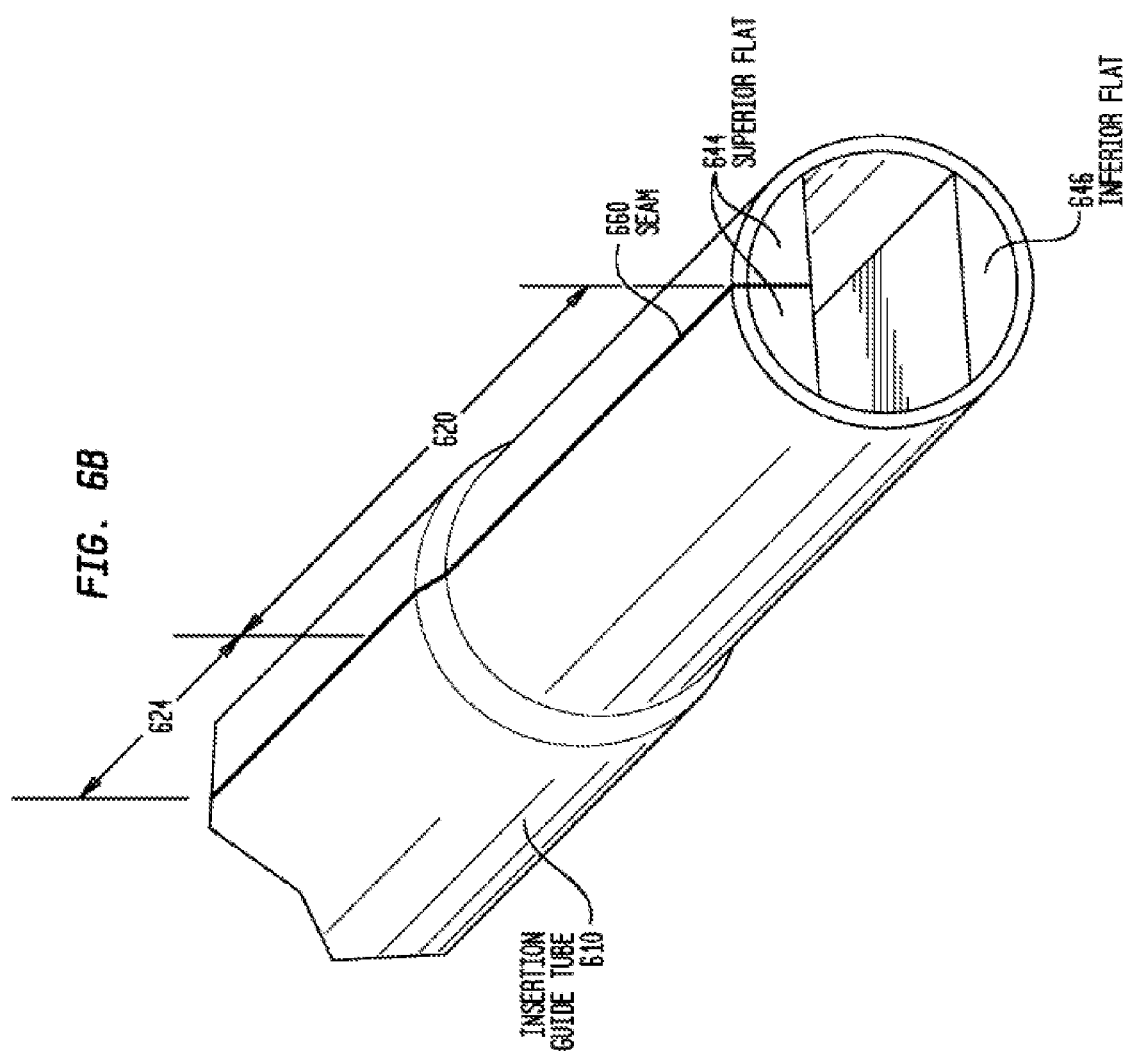
FIG. 6B is a perspective view of the portion of the guide tube illustrated in FIG. 6A.

FIGS. 6A-6D are different views of but some exemplary embodiments of insertion guide tube 210, referred to herein at insertion guide tube 610. For ease of description, features of the guide tube will be described with reference to the orientation of the guide tube illustrated in the figures. FIG. 6A is a partial cross-sectional view of an embodiment of insertion guide tube 210, referred to herein at insertion guide tube 610. As can be seen, insertion guide tube 610 includes an anti-twist section 620 formed at the distal end of the guide tube. Anti-twist section 320 is contiguous with the remaining part of guide tube 610. Guide tube 610 has a lumen 640 which, in proximal section 624 has a vertical dimension 626, and an distal anti-twist section 620 has a smaller vertical dimension 634 described below. The vertical dimension of lumen 640 decreases from dimension 626 to dimension 634 due to a ramp 648 at the proximal end of anti-twist section 642.

Anti-twist section 620 causes a twisted electrode assembly traveling through guide tube 610 to return to its untwisted state, and retains the electrode assembly in a straight configuration such that the orientation of the electrode assembly relative to the insertion guide tube 610 does not change.

As shown in FIG. 6C, electrode assembly 145 has a rectangular cross-sectional shape, with the surface formed in part by the surface of the electrode contact, referred to herein as top surface 650, and the opposing surface, referred to herein as bottom surface 652, are substantially planar. These substantially planar surfaces are utilized in embodiments of the insertion guide tube described herein.

Figure 6D:
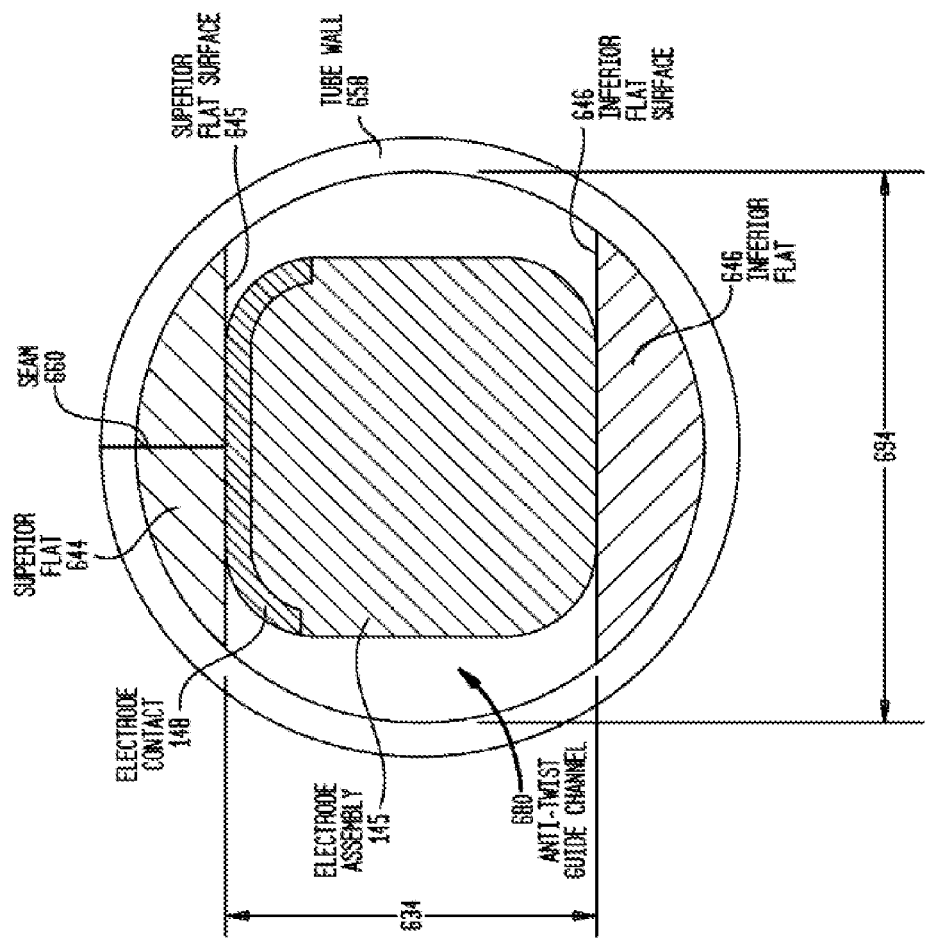
FIG. 6D is a cross-sectional view of the conventional electrode assembly of FIG. 6C positioned in the insertion guide tube illustrated in FIGS. 6A and 6B.

Tube wall 658 in anti-twist section 620 has surfaces 644 and 646 which extend radially inward to form an anti-twist guide channel 680. Specifically, a superior flat 644 provides a substantially planar lumen surface along the length of section 620. As shown best in FIGS. 6A, 6B, and 6D, superior flat 644 has a surface that is substantially planar and which therefore conforms with the substantially planar top surface 650 of electrode assembly 145. Similarly, inferior flat 646 has a surface that is substantially planar which conforms with the substantially planar bottom surface 652 of electrode assembly 145. As shown in FIG. 6D, when a distal region of electrode assembly 145 is located in anti-twist section 620, the surfaces of superior flat 644 and inferior flat 646 are in physical contact with top surface 650 and bottom surface 652, respectively, of the electrode assembly. This prevents the electrode assembly from curving, as described above.

Figure 7:
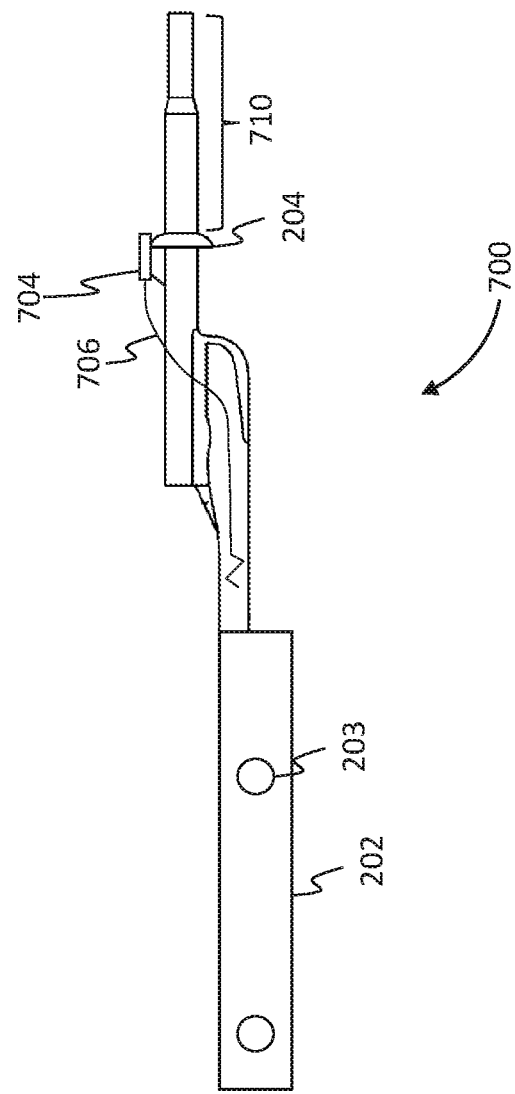
FIGS. 7 and 8 depict side views of respective exemplary embodiments of exemplary electrode array insertion guides.
Figure 8:
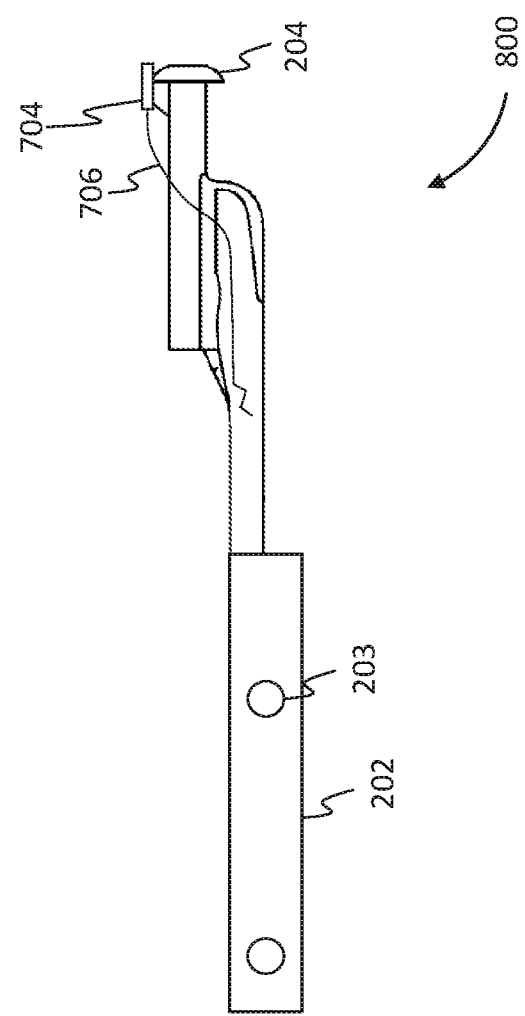

FIG. 7 depicts an exemplary embodiment of a cochlear electrode array insertion guide 700. In an exemplary embodiment, the insertion guide 700 corresponds to that of the insertion guide 200 detailed above, with the exception of the addition of acoustic stimulation generator 704, and the modifications to the tool so as to support the generator and the associated components thereof (e.g., electrical leads 706 (only the "distal" portion of the lead (distal relative to the tool 800) is depicted, the "break" being conceptual), etc.— more on this below). Accordingly, FIG. 7 depicts a cochlear electrode array insertion guide comprising an array guide (e.g., the insertion guide tube (210 of FIG. 2)) and an active functional component (e.g., generator 704). Some additional details of some exemplary functional components, including some exemplary active functional components, will be described in greater detail below. However, it is briefly noted at this time that not all embodiments of the cochlear electrode array insertion guide include an intracochlear portion. In this regard, FIG. 7 depicts a tool 700 that includes an intracochlear portion 710. This is the portion to the right of stop 204/the portion on the distal side of stop 204 (distal relative to the entire insertion guide). Conversely, FIG. 8 depicts a tool 800 that does not include an intracochlear portion. Instead, stop 204 is configured to be placed against the outside of the cochlea such that the passageway through the tool through which the electrode array is passed is aligned with the pertinent window and/or cochleostomy such that no parts of the tool 800 enters the cochlea.

It is noted that while the teachings detailed herein with respect to extra functionality of the insertion guide are based on the insertion guide detailed above with respect to FIGS. 5A-6D, these teachings can be applicable to other types of insertion guides. Indeed, as will be detailed below, some embodiments of the insertion guides do not have an intra-cochlear portion at all. Accordingly, the teachings above with respect to FIGS. 5A-6D serve as but one example of an insertion guide that the following teachings can be utilized in conjunction therewith.

With reference back to FIG. 7, the exemplary active functional component can be an acoustic stimulation generator, as noted above. In an exemplary embodiment, the embodiment of FIG. 7 (or FIG. 8) enables the middle ear to be bypassed so as to provide a source of acoustic stimulation in an intraoperative ECoG measurement. In this regard, the stimulation generator 704 can be an extra-cochlea bone conduction actuator positioned such that, when the insertion guide is utilized when inserting the electrode array into the cochlea, the acoustic signal generator 704 is pressed against the cochlear promontory, round window, or cochleostomy during insertion. In an exemplary embodiment, the proximity of the acoustic stimulation generator 704 to the cochlea enables such to be utilized as an acoustic stimulation source during intraoperative ECoG measuring. In an exemplary embodiment, the acoustic stimulation generator 704 is a bone conduction device as detailed above. In an exemplary embodiment, the acoustic stimulation generator 704 is an electromagnetic actuator that is configured to vibrate when subjected to a current via the electrode lead 706. Alternatively, in an exemplary embodiment, the acoustic stimulation generator is a piezoelectric actuator that is configured to vibrate when subjected to a current via the electrode lead 706. In these embodiments, these actuators can be actuated for a bone conduction device, as noted above. That said, in some alternate embodiments, the acoustic stimulation generator can be a speaker. Element 704 can be any device that can enable stimulation having utilitarian value for an ECoG measurement.

Figure 9:
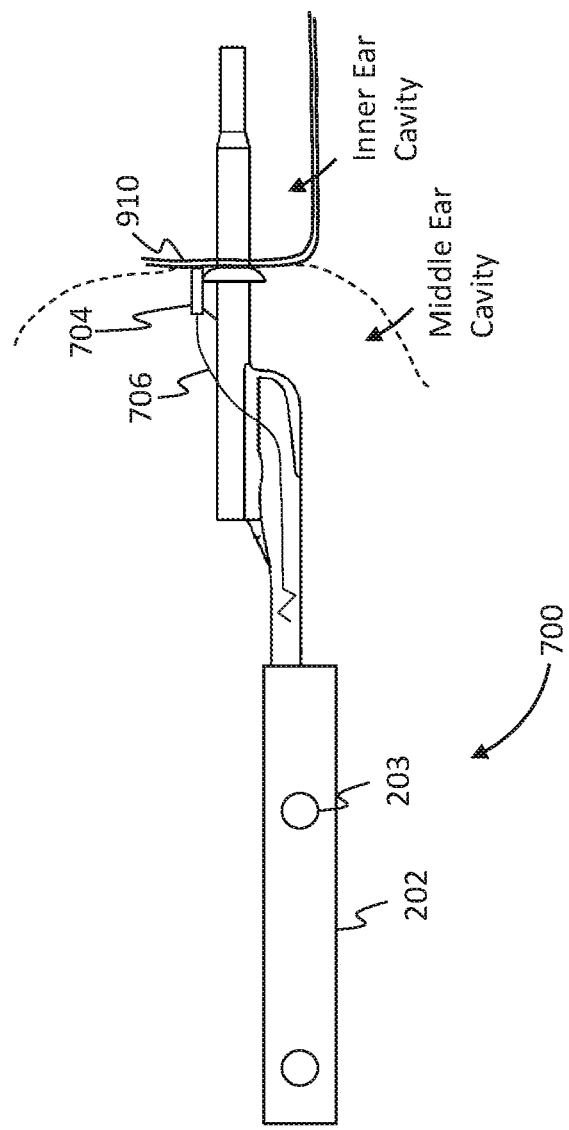
FIGS. 9-10B depicts side views of various exemplary embodiments of various insertion guides in use.

The embodiments of FIGS. 7 and 8 are such that the generator 704 abuts the outside of the cochlea during use so as to establish physical contact with the outside of the cochlea. FIG. 9 depicts an exemplary scenario of use, where element 910 is the wall of the cochlea that separates the middle ear cavity from the inner cavity. In an exemplary embodiment, generator 704 abuts the cochlear promontory. In an exemplary embodiment, generator 704 abuts the round window and/or oval window. With respect to the "and/or" it is noted that while the embodiments depicted herein indicate a single generator, in alternative embodiments, two or more generators can be utilized in an array such that one contacts the oval window and the other contacts the round window. In an exemplary embodiment, these generators can operate out of phase such that a first generator depresses the round window while a second generator provides no force against the oval window, and then the second generator depresses the oval window while the first generator provides no force against the round window. An exemplary embodiment of a structure configured to operate in such a manner or a variation thereof is detailed in U.S. patent application Ser. No. 15/159,335, entitled "Implantable Hearing Prosthesis With Dual Actuation" filed on May 19, 2016, to the inventor Joris Walraevens. Any force generator/vibration generator that can establish stimulation to enable ECoG measurement can be utilized in at least some exemplary embodiments.

In any event, it is again noted that the generator can be located anywhere on the guide that the generator can have utilitarian value with respect to establishing stimulation to enable ECoG measurements. In an exemplary embodiment, the generator can be located such that, during use, the generator is not necessarily in direct contact with the cochlea providing that such has the aforementioned utilitarian value with respect to generating stimulation enabling ECoG measurement.

Figure 10A:
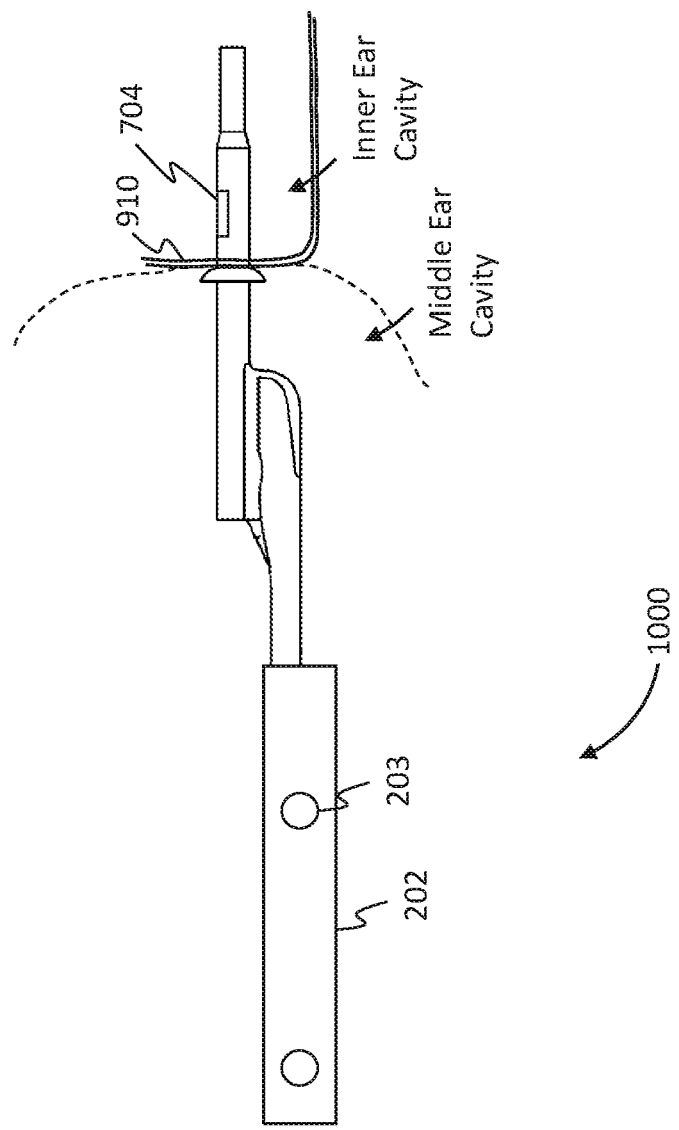
Figure 10B:
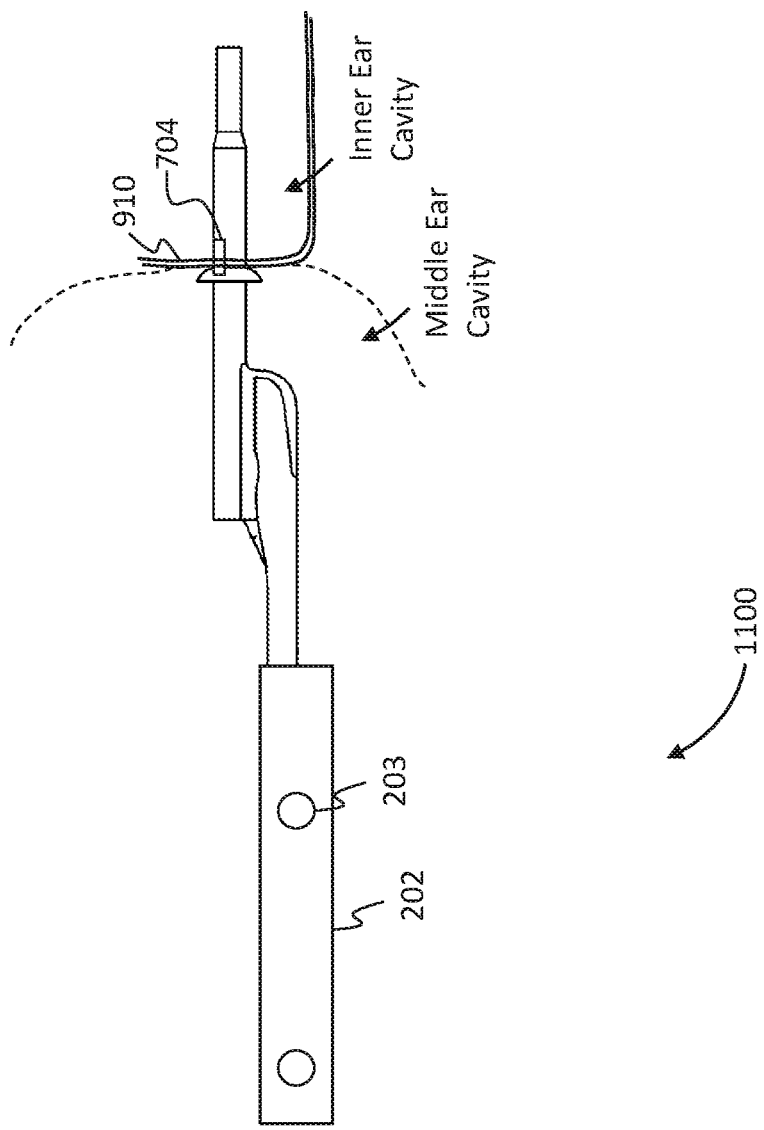

While the embodiments detailed above have focused on the generator being located entirely outside the cochlea (e.g., entirely inside the middle ear), in an alternative embodiment, the generator is located inside the cochlea during use. FIG. 10A depicts an exemplary insertion regime utilizing exemplary electrode array insertion guide 1000 where the generator 704 is located entirely in the inner cavity (in the cochlea) when the insertion guide is fully inserted into the inner ear cavity. Still further, FIG. 10B depicts an exemplary insertion regime utilizing exemplary electrode array insertion guide 1100 where the generator is located in the wall that separates the middle ear cavity from the inner ear cavity when the insertion guide is fully inserted into the inner ear cavity. In an exemplary embodiment, a portion of the generator 704 is located in the middle ear cavity, and another portion of the generator 704 is located in the wall 910 and/or in the inner cavity when the insertion guide 1100 is fully inserted into the cochlea. In an exemplary embodiment, the guide is such that the entire generator 704 is located in the wall 910 (i.e., in the hole through the wall) when the insertion guide 1100 is fully inserted into the inner ear cavity. That is, no part of the generator is located in the middle ear cavity where the inner ear cavity (where, for the purposes of this paragraph only, the volume corresponding to the hole that is formed in the cochlea so that the array can pass from the middle ear cavity to the inner ear cavity is neither in the middle ear cavity nor in the inner ear cavity). In an exemplary embodiment, the guide is such that a portion of the generator 704 is located in the wall 910 when the insertion guide 1100 is fully inserted into the inner ear cavity, and a portion of the generator is located in the inner ear cavity when the insertion guide is fully inserted into the inner ear cavity.

Figure 11:
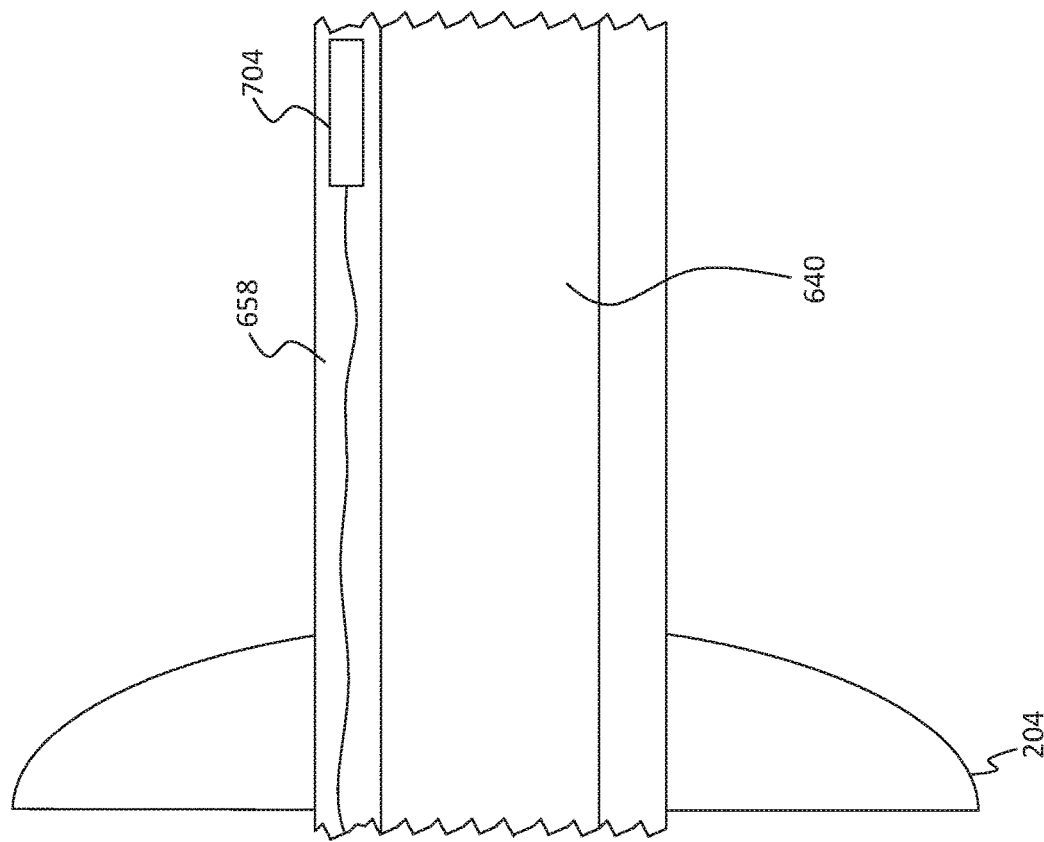
FIGS. 11-18 depict cross-sectional views of portions of the insertion guide tube of exemplary embodiments of the electrode array insertion guide.

FIG. 11 depicts an exemplary cross-section of an exemplary insertion guide where the frame of reference is seen relative to the stop 204, and the distance between the closest service of the stop 204 and the generator 704 is greater than the thickness of the wall of the cochlea between the middle ear cavity in the inner ear cavity. Thus, in this exemplary embodiment, the entire generator 704 is located entirely within the inner ear cavity when the insertion guide is fully inserted into the inner ear cavity.

As can be seen in this exemplary embodiment, the generator 704 is located or otherwise embedded in the tube wall 658 of the insertion guide. In the end exemplary embodiment depicted in the figure, the generator 704 is located in the proximal section 624 of the insertion guide tube 610. That said, in an alternative embodiment, the generator 704 can be located in the anti-twist section 620. The generator can be embedded anywhere within the insertion guide that can enable the teachings detailed herein and/or variations thereof. While the embodiment depicted in FIG. 11 shows only one generator 704, in an alternate embodiment, two or more generators can be located in the wall 658 or otherwise embedded in the wall 658 such that two or more generators are located inside the cochlea when the guide is fully inserted in the cochlea.

Figure 12A:
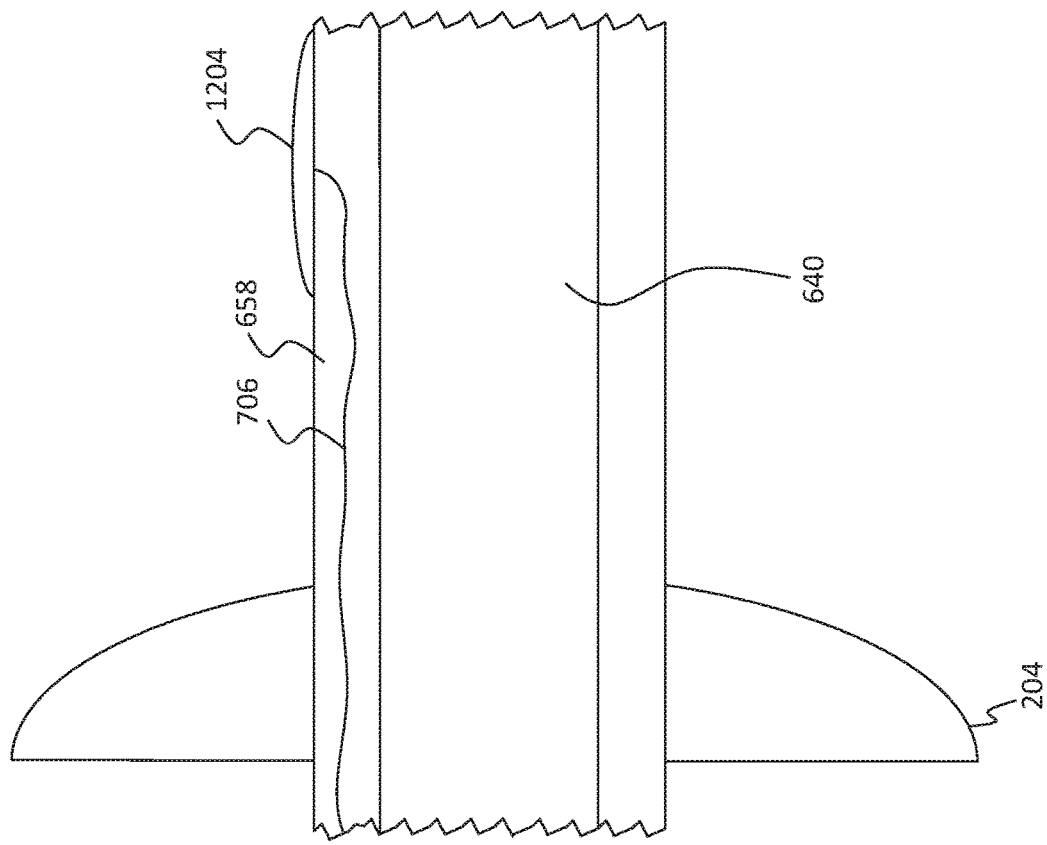

FIG. 12A depicts an alternate embodiment where the generator 1204, which can correspond to any of the generators detailed herein or any other generator for that matter that can have utilitarian value with respect to enabling the teachings detailed herein, is located on the outside of tube wall 658. As can be seen, lead 706 leads from the outside of the inner ear cavity/from the guide handle section into the inner ear cavity to the actuator 1204. In the embodiment depicted in FIG. 12A the actuator is streamlined so as to not interfere or otherwise enable relative ease of insertion of the proximal section 624 of the guide into the cochlea.

Figure 12B:
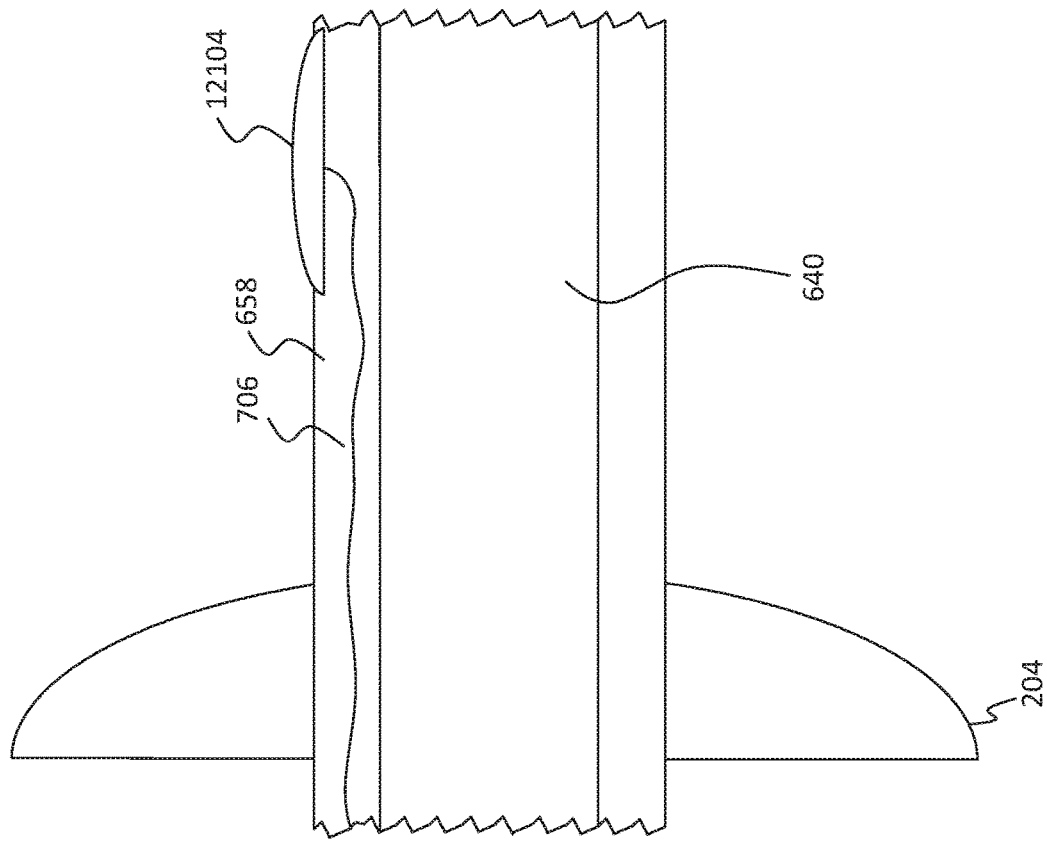
Figure 12C:
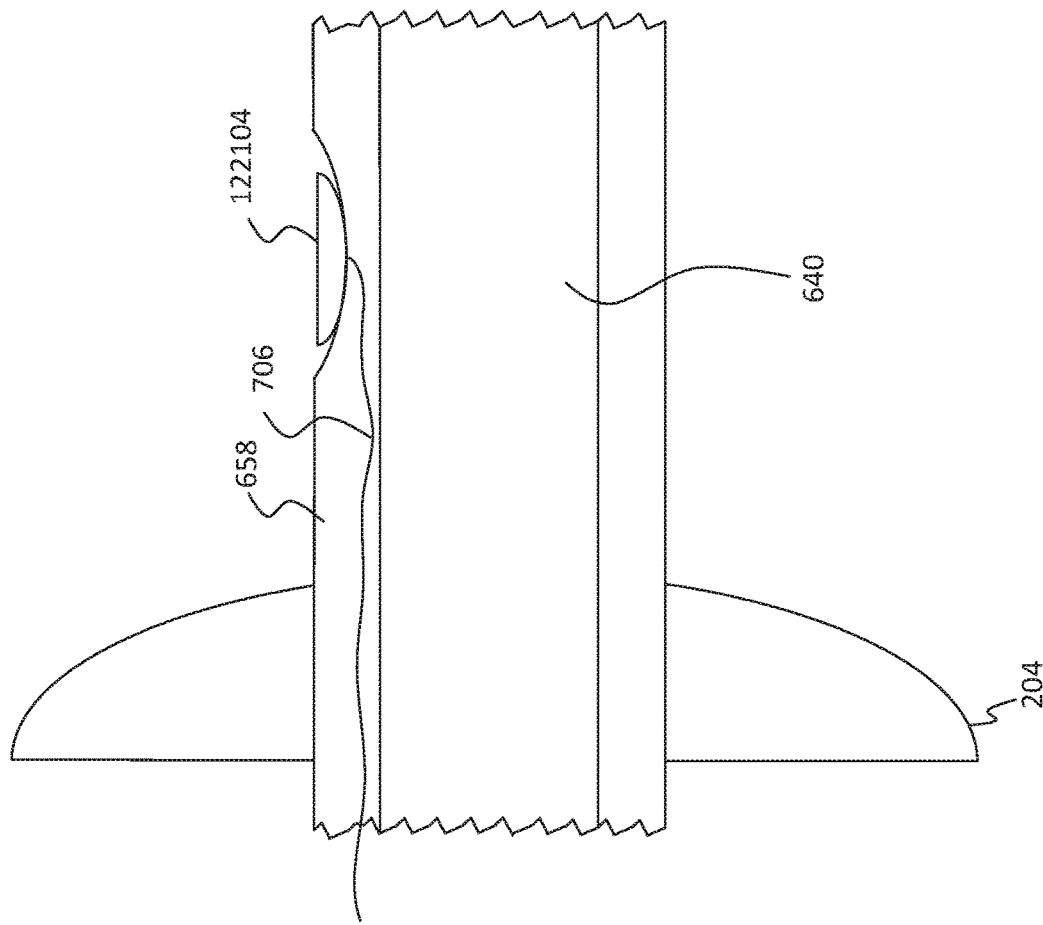

While the embodiment of FIG. 12A depicts the generator located entirely on the outside surface of tube wall 658, in an alternate embodiment, a portion of the generator can be located or otherwise embedded in the tube 658, and another portion of the generator can be proud of the tube wall 658, as can be seen with respect to generator 12104 in FIG. 12B. Still further, FIG. 12C depicts an exemplary embodiment where a cavity is located in tube wall 658, and a generator 122104 is located within that cavity. In some embodiments, the generator is not proud of the outer tube wall surface, and in some embodiments, the generator is proud of the outer tube wall surface. In an exemplary embodiment, the area around the generator can be filled with another material so as to establish a smooth outer wall.

Figure 13:
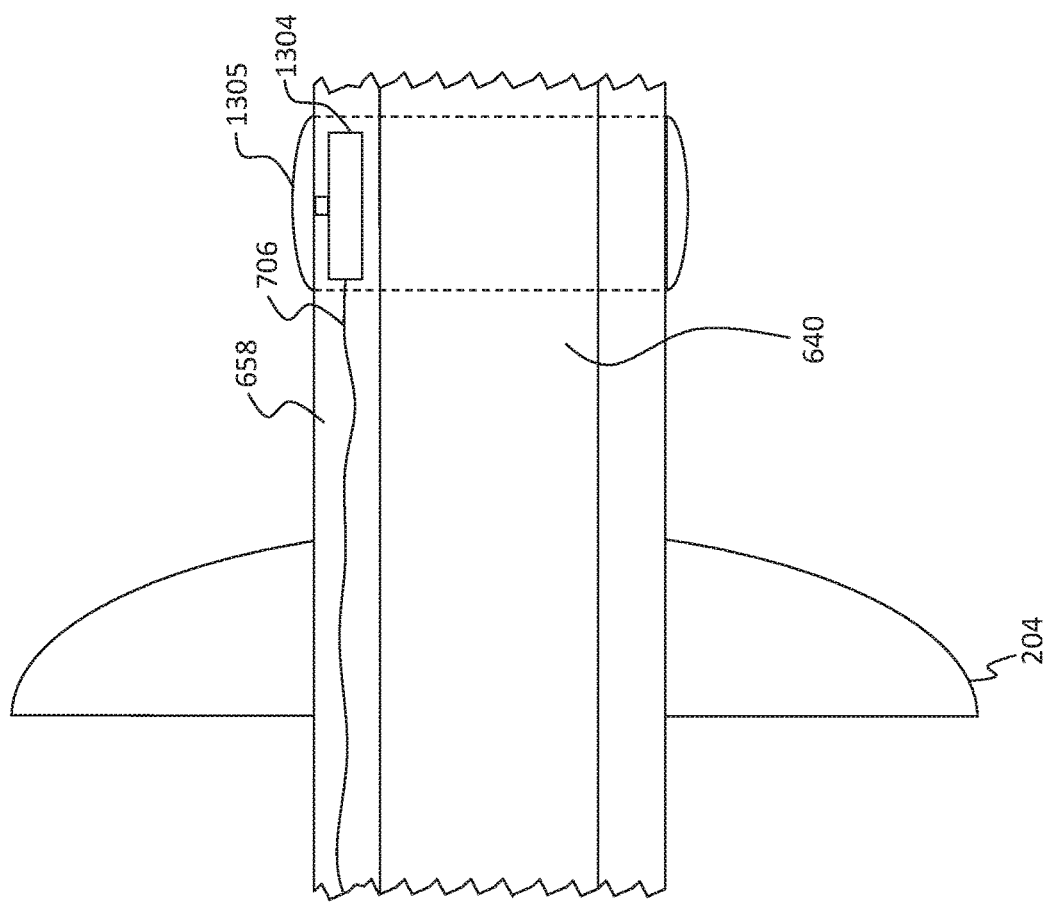

FIG. 13 depicts another exemplary embodiment, where the generator 1304 is embedded in the tube wall 658, but is in vibratory communication with a band 1305 that extends about the tube wall 658. In an exemplary embodiment, the generator 1304 vibrates when subjected to an electric signal via the leads 706, and there are vibrations conducted via a conductor, such as a piece of metal or the like, to the band 1305. In an exemplary embodiment, the band 1305 can be a titanium band. When the vibrations are conducted to band 1305, the band will vibrate.

Figure 14:
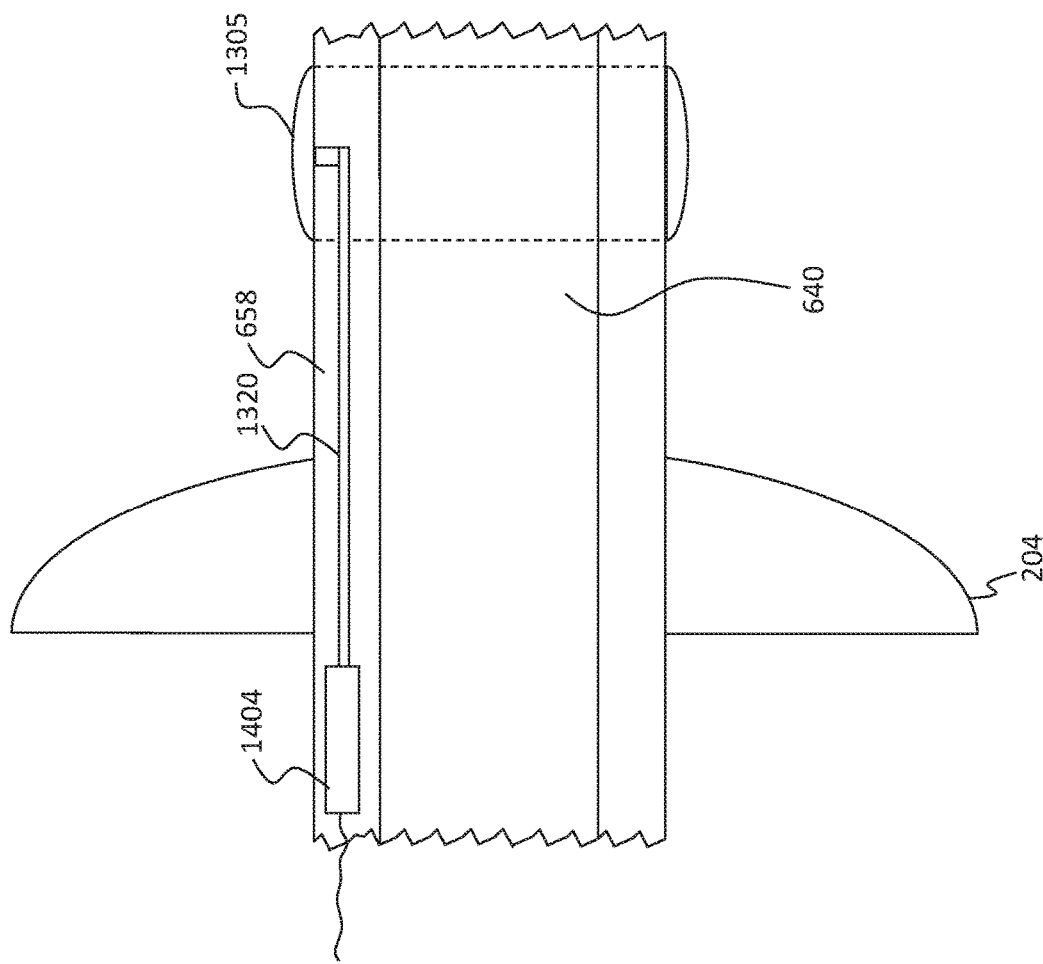

While the embodiments detailed above have been directed towards the scenario where the generator is located within the cochlea when the insertion guide is fully inserted in the cochlea, in an alternate embodiment, the generator 1404 is located entirely outside the cochlea when the guide is fully inserted in the cochlea, and a conductive path leads to a component that is located inside the cochlea when the guide is fully inserted in the cochlea that vibrates upon actuation or otherwise energize men of the generator. This can be seen in FIG. 14, where element 1404 is the generator, element 1320 is a vibratory conductive component (e.g., a piece of metal, such as a wire or a tube embedded in the tube wall 658) that conducts vibrations to the band 1305. In an exemplary embodiment of such a conductive element is disclosed in U.S. patent application Ser. No. 12/957,085, entitled "Hearing Prosthesis Having A Flexible Elongate Energy Transfer Mechanism," to inventor Peter B. J. Van Gerwen, filed on Nov. 30, 2010.

Figure 15:
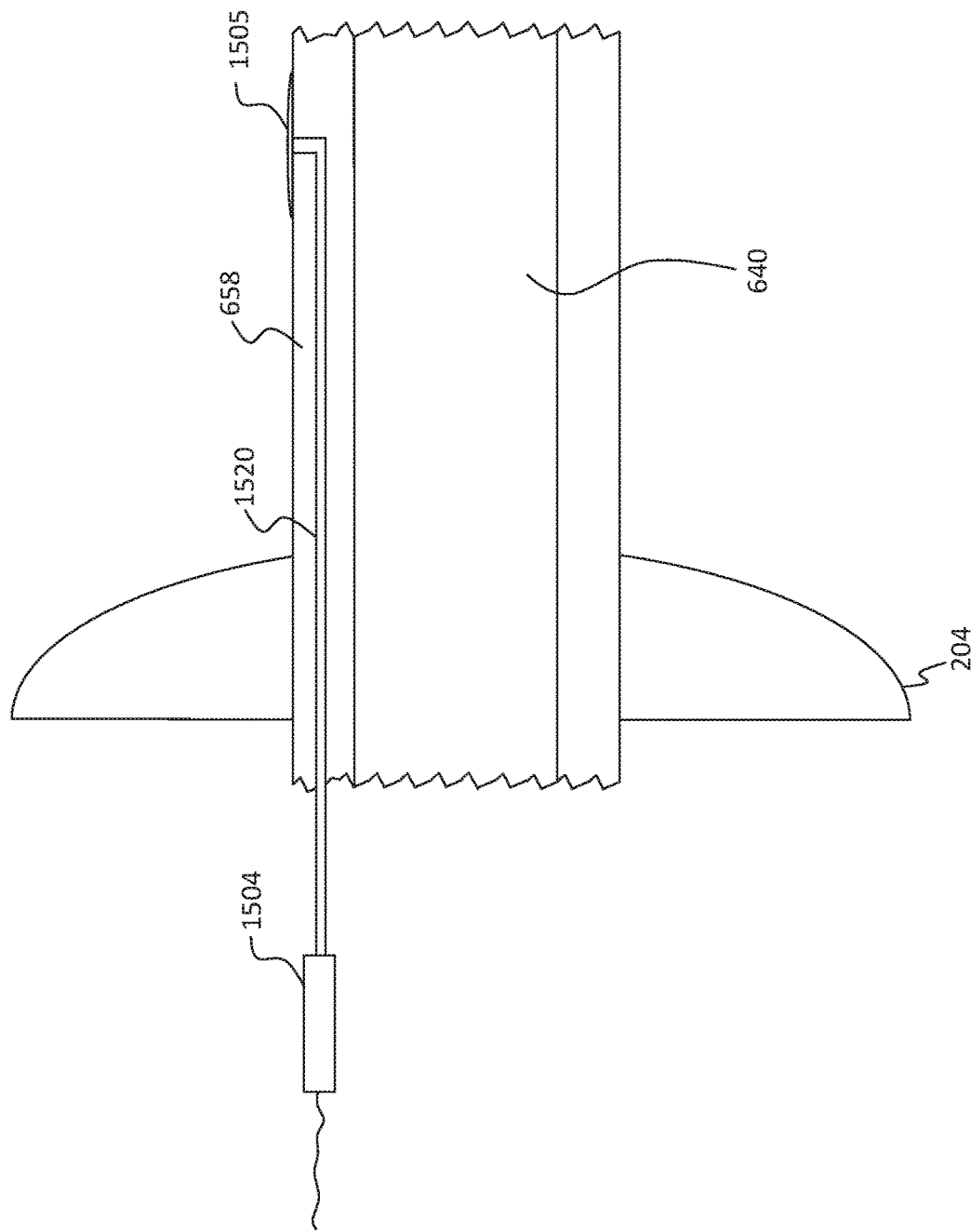
Figure 16:
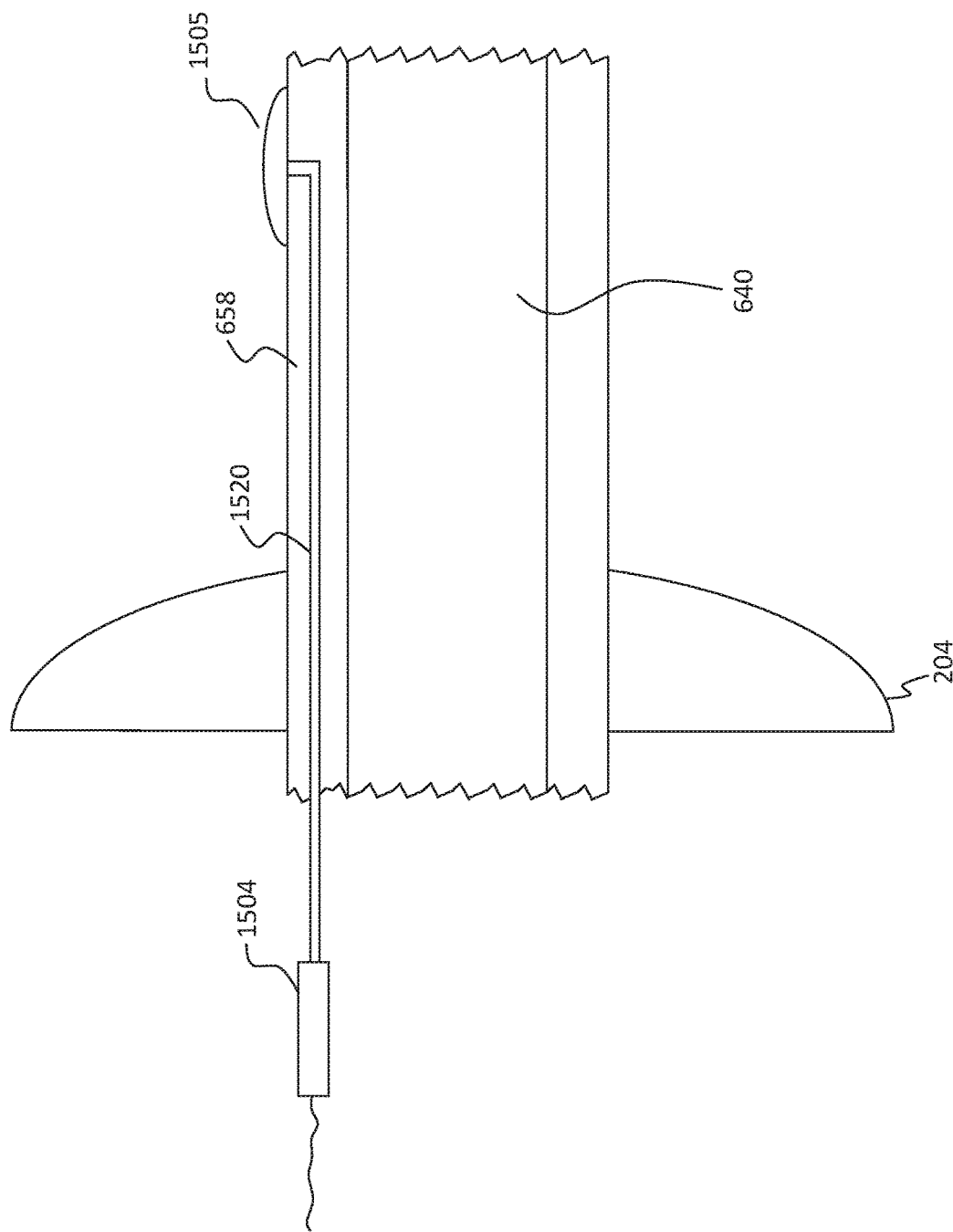

FIGS. 15 and 16 present an alternate embodiment where the generator 1504 is located entirely outside the cochlea when the guide is fully inserted in the cochlea. Here, generator 1504 is in fluid communication with a diaphragm 1505 via conduit 1520. The generator pulses so as to variably increase and/or decrease the pressure within the conduit 1520, which corresponds to an expansion and/or contraction of diaphragm 1505. FIG. 15 depicts the diaphragm 1505 in the contracted state, and FIG. 16 depicts the diaphragm 1505 in the expanded state. As will be understood, expansion and/or contraction of the diaphragm at a sufficient frequency with a sufficient magnitude will cause waves of fluid motion within the cochlea, and thus will provide the stimulus for an ECoG measurement.

Figure 17:
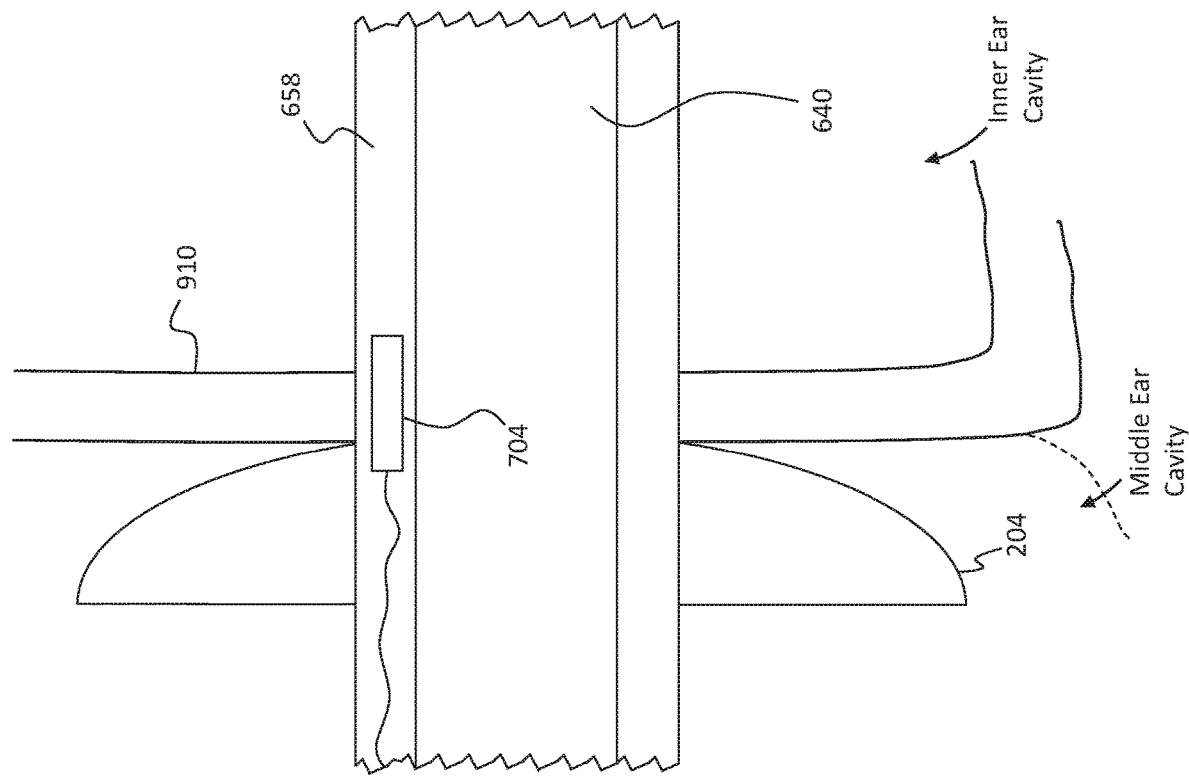

FIG. 17 depicts an exemplary embodiment of the insertion guide where the generator 704 can be located such that it is in the hole in the wall 910 of the cochlea when the guide is fully inserted into the cochlea. It is noted that while the embodiment of FIG. 17 depicts the generator embedded in the wall 658, any of the other embodiments detailed herein with respect to the location of the generator can be applicable to the embodiment of FIG. 17. It is noted that while the embodiment of FIG. 17 presents the location of the generator 704, in an alternative embodiment, the location of the output component (e.g., band 1305, diaphragm 1505, etc.) alone or in combination with the generator can be located in hole in the wall 910 of the cochlea through which the guide is inserted when the guide is fully inserted into the cochlea.

Figure 18:
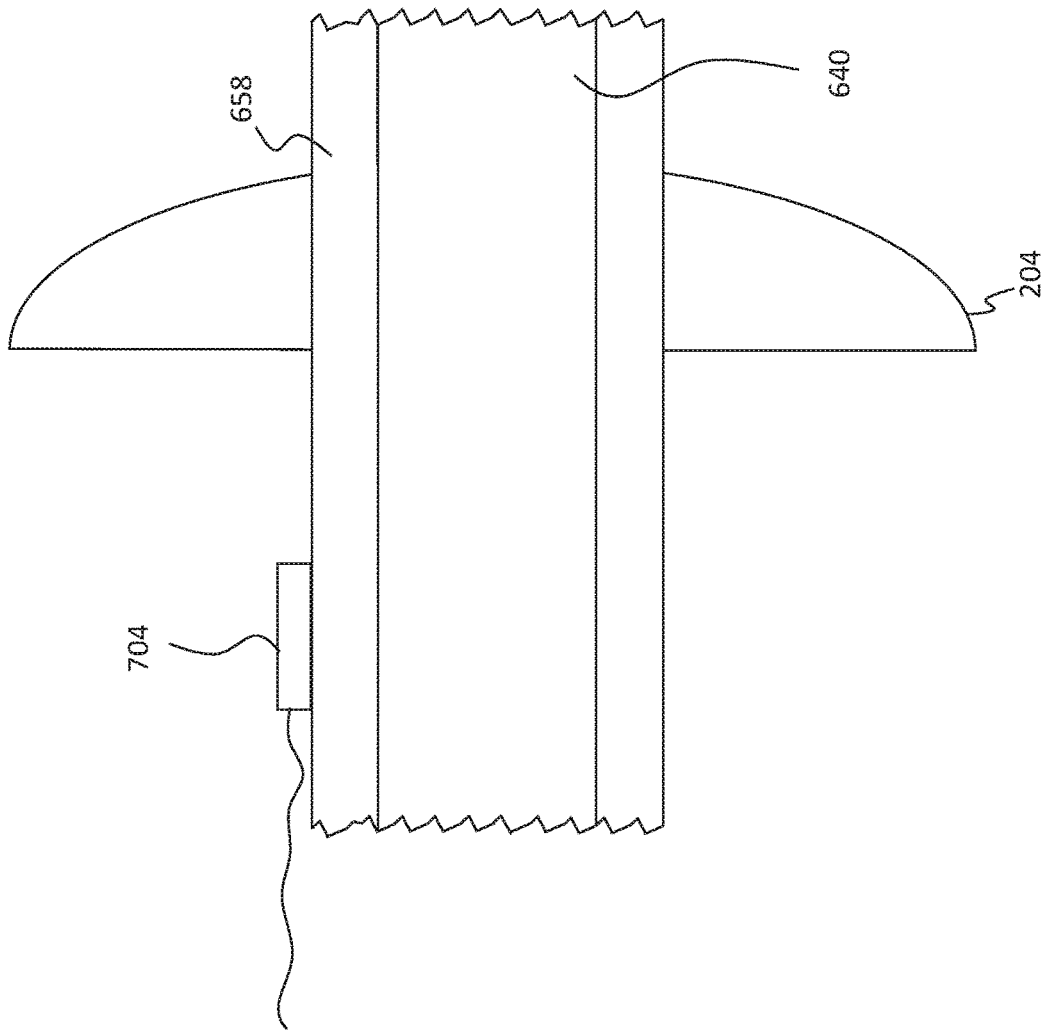

FIG. 18 depicts another exemplary embodiment where the generator 704 is located on the outside of the insertion guide tube on the proximal side of the stop 204. In an exemplary embodiment, a vibrationally conductive path of material different than that made up of the tube can extend from the generator 704 to a location inside the cochlea (e.g., concomitant taunts with the embodiment of FIG. 14, etc.). Still further, the embodiments of FIGS. 15 and 16 can be practiced except where the generator is located outside the insertion guide tube. Note also that while the embodiments depicted in FIGS. 14, 15, and 16 utilize a component that establishes a vibrational path from the generator to the output component that is of a different material than that of the insertion guide tube (e.g., a wire or the like made of metal, the fluid filled tube, etc.), in an alternate embodiment, the material of the insertion guide tube itself provides the medium for the vibrations to be transferred from outside the cochlea to inside the cochlea. This embodiment is depicted in FIG. 18.

It is noted that the embodiments detailed above can enable intraoperative ECoG measurements without a functioning middle-ear, such as a functioning middle ear that is utilized to relay acoustic stimulation from an in-the-ear receiver to the cochlea. In an exemplary embodiment, this can have utility with respect to recipients with middle ear infections and/or pediatric cochlear insertions or combined conductive/sensorineural hearing loss.

In an exemplary embodiment, the generators detailed herein are configured to output stimulation no more than 50 dBs, no more than 55 dBs, no more than 60 dB, no more than 65 dB, no more than 70 dB, no more than 75 dB, no more than 80 dB, no more than 85 dBs, or no more than 90 dB, or any value or range of values therebetween in 1 dB increments (no more than 82 dBs, no more than 84 dBs, a range from 50 dBs to 87 dBs). In an exemplary embodiment, the output of the generator cannot output anymore output than the aforementioned values.

In view of the above, it is to be understood that in an exemplary embodiment, there is an electrode array insertion guide, such as by way of example only and not by way of limitation, those detailed above, wherein the insertion guide comprises an assembly configured to provide direct array insertion functionality and ancillary array insertion functionality to a user thereof. The direct array insertion functionality is just that, the functionality of inserting an electrode array into the cochlea. The ancillary array insertion functionality is a functionality having utilitarian value related to the insertion of the array in the cochlea. In view of the above, an exemplary ancillary array insertion functionality of the guide enables ECoG measurement. As will be understood from the above, in an exemplary embodiment, exemplary guides include an extra-cochlea bone conduction actuator system, and the ancillary array insertion functionality is output of vibrations directly to the cochlea by the system. By "output of vibrations directly to the cochlea," it is meant that the output is provided to the wall of the cochlea separating the inner cavity from the middle ear cavity (e.g., output directly to the cochlear promontory), that the output is provided in the hole in the wall of the cochlea/passageway from the middle ear to the inner ear, and/or inside the cochlea.

Figure 19:
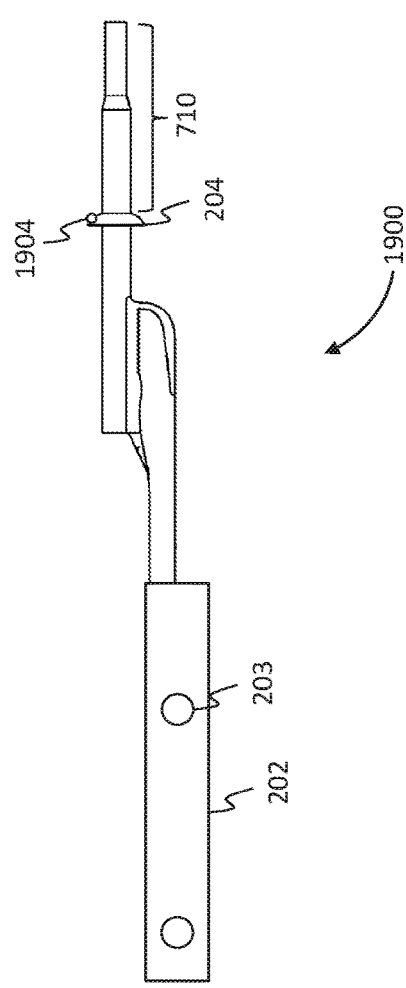

Still further, in view of the above, it can be seen that in an exemplary embodiment, there is a device, comprising a cochlear implant electrode array insertion guide having a plurality of functional capabilities. While two of the functionalities detailed correspond to that of an electrode array support and providing an acoustic stimulation for an ECoG measurement, another exemplary functionality is that of an ECoG electrode. In this regard, in an exemplary embodiment, there is an electrode array insertion guide comprising an ECoG electrode. Along these lines, FIG. 7 depicts an exemplary embodiment of a cochlear electrode array insertion guide 1900. In an exemplary embodiment, the insertion guide 1900 corresponds to that of the insertion guide 200 detailed above, with the exception of the addition of electrode 1904, and the modifications to the guide so as to support the electrode and the associated components thereof (e.g., electrical leads, etc.—more on this below). Accordingly, FIG. 19 depicts a cochlear electrode array insertion guide comprising a first functionality (the array guide—the insertion guide tube (210 of FIG. 2)) and a second functionality functional (an ECoG electrode—the electrode 1904).

Figure 20:
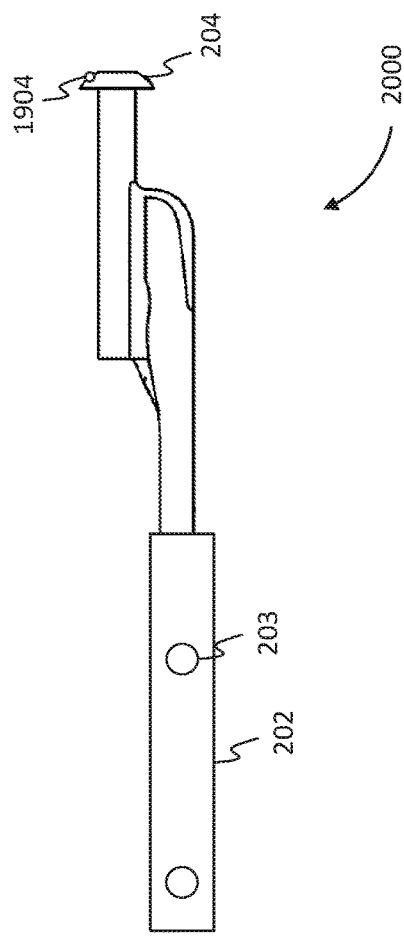

Again, not all embodiments of the cochlear electrode array insertion guide include an intracochlear portion. In this regard, FIG. 19 depicts a guide 1900 that includes an intracochlear portion 710. This is the portion to the right of stop 204/the portion on the distal side of stop 204 (distal relative to the entire insertion guide). Conversely, FIG. 20 depicts a guide 2000 that does not include an intracochlear portion. Instead, stop 204 is configured to be placed against the outside of the cochlea such that the passageway through the guide through which the electrode array is passed is aligned with the pertinent window and/or cochleostomy such that no parts of the guide 2000 enters the cochlea.

Figure 21:
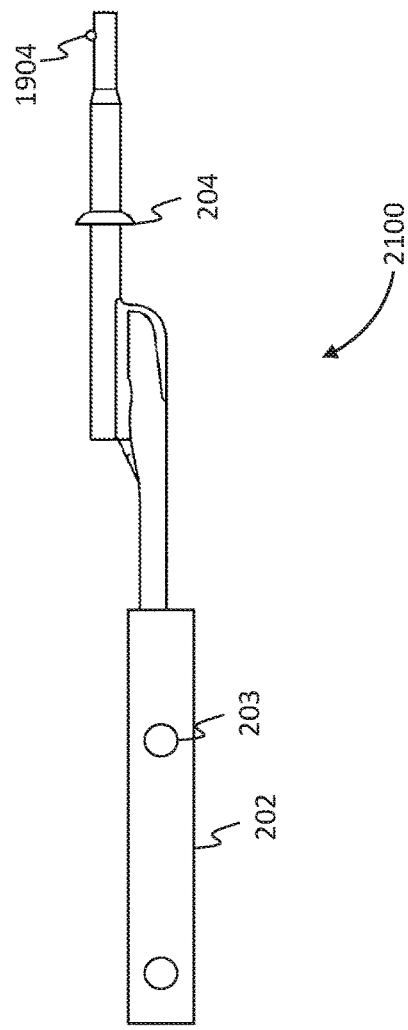

FIG. 21 depicts another exemplary embodiment of an insertion guide 2100, where the electrode 1904 is mounted in the intracochlear portion/on the intracochlear portion. It is briefly noted that while the embodiments depicted in the FIGS. depict the electrode 1904 as being partially embedded in the body of the insertion guide, in some alternate embodiments, the electrode can be fully embedded in the body of the insertion guide while in other embodiments, the electrode can be fully proud of the body of the insertion guide. Any arrangement of the electrode that can enable the teachings detailed herein can be utilized in at least some exemplary embodiments.

Figure 22:
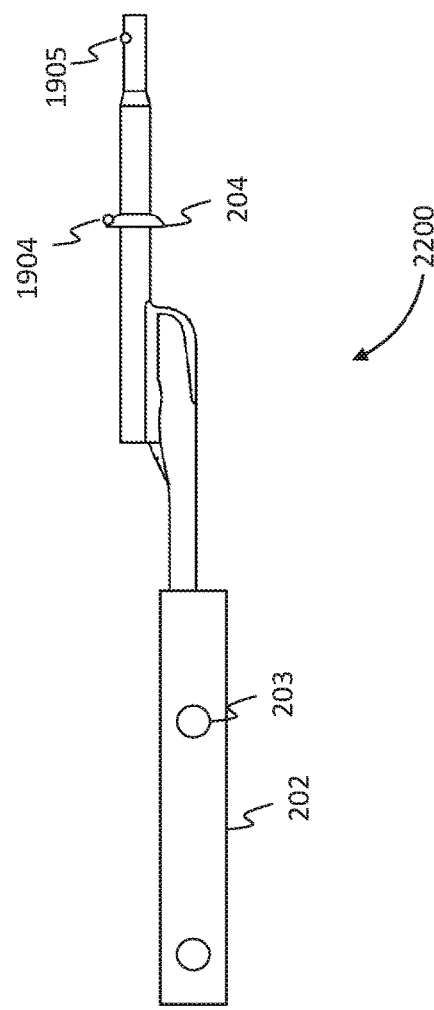

FIG. 22 depicts another exemplary embodiment of an insertion guide 2200, where there is an electrode 1904 located on the stop 204, and thus representing an extra cochlear electrode when the guide 2200 is fully inserted, and an electrode 1905 located on the intracochlear portion of the guide. Thus, exemplary embodiments can include two or more electrodes that are part of the insertion guide.

Figure 23:
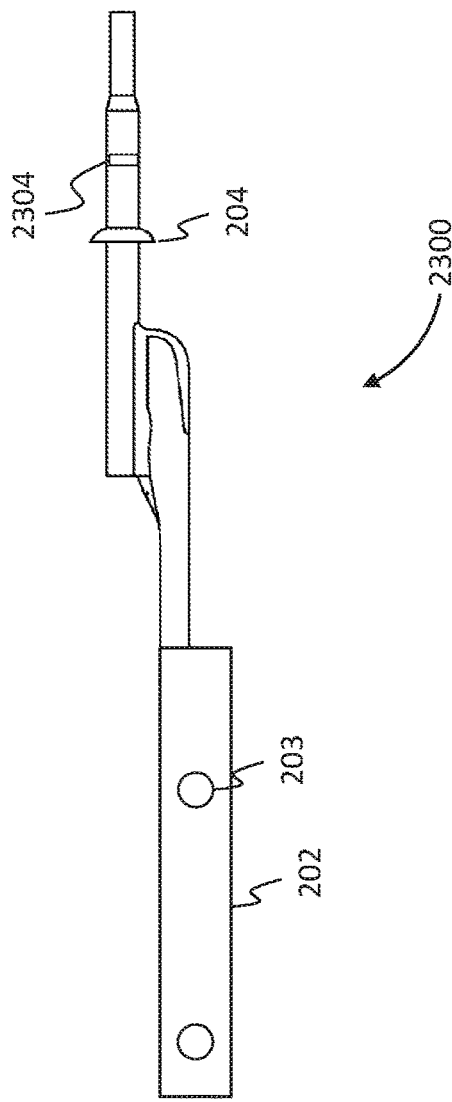

Note also that while the embodiments depicted above have been described in terms of utilizing a ball electrode, in some alternate embodiments, other types of electrodes can be utilized. To this end, FIG. 23 depicts an exemplary insertion guide 2300 that includes a band electrode 2304 in the intracochlear portion of the guide (which can be slit in embodiments where the insertion tube is split, which split facilitates removal of the insertion guide after insertion of the electrode array into the cochlea. Any type of electrode that can enable the ECoG measurements can be utilized in at least some exemplary embodiments.

Figure 24:
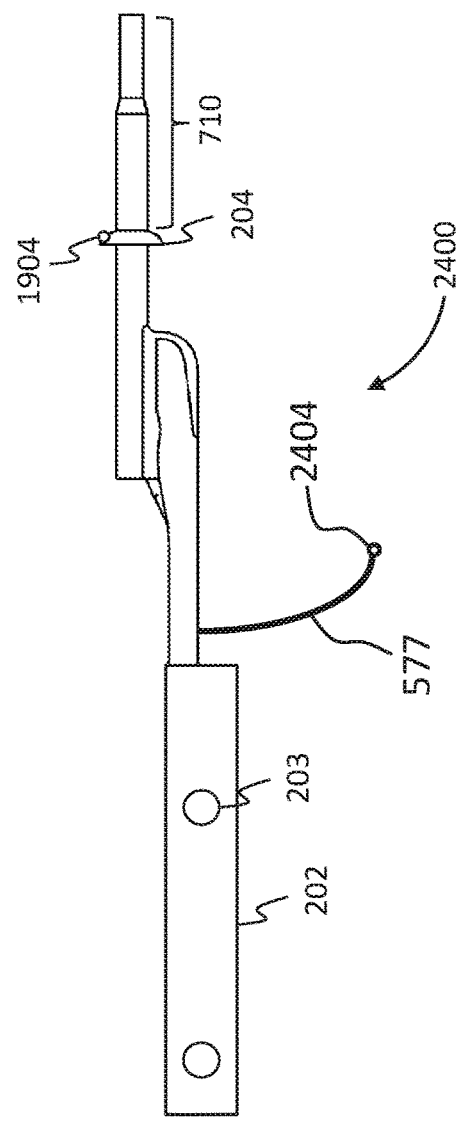

As will be described in much greater detail below, the electrodes 1904 and 1905 and 2304 are so-called measurement electrodes that are utilized in an ECoG system. Corollary to this is that at least some exemplary embodiments of insertion guides include so-called reference electrodes or return electrodes. To this end, FIG. 24 depicts an exemplary insertion guide 2400, which includes a measurement electrode 1904 mounted on the stop 204, and a reference electrode 2404 mounted on a flexible support 577. In an exemplary embodiment, when the insertion guide is fully inserted into the cochlea (i.e., the stop 204 hits the outer wall of the cochlea at the cochleostomy), and positioned at the proper angular orientation (about the longitudinal axis of the guide), the reference electrode 2404 is applied against tissue of the recipient at a proper location (e.g., in the middle ear cavity) underneath the skin of the recipient owing to the fact that the anatomy of the human being is generally the same from one human being to the other. While the exemplary embodiment depicted in FIG. 24 depicts the reference electrode 2404 being located at the "bottom" of the insertion guide, the reference electrode 2404 can be located at other places. Note also that while the embodiment depicted in FIG. 24 depicts the support 577 position at about the midway portion of the guide, in other embodiments, the support 577, and thus the reference electrode 2404, can be positioned closer to the distal end or closer to the proximal end. Note also that while the embodiment depicted in FIG. 24 depicts only a single reference electrode, in an alternate embodiment, two or more reference electrodes can be utilized. Any arrangement of reference electrodes that can have utilitarian value can be utilized in at least some exemplary embodiments.

FIG. 25 depicts an alternate embodiment of an insertion guide 2500 where a support structure 577 extends from the top portion of the guide 2500 and supports a ball electrode 1904 (or some other type of electrode) away from the stop 204. In an exemplary embodiment, this can have utilitarian value with respect to positioning the ball electrode 1904 against an outside of the cochlea at a location in direct contact to the round window and/or the oval window when the insertion guide is fully inserted in the cochlea. In an alternative embodiment, this can have utilitarian value with respect positioning the ball electrode such that the ball electrode is not in direct contact with the round window and/or the oval window when the insertion guide is fully inserted into the cochlea. Such can also have utilitarian value with respect to placing the electrode 1904 against the outer wall of the cochlea at a location away from the cochleostomy.

In this exemplary embodiment, structure 577 is a flexible structure that is configured to flex so as to accommodate the fact that the insertion guide 2500 can be utilized differently in some scenarios and/or to accommodate the fact that human physiological structure can slightly vary from recipient to recipient. In an alternate embodiment, structure 577 is a structure that is configured to press the electrode 574 against the outside of the cochlea so as to hold the electrode 574 against the tissue as a result of spring forces or the like. Indeed, in an exemplary embodiment, structure 577 can be a spring.

FIG. 26 depicts another exemplary embodiment where a support structure 578 supports a spring-loaded plunger 579 that supports the electrode 1904 at the end of a spring-loaded cylinder. In this embodiment, plunger 579 is configured to accommodate the movements of the guide 2600 relative to the cochlea, such that the ball electrode 1904 is positioned against the outer wall of the cochlea prior to full insertion of the guide 2600 into the cochlea (i.e., prior to the stop 204 contacting the outside wall the cochlea). In this regard, the configuration of the plunger 579 is such that the force applied to the electrode 1904 against the tissue of the recipient is always greater than any force that would pull the electrode 574 away from the tissue resulting from the movement of the guide slightly away from the cochlea during use of the guide. Indeed, in an exemplary embodiment, there can be utilitarian value with respect to practicing ECoG measurements without the guide 2600 fully inserted into the cochlea, if only so as to provide relief to the surgeon (if the surgeon is not constantly applying a force against the cochlea, his or her hands will not be as stressed relative to that which would be the case if the surgeon had to constantly apply force against the cochlea).

Figure 27:
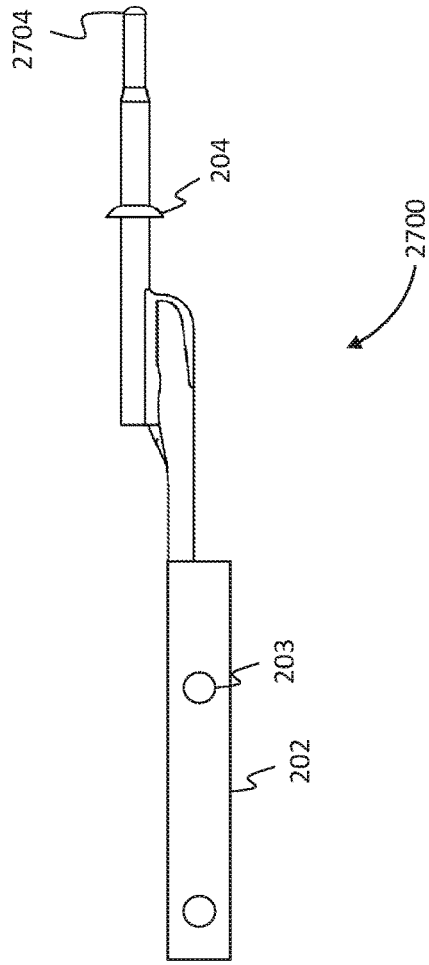
Figure 28:
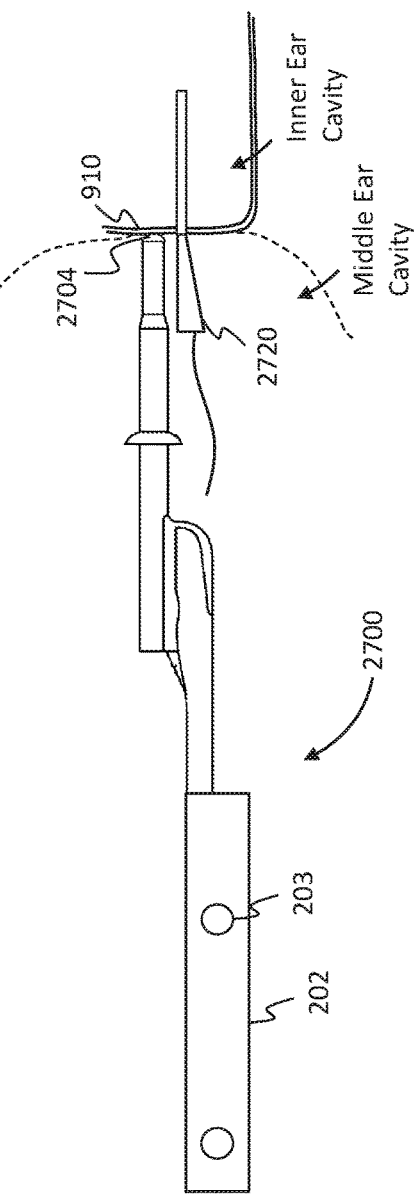
FIG. 28 depicts an exemplary use of an exemplary electrode array insertion guide.

Indeed, corollary to the scenario where ECoG measurements are taken in a regime where the insertion guide is not fully inserted into the cochlea, an exemplary embodiment entails taking ECoG measurements utilizing electrodes of the insertion guide where the insertion guide is completely outside the cochlea. FIG. 27 depicts an exemplary embodiment of such an insertion guide, where the tip of the insertion guide includes a reference electrode 2704. In an exemplary scenario of use, the insertion guide 2700 is completely withdrawn from the cochlea, and the tip is placed against the outer wall of the cochlea, such as on the cochlear promontory, and then ECoG measurements are taken utilizing the reference electrode 2704 as the reference electrode. FIG. 28 depicts an exemplary scenario of utilization of the embodiment of FIG. 27, where the electrode 2704 is placed against the outer wall 910 of the cochlea, subsequent to full implantation of the electrode array 2720. Is also noted that an exemplary scenario of use can be such that the insertion guide 2700 is utilized for ECoG measurements before the electrode array 2720 is inserted into the cochlea, as well as after the electrode array 2720 is inserted into the cochlea.

It is noted that embodiments of the insertion guide having the acoustic stimulation generator can be combined with embodiments of the insertion guide having the measurement electrode. To be clear, any feature of any embodiment detailed herein can be combined with any other feature of any embodiment detailed herein, unless otherwise noted. To this end, FIG. 29 depicts an exemplary insertion guide that has a plurality of functionalities beyond the functionality of inserting the electrode array into the cochlea. In particular, as can be seen, the insertion guide 2900 includes an acoustic stimulation generator 704 and a reference electrode 1904. In this exemplary embodiment, lead 706 from the generator 704 and lead 2406 from the electrode 1904 lead to a junction box in the hand guide, and then a lead/a plurality of leads extends to a connector 2410. The connector 2410 can be connected to an ECoG system as will be described below.

FIG. 30 depicts an alternate embodiment of an insertion guide 3000 where the generator 704 is located closer to the distal end. This can have utilitarian value with respect to providing vibrations to the cochlea while the insertion guide is positioned as seen in FIG. 28 in that the generator is located closely to the tip of the insertion guide. In an exemplary embodiment, a material that is conducive to vibrations can extend from the generator 704 to the tip, or to the electrode 2704. That said, in an alternate embodiment, the housing of the generator 704 can abut or otherwise be in contact with the backside of the electrode 2704. In an exemplary embodiment, the vibrations are transferred from the generator 704 directly or indirectly to the electrode 2704, and then to the wall of the cochlea 910 so as to provide stimulation for an ECoG measurement.

That said, while the embodiment depicted in FIG. 30 has the generator 704 located in the intracochlear portion, consistent with the embodiments detailed above, an exemplary embodiment, the generator 704 can be located in the portion of the guide outside the cochlea when the guide is fully inserted into the cochlea, and the guide itself or additional material conducive to establishing a path for vibrations/conducive to conducting vibrations can extend from the generator to the electrode 2704. Thus, an exemplary scenario of use entails placing the tip of the guide 3000 on the outside wall of the cochlea, such as the cochlear promontory, such as that depicted in the scenario of use of FIG. 28, and activating the generator 704 so as to provide acoustic stimulation to the cochlea, and utilizing the electrode 2704 is part of a measurement electrode of an ECoG system.

Figure 31:
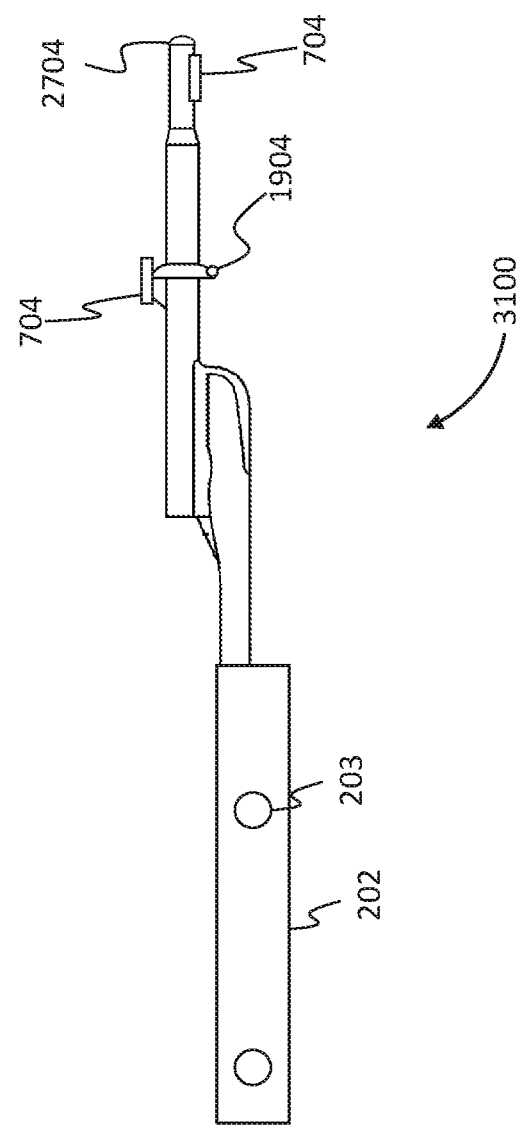

Consistent with the teachings detailed above that embodiments can include two or more generators 704 and two or more electrodes, FIG. 31 depicts an exemplary insertion guide 3100 that includes such dual components. In an exemplary scenario of use, the generator 704 mounted on the stop and the electrode 1904 can be utilized during a first ECoG measurement where the insertion guide is fully inserted into the cochlea. In another exemplary scenario of use, the generator 704 mounted on the intracochlear portion of the guide and the electrode 2704 on the tip of the guide can be utilized during a second ECoG measurement where the guide is completely out of the cochlea. To be clear, some embodiments can utilize one generator for both scenarios, and some embodiments can utilize one electrode for both scenarios. For example, in at least some exemplary embodiments, the electrode 2704 can be utilized for both scenarios. Still further, an exemplary scenario could utilize the generator 704 mounted on the stop for both scenarios, such as in an embodiment where a sufficiently conductive path is present for vibrations to travel between the generator 704 to the electrode 2704.

Figure 32:
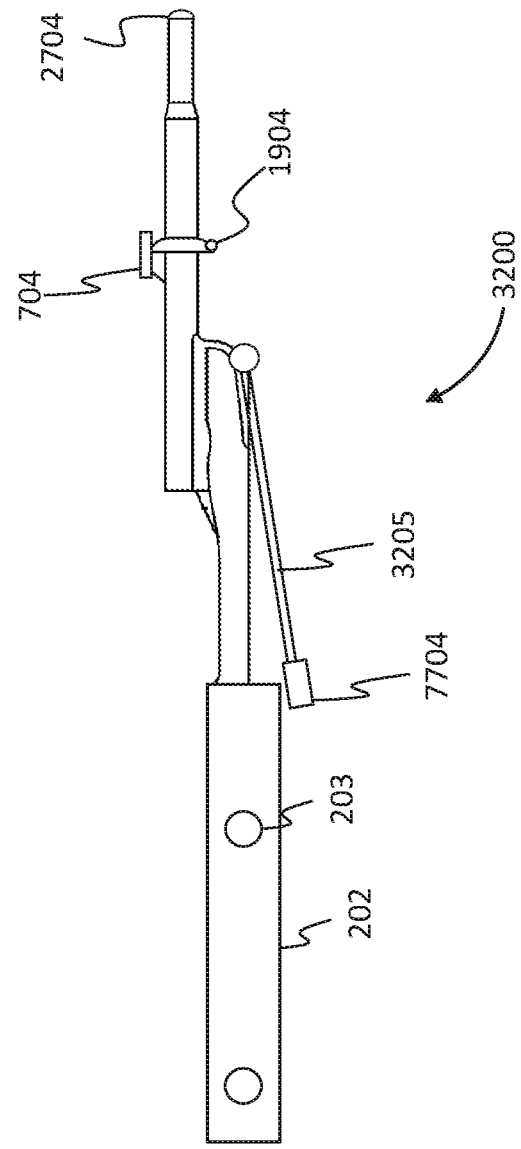
Figure 33:
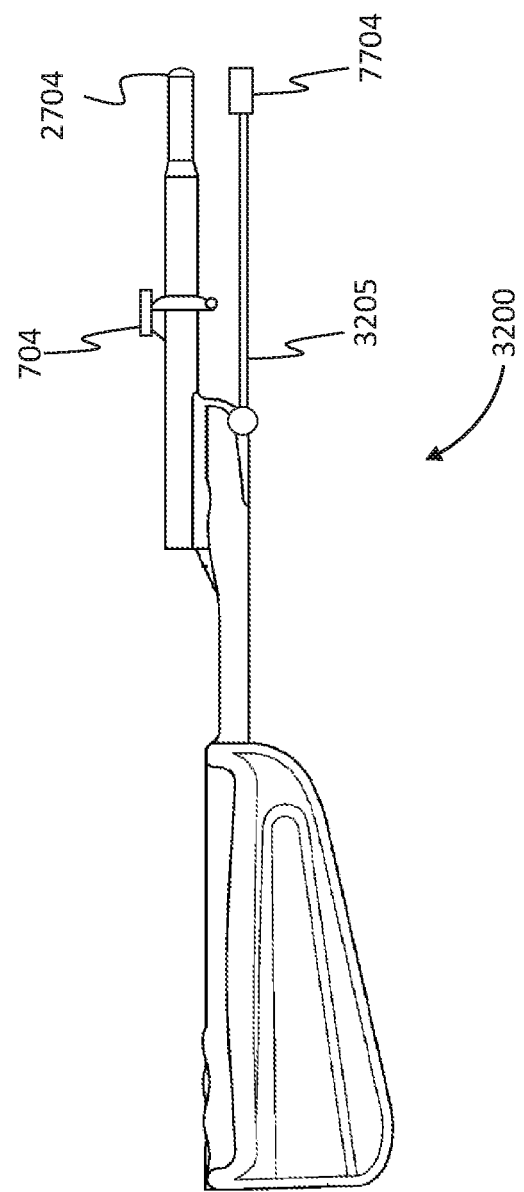

While the embodiments detailed above have depicted the generator and the electrodes as static components relative to the rest of the guide (static in the sense that the overall positions thereof do not change relative to the guide/changes in the position of the guide change the positions of the electrodes and generators), FIG. 32 depicts an alternate embodiment where a stimulation generator 7704 is mounted or otherwise adjustable in a manner somewhat analogous to a switchblade. In this regard, generator 704 is mounted on a beam 3205 that is hingedly supported/connected to the guide 3200. In an exemplary scenario of use, the insertion guide 3200 is utilized to insert the electrode array in the configuration depicted in FIG. 32. In an exemplary scenario of use, ECoG measurements are taken utilizing the guide 3200 in the configuration of FIG. 32 while the guide is fully inserted into the cochlea. For example, generator 704 can be utilized in conjunction with electrode 1904. Still further, providing there is sufficient vibratory conduction between the generator 704 and the electrode 2704, guide 32 is utilized in the scenario of use detailed above with respect to FIG. 28. That said, in another exemplary scenario of use, the generator 7704 is moved by articulating the beam 3205 about the hinge so that the generator 7704 is positioned as seen in FIG. 33. In an exemplary scenario of use, the electrode 2704 is positioned against the outer wall of the cochlea, and the generator 7704 is also positioned against the outer wall of the cochlea, and ECoG measurements are taken utilizing the generator 7704 as the source of acoustic stimulation.

Thus, embodiments of the electrode array insertion guides can include embodiments where the additional functional components can be moved in and out of position on an as-needed basis.

Figure 34:
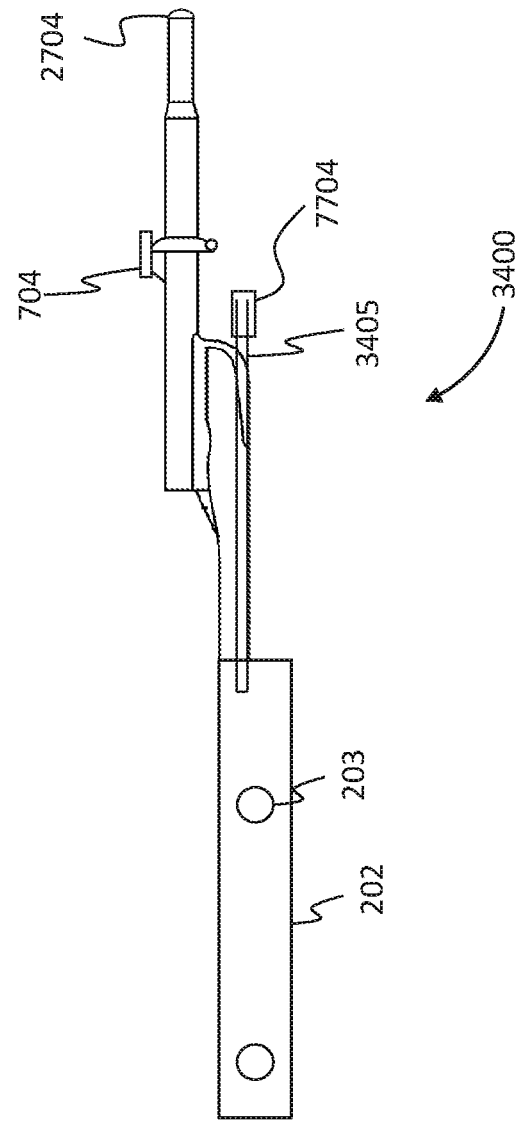
Figure 35:
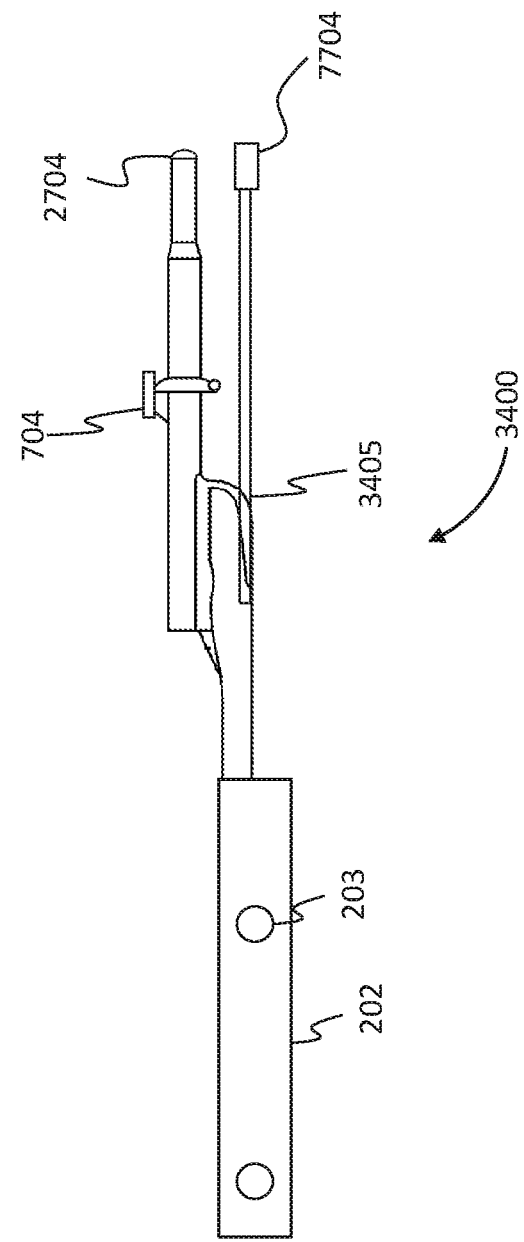

Note that the embodiment of FIG. 32 is but exemplary. In an alternate embodiment, such as that seen in FIG. 34, the generator 7704, supported by telescoping boom 3405, telescopes out of the guide 3300 (FIG. 35 depicts the generator 7704 telescoped out of the guide).

Note that in an alternate embodiment, the boom 3405 and the generator 7704 can be fixed to the guide in a manner analogous to fixing a bayonet to a rifle. In an exemplary scenario use, the various actions detailed herein are executed, and then subsequent withdrawal of the guide from the cochlea, boom 3405 is attached to the guide, and then ECoG measurements are commenced utilizing the generator 7704. In an exemplary embodiment, a connector can be provided at the base or another location of the boom 3405 so as to place the generator 7704 into electrical communication with a lead assembly in the body of the guide so that upon connection of the boom 3405 to the guide, electrical signal can be provided to the generator 7704 so as to actuate the actuator therein so as to cause the generator 7704 to vibrate or otherwise output stimulation so that in ECoG test can be executed.

Figure 36:
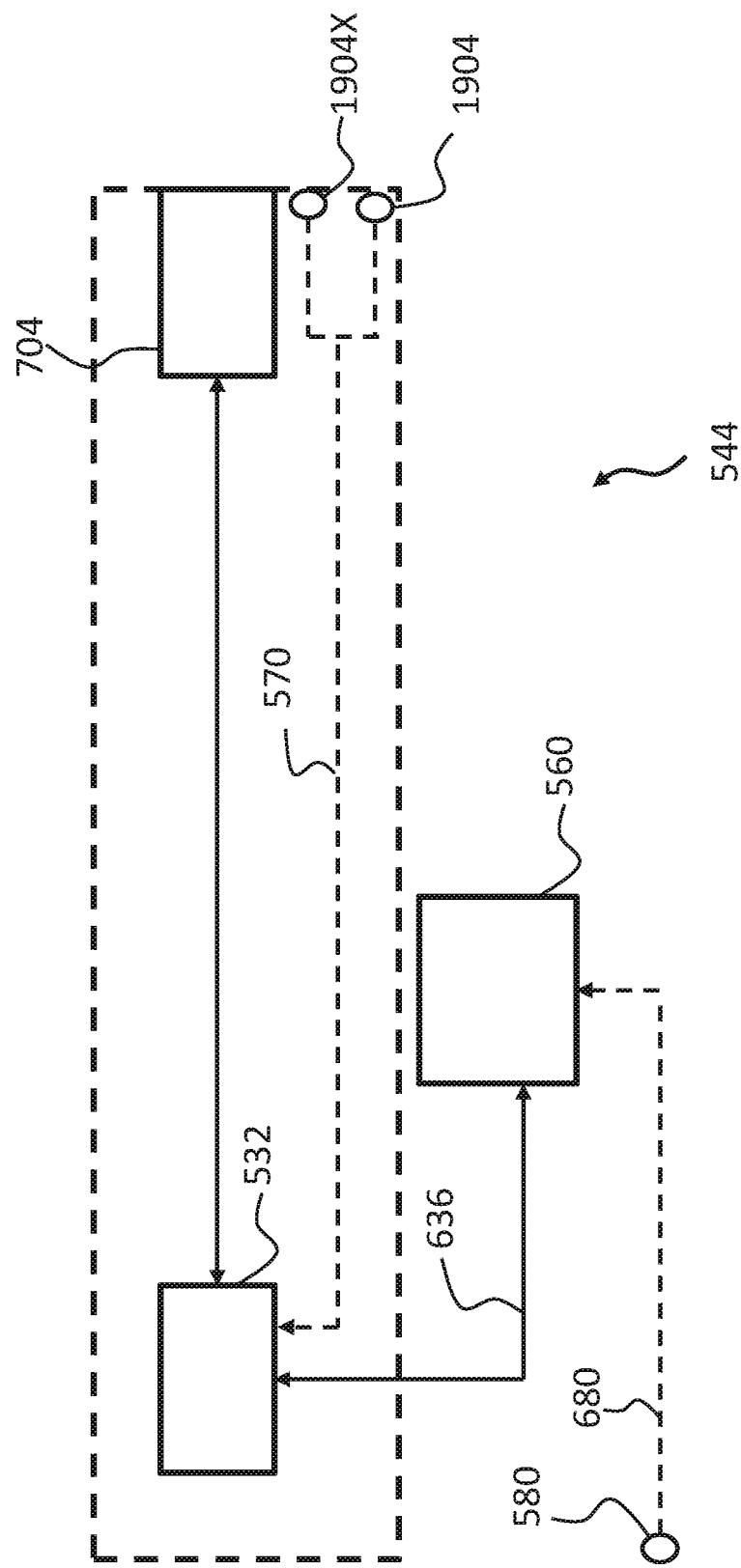
FIGS. 36-37 depict exemplary functional block diagrams associated with the exemplary electrode array insertion guides.

In an exemplary embodiment, utilization of the guide of FIG. 29 is such that the electrode can be positioned adjacent the round window niche/cochleostomy so as to function as a sense electrode for an extra cochlear ECoG system. To this end, FIG. 36 depicts a functional block diagram of a system 544, at least part of which can be included in the insertion guide. More specifically, FIG. 36 depicts a functional block diagram of a system 544 usable with the insertion guides detailed herein and/or variations thereof, system 544 includes a communications unit 532 that receives and/or transmits signals to communicate with a remote component, such as a data recorder. In an exemplary embodiment, the output of unit 532 is transferred to connector 2410 of FIG. 29. In an exemplary embodiment, receiver/transmitter unit 532 is configured to receive signals from a remote unit so that the system 544 can utilize those signals so that the system 544 can utilize those signals to implement the telemetric operations/the ECoG and methods detailed herein and/or variations thereof as will be described in greater detail below. The unit 532 is also configured to transmit signals to the remote unit so as to transmit the telemetric information gathered by the system 544 as will be detailed below. As can be seen from FIG. 36, communications unit 532 is in two-way communication with stimulation arrangement 704, which corresponds to any of the generators detailed herein and/or variations thereof. FIG. 36 depicts two-way communication between units 532 and 704. That said, in an alternate embodiment, there is only one-way communication between these two components. (It is noted at this time that any disclosure herein of one-way communication corresponds to an alternate disclosure of two-way communication, and vice versa providing that the art enables such, unless otherwise specifically noted.) The communication between unit 532 and unit 704 permits the stimulation arrangement 704 to output energy to evoke a hearing percept based on received signals by the communications unit 532 to evoke a hearing percept according to the teachings detailed above.

Still with reference to FIG. 36, system 544 includes a test unit 560 that can correspond to a processor or the like configured to implement testing according to the teachings detailed herein and/or variations thereof. It is noted that while the test unit 560 is depicted as being separate from the guide 2900 (the portions inside the dashed line), in some alternate embodiments, the units are integral with one another. Any arrangement that can enable the teachings detailed herein and/or variations thereof to be practiced can be utilized in at least some exemplary embodiments. As can be seen, test unit 560 is in two-way communication with the communications unit 532 via signal line 636.

Test unit 560 is also in communication with one or more of measurement electrodes 1904 and, optionally, 1904X (and others not shown, in some embodiments) via communication with unit 532 which is in turn in signal communication with those electrodes via signal line 570, and is also in communication with one or more reference electrodes 580 via signal line 680, where reference electrode 580. (While the embodiment of FIG. 36 depicts the reference electrode as not being part of the insertion guide, in an alternate embodiment, reference electrode can be part of the insertion guide as detailed above, and, in an exemplary embodiment, signal line 680 thus can extend to unit 532 in a manner analogous to signal line 570.

It is noted that while some embodiments depict the reference electrode 580 as being separate from the implant, in an alternate embodiment, the reference electrode is part of the implant or otherwise supported by the housing that houses, for example, the receiver/stimulator unit of the cochlear implant. In this regard, in an exemplary embodiment, the inductance coil of the cochlear implant can be utilized to communicate with the reference electrode. Accordingly, in an exemplary embodiment, signal line 680 entails an inductance coil communication system located between electrode 580 and unit 560. Any placement of the return electrode 580 that can enable the teachings detailed herein and/or variations thereof can be utilized in at least some exemplary embodiments.

It is briefly noted that some embodiments according to the teachings detailed herein are practiced without any electrodes located in the cochlea. That is, all electrodes are located outside the cochlea and are thus extra cochlear electrodes. Thus, an exemplary embodiment entails executing some or all of the teachings detailed herein and/or variations thereof in a noninvasive manner with respect to the cochlea (although embodiments will include an invasive process or device associated with the recipient in general). In an exemplary embodiment, the electrodes are arrayed or otherwise positioned so as to measure or otherwise detect signals indicative of the cochlear function.

Figure 37:
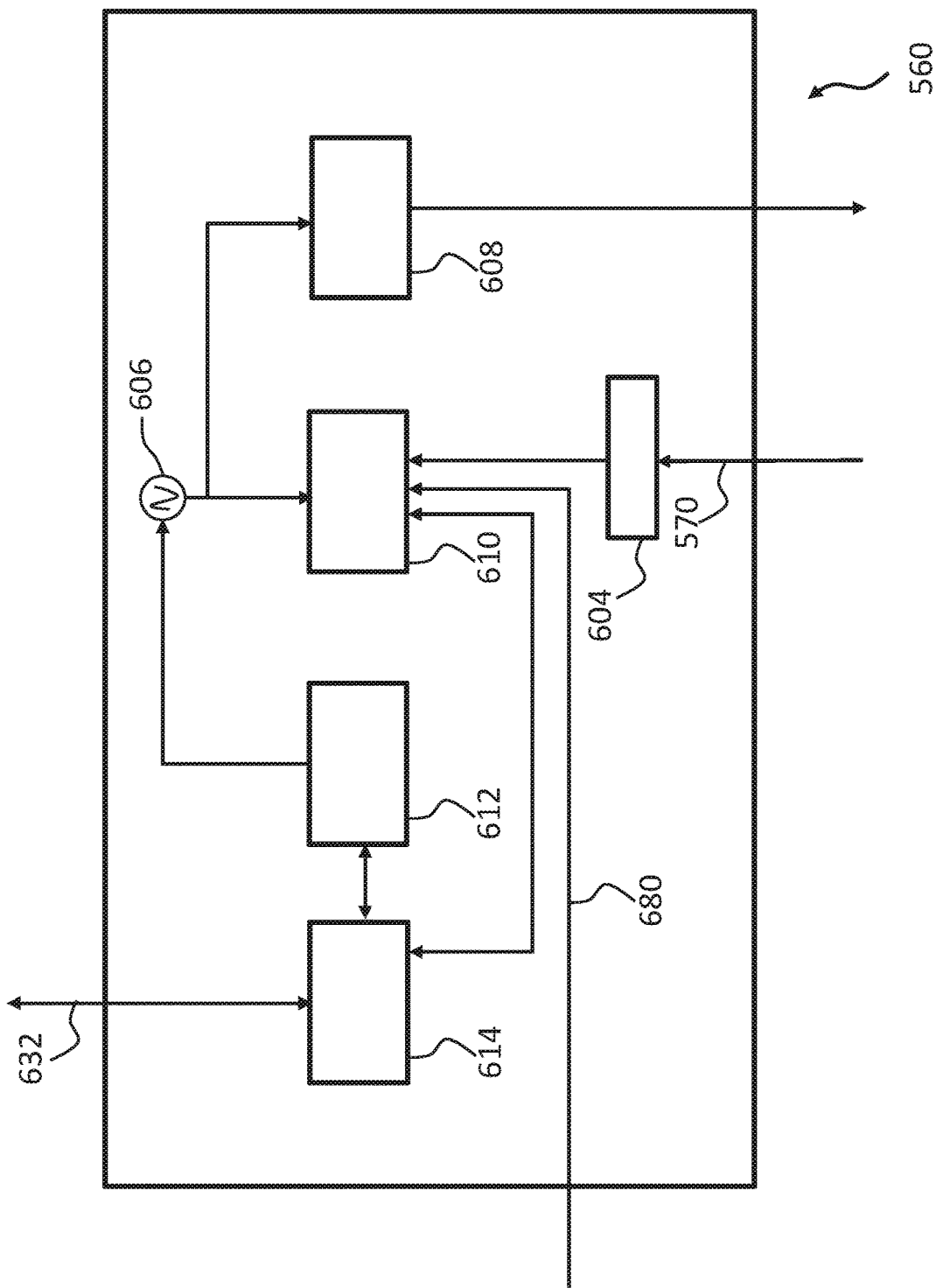

FIG. 37 presents additional details of test unit 560. It is again noted that the teachings associated with the test unit 560 are exemplary in nature, and can be implemented in any manner that will enable the teachings detailed herein. Indeed, the teachings detailed herein are presented for purposes of compactness and ease of understanding by referring to a "test unit." It is noted that one or more or all of the functionalities detailed herein associated with the test unit can be distributed through other portions of the prosthesis. In this regard, any prosthesis that enables the functionality detailed herein can be utilized in at least some exemplary embodiments. With this in mind, an exemplary embodiment includes a measurement system having test unit 560 that includes an electrophysiology measurement (EP) device 604, such as an electrocochleography (EC) measurement device, interconnected thereto. The electrophysiology measurement device 604 is configured to measure the electrical potential(s) associated with the cochlea and/or auditory nerve in response to test signals that are generated by the test unit 560 and supplied to the stimulation arrangement 704 (either indirectly through unit 532, or, in some other embodiments, where the test unit 560 is actually a part of the guide as well, directly to stimulation arrangement 704), where a component of the system generates stimulation signals based on that output that is utilized to actuate the stimulator arrangement 704. It is noted that while the embodiments detailed herein concentrate on the electrical potential, alternate embodiments can be utilized to measure other features associated with the cochlea and/or auditory nerve. Any measurement of any physiological feature that can enable the teachings detailed herein and/or variations thereof to be practiced can be utilized in at least some exemplary embodiments. Herein, any disclosure of the measurement of electrical potentials with the sensation of electrical potentials corresponds to a disclosure of the measurement and/or sensation of any electrical phenomenon/characteristics associated with electrophysiology (e.g., electrocochleography) and/or the disclosure of a measurement and/or sensation of any electrical phenomenon/characteristics associated with electrophysiological signals that can enable the teachings detailed herein and/or variations thereof (e.g., measurement of higher evoked potentials (e.g., higher than ECoG)).

In an exemplary embodiment, the measured electrical potential(s) may be output as measurement signals by the electrophysiology measurement device 604 to the test unit 560 and processed/output to a user to assess various features associated with the recipient pre- and/or post-implantation of the electrode array. The electrophysiology measurement device 604 may be provided to measure or otherwise detect/sense cochlear microphonic, summating potential and/or compound action potential of the auditory nerve and the auditory nerve neurophonic in response to the noted test signals. The cochlear microphonic, summating potential is the electrical potential generated at the hair cell level in the cochlea. In some exemplary embodiments, such summating potential has a predeterminable latency range following stimulation. Further, the summating potential can have, in some exemplary embodiments, a predeterminable durational range (e.g., directly related to the test signal duration) and predeterminable absolute amplitude range. Such predeterminable ranges are employed by test unit 560 in at least some exemplary embodiments to facilitate processing of the measured potential values output by electrophysiology measurement device 604.

The action potential of the auditory nerve is an electrical response that is generated by the cochlear end of the VIII cranial nerve and is typically viewed as representing the summed response of the synchronous firing of thousands of auditory nerve fibers. That is, the size of the action potential reflects the number of nerve fibers which are firing simultaneously. In the absence of adverse pathology, the action potential can have a predeterminable latency range (e.g., about 1.30 milliseconds to 1.70 milliseconds). Its duration can also have a predeterminable range (e.g., about 0.80 milliseconds to 1.25 milliseconds), with a predeterminable absolute amplitude range (e.g., between about 0.60 millivolts and 3.00 millivolts). Such predeterminable ranges can be employed in some embodiments by test unit 560 to facilitate processing of the measured potential output from electrocochleography measurement device 604. It is noted that measurement signal values corresponding with the measured magnitude of the summating potential and/or action potential and/or a ratio thereof can be extracted and processed by the test unit 560 in at least some exemplary embodiments to assess the interface between the implantable transducer and middle ear component or inner ear of the recipient, e.g., the actuator of stimulation arrangement 550. As will be described in greater detail below, this assessment of the interface is utilized in some exemplary methods to determine whether or not adjustments to the prosthesis can have utilitarian value relative to not making adjustments to the prosthesis, etc.

In some embodiments, to enable measurement of the summating potential and/or action potential, the test unit 560 comprises one or more measurement electrodes 1904/1904X. To be clear, an electrocochleography measurement electrode can be positioned as part of the insertion guide at a variety of locations, thus permitting that electrode to be positioned at a variety of locations inside the recipient (as is also the case with other types of electrography measurement electrodes).

Referring again to FIG. 37, the test unit 560 can comprise a signal generator 606, a reference transmitter 608, a signal processing unit 610, a test control processor 612, and a communication unit interface 614 that communicates with the communication unit 532 via signal line 632. By way of example, the test control processor 612 may provide signals for setting signal generator 606 to output reference signals at a predetermined frequency, or plurality of frequencies across a predetermined range, or a broadband reference signal, e.g., a click. The output reference signals may be provided to the reference transmitter 608, which in turn outputs test signals to the particular stimulation arrangement 704 (either directly or indirectly) and the signal processing unit 610. The signal processing unit 610 can analyze and/or store data based on the signals so as to enable an evaluation of the performance and positioning of the hearing prosthesis and/or a physiological aspect of the recipient. In an exemplary embodiment, the unit 610 is in communication with a non-transitory computer-readable medium having recorded thereon, a computer program for executing one or more or any of the method actions detailed herein associated with the unit 610. In certain applications, it is utilitarian for the test control processor 612 to provide signals to the signal generator 606 to output reference signals that are swept across or inherently broadband to encompass a predetermined frequency range (e.g., a frequency range that encompasses a predetermined or determinable resonant frequency of an implantable stimulation arrangement 704). Any arrangement of test signals and control regimes that will enable the teachings detailed herein and/or variations thereof to be practiced can be utilized in at least some exemplary embodiments.

Figure 38:
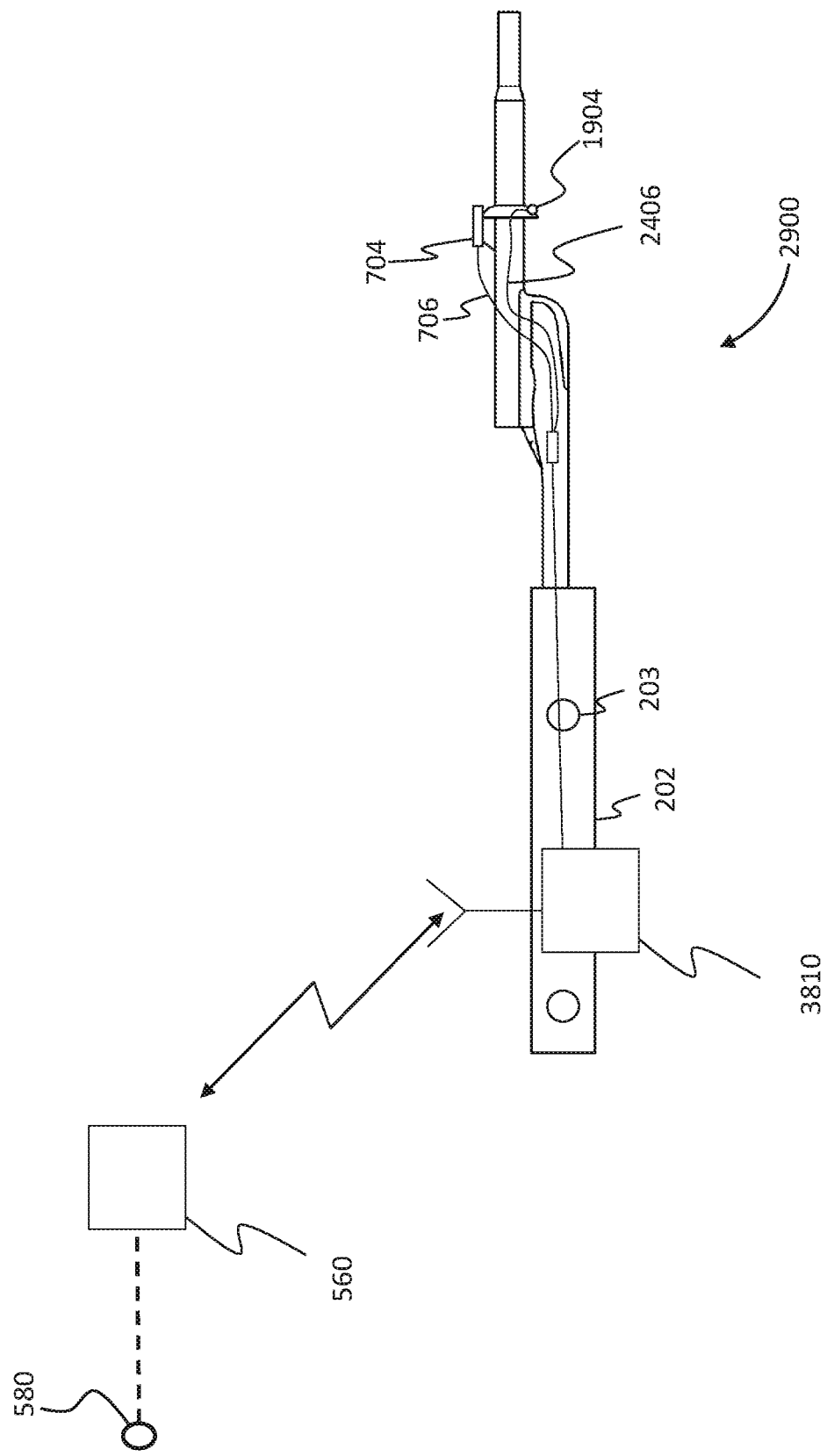
FIGS. 38-39 depict side views of exemplary embodiments of exemplary electrode array insertion guides.

It is briefly noted that while the embodiment of FIG. 36 is presented in terms of the test unit 560 being separate from the guide 2900, in some other embodiments, test unit 560 is located in the guide, the test unit 560 being in signal communication with the communication unit via an electrical connector therein and/or via hard wiring between the components. That said, in other embodiments, the test unit 560 can include its own communication unit so as to enable communication with the various components utilized in the system. Note further that in some other exemplary embodiments, wireless communication between one or more of the components can be utilized. FIG. 38 depicts an exemplary embodiment where a wireless transmitter/receiver 3810, corresponding to the communication unit 532, is in wireless communication via a wireless link with the test unit 560. Any arrangement that can enable the teachings detailed herein and/or variations thereof to be practiced can be utilized in at least some exemplary embodiments.

It is briefly noted that while the embodiments presented above have been described in terms of the utilization of the signal generator 606 generating a signal, in an alternative embodiment, a signal upon which the basis of the telemetric teachings detailed herein are implemented can be based on a sound that is captured by the sound capture device of the hearing prosthesis, whether that be located outside of the recipient in the case of a partially implantable hearing prosthesis or within the recipient in the case of a fully implantable hearing prosthesis.

As noted above, the electrophysiology measurement device 604 provides, in some exemplary embodiments, measured electrical potential values to test unit 560 and/or another device of the prosthesis. More particularly, the measured potential values are provided to the signal processing unit 610 in the exemplary embodiment presented in FIG. 37. In turn, the signal processing unit 610 can process the measured potential values in accordance with preset algorithms. For example, utilizing the stored reference signal information and stored algorithms corresponding with one or more of the above noted predeterminable ranges, the signal processing unit 610 is configured in some embodiments to selectively extract the summating potential and/or action potential from the measured potential values. Still further, the processing unit 610 is further configured to process the extracted values (e.g., average the values and/or otherwise successively compared these values to determine whether and/or when a predetermined threshold or maximum value is reached (e.g., thereby indicating a desired interface).

Figure 39:
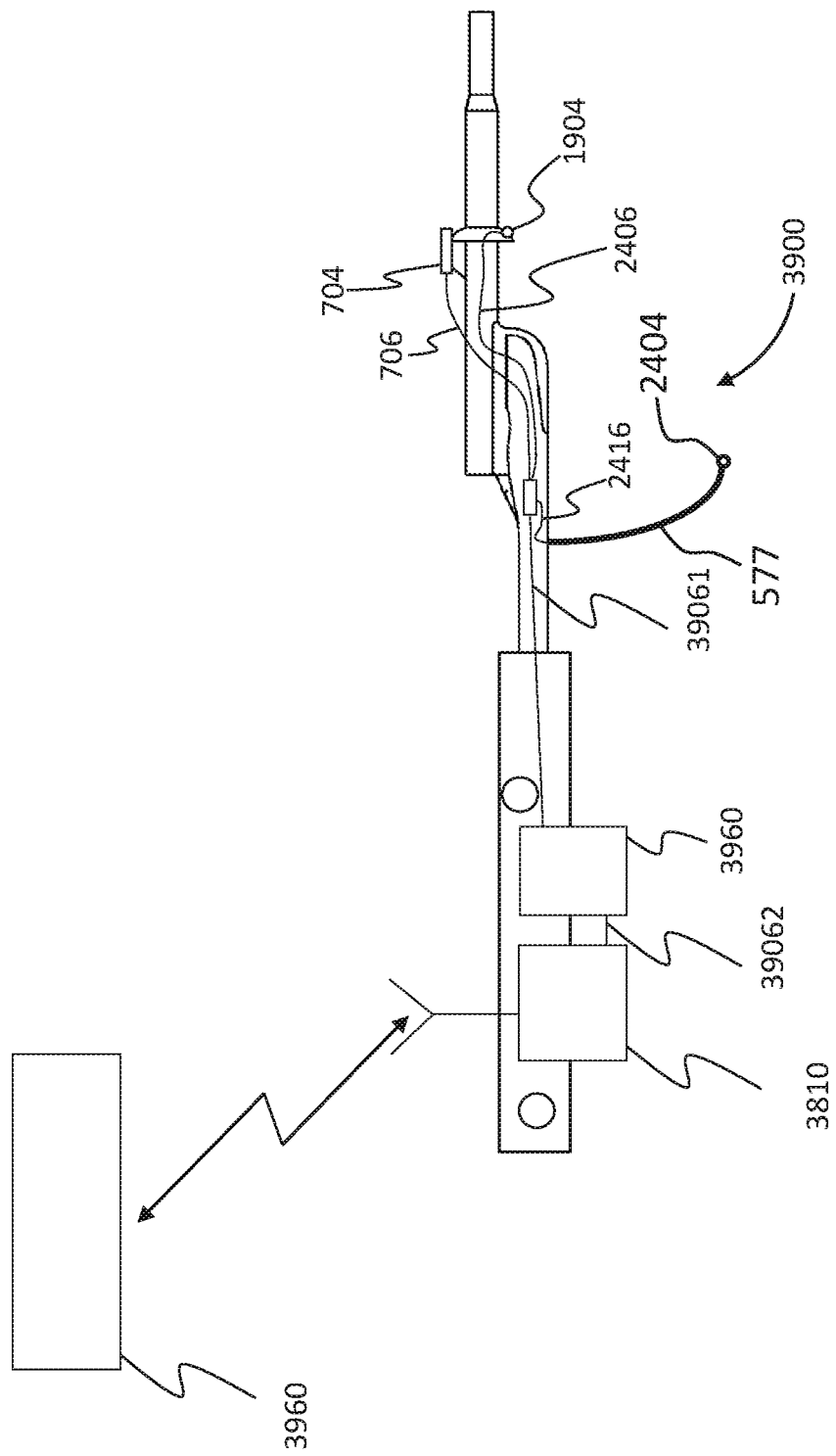

As briefly noted above, in at least some exemplary embodiments, some exemplary insertion guides can include a self-contained ECoG system. FIG. 39 depicts such an exemplary embodiment of an insertion guide 3900. Insertion guide 3900 contains a complete ECoG system. As can be seen, the insertion guide 3900 further includes a reference electrode 2404, which is in signal communication with the electrical leads of the system via lead 2416. Lead 39061 extends from the connector to test unit 3960, which can correspond to test unit 560 detailed above. Test unit 3960 is in signal communication with communication unit 3810 via lead 39062. Communications unit 3810 can be in wireless communications with remote device 3960. In an exemplary embodiment, the remote device 3960 is a data storage device/data recording device that records the data transmitted via the communications unit 3810. For example, 3960 can be a desktop and/or a laptop computer having memory therein to record the data. In an alternate embodiment, device 3960 can be a control unit or the like, again such as a computer, that can control the ECoG system of the guide 3900. That said, in an exemplary embodiment, the guide 3900 includes an activation switch or the like so that the ECoG system can be activated and/or deactivated by the surgeon or other healthcare professional.

Figure 40:
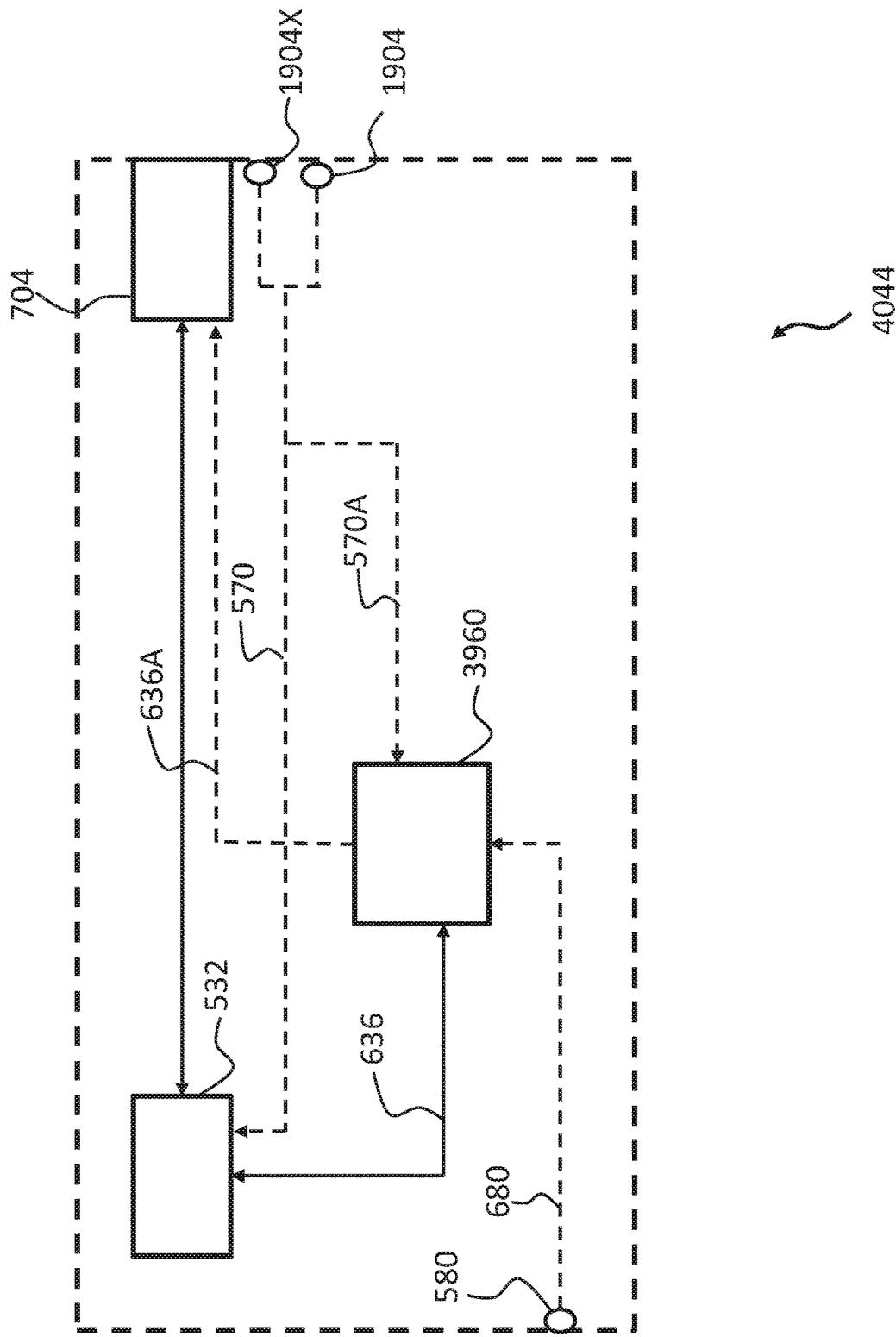
FIG. 40 depicts an exemplary functional block diagram associated with the exemplary electrode array insertion guides.

FIG. 40 depicts an exemplary schematic of the ECoG system 4044 of the guide 3900, or system 4044 is entirely integrated into the guide 3900 (e.g., the communication unit 532 and the test unit 3960 are integrated into the handle of the guide (either in or on the handle)) and the electrodes and the generator are supported by the guide in accordance with the teachings detailed herein and/or variations thereof. As can be seen, test unit 3960 is in signal communication with communication unit 532 via signal line 636. Through communication unit 532, the test unit 3960 can indirectly communicate with the generator 704 and the electrodes 1904 and 1904X. That said, alternatively and/or in addition to this, test unit 3960 can be in communication with the electrodes via signal line 570A and with the generator via signal line 636A. Further, the reference electrode 580 can be in communication with the communication unit 632 instead of and/or in addition to direct communication with the test unit 3960. Note also that in an exemplary embodiment, the reference electrode 580 can be a remote unit that is not part of the insertion guide. Any arrangement that can enable the teachings detailed herein can be utilized in at least some exemplary embodiments.

Figure 41:
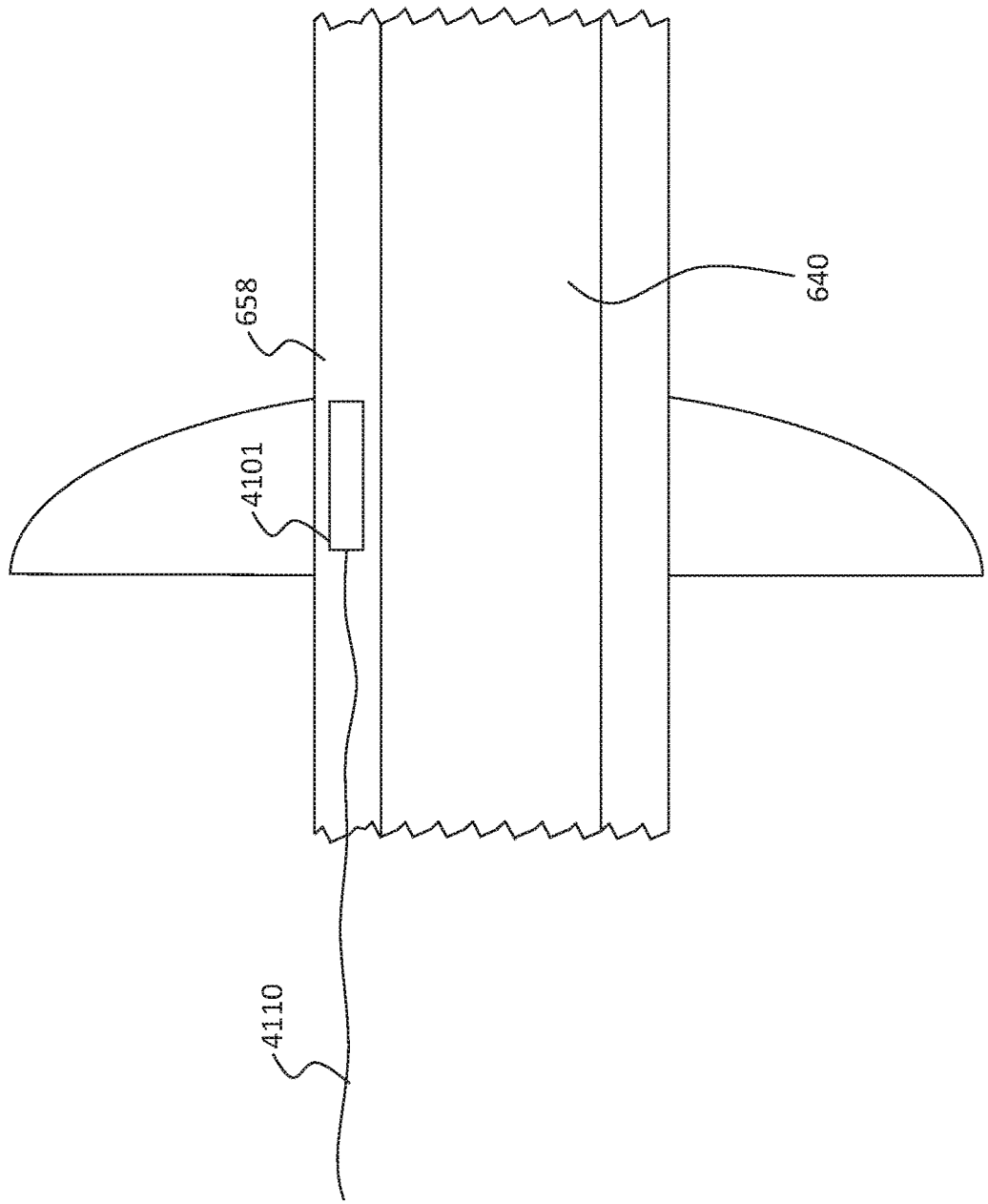
FIGS. 41-44 depict cross-sectional views of portions of the insertion guide tube of exemplary embodiments of the electrode array insertion guide.

FIG. 41 depicts another exemplary embodiment of an insertion guide that has a functionality beyond that of an electrode array support/an electrode array insertion device. Particularly, the embodiment of FIG. 41 depicts a portion of the insertion guide tube at the stop 204 where a sensor 4101 is located in the wall 658 of the tube, although in other embodiments, the sensor 4101 is located on the inside wall of the tube and in other embodiments, the sensor 4101 is located on the outside wall of the tube. In this exemplary embodiment, the sensor is configured to sense or otherwise detect individual electrodes in the array as they pass by the sensor as the electrode array is inserted through the lumen 640 into the cochlea, and output a signal via lead 1410 indicative of at least one of an electrode passing the sensor 4101 or, in a more sophisticated embodiment, the speed of the electrode/electrode array passing by sensor 4101. In an exemplary embodiment, the sensor 4101 can be a sensor that utilizes capacitive sensing. In an exemplary embodiment, it could be a Hall effect sensor. In some embodiments, the sensor could be a sensor that comes into direct contact with the electrodes of the electrode array. In an exemplary embodiment, there is a system that receives the signal from lead 1410 and outputs data indicative of the insertion speed of the electrode. In an exemplary embodiment, the system can be a personal computer with an algorithm that analyzes the signal 4110, and outputs data to the surgeon. Exemplary output can be output by a speaker or the like indicating the speed of the insertion of the electrode array. Exemplary output can be output by a visual device indicating the speed of insertion of the electrode array. Exemplary output can correspond to the speed of insertion, a go/no go data package (e.g., insertion too fast/insertion speed fine). Such can be done via audio and/or visual devices. For example, a green light can indicate acceptable speed and a red light can indicate an unacceptable speed. Moreover, the system can be binary. The activation of the light will indicate that the speed is too fast/the audio indication (which could be a buzzer or a tone, etc.) activates when the insertion speed is too fast. The alternative could also be the case. The tone and/or light can be activated while the insertion speed is acceptable, and the tone or light is deactivated when the insertion speed is unacceptable.

Figure 42:
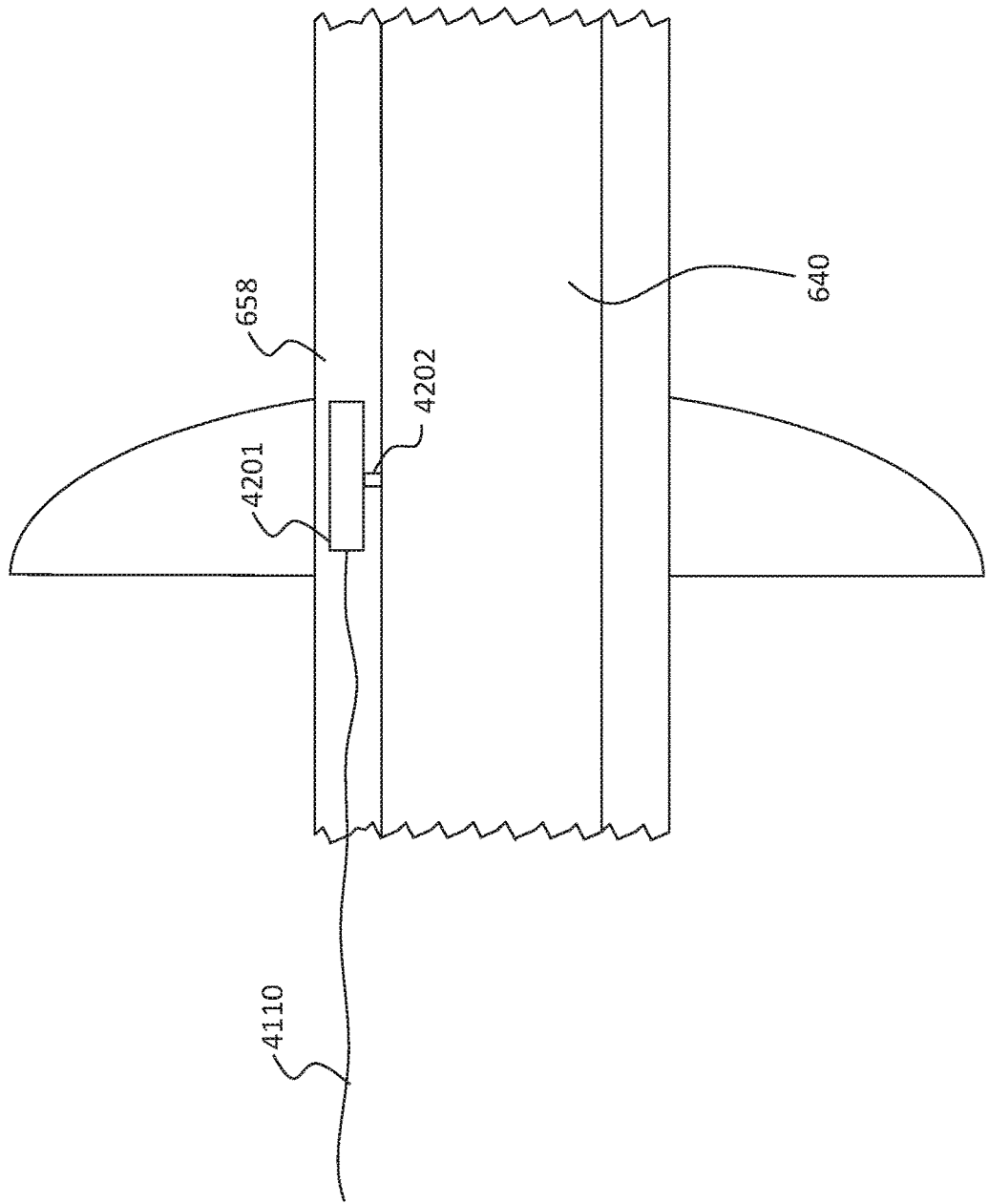

FIG. 42 depicts an alternate embodiment, wherein the sensor 4201 is a visual sensor. For example, optics 4202 view the inside of the insertion guide tube 610/view the lumen. Indicia on the array, such as markings provided especially for this purpose, or, in an alternative embodiment, the electrodes themselves, can be counted or otherwise detected via the sensor 4201 and thus the speed determined or otherwise deduced. In an exemplary embodiment, the sensor 4201 is a photosensor. In an exemplary embodiment, the sensor is a CCD. Any arrangement that can be utilized to visually sense the passage of the array can be utilized in at least some exemplary embodiments.

In an alternate embodiment, sensor 4201 utilizes a sound or a radio wave or the like to detect the passage of the array and deduce the speed thereof. In an exemplary embodiment, a Doppler shift or the like can be utilized. Thus, in an exemplary embodiment, sensor 4201 can generate a sound wave and/or a radio wave, and receive the soundwave and/or radio wave. Thus, the sensor can be akin to a sonar sensor and/or a radar sensor.

Figure 43:
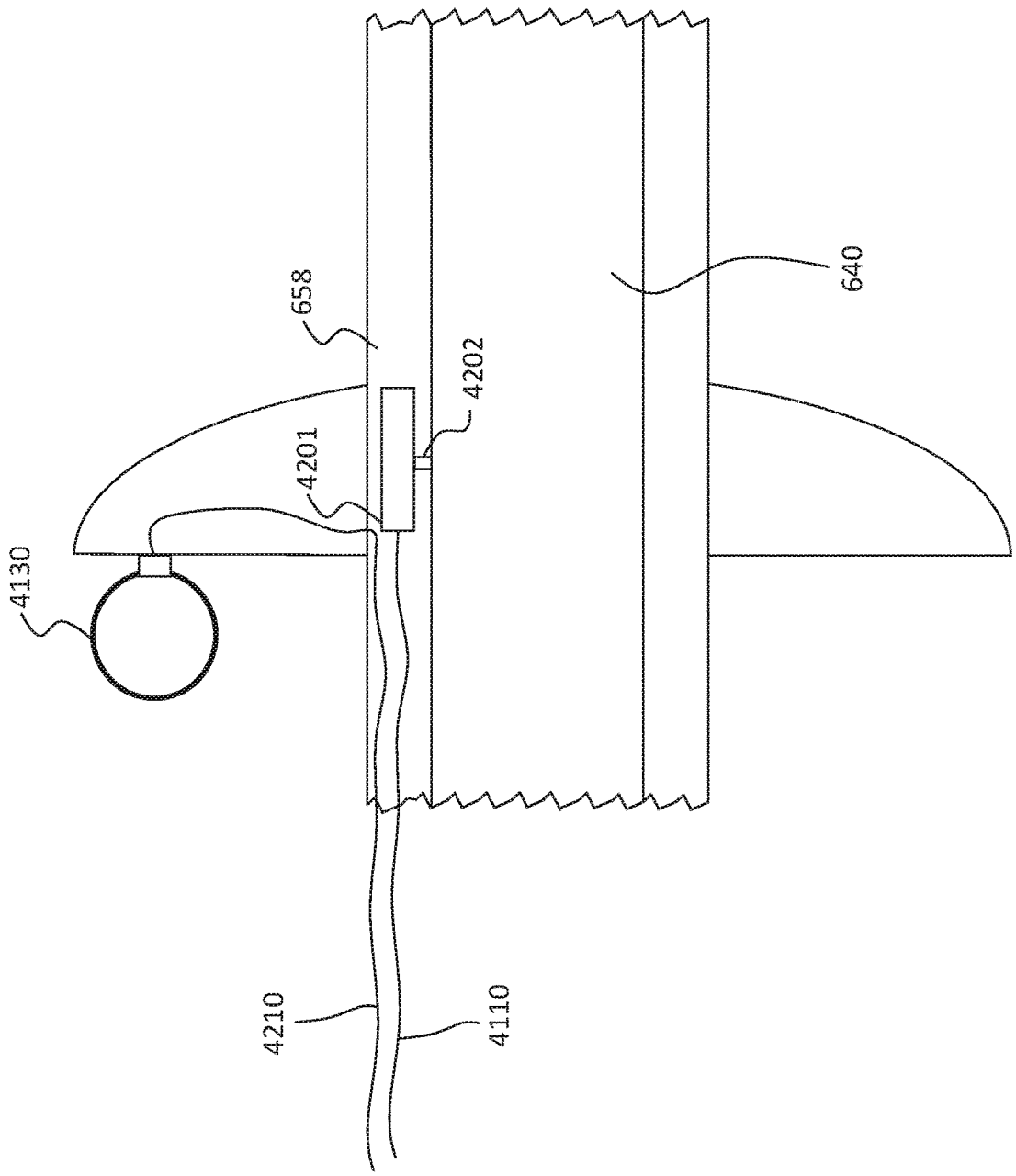

In an exemplary embodiment, lead 4110 is connected to a processor that can determine the speed and/or can utilize the information from sensor 4201 or 4101 or any other sensor to determine the insertion depth of the electrode array. In an exemplary embodiment, the processor can be part of the guide. Indeed, concomitant taunts with the teachings detailed above with respect to the integrated ECoG system, the guide can include a processor or other device that receives the input from the lead 4110 and analyzes that input to output data to the user. Thus, in an exemplary embodiment, the guide can have an output device (e.g., a light (LED, etc.), located on the stop as seen in FIG. 43) that provides the user with data. A plurality of output devices can be utilized (e.g., two lights, one red/one green, although it is noted that in some alternate embodiments, an LED that can change colors is utilized). In this regard, FIG. 43 depicts an exemplary insertion guide that includes a light 4120. The light is in signal communication with a processor (not shown) via lead 4210. In an exemplary embodiment, the sensor 4201 provides a signal to the processor via lead 4110, and that processor analyzes the signal, and provides output via lead 42102 activate light 4130 to indicate information regarding the insertion speed and/or the distance. In an exemplary embodiment, an array of lights is arrayed about the outer periphery of the stop. In an exemplary embodiment, these lights are variously activated and/or deactivated to indicate the speed and/or the location of the array in an analog and/or a digital manner. Note also that while the embodiment presented in FIG. 43 relies on a remote processor remote from the sensor 4102, in an alternate embodiment, the sensor can include processing capabilities and/or can be such that it can output a signal directly to the lights 4130 and/or a plurality of lights and/or other output devices (speakers—the output could be clicks like a Geiger counter or some other sound that indicates distance and/or speed, etc.). Indeed, in an exemplary embodiment, the remote processor is not needed.

In an exemplary embodiment, the sensors utilized to monitor the speed and/or location of the array within the lumen 640 utilize or otherwise implement capacitive coupling between the electrodes and the array and the sensor.

While the embodiments depicted in FIGS. 41 and 42 depict a single sensor, in alternate embodiments, a plurality of sensors are utilized. Indeed, the sensors can be arrayed such that the sensors are located "out of phase" with respect to each other and the electrodes of the array such that the sensors can be "tripped" more frequently than that which would be the case utilizing one sensor or a sensor having spacing the same as or greater than the distance between electrodes. This can have utilitarian value with respect to not having to wait for feedback from only one sensor to determine the speed and/or location of the array. For example, in an insertion guide having a plurality of sensors located out of phase with each other relative to the electrode spacing, an electrode or other indicia on the array can pass the first sensor, and then pass a second sensor, and/or a third sensor, and/or a fourth sensor, etc. prior to another electrode passing the first sensor. Thus, this provides additional data points to deduce the speed and/or location of the array. Note also that while the embodiments depicted in the FIGS. depict the sensor located at the top of the insertion guide tube, in an alternate embodiment, the sensors can be located on the bottom. Such can have utilitarian value in embodiments where the electrodes are located on the bottom of the array as opposed to on the top of the array.

Note also that while the sensors are depicted as being proximate the stop, in alternative embodiments, the sensors can be located elsewhere. Indeed, in an exemplary embodiment, the sensor can be located at the tip or proximate to the tip of the insertion guide. In this regard, the sensor can provide an indication to the surgeon or the like when the array first leaves the tube. Again, sensors can be arrayed at a number of locations. Any arrangement of sensors that can enable the teachings detailed herein can be utilized in at least some exemplary embodiments.

It is noted that at least some embodiments that utilize the electrode or other devices to measure or otherwise monitor insertion speed and/or insertion depth do so without measurements of the impedance of individual electrodes as the array is inserted into the conductive perilymph. That is, in an exemplary embodiment, the insertion guide is configured so as to monitor insertion speed and/or insertion depth without the presence of perilymph between the sensor of the guide (e.g., electrode) and the electrode array. However, in some alternate embodiments, measurement of either voltage induced in the perilymph due to stimulation current being passed from one intro cochlear electrode contact to another, with the impedance and passing current from a stimulating contact on the array to a return contact on the sheath, could be used to infer the proximity of a contact passing through the sheath, and thus can be utilized to monitor insertion speed and/or insertion depth based on the inference the proximity of the contact.

Figure 44:
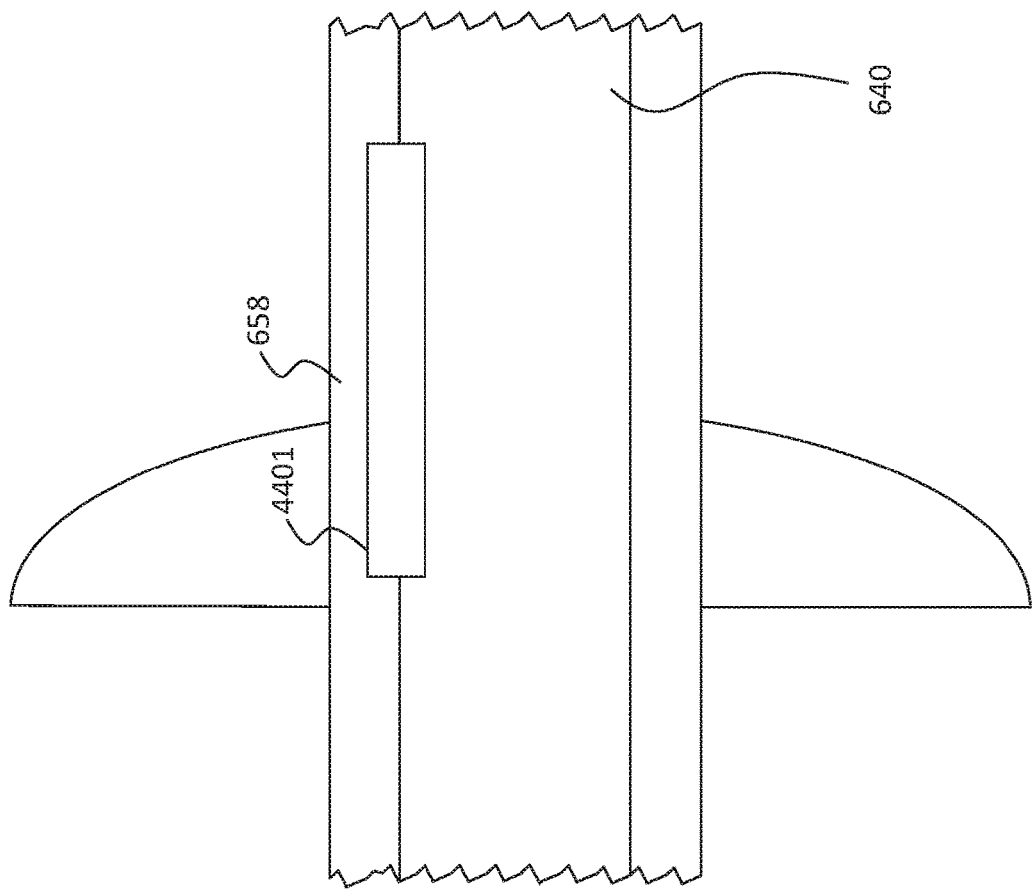
Figure 45:
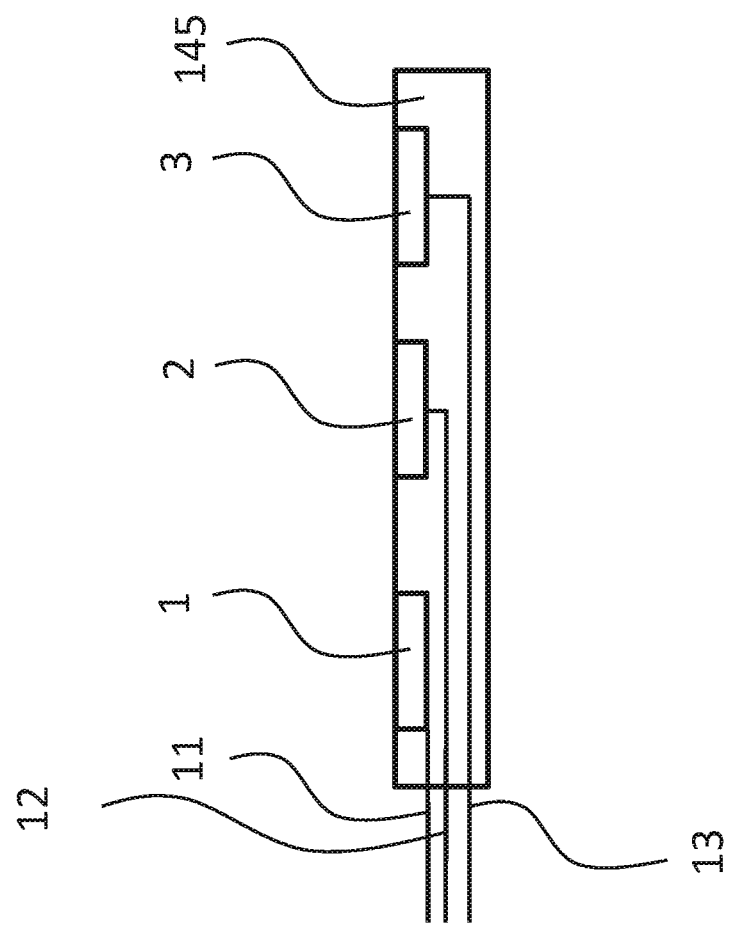
FIG. 45 is a quasi-functional schematic of an electrode array according to an exemplary embodiment.

FIG. 44 depicts a portion of an exemplary insertion guide that is configured to enable testing for an open circuit between two or more electrodes of the electrode array as the array passes through the lumen 640. Briefly, component 4401 is made of a conductive material that essentially "shorts" two electrodes of the electrode array as they pass by in contact with the component 4401. As will be detailed below, component 4401 can be a flexible component so as to provide a compressive force on the outside of the electrode array so as to establish sufficient electrical conductivity between an electrode, component 4401, and another electrode. In general terms, FIG. 45 depicts a quasi-functional diagram of a portion of electrode array 145, depicting electrodes 1, 2, and 3, which are respectively connected to leads 11, 12, and 13, which leads extend from the respective electrodes to the proximal end of the electrode array assembly, and then to a receiver/stimulator thereof. While only three electrodes and three leads are depicted in FIG. 45, it is to be understood that in at least some embodiments, more electrodes and more leads are present in electrode array 145. Only three electrodes and only three leads are depicted in FIG. 45 for clarity.

In isolation, without any contact with any outer material other than air, to test for a short, a source of current is applied to any one of the leads 11, 12, or 13. If current is detected (this phenomenon is described generally—in at least some exemplary embodiments, the "detection" corresponds to a given functionality of the receiver/stimulator that can be telemetrically transmitted and analyzed—more on this below) at any one of the other leads 11, 12, and/or 13, a determination can be made that a short exists. This is because the impedance between the electrodes 11, 12, and 13 should be relatively high (the material connecting the electrodes 148 is typically made of silicone). The leads 11, 12, and 13 are insulated from one another and from the electrodes other than the respective electrodes associated with the respective leads.

Conversely, to detect for an open, in the absence of contact with any other material other than air, because of the high impedance between the respective electrodes, and the aforementioned electrical insulation, there is nothing to close the circuit between a source of electrical current applied to one lead, and a detector (again, this is used generally—more on this below) located at any of the other leads.

Accordingly, in an exemplary embodiment, the apparatus 4401 is configured to enable testing for an open circuit between two electrodes by utilizing conductive material that is sufficiently conductive to test for an open circuit when placed into contact with two or more electrodes of the electrode array 144. In use, component 4401 extends a sufficient distance into the lumen 640 and has sufficient length such that it can contact two electrodes as the electrode array passes by component 4401. In an exemplary embodiment, the entire component 4401 is made of a requisite conductive material. In an exemplary embodiment, only a portion thereof is made of the requisite conductive material. By way of example only and not by way of limitation, at least the bottom surface (the surface that faces the electrodes/the surface that comes into contact with the electrodes) can be made of the requisite conductive material, or at least coated with the requisite material or otherwise the requisite material is attached to the interior thereof). In an exemplary embodiment, only a portion of the component 4401 is made of the requisite conductive material. Any arrangement that can enable the testing of an open circuit while electrode array assembly is being passed can be utilized in at least some embodiments.

In an exemplary embodiment, the material of the component 4401 and/or other material forming a portion of the component 4401 and/or any other material that enables testing for an open circuit has a "midrange" impedance, or at least enables the establishment of a midrange impedance between two or more electrodes, such that both testing for an open circuit and testing for a short circuit can be implemented. In other exemplary embodiments, the component 4401 has a relatively high range impedance.

In an exemplary embodiment, the component 4401 is configured to provide a controlled impedance between two or more electrodes that will enable at least testing for an open circuit between two electrodes, if not both testing for an open circuit and testing for a short circuit between two electrodes.

Thus, in an exemplary embodiment, the component 4401 is configured to enable two types of conductivity testing of the electrode array (e.g., testing for an open circuit and testing for a short circuit) in some embodiments.

Figure 46:
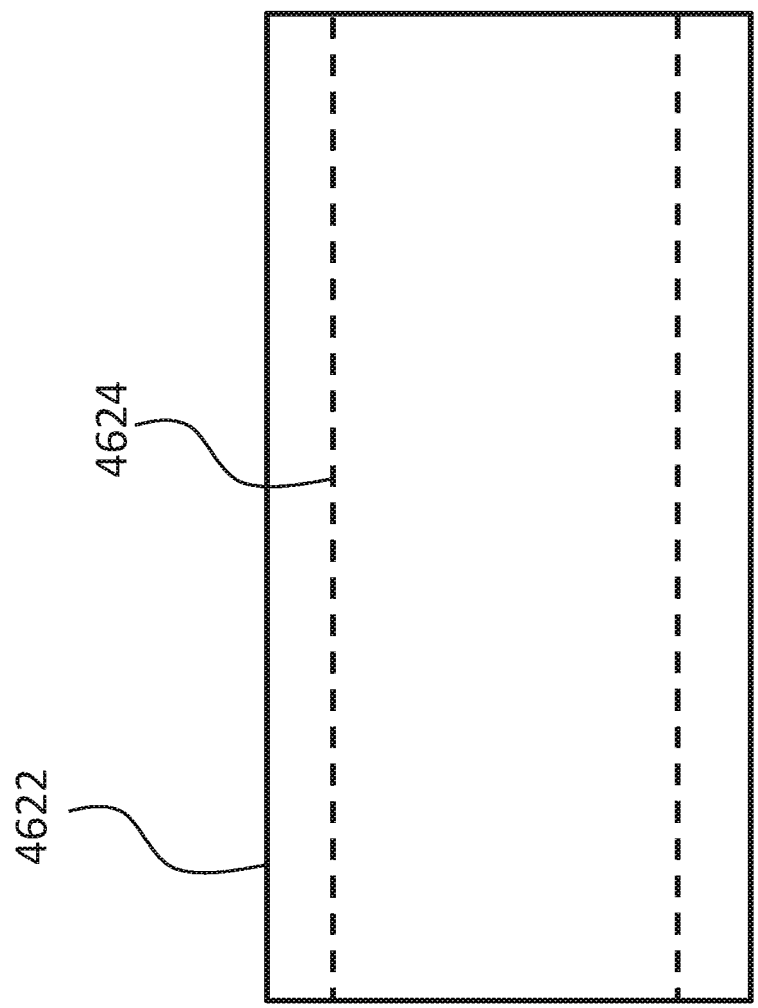
FIG. 46 is a schematic of a conductive apparatus according to an exemplary embodiment.

FIG. 46 depicts an exemplary conductive apparatus 4622 in the form of an elongate cylinder having a passage 4624 therethrough, wherein the passage 4624 is sized and dimensioned to receive the electrode array 145 therein such that at least two electrodes of the electrode array 145 contact the interior walls of the passage 4624 to establish electrical conductivity between the electrodes. In an exemplary embodiment, the conductive apparatus 4622 is configured such that an impedance between any two locations on the interior surface of the passage 4624 within a distance corresponding to the distance between two electrodes of the electrode array 145 that will be inserted or otherwise located within passage 4624 is less than about 500 ohms (or any other value that will enable testing for an open circuit between two electrodes—more on this below). In this regard, it is noted that all disclosures of impedance and related phenomenon detailed herein both correspond to the structure being described, and how the structure is arranged or otherwise used. That is, because impedance varies both with respect to distance and with respect to material type (along with some other features) and it is the resulting impedance that imparts utilitarian value on to the teachings detailed herein, as opposed to the specific impedance of a given material or the like, any disclosure herein regarding material properties also corresponds to the functionality of the resulting apparatuses when utilized according to the teachings detailed herein and/or variations thereof.

Figure 48A:
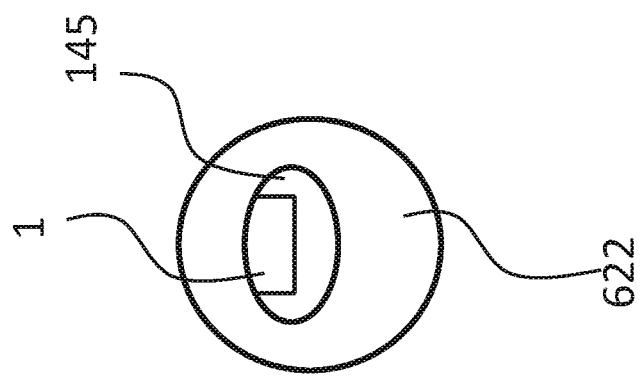
FIG. 48A depicts the view of FIG. 7, along with a cross-sectional view of an electrode array located in the conductive apparatus.

FIG. 48A depicts the conductive apparatus 4622 located in the insertion guide tube 610 of the insertion guide. In an exemplary embodiment, the interior of the conductive apparatus at the ends thereof is rounded so as to provide a smooth interface between the interior wall of the tube wall 658 and the "bump up" that is the interior of conductive apparatus 4622. That is, because the interior of conductive apparatus 4622 is proud of the interior wall of the tube wall 658, ramping can be used so as to avoid binding or otherwise catching the electrode array one the edges of the conductive apparatus 4622.

Briefly, the embodiments utilizing apparatus 4622 and variations thereof to "short" two electrodes rely on, in some embodiments, the ability of the receiver/stimulator of the cochlear implant to provide an electrical signal to one of the electrodes and sense a voltage and/or current at the other of the electrodes. In an exemplary embodiment, a device is in inductance communication (or any other applicable communication format that will enable the teachings detailed herein and/or variations thereof to be practiced) with the receiver/stimulator of the cochlear implant so as to communicate data therefrom indicating whether or not an open circuit is present. Indeed, in an exemplary embodiment, the device that is in inductance communication with the receiver/stimulator is the device that initiates the current to one of the electrodes and the first instance. In an exemplary embodiment, the communication can correspond to the communication that transcutaneously takes place between the external component 142 and the implantable component 144 vis-à-vis the system of FIG. 1. That is, in an exemplary embodiment, the communication from the receiver/stimulator and/or to the receiver/stimulator can be executed utilizing techniques that are the same as, or at least analogous to, the transcutaneous communication that takes place while the cochlear implant 100 is implanted in a recipient fully and completely beneath the skin.

Figure 47:
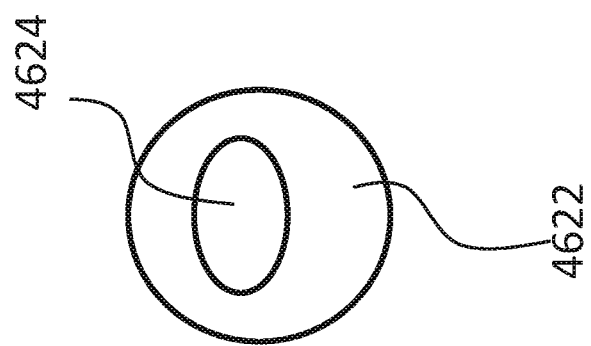
FIG. 47 is another view of the conductive apparatus of FIG. 46.

FIG. 47 depicts a view looking down the longitudinal axis of the conductive apparatus 4622 (i.e., looking from the left or the right with respect to the frame of reference of FIG. 46). It is noted that the geometric shapes presented in these FIGS. are but exemplary. Any configuration that will enable the teachings detailed herein and/or variations thereof to be practiced can be utilized.

It is further noted that while the embodiment depicted in FIG. 46 and FIG. 47 is depicted as a monolithic component (in an exemplary embodiment, the entire body 4622 is made from a conductive material, and thus conductive apparatus 4622 is a tube or cylinder of conductive material), in an alternative embodiment, the conductive apparatus 4622 can be a multilithic component. Indeed, in an exemplary embodiment, the walls of the passageway 4624 can be coated with a conductive material (e.g., gold), and the remainder of the conductive apparatus 4622 is made of a relatively nonconductive material (e.g., rubber, silicone, etc.). In this regard, for embodiments where the conductor used to test for the open circuit is movable in and out of position, the impedance range of the conductor can be very low.

It is noted that in an exemplary embodiment, the entire body 4622 and/or a portion thereof (e.g., the portion making up the walls of the passageway 4624) is a conductive foam or conductive polymer. Typically, this is foam or polymer containing conductive elements (e.g., loaded with silver, gold, carbon, etc.). This can have utilitarian value with respect to deforming around the electrode array as the electrode array passes through body 4622. Accordingly, such can have utilitarian value with respect to contracting as the localized width of the electrode array relative to body 4622 becomes wider as the electrode array is passed therethrough during insertion of the electrode array.

Figure 48B:
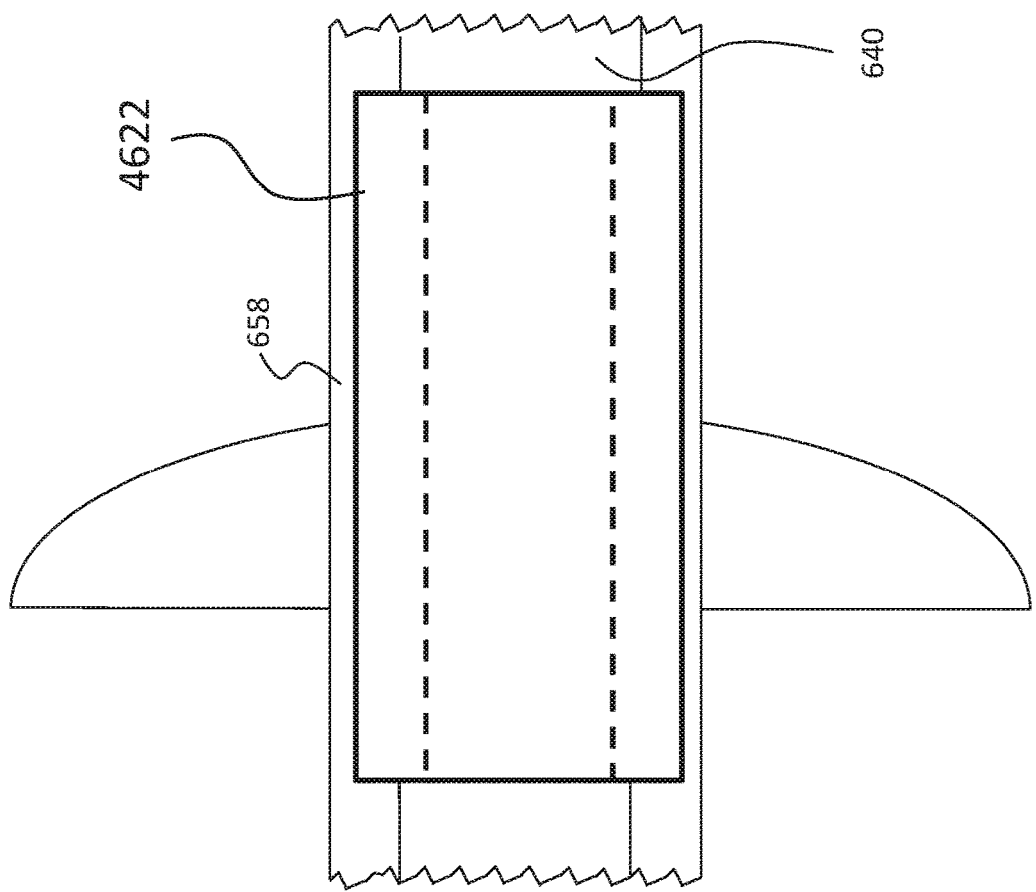
FIG. 48B depicts a cross-sectional view of a portion of the insertion guide tube of exemplary embodiments of the electrode array insertion guide.
Figure 49:
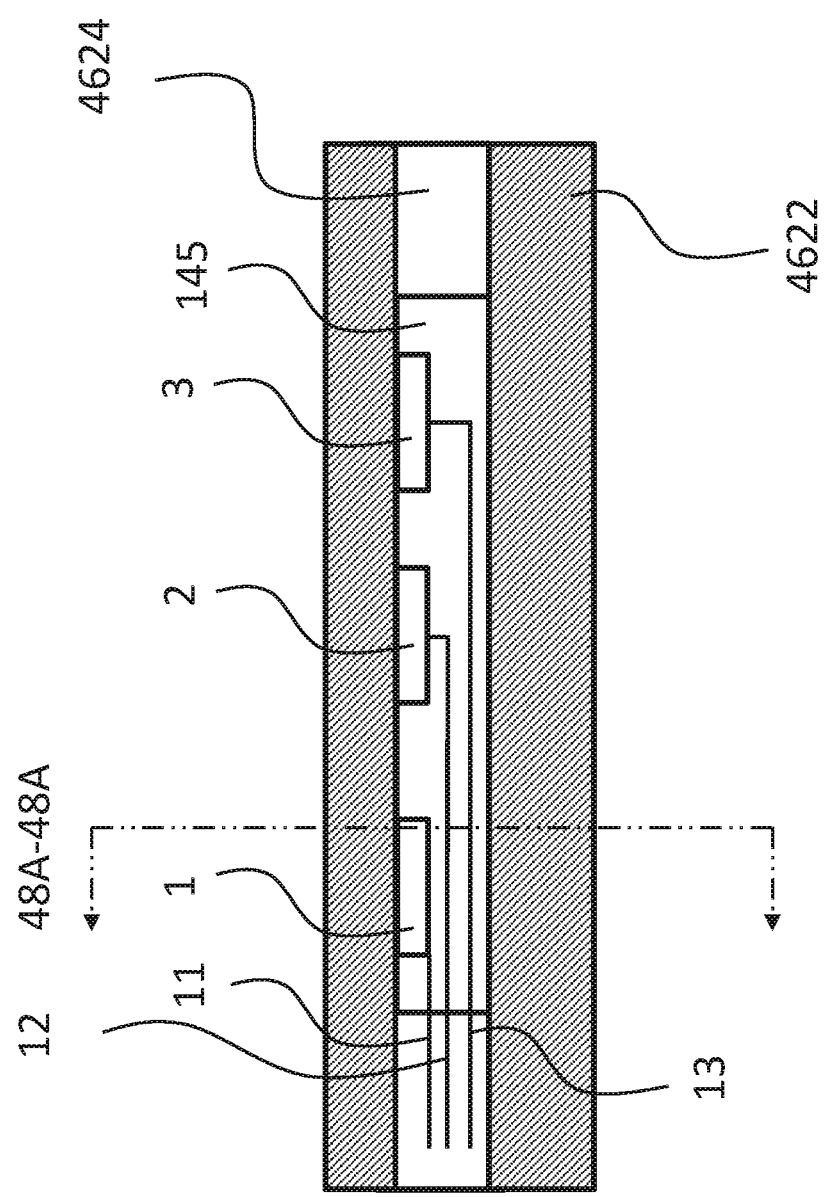
FIG. 49 depicts an exemplary scenario associated with testing an electrode array for an open circuit utilizing a component of an insertion guide.

FIG. 48A depicts the view of FIG. 47, with the addition of the electrode array 145 being located in the passage 4624 (the array is shown in cross-section). More particularly, the view of FIG. 48 depicts a cross-sectional view of an electrode array 145 taken at a location where electrode 1 is located. FIG. 49 presents FIG. 48A in greater context, which depicts a side view of a cross-section through the conductive apparatus 4622 with the electrode array 145 located therein.

As can be seen, the electrodes are in contact with the inner surface of the passageway 4624. In this embodiment, the contact is sufficient to provide electrical conductivity from electrode 1 to electrode 2 and/or electrode 3 such that testing for an open circuit between one of these electrodes can be implemented. Corollary to this is that the conductive apparatus 4622 is configured to maintain the requisite contact to enable testing for an open circuit between two or more of the electrodes and/or be placed and held in that configuration for such testing to be executed. In an exemplary embodiment, conductive apparatus 4622 is made of a conductive foam material, wherein an interference fit is established between the electrode array 145, and thus the electrodes 148, and the inner surface of the passage 4624. In an exemplary embodiment, the interference fit ensures that sufficient contact will be made between the inner surface of the passage 4624 and the respective surfaces of the electrodes 148. In an exemplary embodiment, the use of foam ensures or otherwise substantially lessens the chance that the array 145 will be damaged due to contact between the array and the conductive apparatus 4622. This will be described in greater detail below.

Figure 50A:
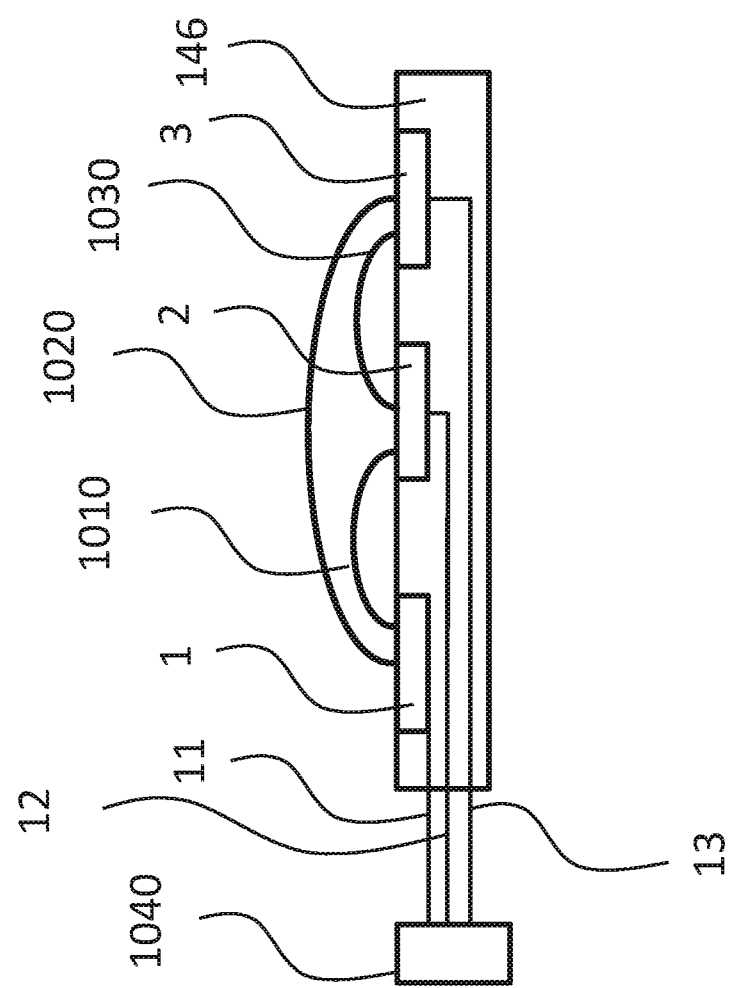
FIG. 50A depicts a conceptual diagram depicting a test for an open circuit.

FIG. 50A presents a functional representation of the functionality of the conductive apparatus 622, where hypothetical leads 1010 and 1020 are located between electrodes 1 and 2 and between electrodes 1 and 3, respectively. Also shown is hypothetical lead 1030, which is located between electrodes 2 and 3. These leads place the various electrodes into electrical conductivity with one another so that testing for an open circuit can be executed. Also depicted by way of black box format is a current generator/detector 1040, which is configured to apply current to one or more of the leads 11, 12, 13, and detect a current (if there is no open circuit) at one or more of the other of leads 11, 12, 13. The current generator/detector 1040 is but a functional representation of the operation of the receiver/stimulator 180 and/or a test device. That said, in some alternate embodiments, current generator/detector 1040 can be an ohmmeter and/or a multimeter, albeit one adapted for the types of voltage and current suitable for testing of a cochlear electrode array or other array to which the teachings detailed herein are applicable.

Briefly, in an exemplary embodiment, a current is applied by current generator/detector 1040 to lead 12. Current generator/detector 1040 "looks" for a current at either or both of leads 11 and 13. (In an exemplary embodiment, the insertion guide includes a generator configured to generate current at a programmed amount through lead 12 and return it through one or all of the remaining electrodes. In an exemplary embodiment, the guide provides an output indicative of voltage required to drive this amount of current. In an exemplary embodiment, if the voltage is above a certain threshold, it is deemed an open circuit. Otherwise, it is assumed the current is flowing and thus this circuit is closed.) Because the conductive apparatus 622 has placed electrode 2 into electrical conductivity with electrodes 1 and 3 via hypothetical leads 1010 and 1030, a current should register at one or both of leads 11 and 13 (or only one of the leads if only one of the hypothetical leads 1010 and 1030 or present) thus indicating that there is no open circuit between current generator detector 1040 and electrode 2.

Note that by "looking" for a current at two or more leads, the scenario where an open circuit exists with respect to one of the other leads, which open circuit could give a "false-negative" with respect to the lead under test can be accounted for in an exemplary embodiment. For example, if lead 12 is being tested (or, more precisely, testing for an open circuit is being performed between current generator/detector 1040 and electrode 2), and if only one lead, such as lead 11, was being utilized for the test, failure to detect a current by current generator/detector 1040 at lead 11 would not necessarily indicate a break for an open circuit associated with lead 12. This is because lead 11 could have failed. However, if a current is detected at lead 13 but not lead 11, it can be surmised that lead 12 is in proper working order, and lead 11 has experienced a failure mode. That is, it can be extrapolated or otherwise inferred that lead 11 has failed in some manner (i.e., the open circuit is between current generator/detector 1040 and electrode 1). In this regard, exemplary embodiments include algorithms to more quickly test a plurality of circuits in view of the fact that deductive logic can be utilized when more than two electrodes are placed into electrical conductivity with one another via conductive apparatus 622.

Note further that to test for a short circuit, the hypothetical leads are removed from the electrodes (e.g., the electrode array is moved away from conductive apparatus 4622). A current is applied to one or more of the leads, and current is looked for at one or more of the other leads. No current (or only specific current—more on this below) should be detected because the hypothetical leads have been removed.

Figure 50B:
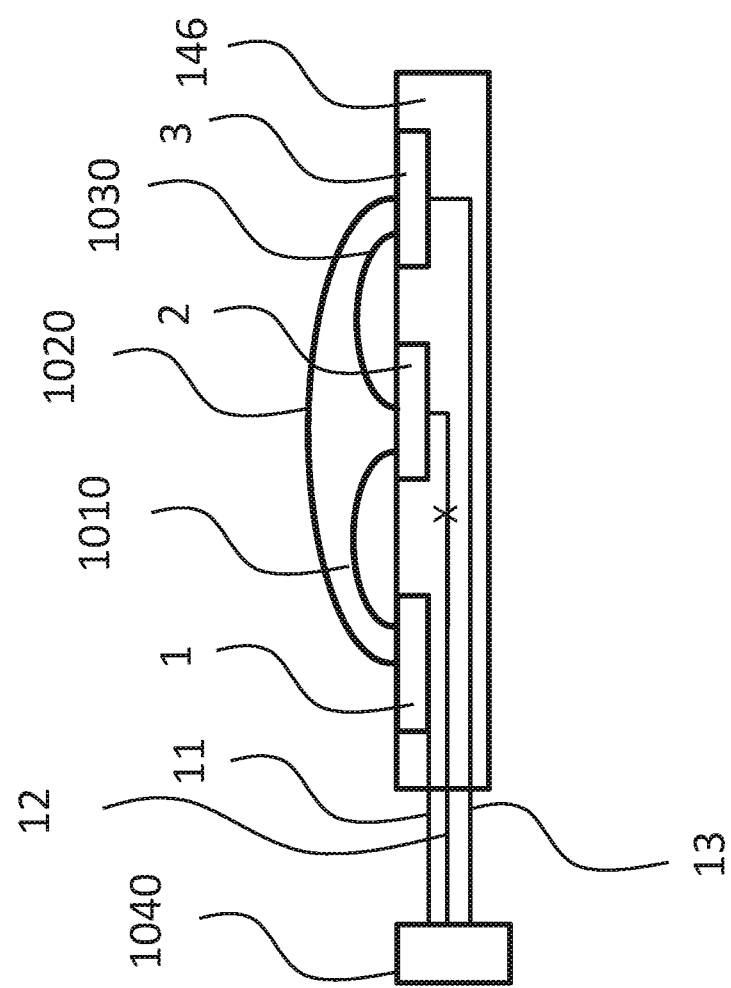
FIG. 50B depicts a conceptual diagram depicting an open circuit that can be detected utilizing the test for an open circuit.

FIG. 50B presents a hypothetical open circuit scenario, where lead 12 has experienced a break at the location indicated by the "X." In an exemplary method, a current is applied by current generator/detector 1040 to lead 12. Current generator/detector 1040 "looks" for a current at either or both of leads 11 and 13. Because the conductive apparatus 4622 has placed electrode 2 into electrical conductivity with electrodes 1 and 3 via hypothetical leads 1010 and 1030, a current will not register at either of leads 11 and 13 (or only one of the leads if only one of the hypothetical leads 1010 and 1030 or present) thus indicating that there is an open circuit, most likely between current generator detector 1040 and electrode 2.

Note that by "looking" for a current at two or more leads, it can be immediately deduced that there is a fault between current generator/detector 1040 and electrode 2 (or a simultaneous fault in electrodes 1 and 3, which can be addressed by running the test by applying current at lead 11 and/or lead 13 and looking at lead 12).

In an exemplary embodiment, a common ground impedance (voltage required to drive a current between a chosen electrode and all the other electrodes shorted together) is measured for each electrode in turn many times a second (1, 2, 3 . . . 22, 1, 2, 3 . . . 22, 1, 2, 3 . . . 22, etc.). In this way, whatever electrodes are in contact with the contacts in the sheath, such will show up as low impedance. As the electrode array advances through the sheath, the low impedance point will travel down the array from electrode 22 to electrode 1. An open circuit will be evident as the electrodes that never go to low impedance.

Note further that in at least some exemplary methods, the methods are not executed to detect which lead or which connection is open or otherwise has experienced a failure mode. A determination that there is some failure anywhere will typically be utilitarian in that a determination can be made in view of the single failure detection that the cochlear implant 100 should not be implanted in the recipient at that time. In an exemplary embodiment, a new cochlear implant 100, such as a cochlear implant 100 located in a new apparatus 400, will be obtained, and a new round of testing for an open circuit will be executed. Such is also the case with respect to detecting which particular electrodes are associated with a short circuit.

Note that by way of example only and not by way of limitation, in an exemplary embodiment, a failure mode can correspond to a break in a lead and/or a disconnect between a lead and an electrode, which failure mode can typically result in an open circuit. In an exemplary embodiment, this can occur during shipping of the apparatus 400.

Figure 51B:
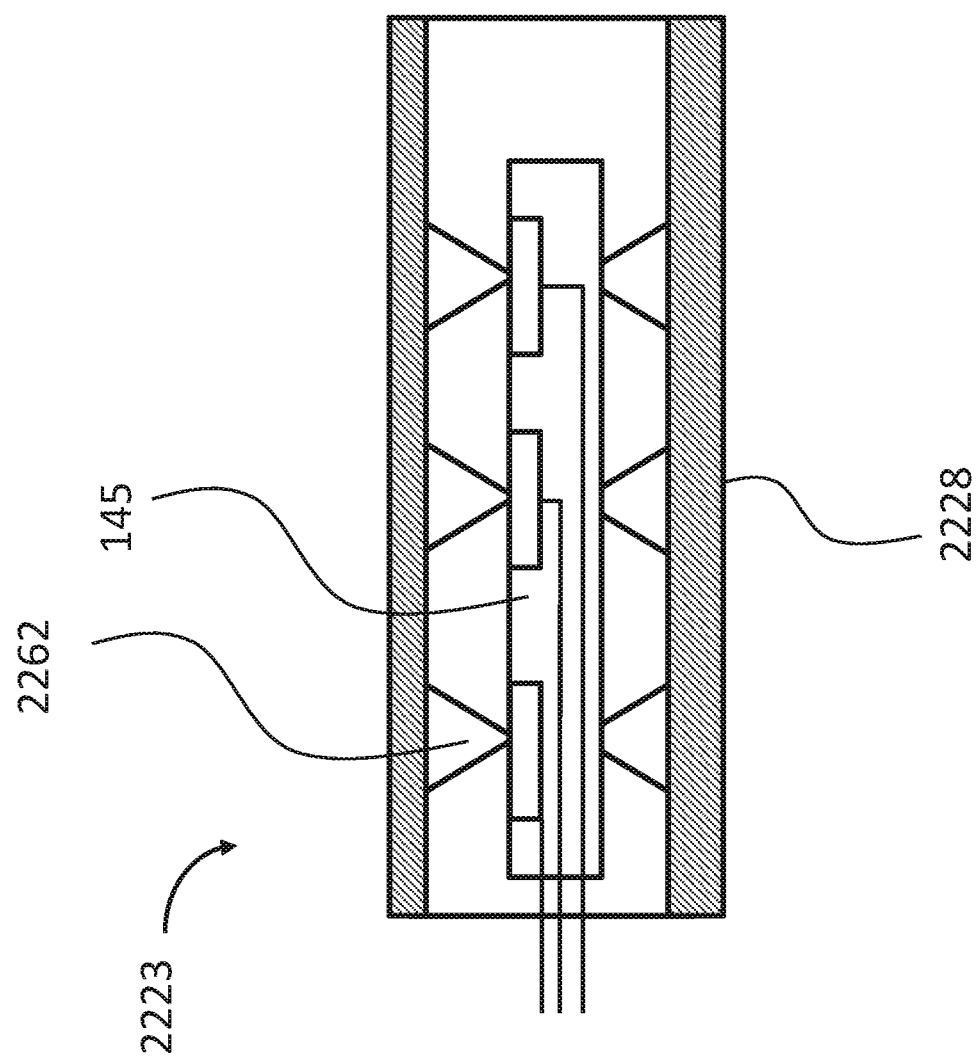
Figure 51C:
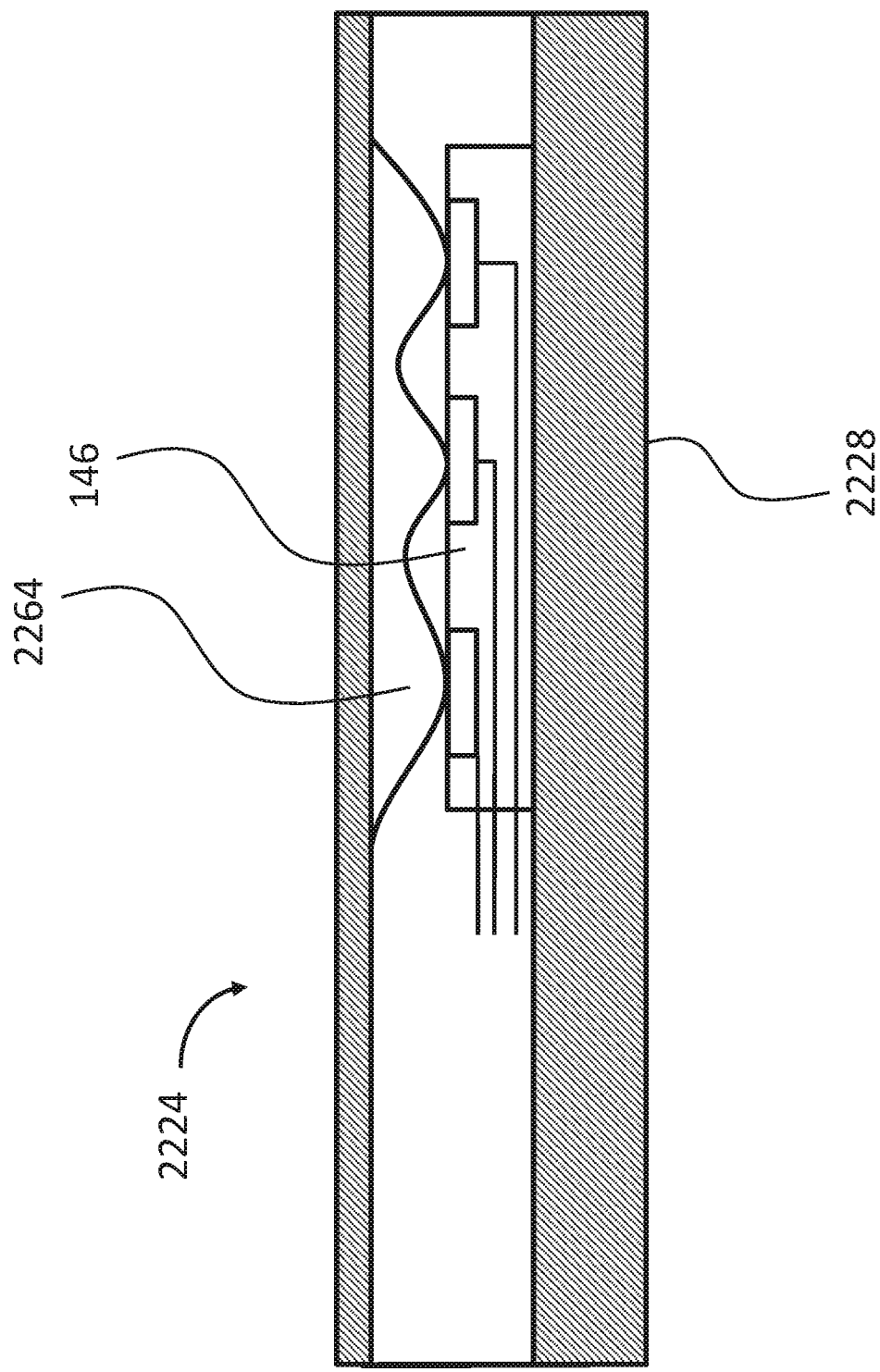

It is further noted that in an exemplary embodiment, instead of a solid or contiguous conductive component that contacts the various electrodes, separate contacts 2262 supported by conductive body that extends between the contacts can be configured to be compressible, at least with respect to the portions on the tip, as can be seen in FIGS. 51A and 51B. In an exemplary embodiment, element 4622 is replaced by conductive apparatus 2223. Alternatively, and/or in addition to this, the contacts 2262 can be supported on a flexible material that flexes to provide space. The contact can also be spring loaded in another exemplary embodiment (more on this below). FIG. 51C depicts another exemplary embodiment of a conductive apparatus 2224 that can be utilized in place of element 4622. Also, in this exemplary embodiment, the conductors 2262 can be located only at the top of the conductive apparatus 2223, instead of all the way around, as is the case with the embodiment of FIG. 50C.

It is further noted that variations of the concepts depicted herein can be implemented to enable the teachings detailed herein. Instead of utilizing triangular contacts as seen, square contacts can be utilized. Still further, undulating contact surfaces can be utilized such that the crests of each undulation are in phase with the respective electrodes (e.g., aligned with the centers of the electrodes) of the electrode array. FIG. 50C depicts an exemplary embodiment of a conductive apparatus 2224 utilizing a "wavy" contact surface, where contact apparatus 2264 can be seen to have crests that are in phase with the electrodes of the electrode array 145.

In an exemplary embodiment, any of the teachings of U.S. patent application Ser. No. 15/164,789, filed on May 26, 2016, to Inventor Grahame Walling, for testing for an open circuit can be incorporated into an insertion guide with the requisite modifications to enable open circuit testing.

Figure 52:
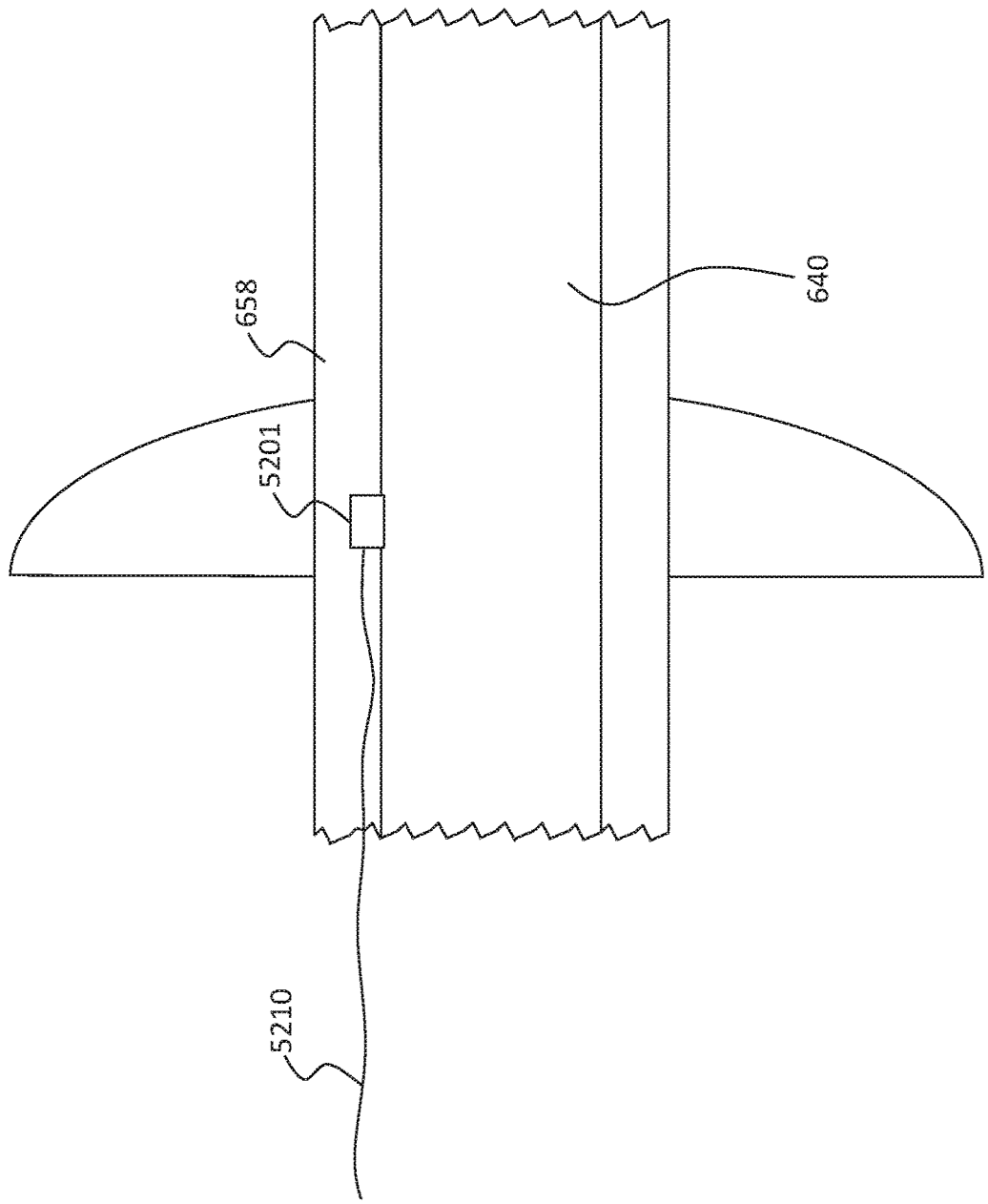
FIG. 52 depicts an exemplary cross-sectional view of an exemplary embodiment of an exemplary insertion guide.

While the embodiments detailed above have been directed towards a device that shorts two electrodes, an alternate embodiment utilizes an electrode in the insertion guide to establish a capacitive coupling with the electrodes of the electrode array as the electrodes of the electrode array pass by the electrode of the insertion guide. FIG. 52 depicts an alternate embodiment of an electrode array insertion tube having another functionality beyond that associated with supporting and/or guiding the electrode array into the cochlea. In this regard, element 5201 is an electrode that is utilized as part of an open circuit testing system. Here, electrode 5201 can establish a capacitive coupling between the electrodes in the array and the insertion guide in general, and the electrode 5201 in particular.

Figure 53:
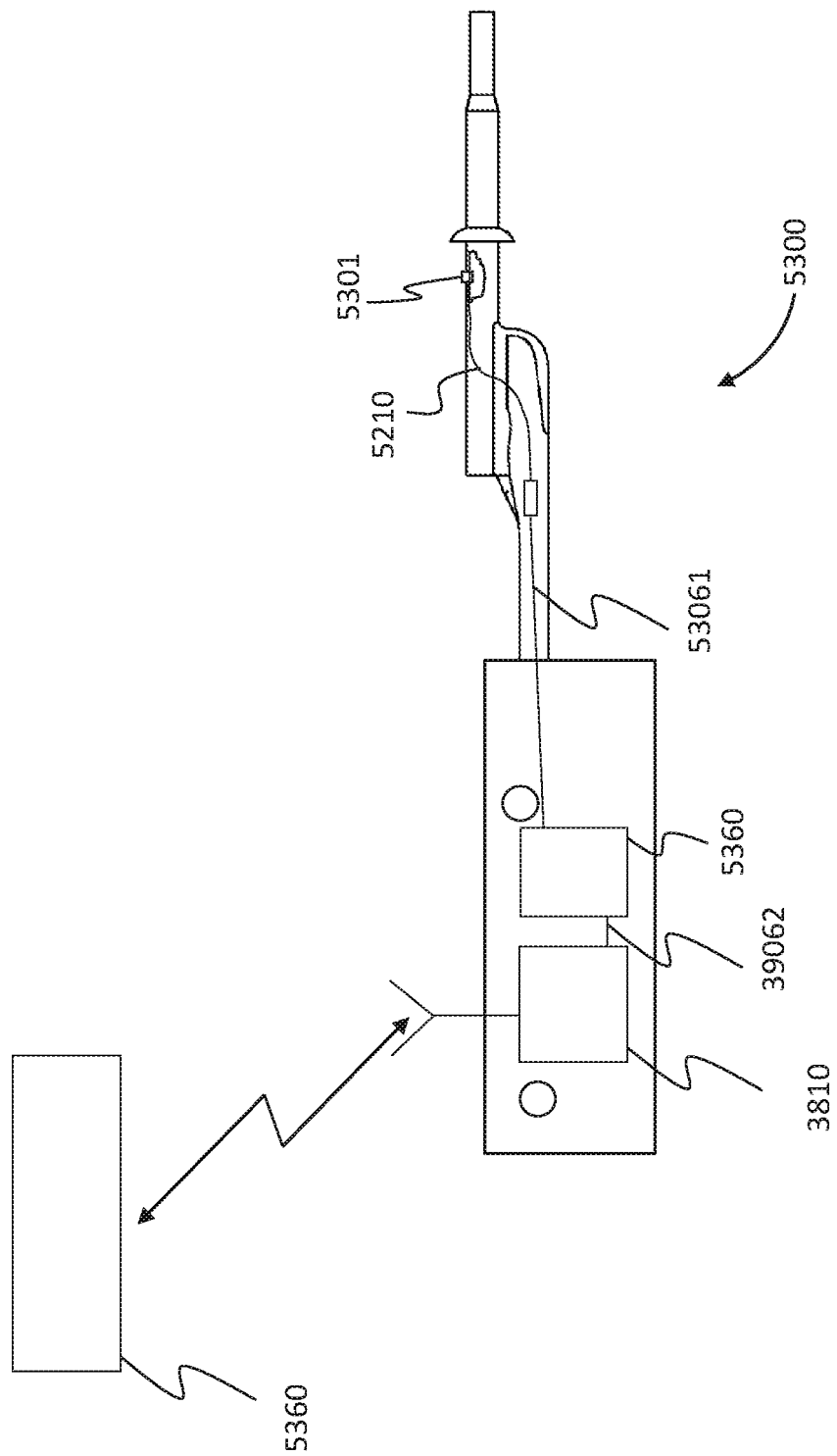
FIGS. 53-54 depict side views of exemplary embodiments of exemplary electrode array insertion guides.

As can be seen, electrode 5201 is connected to a lead 5210. In an exemplary embodiment, this lead energizes the electrode with an electrical current. In an alternate embodiment, this lead provides a return path in a scenario where the electrodes of the electrode array are energized. FIG. 53 depicts an exemplary embodiment of an insertion guide 5300 having the electrode 5301 to establish the capacitive coupling with the electrodes of the electrode array. Here, electrode 5301 is located to the left (proximally) of the stop 204. FIG. 53 depicts a cutout view of the tube of the insertion guide showing electrode 5301 extending into the lumen. Lead 5210 can be seen extending from electrode 5301 to a coupling, to which is connected a lead 53061, which in turn extends to test unit 5360. Test unit 5360 is configured to energize the electrode 5301 in at least some exemplary embodiments. In some alternate embodiments, test unit 5360 is configured to receive current from electrode 5301 in the case where the electrodes of the array are energized. At a minimum, test unit 5360 can be a voltage/energy source, such as an assembly having circuitry to provide a controlled current at a control voltage to electrode 5301. In an exemplary embodiment, test unit 5360 includes a battery to provide the source of the current. In an alternate embodiment, test unit 5360 is an assembly having circuitry configured to receive an electrical current from lead 53061 and analyze the current or at least determine whether a current is present. Indeed, in an exemplary embodiment, in view of the binary nature of an open circuit, unit 5360 can be a simple circuit that energizes an indicator upon the absence of a received current. By way of example, test unit 5360 can include a transistor or the like or some form of relay that is activated and/or deactivated upon the reception of a current through lead 53061. The activation and/or deactivation of this transistor or the relay activates an indicator, such as an LED, or disables the indicator (e.g., turns off the LED) indicating an open circuit. In an exemplary scenario, upon failure of current from lead 53061 reaching test unit 5360, a relay is closed and a circuit is accordingly closed to illuminate an LED, providing an indication to the surgeon that an open circuit is present in the electrode array. In an exemplary embodiment, this can be combined with the teachings detailed herein regarding the utilization of the insertion guide to provide an indication or otherwise determine the position of the electrode array and/or the speed of insertion. For example, such teachings can be correlated to the embodiment to test for the open circuit, so that an indication to the surgeon of an open circuit is not provided simply because electrode 5301 is not in capacitive coupling with an electrode of the electrode array, because the electrode 5301 is in between electrodes of the electrode array. Still further, in an exemplary embodiment, the system of FIG. 53 can be combined with or otherwise used in conjunction with devices that can indicate whether or not an electrode of the electrode array is proximate the electrode 5301 or otherwise at a location where capacitive coupling between the electrode can be established. The system of FIG. 53 is configured so as to only provide an indication of an open circuit when a determination has been made that the electrode of the electrode array is proximate the electrode 5301 or otherwise at a location where capacitive coupling between the electrode can be established.

Figure 54:
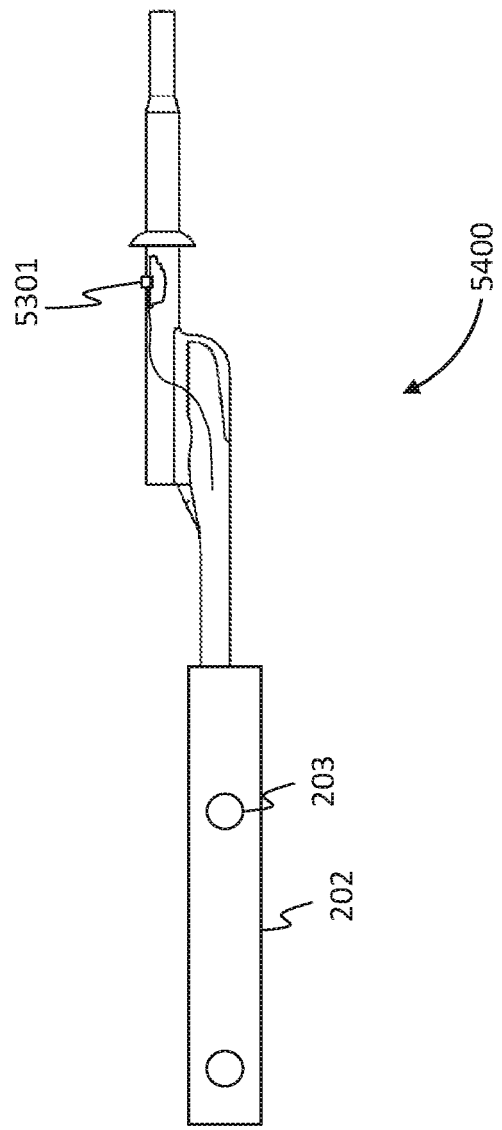

The embodiment seen in FIG. 53 includes communication unit 3810 in signal communication with the test unit 5360 via lead 39062. In an exemplary embodiment, communication unit 3810 can be the communication unit detailed above. As can be seen, communication unit 3810 can be in wireless communication with a remote device 5360. That said, in some alternate embodiments, this communication can be wired. In an exemplary embodiment, the remote device 5360 can be a laptop and/or a desktop computer that is also in signal communication with the receiver/stimulator of the cochlear implant. In an embodiment where test unit 5360 outputs a current to electrode 5301, the receiver/stimulator of the cochlear implant can detect this current via the electrodes (providing there is no open circuit—if there is, no detection will occur, thus indicating the open circuit) of the electrode array, and communicate such to device 5360, whereby device 5360 can provide an indication that there is a reason not an open circuit. Indeed, it is noted that in such an exemplary embodiment, the insertion guide 5300, in some embodiments, need not be in signal communication with remote device 5360. In this regard, it is sufficient that test unit 5360 simply provide a controlled current to the electrode 5301. FIG. 54 provides such an exemplary embodiment of an insertion guide 5400, where test unit 5460 is a current generator apparatus, such as an apparatus that includes a battery with or without circuitry to provide a controlled output current to electrode 5301. In this embodiment, providing that the receiver/stimulator of the cochlear implant is in telemetric communication via the inductance coil with a component that can indicate whether or not the electrodes of the electrode array have received a current, a remote device in signal communication with the receiver/stimulator can provide the indication to the surgeon of an open circuit. That is, the guide 5400 simply provides the electrical signal for testing of the open circuit.

That said, in an alternate embodiment where electrode 5301 receives or otherwise detects current/voltage (such as would be the case if there is no open circuit and the given electrodes of the electrode array are energized at least as they pass electrode 5301), the test unit 5460 can analyze the received signal (which can be a binary analysis that the signal is present or is not present) and provide an indication to the user that an open circuit exists and/or that no open circuit exists, or at least provide an indication to the user of the required voltage to push the current or some other indicia that will indicate the presence of an open circuit. In an exemplary embodiment, an LED or the like can be mounted on the guide at a location visible to the surgeon while inserting the electrode array. The LED can be activated (it can be a red LED, for example) to indicate an open circuit. As will be understood, this embodiment can also be practiced without being in communication with another component, such as the computer 5360. Still, in some alternate embodiments, there can be utilitarian value with respect to communicating to another device that could have additional logic circuitry so as to perform a more sophisticated analysis or so as to provide a better indication or more informative indication.

Embodiments include an insertion guide by itself or an insertion guide that is used in conjunction with other components that can provide an indication to the surgeon or other healthcare professional that an open circuit is present. Any type of indication that can be provided to the surgeon or healthcare professional that will indicate the presence of an open circuit can be utilized in at least some exemplary embodiments.

It is briefly noted that while the embodiments depicted herein utilize one electrode located at the top of the tube for open circuit testing, in other embodiments, a plurality of electrodes can be utilized. Still further, while the embodiments depicted in the FIGS. depict a box electrode for open circuit testing, alternate embodiments can utilize other types of electrodes, such as by way of example, ball electrodes. Indeed, in an exemplary embodiment, the electrode is a band electrode that extends completely about the axis of the lumen 360°. Any number of electrodes at any spacing and any configuration that can enable open circuit testing can be utilized in at least some exemplary embodiments.

It is briefly noted that in an exemplary embodiment, the electrode 5301 utilized to test for open circuit can also be utilized as the insertion speed and/or insertion depth measurement electrode detailed above and vis-a-versa. This is also the case in embodiments where a plurality of electrodes are utilized to test for an open circuit.

In view of the above, it can be seen that in an exemplary embodiment, there is an insertion guide for an electrode array that includes an active functional component, wherein the active functional component enables the measurement of the insertion speed and/or insertion depth of the electrode array. In an exemplary embodiment, the active functional component is an electrode of an open circuit monitor configured to establish a capacitive coupling between the electrodes of the electrode array in the electrode of the insertion guide. In an exemplary embodiment, the active functional component of the electrode array insertion guide enables at least one of array insertion speed monitoring or array insertion depth monitoring. Note that this is distinguished from utilizing indicia on the insertion guide in a passive manner to determine speed and/or insertion depth.

Note also that with respect to the embodiments where the guide includes lights and/or speakers and/or other data conveyance devices (e.g., a vibrator that vibrates in the user's hand to provide indication of a phenomenon associated with the electrode array, etc.), the active functional component can be thus an indicator to a user of the insertion guide of a phenomenon associated with insertion of the array. As detailed above, such phenomena can include insertion speed and/or insertion depth. As will be described in greater detail below, such phenomena can also include array orientation, etc. in an exemplary embodiment, any phenomenon associated with the insertion of the electrode array can be used as a basis to provide an indicator to the user of such phenomenon. It is noted that the electrode array orientation can include the orientation about the electrode axis, as well as rotation about the other two axes. By way of example only and not by way of limitation, orientation can be related to rotation about one or more of these axes.

In view of the above, it can be seen that the guide can have a first functionality corresponding to an electrode array support, and a second functionality corresponding to an electrode array open circuit protection functionality for detecting an open circuit in the electrode array.

Figure 55:
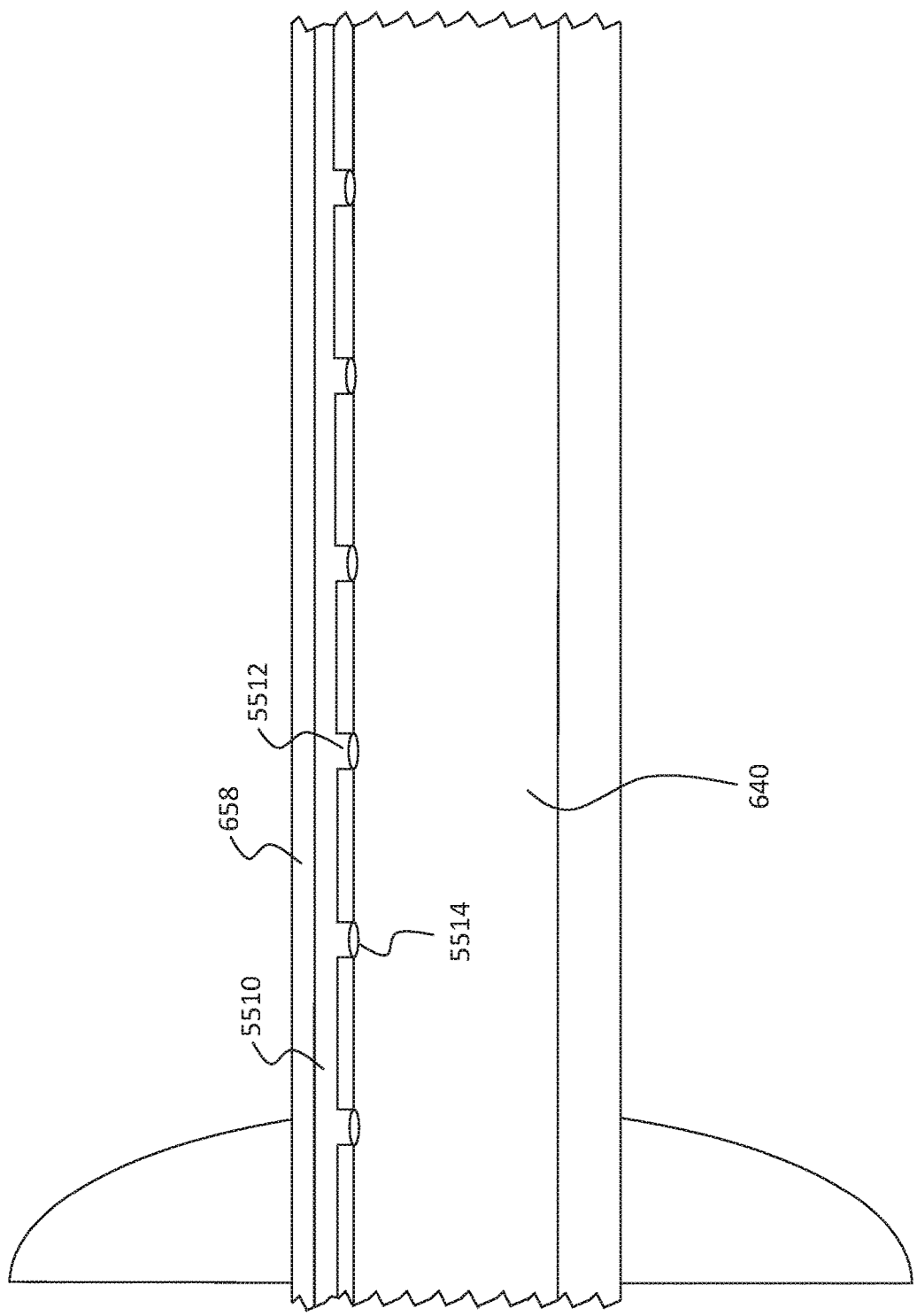
FIGS. 55-56 depict exemplary cross-sectional views of an exemplary embodiment of an exemplary insertion guide.

FIG. 55 depicts an alternate embodiment of a portion of an electrode array insertion guide. As can be seen, a fluidic passage 5510 is located in the wall 658 of the insertion guide tube 610. A plurality of passageways 5512 extend downward from the fluidic passage 55102 orifices 5514 that open into the lumen 640. In an exemplary embodiment, the fluidic passage 5510 is utilized to conduct fluids from outside the cochlea into the lumen 640. In an exemplary embodiment, these fluids can be drugs that have utilitarian value vis-à-vis insertion into the cochlea. In an exemplary embodiment, the electrode array insertion guide is configured to connect to a reservoir of such drug(s), which can be provided to the fluidic passage 5510 under pressure, so as to be "injected" or otherwise transferred into the lumen 640. In an exemplary embodiment, the drugs are injected or otherwise transferred into the lumen 640 as the electrode array is being inserted. In an exemplary embodiment, this can coat at least a portion of the electrode array, and the drugs are transferred into the cochlea as the electrode array moves into the cochlea out of the insertion guide.

Note also that in an exemplary embodiment, a back pressure can be established in the lumen 640 so as to "push" the fluid injected or otherwise transferred into lumen 640 out of the end of the insertion sheath so that the drugs can be delivered to the cochlea irrespective of whether or not the drugs become coated onto the electrode array.

In an exemplary embodiment, the drugs perform a lubrication function between the electrode array and the interior walls of the tube wall 658. In an exemplary embodiment, the drugs are anti-inflammatory drugs, and these anti-inflammatory drugs exhibit lubrication properties that can be utilized to implement the embodiment of FIG. 55.

Thus, it is to be understood that in an exemplary embodiment, there is a device, such as the guide of FIG. 55, that provides a functionality of an electrode array guide, and drug delivery functionality in a manner that lubricates the insertion guide with respect to the array.

Figure 56:
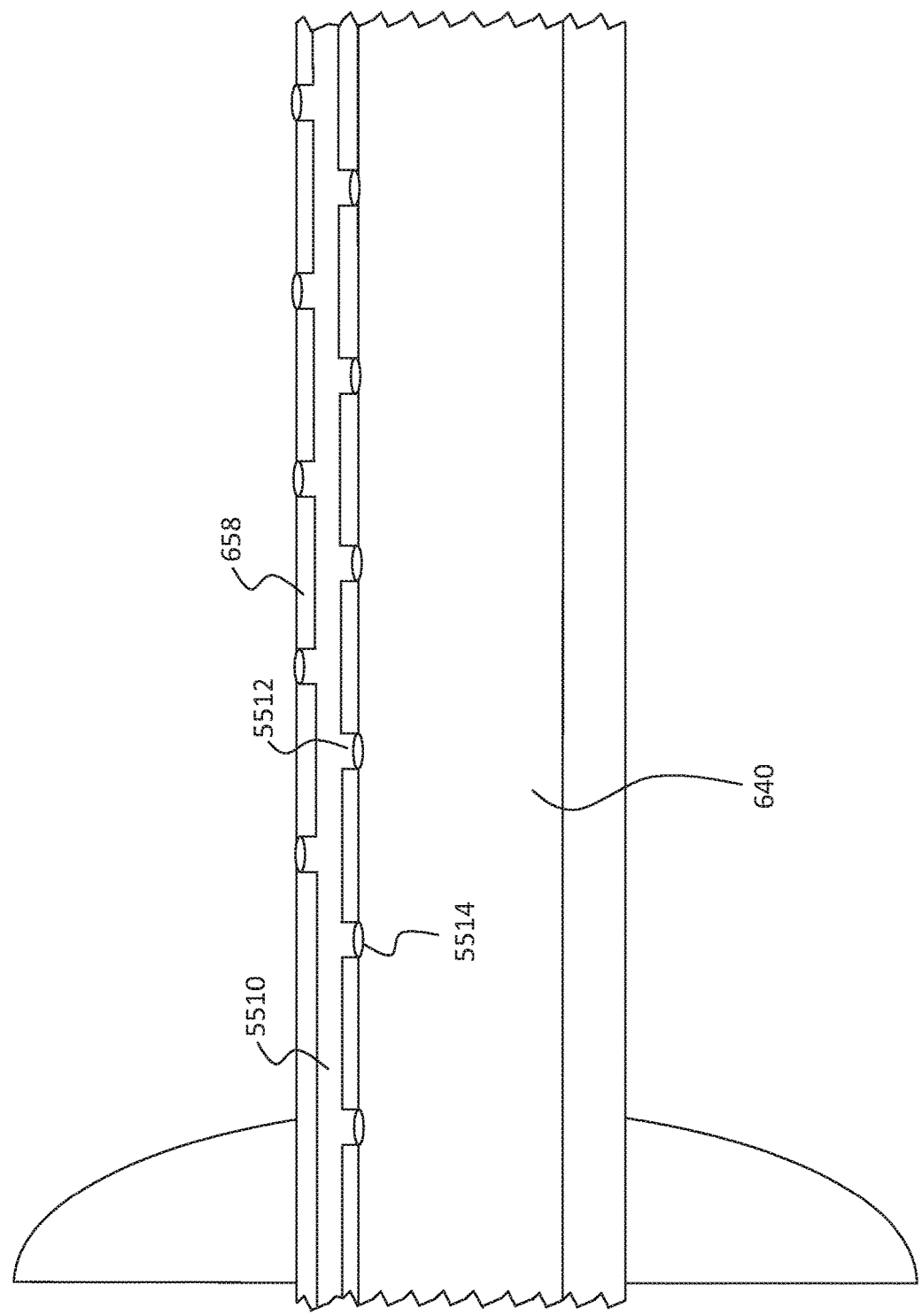

FIG. 56 depicts an alternate embodiment of an insertion guide having drug delivery functionality. As can be seen, fluidic passage 5510 also has passageways 5512 and outlet ports 5514 to the outside of the insertion guide tube 610. In an exemplary embodiment, this can enable the injection or otherwise transfer of the fluid in passageway 5510 into the cochlea in directions normal to the longitudinal axis of the insertion guide. It is noted that in alternate embodiments, the guide only has orifices located on the outside of the tube wall 658. This is the opposite of the embodiment depicted in FIG. 55, which has orifices located only on the inside of the tube wall 658.

In an exemplary embodiment, the insertion guide enables the administration of drugs into the cochlea concurrently with insertion of the electrode array. By way of example only and not by way of limitation, the drugs are injected or otherwise transferred into the cochlea at the same time that the electrode array is being inserted into the cochlea. In an exemplary embodiment, the rate of drug delivery relative to the total amount of drugs delivered via the insertion guide or in total is at least about 1 to 1 with the length rate of insertion of the electrode array relative to the total length of the electrode array. For example, if the total amount of drugs to be delivered is A and the length of the electrode array is X, and the rate of insertion of the electrode array is $1/30^{th}$ the length of the electrode array every second, about $1/30^{th}$ of A will be delivered every second. That said, in an alternate embodiment, the guide can be utilized to administer a first quantity of drug first, followed by insertion of the electrode array, followed by the administration of a second quantity of drug. Still further, in an exemplary embodiment, the guide can be utilized to administer a first quantity of drug first, and a second quantity of drug while the electrode array is being inserted into the cochlea, and then a third quantity of drug. Still further, in an exemplary embodiment, the guide can be utilized to administer a first quality of drug first, and then a second quality of drug while the electrode array is being inserted in the cochlea, where the second quantity and the first quantity constitutes the total quantity of the drug administered, at least with respect to the utilization of the insertion guide.

It is noted that while the above ratios are provided in exact terms, it is to be understood that there can be considerable tolerance with respect to variations of a drug delivery regime relative to an electrode array insertion regime. In this regard, it is noted that at least some embodiments of the insertion guide provide drug delivery functionality that enables drug delivery to be correlated with insertion depth of the electrode array. This correlation can be relatively loose, and need not be exact.

Figure 57:
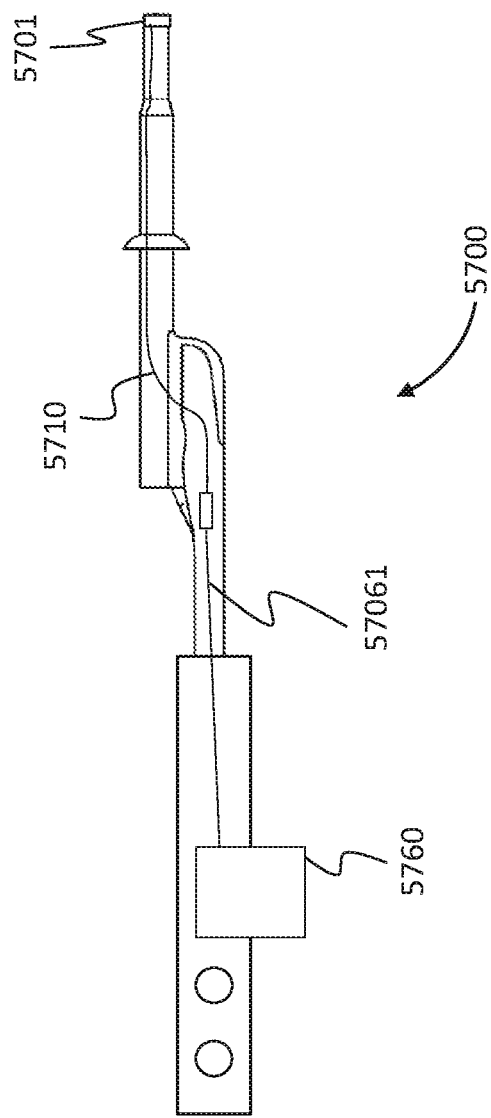
FIG. 57 depicts an exemplary side view of an exemplary embodiment of an exemplary insertion guide.
Figure 58:
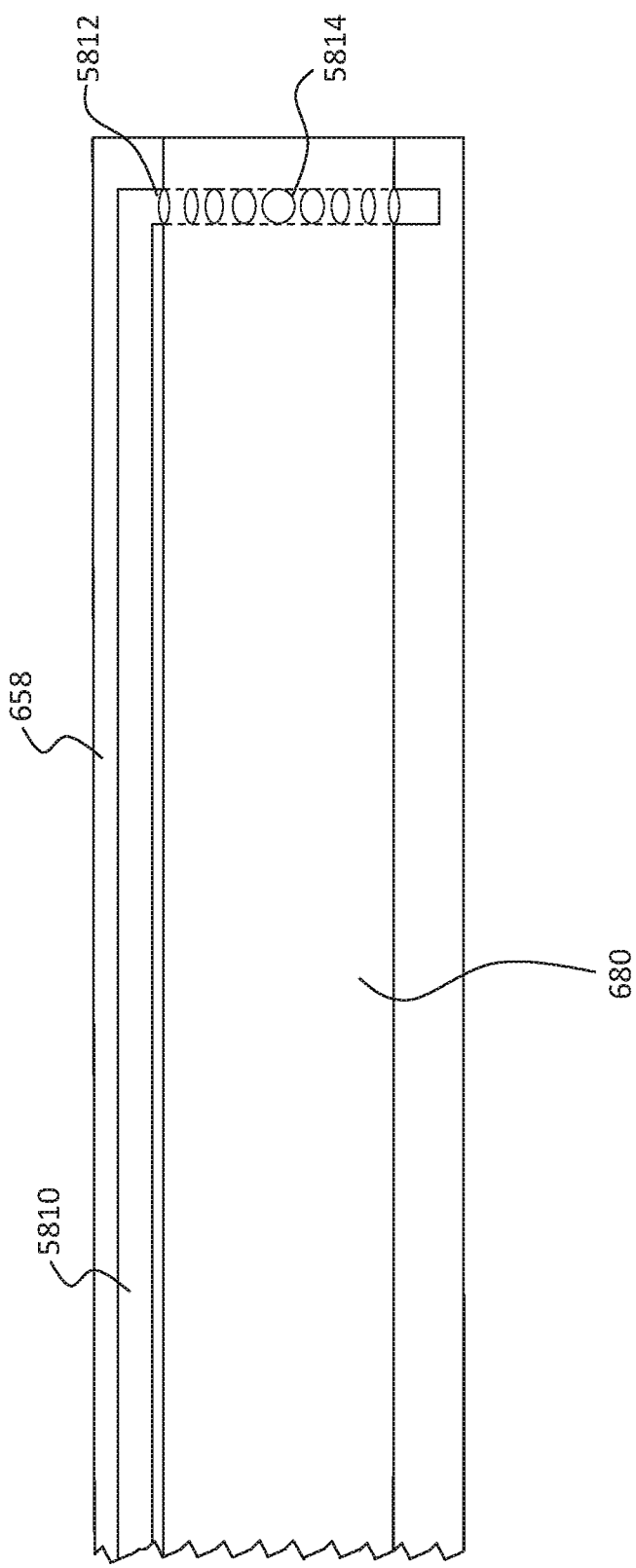
FIG. 58 depicts an exemplary cross-sectional view of an exemplary portion of an exemplary insertion guide.

While the embodiments of FIGS. 55 and 56 concentrate on delivering the drug along the axial length of the insertion guide, in an alternate embodiment, the drug is delivered at the tip of the insertion guide. FIG. 57 depicts an exemplary embodiment of an insertion guide 5700, where a drug delivery device 5701 is located at the tip. In an exemplary embodiment, drug delivery device 5701 constitutes a fluidic passage 5812 (with reference to FIG. 58, which depicts the tip of the guide) that extends about the axis of the lumen (or anti-twist guide-channel 680, if such is utilized). Orifices 5814 are in fluidic communication with this fluidic passage 5812. The fluidic passage 5812 is in fluid communication with a fluidic passage 5810, corresponding to fluidic passage 5710 of FIG. 57. In an exemplary embodiment, a fluid substance, such as a liquid drug, is transported through fluidic passage 5812, and then injected or otherwise transferred out of orifices 5814. In an exemplary embodiment, this coats the electrode array with the drug about the entire circumference thereof as the electrode array is pushed through the tip of the insertion guide into the cochlea, the electrode array transporting the drug into the cochlea as the electrode array is transferred into the cochlea. In an alternate embodiment, the orifices extend outward instead of inward. In an exemplary embodiment, the orifices extend both outward and inward.

FIG. 57 depicts an exemplary embodiment where a drug reservoir 5760 is located in the handle. The drug reservoir 5760 is in fluid communication with fluid passage 5710 via fluidic conduit 57061. In an exemplary embodiment, guide 5700 is configured to transport the drug contained in the reservoir 5760 to the drug delivery device 5701 (or any other drug delivery device—the embodiment of FIG. 57 is not mutually exclusive to that configuration and/or the configuration of FIG. 58—again, any feature of any embodiment detailed herein can be combined with any feature of any other embodiment detailed herein unless otherwise noted). In an exemplary embodiment, the guide includes an actuation device that enables the surgeon or the like to activate drug delivery. In an exemplary embodiment, a plunger device can be located in the handle that pressurizes the drug in reservoir 5760 so as to reject the drug from the guide 5700. In an exemplary embodiment, the guide 5700 is configured to be "charged" with the drug. In an exemplary embodiment, a connection between reservoir 5760 and the outside of the guide is present, where a surgeon or other healthcare professional can insert the drug into the reservoir 5760. Indeed, in an exemplary embodiment, the reservoir 5760 can include a self-sealing diaphragm or the like that enables a surgeon or other healthcare professional to insert a needle of a syringe therethrough, and inject the drug from the syringe into the reservoir 5760 so as to "charge" the guide with the drug. (This is analogous to the device that vaccines, etc., are stored in, where a healthcare professional inserts a needle into the diaphragm and withdraws the drug prior to giving an injection, except here, the drug is injected into the container as opposed to withdrawn from the container.) This can have utilitarian value with respect to managing the drugs. In this regard, in at least some exemplary embodiments, the drug need only be inserted into the guide right before the use of that drug, thus avoiding a scenario where the drug becomes unstable due to age or temperature or the like.

Figure 59:
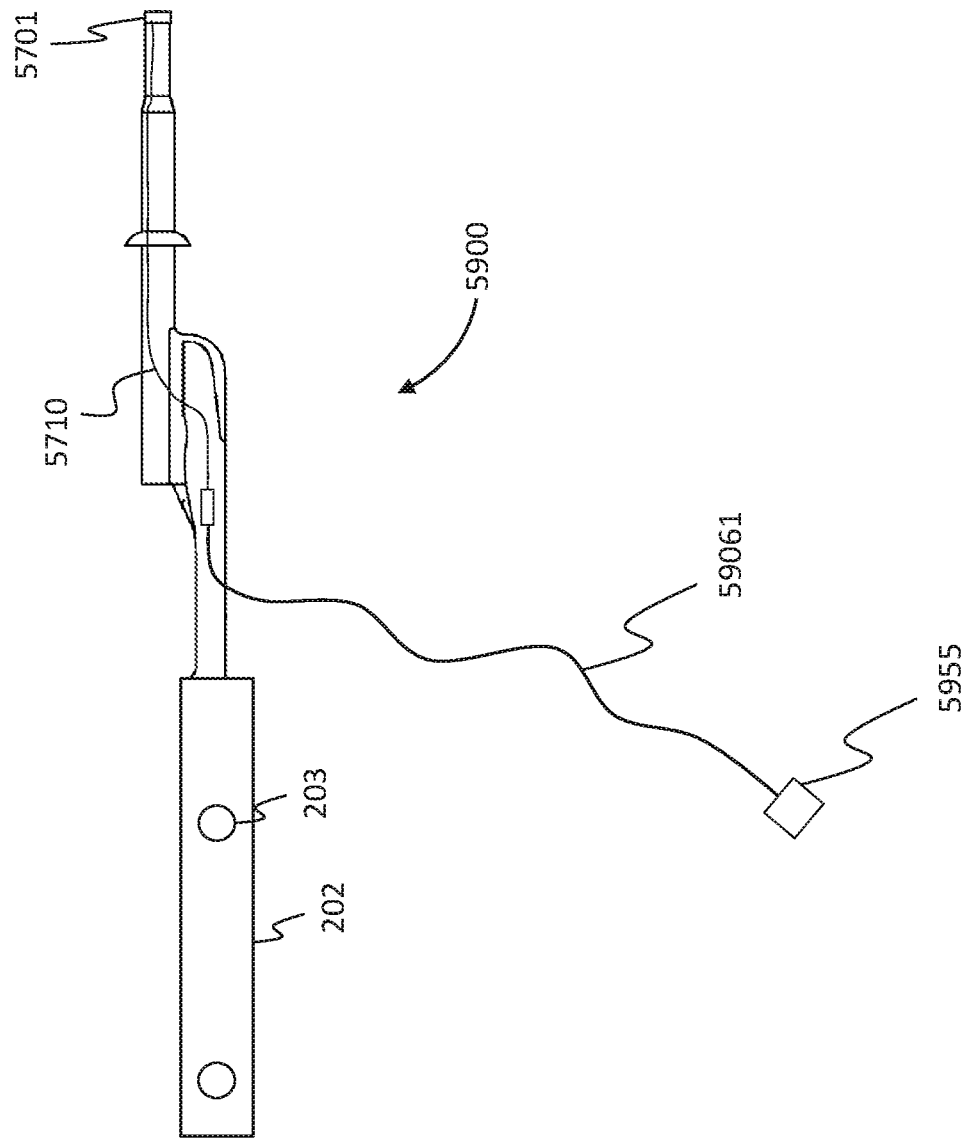
FIG. 59 depicts an exemplary side view of an exemplary embodiment of an exemplary insertion guide.

That said, in an alternate embodiment, a fluidic connection to a reservoir of the drug located remote from the guide 5700 can be utilized. Indeed, in an exemplary embodiment, a conduit can extend from the guide 5700 to a remote syringe, where a healthcare professional other than the person handling the guide 5700 operates the drug delivery. To this end, FIG. 59 depicts an exemplary embodiment of an insertion guide 5900, that includes a flexible fluid conduit 59061 extending from a connector 5955 to fluidic passage 5710. In an exemplary embodiment, coupling 5955 is configured to be connected to a reservoir of a drug or the like, and the drug can be transferred through conduit 59061 under pressure. In an exemplary embodiment, coupling 5955 can be snapped coupled or otherwise screwed onto the reservoir the drug. In an exemplary embodiment, connector coupling 5955 has a diaphragm or the like that can be pierced by a syringe. In an exemplary embodiment, a healthcare professional inserts the needle of the syringe through the diaphragm in connector 5955, and then injects the drug by depressing the handle of the syringe, thus delivering the drug to the guide 5900, and ultimately to the recipient. This structure of the connector 5955 can be analogous to the structure of an IV tube where a healthcare professional can interact a drug into the IV without having to pierce the skin again because the skin is already pierced.

In view of the above, it is to be understood that in an exemplary embodiment, there is an electrode array insertion guide comprising an assembly configured to provide direct array insertion functionality and ancillary array insertion functionality to a user of the guide where the ancillary functionality can be drug delivery functionality.

Figure 60:
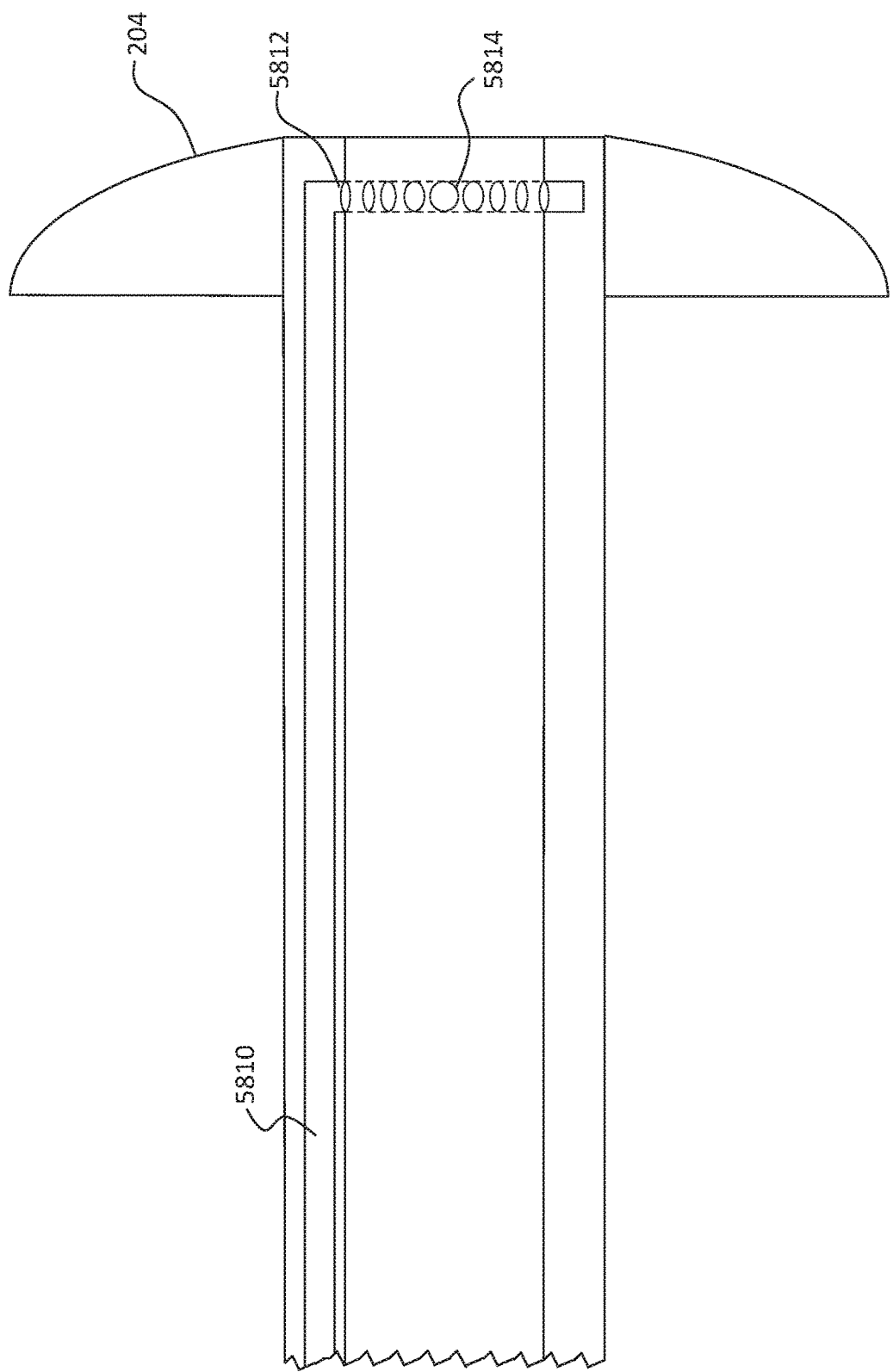
FIG. 60 depicts an exemplary cross-sectional view of an exemplary portion of an exemplary insertion guide.

It is noted that while the embodiments depicted above focused on the orifices of the drug delivery system of the guide being located in the intracochlear portion of the guide, the orifices can be located elsewhere, such as in the portions of the guide that are not inserted into the cochlea. The orifices of the drug delivery system can be located anywhere within the guide that has utilitarian value. Also, it is noted that the teachings associated with the drug delivery systems detailed herein are not limited to an insertion guide that is inserted into the cochlea. In this regard, FIG. 60 depicts an exemplary portion of an exemplary insertion guide that does not have a component that is configured to be inserted into the cochlea, where the orifices 5814 are arrayed on the inside of the tube at the location of the stop 204.

Figure 61:
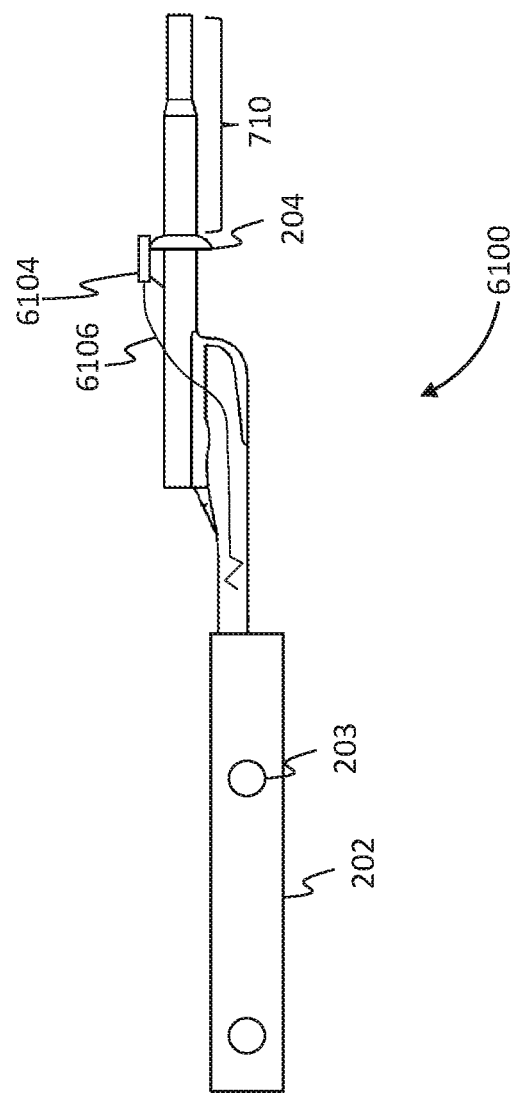
FIGS. 61-63 depict side views of exemplary embodiments of exemplary electrode array insertion guides.

FIG. 61 depicts another alternate embodiment of an insertion guide 6100 for a cochlear array. Here, an ultrasonic transducer 6104 is located on the stop 204. Ultrasonic transducer 6104 is connected to lead 6106, which is in signal communication with a device, not shown, that enables reception and/or analysis of the signal received by transducer 6104. In this regard, guide 6100 includes an ultrasonic transducer positioned on the extra cochlea section of the guide (with respect to the guide when it is fully inserted into the cochlea) such that the working end of the ultrasonic transducer directly abuts the round window and/or the oval window and/or tissue around the cochlea promise and/or the tissue around the round window and/or the oval window. The transducer 6104 can serve as an acoustic source for ultrasonic imaging. This can enable a surgeon or other healthcare professional to verify the array is positioned within the correct scala and check the final position of the array. In an exemplary embodiment, the transducer 6104 enables the teachings of U.S. patent application Ser. No. 13/965,348.

Consistent with the other embodiments detailed herein, while the embodiment of FIG. 61 is depicted as being utilized with a guide that has an intracochlear portion, the teachings associated with this embodiment can be utilized with insertion guides that do not have a component that is inserted into the cochlea.

Figure 62:
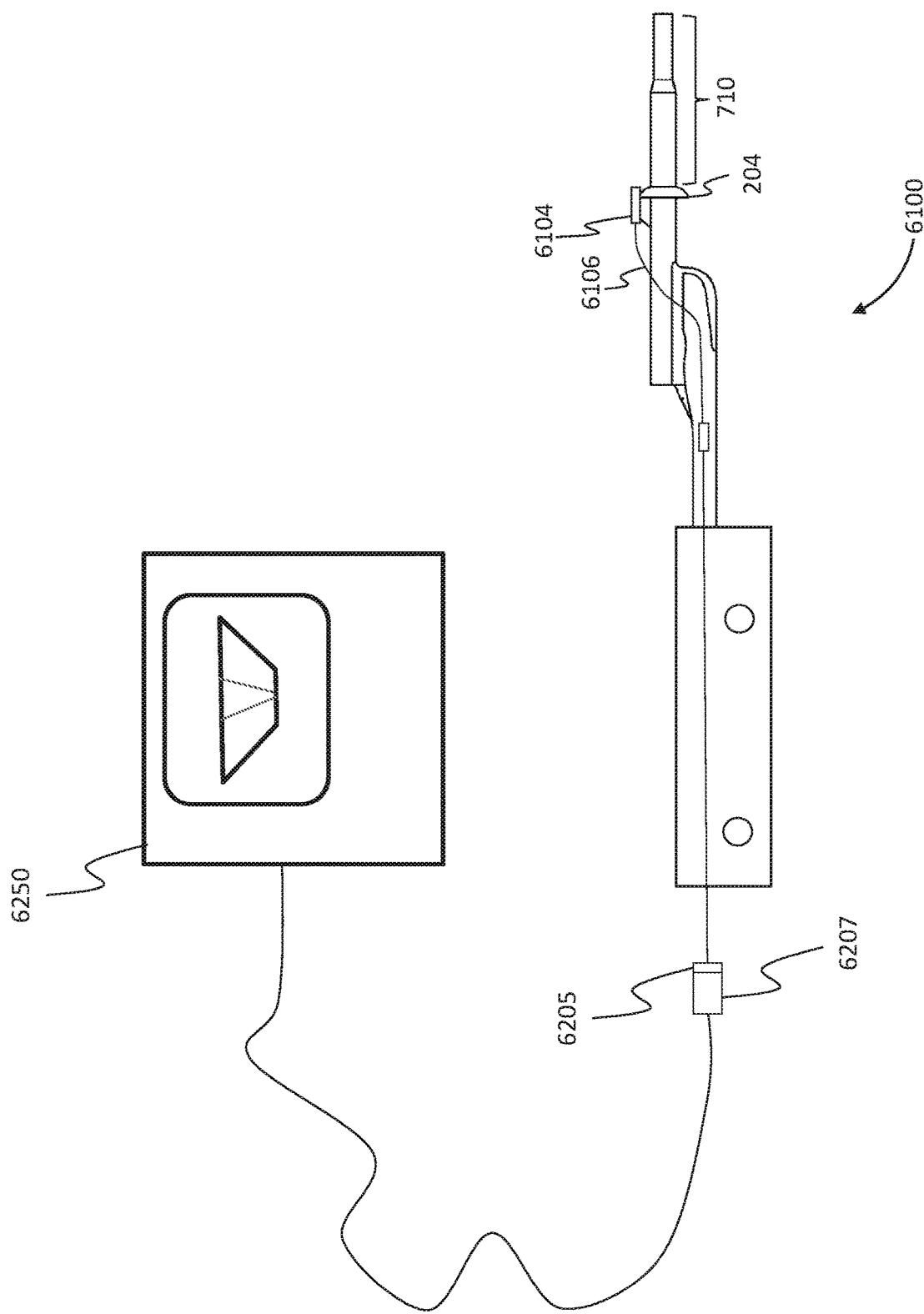

In an exemplary embodiment, the guide 6100 includes a connection that is in signal communication with lead 6106. This connection can enable guide 6100 to be connected to an ultrasonic imaging device that can utilize the signals from the ultrasonic transducer 6104 to create an image. In this regard, it is noted that an exemplary embodiment includes the guide 6100 connected to this ultrasonic imaging device. In this regard, FIG. 62 depicts an ultrasonic imaging system, where a connector 6205 in electrical communication with lead 6106 is connected to connector 6207 which is an electrical communication with an ultrasonic imaging unit 6250, such as that which can be obtained from the General Electric Company or the like. The ultrasonic imaging unit 6250 receives input from the transducer 6104 and generates an image on an LCD screen and/or a cathode ray tube based on the input from transducer 6104.

Thus, in an exemplary embodiment, there is an insertion guide for an electrode array, having an ancillary array functionality in the form of an ultrasonic transmitter and/or receiver.

It is briefly noted that while the embodiment depicted in FIG. 62 represents communication of the insertion guide with an ultrasonic imaging unit, FIG. 62 can be representative of other types of devices in signal communication or otherwise connected to the insertion array guide (e.g., an ECoG analysis program on a laptop or a desktop computer, an open circuit test unit, etc.).

Figure 63:
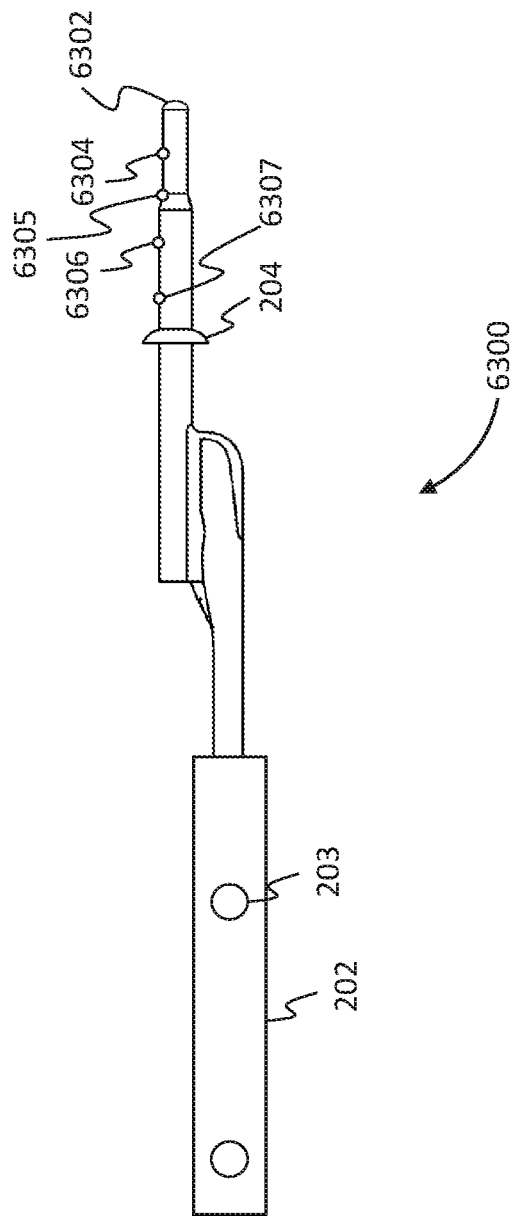

As noted above with respect to the embodiments utilizing the electrode in capacitive coupling with an electrode of the electrode array, the electrodes of the insertion guide can be utilized to deduce certain features associated with the electrode array. While the embodiments detailed above have been directed towards features associated with the state of the electrical system of the electrode array, electrodes can be utilized to deduce a state in which the electrode array is currently in and/or a position of the electrode array. FIG. 63 depicts an exemplary embodiment of an insertion guide 6300 that includes a plurality of electrodes that are located on the exterior of the insertion sheath. As can be seen, there is a tip electrode 6302, an electrode 6304 located on the outer surface of the anti-twist section, and electrode 6305 located at the ramp portion between the anti-twist section in the proximal section, and electrode 6306 located on the proximal section, and another electrode 6307 located on the proximal section. These electrodes are utilized to monitor voltage and/or impedance characteristics between a given electrode of the guide, and one or more electrodes of the electrode array during insertion and/or after insertion into the cochlea. It is briefly noted that while the embodiment depicted in FIG. 63 presents a plurality of electrodes on the insertion guide, it is to be understood that some embodiments can be practiced utilizing only one electrode on the insertion guide. That said, in an alternate embodiment, additional electrodes can be utilized. Note further that while the electrodes are depicted as being present on the top portion of the insertion guide, in an alternate embodiment, the electrodes can be located elsewhere such as on the bottom and/or on the lateral sides of the insertion guide. Indeed, a spread of electrodes can be located on the top, the bottom, and the sides.

In an exemplary embodiment, the electrodes of the insertion guide are utilized to monitor the voltage and/or impedance profile between the given electrodes of the guide and the given electrodes of the electrode array as the electrode array is inserted into the cochlea. In an exemplary embodiment, this can have utilitarian value with respect to providing an indication as to the occurrence of a tip fold over. In an exemplary embodiment, one or more of the electrodes can serve the function as one or more of the electrodes of the teachings of U.S. patent application Ser. No. 14/843,255, filed on Sep. 2, 2015, naming Benjamin Johnston as an inventor. In an exemplary embodiment, these electrodes can have utilitarian value with respect to providing an indication as to the occurrence of buckling of the electrode array. In an exemplary embodiment, one or more the electrodes conserve the functions as one or more of the electrodes of the teachings of U.S. patent application Ser. No. 14/843,259, filed on Sep. 2, 2015, naming Frank Risi as an inventor. In this regard, the electrodes of the insertion guide can be utilized as part of a system that monitors the impedance and/or voltage between the electrodes and the electrodes of the electrode array to determine angular insertion depth.

In an exemplary embodiment, the electrodes of the insertion guide provide an absolute reference for monitoring the voltage and/or impedance between the electrodes of the insertion guide and the electrodes of the electrode array. In this regard, this can have utilitarian value with respect to providing more accuracy than that which results from utilizing the electrodes of the electrode array alone as is done in the aforementioned patent applications described in the prior paragraph.

Figure 65:
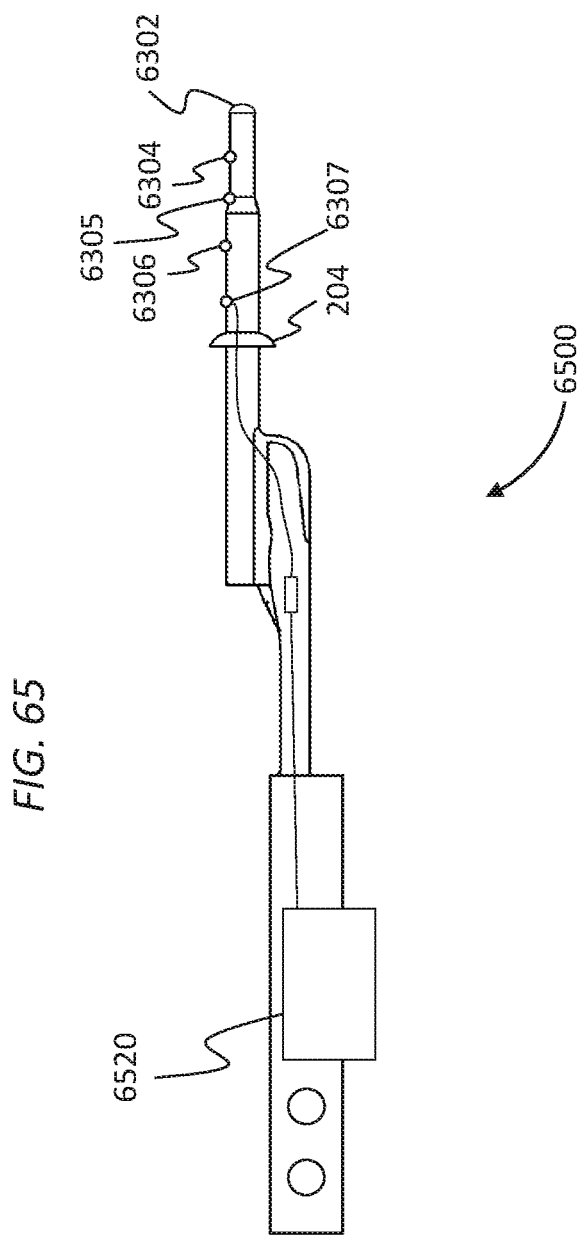
FIGS. 65-67 depict side views of exemplary embodiments of exemplary electrode array insertion guides.

FIG. 65 depicts electrode 6307 in signal communication with a lead that leads to connector 6320. In an exemplary embodiment, connector 6320 is connected to a device that analyzes the output of lead.

Figure 64:
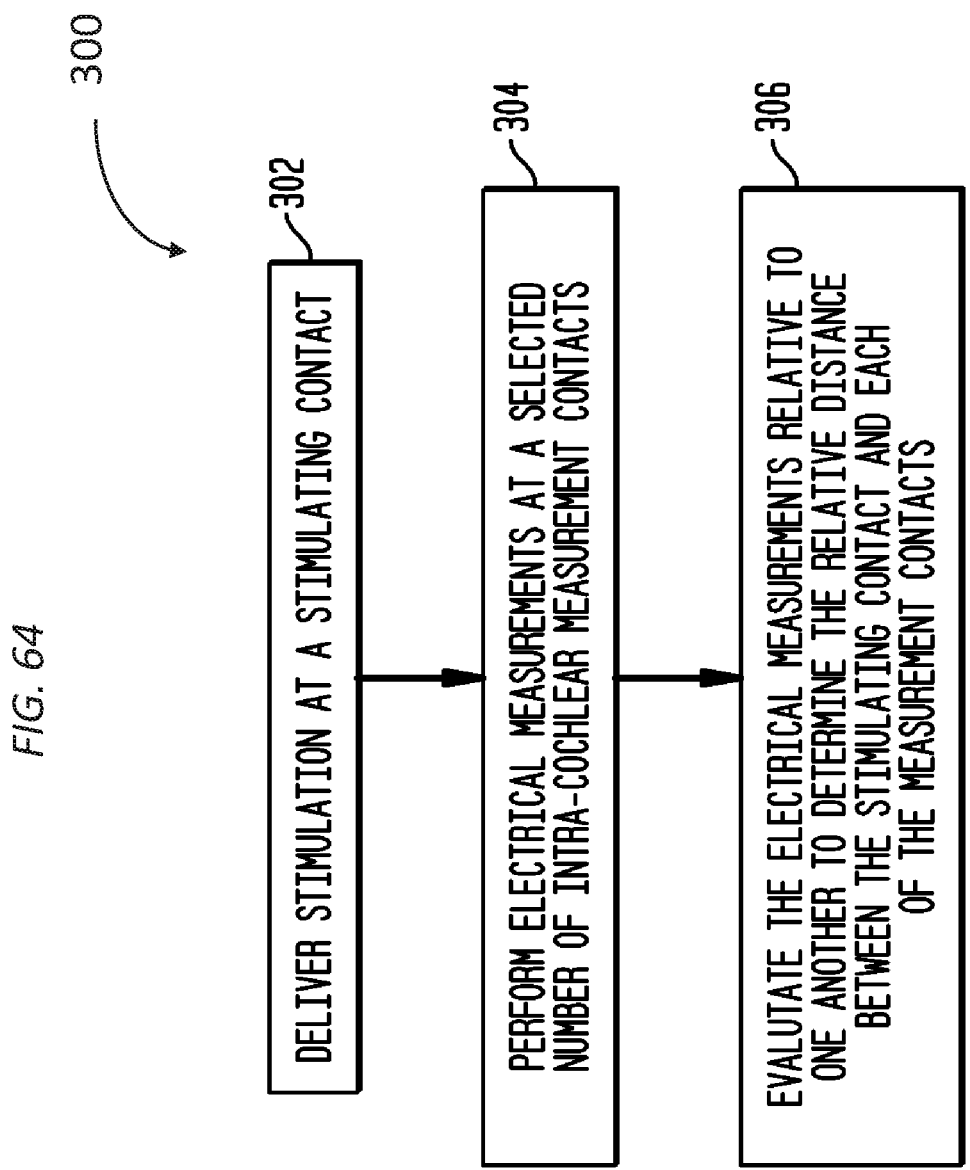
FIG. 64 depicts an exemplary flowchart for an exemplary method according to an exemplary embodiment.

FIG. 64 is a flowchart of a first method 300 for monitoring the physical state of the electrode array through the use of localized stimulation. The method 300 of FIG. 64 is sometimes referred to herein as a localized monitoring method as the method uses the delivery of localized stimulation (i.e., current signals) to induce voltages at a plurality of other contacts. For ease of illustration, method 6400 will be described with reference to the cochlear implant 100 of FIG. 1.

Method 300 begins at 302 where stimulation (i.e., one or more current signals) is delivered/sourced at a selected intra-cochlear electrode of the electrode array. In one specific example, the stimulation is delivered at the most distal/apical electrode of the electrode array and is sunk at one or more of the electrodes of the electrode array insertion guide 6300. The electrode that delivers the current signals, sometimes referred to herein as the "stimulating" or "source" contact (or source electrode) and the electrode that sinks the current signals, namely one or more of electrodes of the guide 6300, is sometimes referred to herein as the "return" contact (or return electrode). Additionally, the two electrodes between which the stimulation is delivered are collectively referred to herein as a "stimulating pair." The remaining electrodes that are not part of the stimulating pair are disconnected from the system ground (i.e., are electrically "floating").

In general, two intra-cochlear contacts are selected for delivery of the stimulation. However, alternative embodiments may use an extra-cochlear contact to source/sink current. Additionally, it is to be that the use of the most distal contacts for sourcing/sinking the current is illustrative and other contacts could be used in alternative embodiments.

While the embodiment described above and herein utilizes the electrodes of the electrode array insertion guide 6300 as sinks, it is to be understood that in an exemplary embodiment, the electrodes of the electrode array insertion guide can be utilized as sources. Thus, any disclosure herein with respect to utilizing the electrodes of the electrode array insertion guide as sinks corresponds to a disclosure of utilizing the electrodes of the electrode array insertion guide as sources.

While this embodiment details utilizing one single electrode of the electrode array insertion guide as a sink (or source), it is to be understood that in alternate embodiments, the electrodes of the electrode array can be utilized as sinks and/or sources sequentially. In this regard, in an exemplary embodiment, during a first temporal period, electrode 6307 can be utilized as a source, and then during a second temporal period, electrode 6306 can be utilized as a source, and then during a third temporal period, electrode 6305 can be utilized as a source, etc. In this regard, because the positions of the electrodes of the electrode array insertion guide are known, it can be possible to triangulate the position of the electrodes of the electrode array.

The electrode array is inserted into the recipient's scala tympani. The scala tympani is substantially filled with a conductive fluid known as perilymph. As such, when current signals are delivered at one of the electrodes of the electrode array insertion guide, at least a portion of the current will spread through the perilymph. For example, the conductive nature of the perilymph will cause at least some current to flow away from the contact. The flow of the current through the perilymph will cause the generation of voltages at the other intra-cochlear stimulating contacts. That is, although the stimulus is localized, due to the conductive perilymph the electric field spreads and induces voltage at the other contacts.

At action 304, following the delivery of the current signals at the apical electrode of the electrode array, measurements are performed at a selected number of other intra-cochlear electrodes of the electrode array utilizing the same electrode of the electrode array insertion guide or different electrodes of the electrode array insertion guide. That is, the voltage induced at the selected other electrodes as a result of the delivery of the current signals at the apical electrode is measured. The electrodes at which the voltages are measured are sometimes referred to herein as "measurement" contacts. In the embodiment of FIG. 64, the measurement contacts may include any of the electrodes of the electrode array insertion guide. Corollary to this, the measurement contacts can include any of the electrodes of the electrode array.

In certain circumstances, the cochlear implant 100 associated with the electrode array is configured to make a plurality of voltage measurements at substantially the same time in response to the delivery of stimulation. In such embodiments, a single set of localized current signals is applied and the voltage induced at a selected number of the measurement contacts is measured substantially simultaneously at the measurement contacts. In other embodiments, the cochlear implant 100 is configured to measure the voltage at a single contact in response to the delivery of a set of current signals. In such embodiments, a plurality of sets of localized current signals are applied in sequence at the most apical electrode of the electrode array and a voltage is measured at a different contact after each sequential stimulation. As such, in the context of FIG. 64, the delivery of single stimulation pattern may refer to the delivery of one set of current signals (with subsequent, substantially simultaneous measurement at each of the selected measurement contacts) or the sequential delivery of a plurality of sets of current signals (with subsequent measurement at one of the selected measurement contacts after each set of current signals are delivered).

As noted above, stimulation delivered at an electrode will have an effect on the other electrodes, and the effect may depend on a number of factors. However, a primary factor that controls the effects of stimulation is the distance between the stimulating electrode and the measurement electrode. For example, in the embodiment of FIG. 64, when stimulation is delivered at the most apical electrode of the electrode array, the voltage measured electrodes other than electrode 6307 should be increasingly larger for electrodes along the insertion guide and should increase the closer that the electrode is to the tip of the electrode array insertion guide. Therefore, at 306 of FIG. 64, the induced voltages measured at each of the measurement electrodes in response to the single stimulation pattern are evaluated relative to one another to determine the relative distance between the stimulating electrode of the electrode array and each of the measurement contacts (i.e., the contacts at which voltages are measured—where the electrodes of the electrode array insertion guide are utilized as the sinks, the contacts at which the voltages are measured are those electrodes). Evaluation of the voltages relative to one another enables the determination of the physical state of the electrode array based on the evaluation of measurements relative to one another, the cochlear implant 100 or a connected device may generate feedback to a surgeon or other user that provides information about the physical state of the electrode array and/or the occurrence of an adverse event. In this regard, the insertion guides detailed herein can be utilized in conjunction with the electrode array to evaluate or otherwise determine the status of an electrode array as detailed in the '255 patent application.

In view of the above, it is to be understood that in an exemplary embodiment, one or more of the electrodes of the electrode array insertion guide when utilized as a current sink "replace" one or more of the electrodes of the electrode array that are utilized as a current sink when implementing the teachings of U.S. patent application Ser. No. 14/843,255. In view of the above, it is to be understood that in an exemplary embodiment, one or more of the electrodes of the electrode array insertion guide when utilized as a current source "replace" one or more of the electrodes of the electrode array that are utilized as a current source when implementing the teachings of U.S. patent application Ser. No. 14/843,255.

Figure 66:
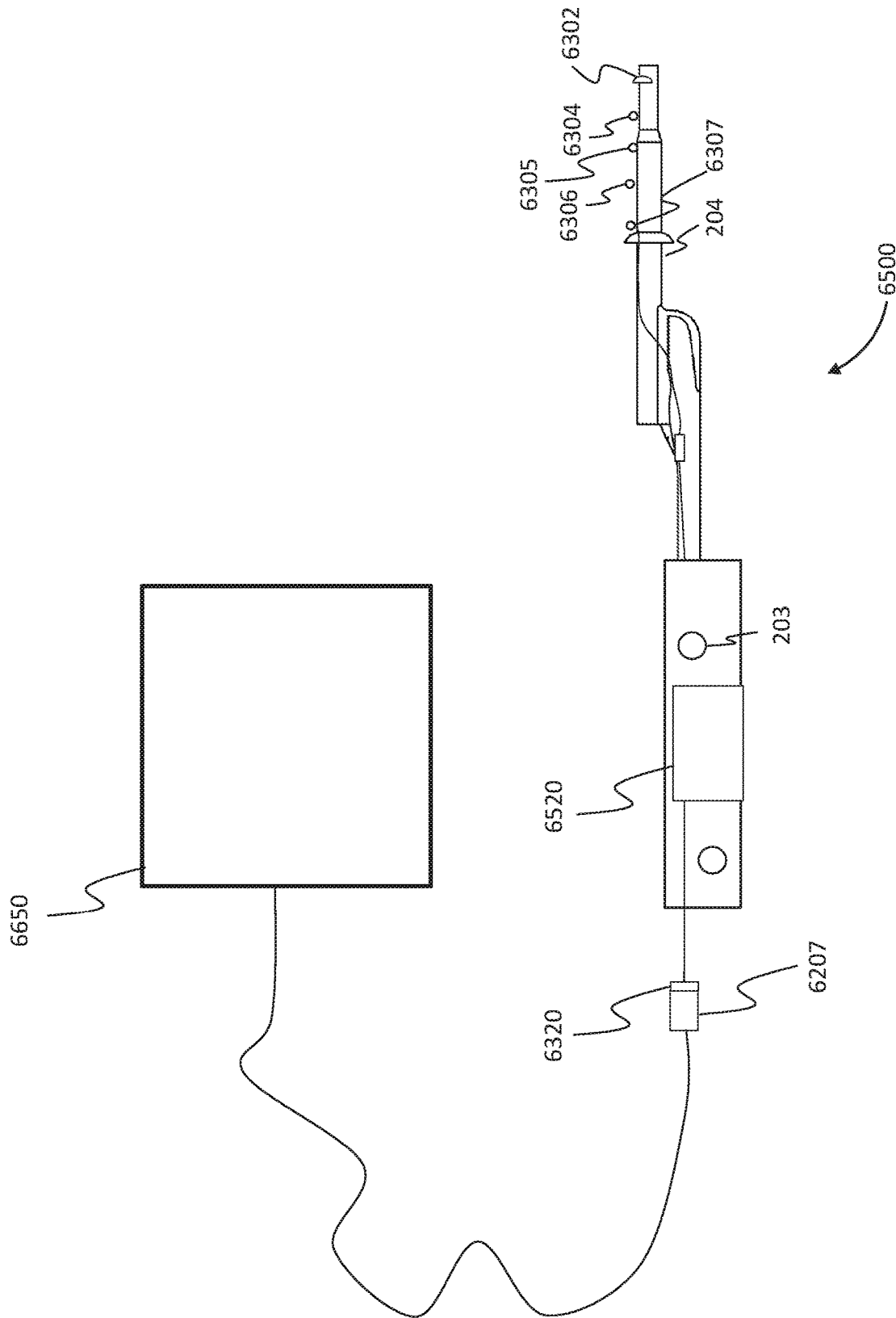

In an exemplary embodiment, the electrode array insertion guide provides source currents from the electrodes thereof. In an exemplary embodiment, the electrode array insertion guide is configured with a current generator that provides a specific current at a specific voltage from the electrode(s) of the guide. In this regard, the electrodes of the electrode array insertion guide operate as a source with respect to the teachings of U.S. patent application Ser. No. 14/843,255. To this end, FIG. 65 depicts an exemplary insertion guide 6500, that provides a current and voltage generator 6520, which is in communication with electrode 6307 via an electrical lead extending therefrom. In an exemplary embodiment, the generator 6520 can also be in communication with the other electrodes of the electrode array insertion guide. In an exemplary embodiment, the generator 6520 includes relays and/or transistors and/or switching components that enable the generator to alternately switch delivery of current from one electrode to the other electrode. In this regard, in an exemplary embodiment, the generator 6520 can have the functionality and/or the structure of the components of the receiver/stimulator of the cochlear implant of U.S. patent application Ser. No. 14/843,255 with respect to generating a source current from the electrodes of the electrode array, when implementing the teachings of that patent application. In an exemplary embodiment, the generator 6520 can be a battery that is connected to circuitry that outputs a stable current at a stable voltage. In an exemplary embodiment, the generator 6520 can be adjustable so as to output different currents at different voltages. Consistent with the teachings detailed herein, the guide 6500 can have a switch or the like to allow the surgeon to activate and/or deactivate the current generator 6520. Alternatively, and/or in addition to this, the guide 6500 can be configured so as to allow selective energizement and/or deenergizement of the electrodes of the guide. While some embodiments permit such as part of the handheld guide, in some alternate embodiments, the guide is configured to be placed into communication with a control unit. For example, as seen in FIG. 66, guide 6500 can be equipped with a connector 6320 in signal communication with the voltage/current generator 6520. The connector can be connected to a connector 6207 that is connected to a control unit 6650, which can be a personal computer or the like. In an exemplary embodiment, the control unit 6650 can control the output of the current generator 6520 with respect to the current, the voltage, and which electrodes are operated as the source. Note further that in some exemplary embodiments, the voltage/current generator 6520 is not part of the guide 6500, but instead is part of the control unit 6650. Indeed, in such an exemplary embodiment, there can be separate leads from each electrode that extend to the connector 6320.

It is noted that in an exemplary embodiment, the control unit 6650 is the implant itself. In an exemplary embodiment, it is the receiver-stimulator unit of a cochlear implant, alone in some embodiments, or when placed into inductance communication with an external component or a component that replicates the functionality of the external component, etc. By way of example only and not by way of limitation, a lead from the guide, such as the lead leading from connector 6207, could clip onto the existing extra cochlear electrode (sometimes referred to as the hardball) of the implant, allowing the implant to look for open circuits, measure voltages, etc., through the electrode on the guide. In this regard, in an exemplary embodiment, the electrodes of the insertion guide can become an extension of the extra cochlear electrode. Accordingly, an embodiment exists where any functionality of the cochlear implant that relies on the extra cochlear electrode can thus also rely on the electrodes of the insertion guide to achieve such functionality. Corollary to this is that in an exemplary embodiment, any of the functions detailed herein that utilize the electrodes of the insertion guide can be executed by the implants in at least some exemplary embodiments when the implant is in signal communication with the implant, or at least when the insertion guide is connected to the extra cochlear electrode of the electrode array.

Still, in at least some exemplary embodiments, the guide 6500 can be configured so that the surgeon or the like can toggle from one electrode to another. For example, the guide can be provided with a switch or a button that the surgeon depresses to selectively energize a given electrode. The electrodes can be energized in sequence by repeatedly pressing the button. In an exemplary embodiment, an indicator on the guide can be provided so as to convey information to the surgeon as to which electrode is being operated as the source. By way of example only and not by way of limitation, an array of LEDs can be arrayed about the insertion stop 204. As a given electrode is energized, the LEDs can light. The LED at the 9 o'clock position could indicate that the closest electrode to the stop has been energized (e.g., electrode 6307). The LED at the 3 o'clock position (when viewing the stop 204 from the surgeon point of view) could indicate that the furthest electrode to the stop has been energized (e.g., electrode 6302). The electrodes in between can correspond to LEDs in between the 9 o'clock position in the 3 o'clock position. Alternatively, LEDs having different colors can be utilized to indicate to the surgeon which electrode is being utilized as a source.

Figure 67:
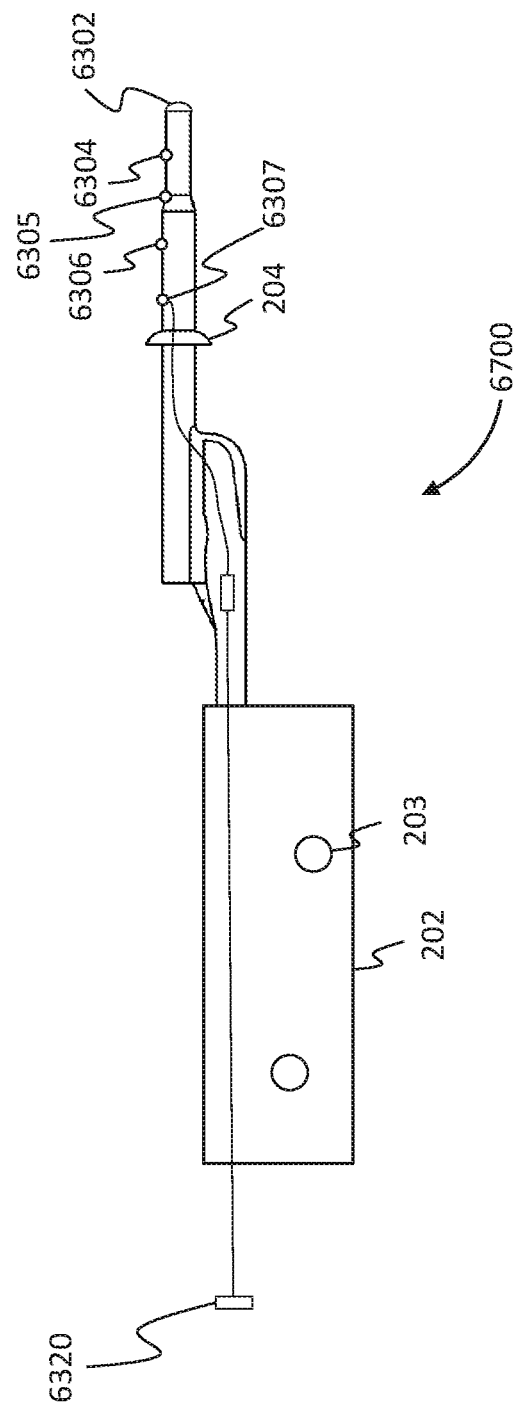

FIG. 67 depicts an alternate embodiment of the electrode array insertion guide, insertion guide 6700, that is utilized as a sink. Here, a lead extends from electrode 6307 to a connector 6320. Other leads also extend in a similar manner, but are not shown. In an exemplary embodiment, connector 6320 can be hooked up to or otherwise connected to a unit that will receive the signal from the electrodes when used as a sink, and analyze that signal in a manner corresponding to how such would be analyzed were that electrode to be part of the electrode array as utilized in U.S. patent application Ser. No. 14/843,255. By way of example only and not by way of limitation, in an exemplary embodiment, a test unit can be a personal computer in signal communication with connector 6320. The personal computer can analyze the output from connector 6320 indicative of the current/voltage at electrode 6307 or any other electrode of the electrode array insertion guide, and analyze the properties of the electrode array in the same manner as that which is done in the '255 patent application. That said, in an exemplary embodiment, the guide 6700 can be placed into signal communication with the receiver/stimulator of the cochlear implant, and the cochlear implant can be configured to utilize the electrodes of the insertion guide as the sink electrode when implementing the teachings of the '255 application. Note also that this is the case with respect to embodiments where the electrodes of the electrode array insertion guide are utilized as the source. That is, connector 6320 can allow the insertion guide to be placed into signal communication with the receiver/stimulator of the cochlear implant, and the cochlear implant can be configured to utilize the electrodes of the insertion guide as the source electrode when implement the teachings of the '255 application.

Note also that in an exemplary embodiment, whether the guide is utilized as a source or a sink for the current, the insertion guide 6700 can be configured to be placed into signal communication with any ancillary equipment utilized in the teachings of the '255 application so as to implement the teachings thereof where the electrodes of the insertion guide are the source or the sink.

Any arrangement of the insertion guide that can enable electrodes thereof to operate as a source or a sink instead of utilizing the electrodes of the electrode array as the respective source or a sink when implementing the teachings of the '255 patent application can be utilized in at least some exemplary embodiments. Thus, in an exemplary embodiment, the guide is configured to interface with any of the components detailed in the '255 patent application to enable such.

The teachings detailed above have utilitarian value with respect to determining or otherwise detecting electrode array tip fold over. The teachings detailed above also have utilitarian value with respect to determining angular insertion depth.

Figure 68:
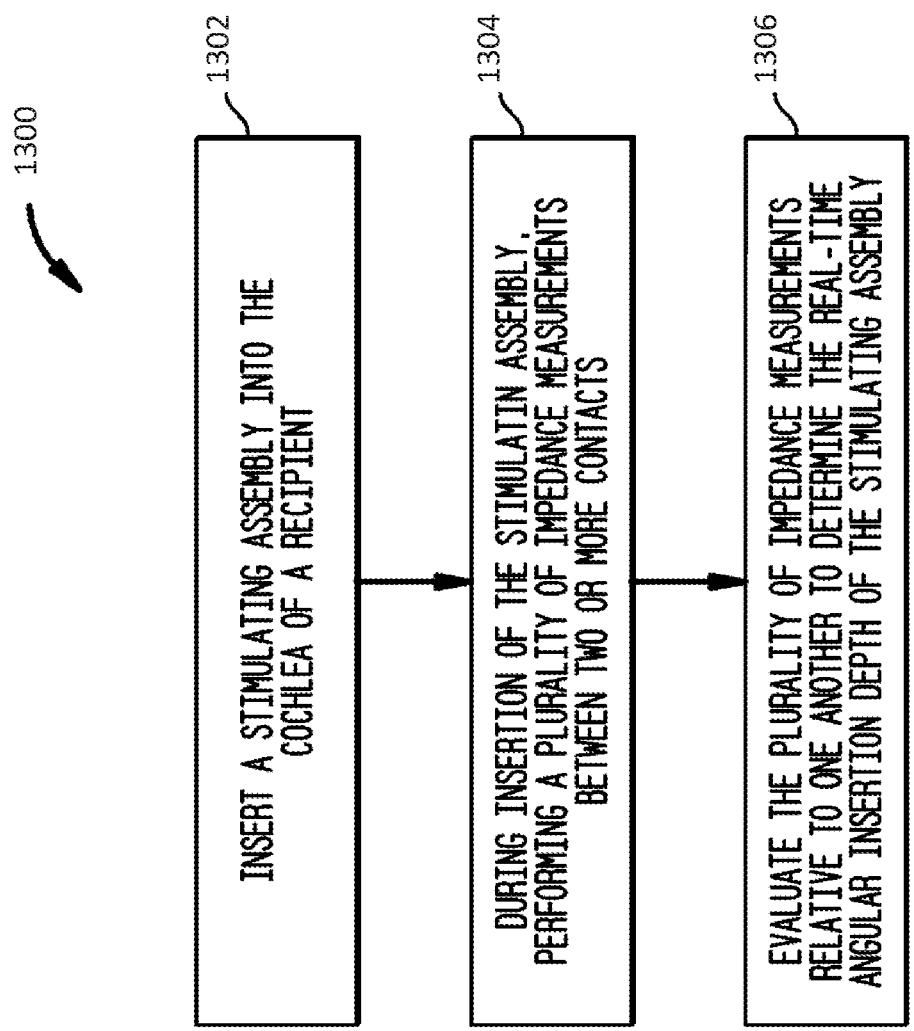
FIGS. 68-70 depict exemplary flowcharts for exemplary methods according to some exemplary embodiments.

FIG. 68 depicts a flowchart of a first intra-operative method 1300 for setting the angular insertion depth of the electrode array utilizing an electrode of the electrode array insertion guide. FIG. 68 illustrates a real-time method that enables the determination of the current/present (i.e., actual) angular insertion depth of the electrode array within the cochlea.

Method 1300 begins at 1302 where the electrode array is at least partially inserted into cochlea. At 1304, during insertion of the stimulating assembly into the cochlea, the impedance between different pairs of intra-cochlear contacts is measured, one contact being an electrode of the electrode array and another contact being electrode of the electrode array insertion guide and used to determine the angular insertion depth of the stimulating assembly.

In one embodiment, to measure the impedance between two intra-cochlear contacts, bipolar electrical stimulation (i.e., one or more bipolar current signals) is repeatedly delivered between a first intra-cochlear contact (e.g., one of the electrodes the electrode array insertion guide) and a second intra-cochlear contact (e.g., one of the electrodes of the electrode array). After the delivery of each set of bipolar stimulation between the first and second intra-cochlear contacts, the impedance between the first and second contacts is measured (e.g., at the second intra-cochlear contact). As with the embodiment detailed above with respect to FIG. 64, the contact that delivers the current signals is sometimes referred to herein as the "stimulating" or "source" contact and the contact that sinks the current is sometimes referred to herein as the "return" contact. Additionally, the two contacts between which the stimulation is delivered are sometimes collectively referred to herein as a "stimulating pair." The remaining contacts that are not part of the stimulating pair are disconnected from the system ground (i.e., are electrically "floating").

It is to be appreciated that impedance measurements are made between two points, thus the impedance may be "measured" at either of the two points (i.e., it is a relative measurement between those two points). However, merely for ease of illustration of certain embodiments presented herein, the return contact of the stimulating pair is sometimes referred to herein as a "measurement" contact.

In general, the impedance between two intra-cochlear contacts in a stimulating pair can be correlated to their physical proximity with one another and their location in the cochlea. Because one of the electrodes is mounted at a known location on the insertion guide, and the insertion guide is inserted into the cochlea by a known amount at a generally known angle, utilizing the electrodes of the electrode array insertion guide can have utilitarian value. The physically closer the contacts of the stimulating pair are to one another, the lower the impedance that will be measured between the contacts. At 1306, again while inserting the electrode array, the impedance-to-proximity relationship is used to evaluate the plurality of impedance measurements relative to one another to determine the relative proximity between the two or more intra-cochlear contacts and thus determine the real-time (current/present) angular insertion depth of the electrode array. As described further below, the method includes the selection of one or more sets/pairs of intra-cochlear contacts for impedance measurement that enables the angular insertion depth of the electrode array to be determined from the relative proximity of the one or more pairs of intra-cochlear contacts.

In an exemplary embodiment, a given electrode of the electrode array will move relative to the electrode of the electrode array insertion guide as the electrode array is inserted in the cochlea. As it travels through the cochlea and curves therein, a given electrode of the electrode array will have a distance from the electrode of the electrode array insertion guide that changes. The distance will grow larger and then grow smaller as the electrode array snakes its way through the cochlea in a manner analogous to how distance between planets expands and contracts. Because the distance is changed, the current and/or voltage measured at a given sink contact will change. This can be utilized to determine the angular orientation according to the teachings of U.S. patent application Ser. No. 14/843,259. Thus, in an exemplary embodiment, whether the guide is utilized as a source or a sink for the current, the insertion guide 6700 can be configured to be placed into signal communication with any ancillary equipment utilized in the teachings of the '259 application so as to implement the teachings thereof where the electrodes of the insertion guide are the source or the sink.

Any arrangement of the insertion guide that can enable electrodes thereof to operate as a source or a sink instead of utilizing the electrodes of the electrode array as the respective source or a sink when implementing the teachings of the '259 patent application can be utilized in at least some exemplary embodiments. Thus, in an exemplary embodiment, the guide is configured to interface with any of the components detailed in the '259 patent application to enable such. To be clear, in an exemplary embodiment, electrode array insertion guide is configured to serve as a source and/or a sink contact in the teachings of the 259 patent application.

To summarize, any of the features detailed above that enable an insertion guide with electrodes to be utilized as source or sink to enable the teachings of U.S. patent application Ser. No. 14/843,255 can be utilized to enable an insertion guide with electrodes to be utilized as source or sink to enable the teachings of U.S. patent application Ser. No. 14/843,259. Thus, the embodiments of FIGS. 63, 65, 66 (with possible modifications to the unit 6650 for angular insertion), and 67 can be utilized to implement the teachings of the '259 application as well.

In view of the above, in an exemplary embodiment, there is an electrode array insertion guide, wherein the guide includes an intracochlear portion configured to be inserted into the cochlea. In this exemplary embodiment, the insertion guide has ancillary functionality of a voltage and/or impedance monitoring of the electrode array via an electrode mounted on the intracochlear portion thereof. It is to be understood that in an exemplary embodiment, the electrode array insertion guide has a functionality of a reference for a measurement system. In view of the above, in an exemplary embodiment, there is a cochlear electrode array insertion guide, comprising an array guide, and an active functional component. In an exemplary embodiment, the active functional component is an indicator to a user of the insertion guide of a phenomenon associated with insertion of the electrode array. In an exemplary embodiment, the phenomenon associated with insertion of the array is an array orientation within the cochlea. In an exemplary embodiment, there is an insertion guide having a functionality voltage and/or impedance monitoring characteristics between two electrodes of the electrode array.

Figure 69:
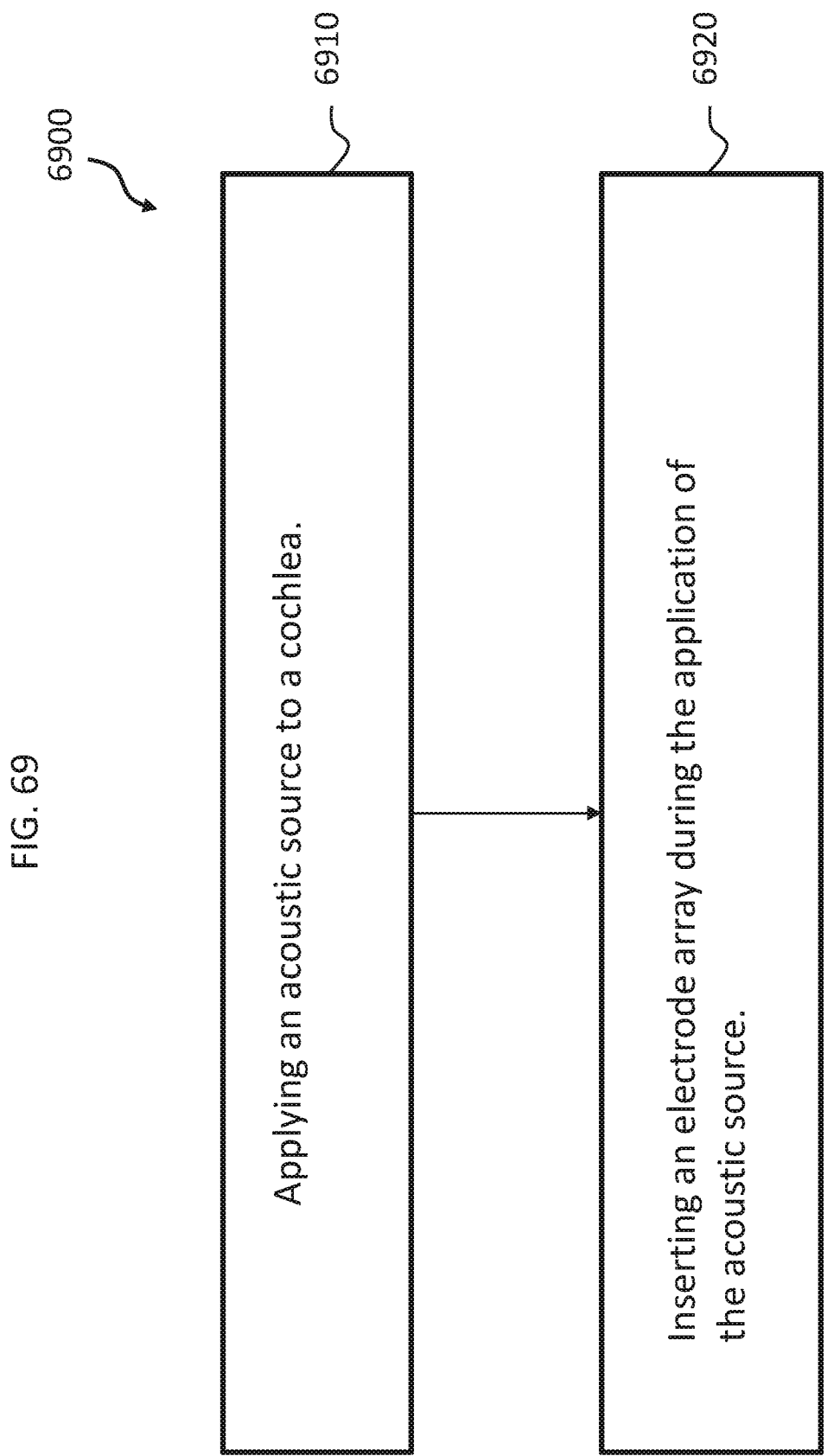

In view of the above, it is to be understood that the insertion guides detailed herein provided utilitarian value with respect to methods. In this regard, FIG. 69 depicts an exemplary flowchart for a method 6900. Method 6900 includes method action 6910, which entails applying an acoustic source to a cochlea. In the exemplary embodiment, this is achieved via the use of the acoustic signal generator mounted on the guide as noted above. Method 6900 further includes method action 6920, which entails inserting an electrode array during the application of the acoustic source. Consistent with the teachings detailed above, the acoustic source could be a bone conduction actuator. In an exemplary embodiment, the acoustic source is operated at a gain of less than about 80 dBs.

Figure 70:
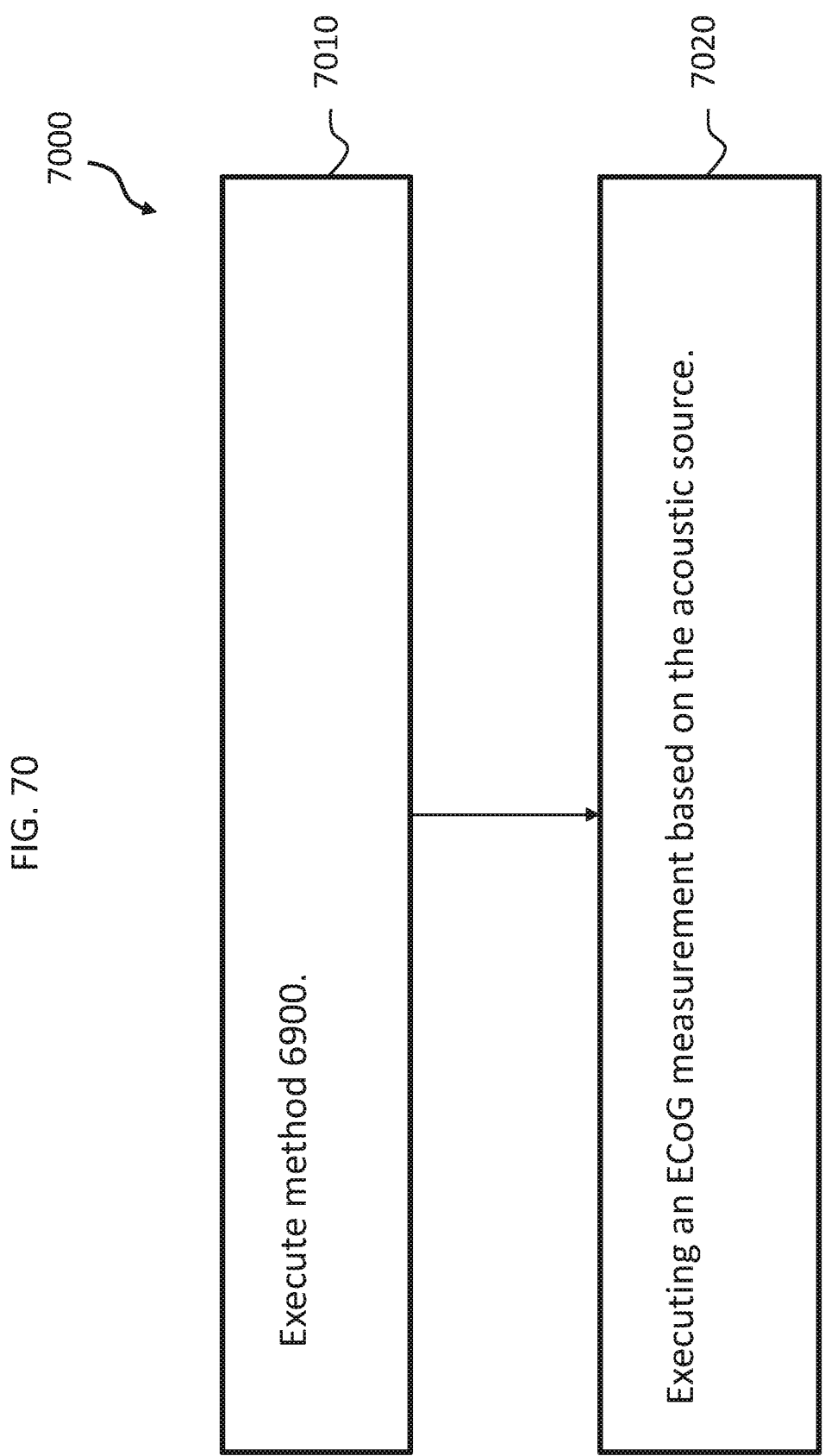

FIG. 70 depicts another exemplary flowchart for an exemplary method, method 7000. Method 7000 includes method action 7010, which entails executing method 6900. Method 7000 further includes method action 7020, which entails executing an ECoG measurement based on the acoustic source. In an exemplary embodiment, this is executed utilizing the devices and systems detailed above. In view of the above, where the insertion guide having the acoustic source signal generator is utilized, in an exemplary embodiment, the acoustic source bypasses the middle ear to provide auditory stimuli for the ECoG measurements. Corollary to method 7000 is that the acoustic source evokes and auditory nerve action potential via bone conduction in at least some exemplary embodiments.

In at least some exemplary embodiments, the execution of the ECoG measurement can have utilitarian value with respect to determining whether or not electrode array is being properly inserted into the cochlea. Accordingly, in an exemplary embodiment, method 7000 can further include the action of temporarily halting the insertion of the electrode array based on the ECoG measurement prior to full insertion of the electrode array. Indeed, in an exemplary embodiment, method 7000 can further include the action of withdrawing a portion of the electrode array from the cochlea based on the ECoG measurement prior to the final insertion of the electrode array into the cochlea.

Still with reference to method 7000, in an exemplary embodiment, the action of inserting the electrode array is executed during a first temporal period and a second temporal period, wherein during the first temporal period, the electrode array is inserted into the cochlea along a first trajectory relative to the very beginning of the cochlea and during the second temporal period, the electrode array is inserted into the cochlea along a second trajectory relative to the very beginning of the cochlea. In this regard, by way of example only and not by way of limitation, the first trajectory can be established by the insertion guide when held at a first angle relative to the outside of the cochlea, or more specifically, relative to the tangent surface at the cochleostomy. In an exemplary embodiment, this angle could be 10°. Because of the nature of the insertion guide, the electrode array would be inserted into the cochlea along a first trajectory controlled by this angle. The second trajectory can also be that established by the insertion guide when held at a second angle relative to the outside of the cochlea, or more specifically, relative to the tangent surface of the cochleostomy. In an exemplary embodiment, this angle can be 15°. Again, because of the nature of the insertion guide, the electrode array would be inserted into the cochlea along a second trajectory controlled by this angle. It is to be understood that the method 7000 further comprises at least one of during the first temporal period or subsequent to the first temporal period, evaluating the ECoG measurement determining that the second trajectory should be adopted for insertion based on the ECoG measurement. In this regard, in an exemplary embodiment, the ECoG measurement could indicate that the electrode array is piercing a wall of the cochlea that it should not be piercing. Thus, there is utilitarian value with respect to changing the angle of orientation of insertion of electrode array into the cochlea. Still further, in an exemplary embodiment, the ECoG measurement could indicate that the electrode array is inserted into the wrong portion of the cochlea. Any data that is conveyed by the ECoG measurement that can have utilitarian value indicating that a different trajectory of electrode array insertion should be utilized, can be used in at least some exemplary embodiments as a basis for which to determine that the trajectory of insertion should be adjusted or otherwise changed.

Still referring back to method 6900, in an exemplary embodiment, the acoustic source is an ultrasonic imaging signal consistent with the utilization of an ultrasonic transducer mounted on the guide as detailed above.

It is noted that in an exemplary embodiment, the insertion guide in general, and the insertion sheath in particular, can be partially formed from or otherwise include layers of thin film circuits with the active components (electrodes, circuits for transducers, MEMS electronics, etc.) needed to produce the added functionality. By way of example only and not by way of limitation, the tube through which the electrode array is inserted could be formed by taking a thin film and laying such flat. Electrical components can be located on the film according to a specific pattern. The film can then be rolled around the mandrel or the like so that the layer stack upon themselves as the film is rolled about the layer. The electronics will thus be located between and/or in the layers and position in the resulting tube accordingly, this tube could be utilized as part of the insertion guide in general, and the lumen through which the electrode array travels during insertion thereof in particular.

Figure 71:
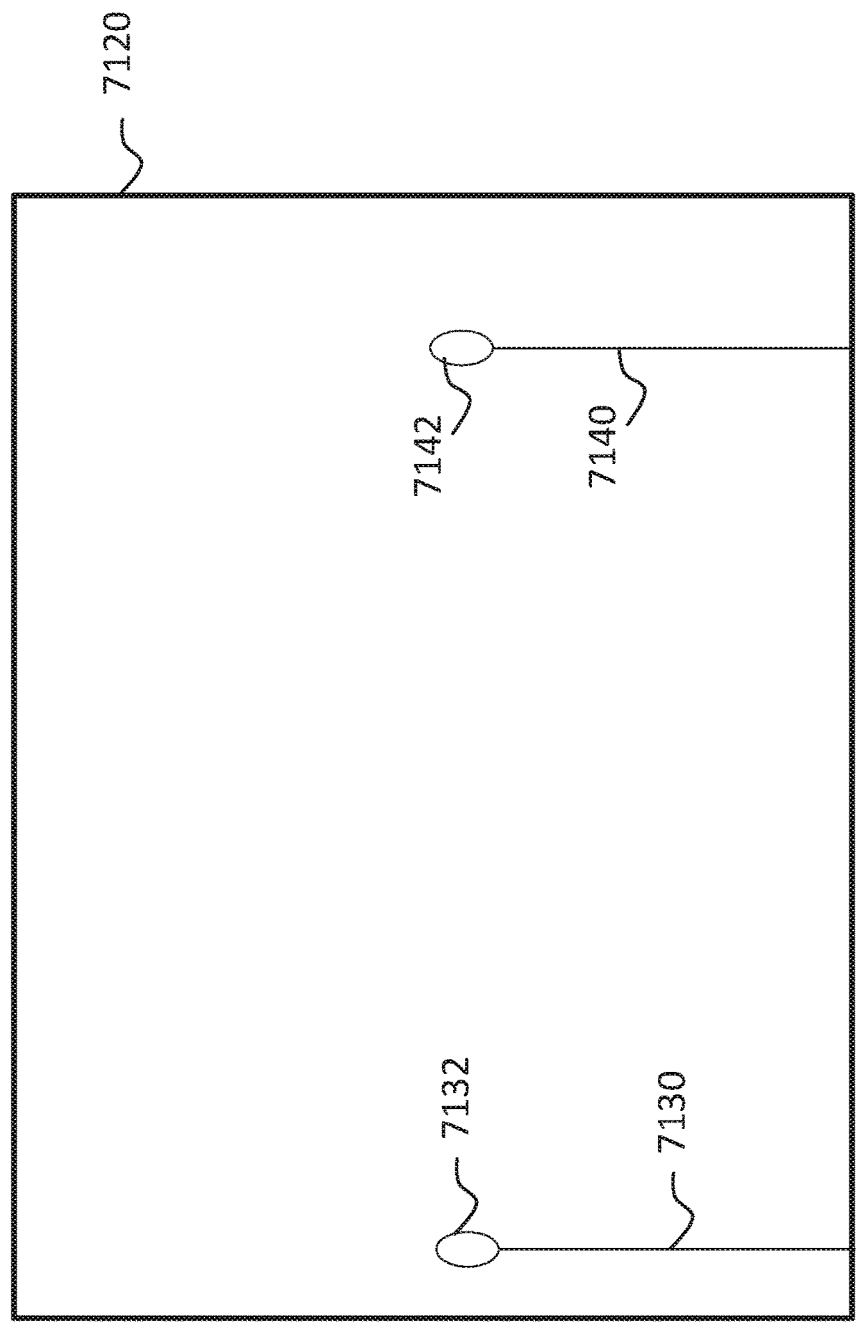
FIG. 71 depicts an exemplary thin-film that is usable for an exemplary embodiment.
Figure 72:
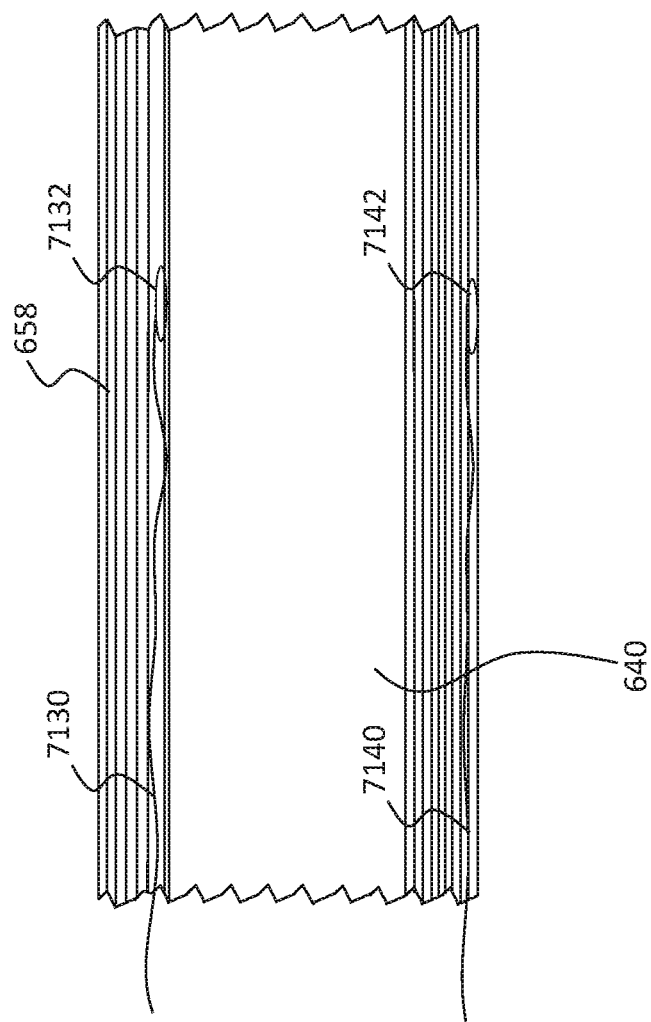
FIG. 72 depicts the results of the utilization of the thin film of FIG. 71.

For purposes of concept illustration, FIG. 71 depicts an exemplary thin-film 7120 having located thereon circuit traces. A first circuit trace includes a lead 7130 and an electrode 7132. A second circuit trace includes a lead 7140 and an electrode 7142. The circuit traces are located on the film 7120 such that, when rolled, the first circuit trace is located closer to the inside of the resulting lumen and the second circuit trace is located close to the outside of the lumen. This is seen in FIG. 72, which depicts a view of the insertion tube showing the positions of the respective circuit traces, and the layers established by the rolling of the film. To be clear, the layers of the film form the tube wall 658 and thus the electrical circuits are embedded in the wall owing to the rolling.

It is noted that the electrode array orientation can include the orientation about/relative to the electrode axis, as well as rotation about the other two axes. By way of example only and not by way of limitation, orientation can be related to rotation about one or more of these axes. Any orientation of the electrode array that can be evaluated or otherwise estimated utilizing the teachings detailed herein and/or variations thereof as a basis in whole or in part to control the electrode array insertion process can be utilized at least some exemplary embodiment in exemplary methods and/or in exemplary apparatuses. It is also noted that in some alternate embodiments, the direction of approach of the electrode array can also be utilized to control the insertion process. In this regard, in an exemplary embodiment, the teachings detailed herein can be utilized to evaluate or otherwise estimate a direction of approach of the electrode array, and the insertion process can be controlled or otherwise adjusted based on the direction of approach.

Figure 73:
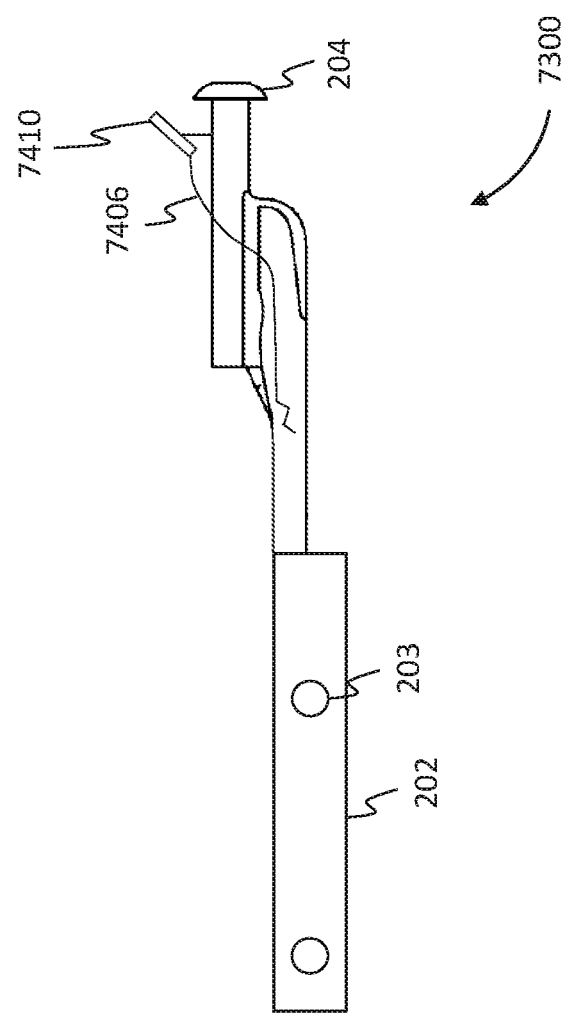
FIG. 73 depicts a side view of an exemplary embodiment of an exemplary insertion guide.

As noted above, the insertion guide can incorporate visual indicators to provide intraoperative feedback to the surgeon. As detailed above, exemplary embodiments have LEDs or the like arrayed about the stop. Still further, in an exemplary embodiment, a liquid crystal display or the like can be incorporated in or on the insertion guide. In this regard, FIG. 73 depicts an exemplary embodiment of an insertion guide 7300 which includes LCD 7410 mounted on the insertion guide tube. LCD 7410 is in electrical communication with other components of the guide and/or other systems remote from the guide via electrical lead 7406. In an exemplary embodiment, the LCD can provide text and/or numerical data to the surgeon during implantation/insertion of the electrode array. The LCD or the other visual indicators can be located anywhere on the guide that will be within the surgeon's immediate field-of-view, but also where the indicator will not obstruct the surgeon's field-of-view of the pertinent portions of the anatomy of the recipient and/or the pertinent portions of the guide 7300 during insertion of the electrode array. In an exemplary embodiment, the indicators provide information pertaining to insertion depth, which can include the absolute depth and/or an indication that the electrode array has reached the intended or programmed stopped depth. Indication can be an insertion speed, which can be absolute speed of insertion or can be an indication that the insertion speed limit has been exceeded. The indication can be an adverse measurement indication. This measurement can be a general indication, such as an indicator that something has gone wrong whatever that is, or specific indication, such as an indication explicitly relating to tip fold-over, basilar membrane contact, scala dislocation, etc.

Figure 74:
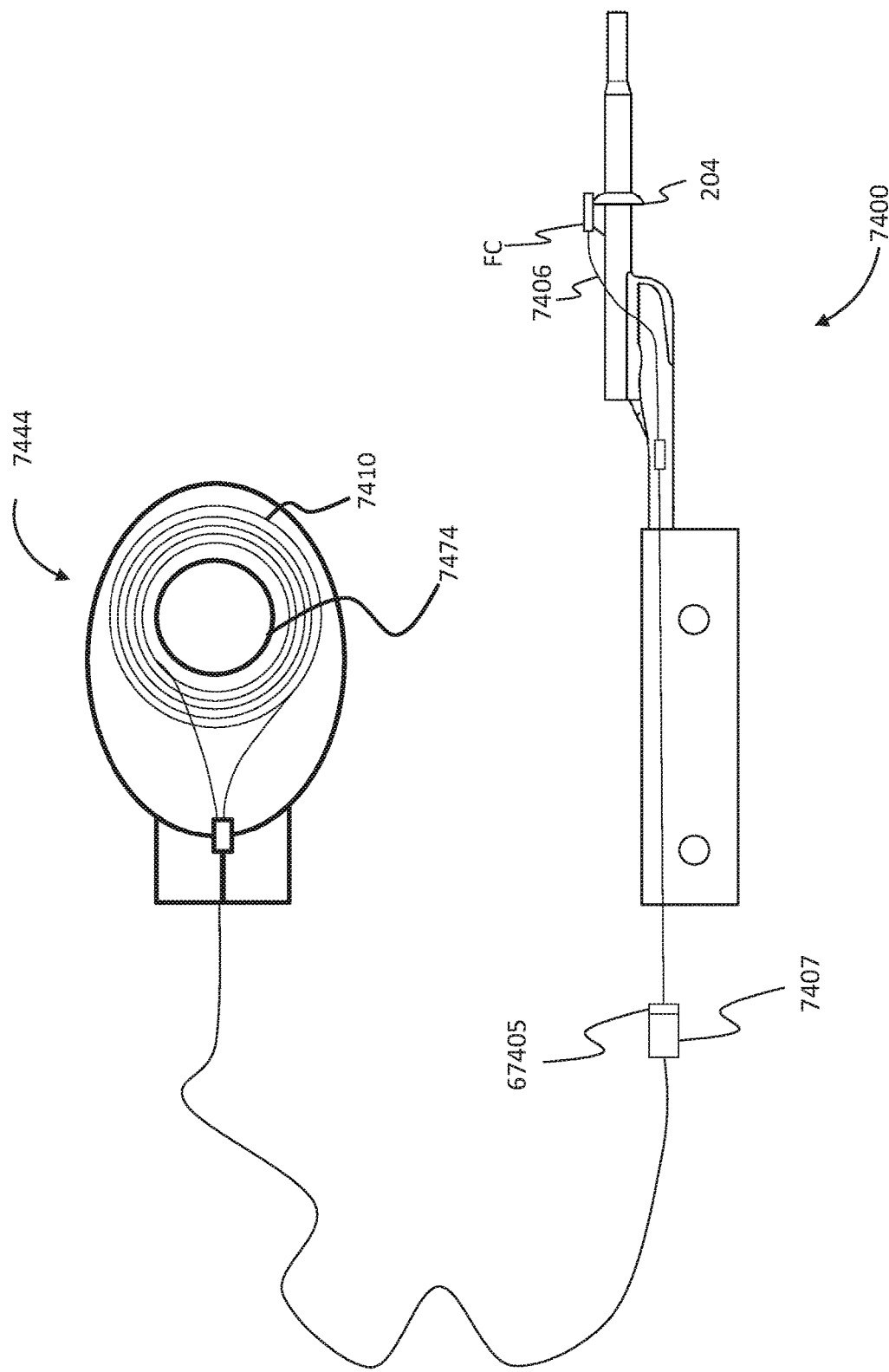
FIG. 74 depicts an exemplary insertion guide—inductance coil combination enabling the insertion guide to communicate with a receiver-stimulator of a cochlear implant.

As noted above, embodiments include an insertion guide configured to communicate with a receiver/stimulator of a cochlear implant. In this regard, FIG. 74 depicts an exemplary insertion guide 7400 which is presented by way of concept. Insertion guide 7400 is a functional component FC mounted thereon. This functional component is representative of any of the additional functionalities of the insertion guide detailed herein and/or variations thereof. For example, element FC could be an electrode, it could be the acoustic stimulation generator, or it could be the ultrasonic transducer. FC could also be any of the indicators detailed herein (e.g., the LCD screen). As can be seen, insertion guide 7400 includes connector 64705 in electrical communication with the functional component FC via electrical lead 746. Connector 64705 is connected to connector 7407 of inductance coil 7444. In an exemplary embodiment, inductance coil 7444 includes coil 7410 configured to establish a magnetic inductance field so as to communicate with the corresponding coil of the receiver-stimulator of the cochlear implant. Inductance coil 7444 includes a magnet 7474 so as to hold the inductance coil 7474 against the coil of the receiver/stimulator of the cochlear implant in a manner analogous to how the external component of the cochlear implant is held against the implanted component, and how the coils of those respective components are aligned with one another. While the embodiment depicted in FIG. 74 depicts no other functional component between the functional component FC and the inductance coil 7444, in an alternate embodiment, one or more of the units detailed herein can be located there between. By way of example, generator 6520 with respect to the insertion guide 6500 detailed above can be located therebetween or otherwise be in signal communication with the leads so as to establish communication with that element with the cochlear implant. In an exemplary embodiment, a communications unit or the like is located between or otherwise is in signal communication with the leads so as to establish communication with the cochlear implant receiver-stimulator. In an exemplary embodiment, the insertion guide includes logic or a processor or other type of control unit that enables the insertion guide to work in conjunction with the cochlear implant so as to execute any of the methods detailed herein, including the methods associated with the '255 and the '259 applications where one or more electrodes of the electrode array insertion guide are utilized in a state of one or more electrodes of the electrode array as taught in those applications.

Figure 75:
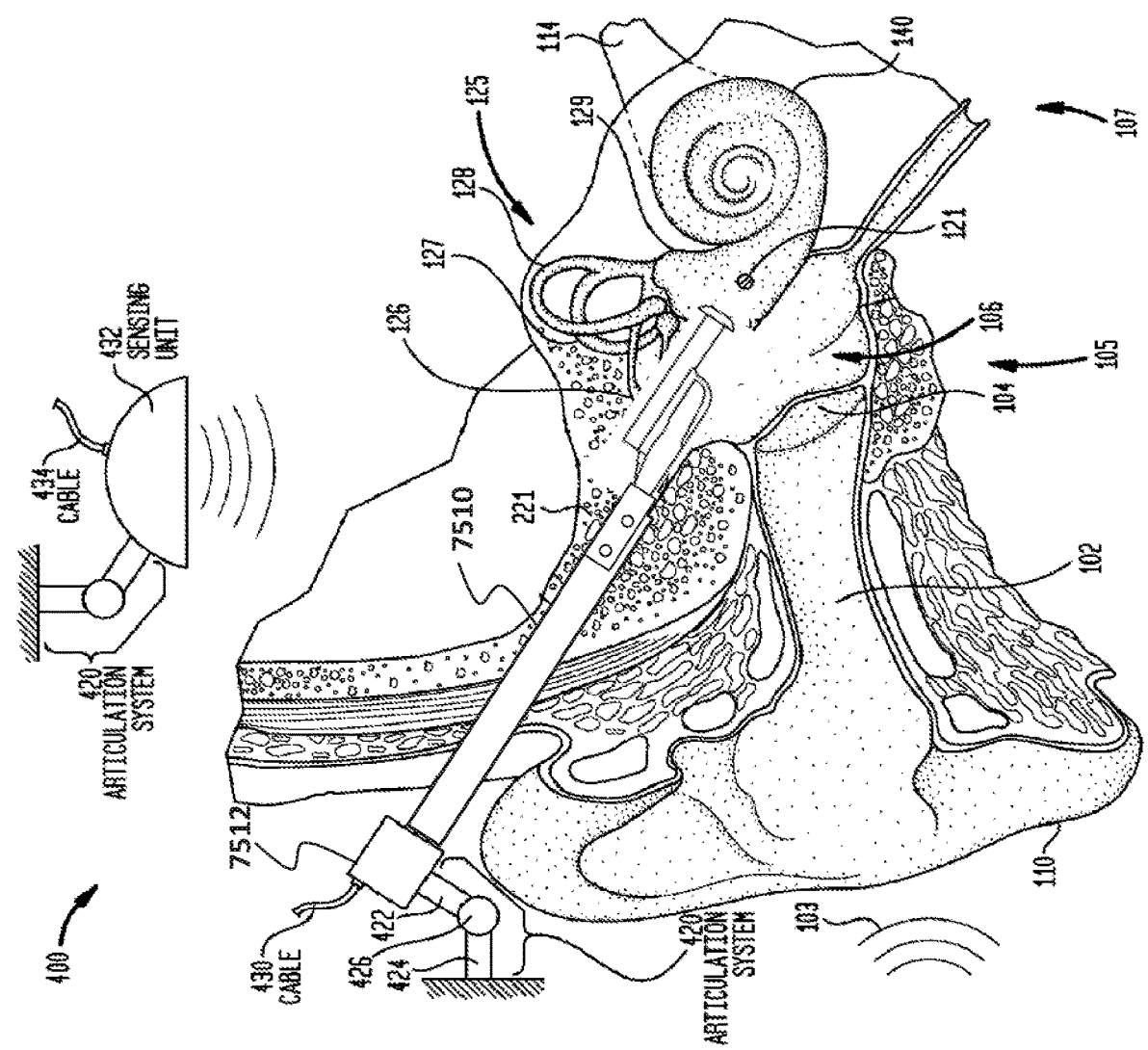
FIG. 75 depicts an exemplary robotic apparatus according to an exemplary embodiment.

It is noted that at least some exemplary embodiments include utilization of the insertion guides detailed herein and/or variations thereof with a robotic electrode array insertion system. In this regard, FIG. 75 is a perspective view of an exemplary embodiment of an insertion system 400. It is noted that the embodiment depicted in FIG. 75 is presented for conceptual purposes only. Features are provided typically in the singular show as to demonstrate the concept associated therewith. However, it is noted that in some exemplary embodiments, some of these features are duplicated, triplicated, quadplicated, etc. so as to enable the teachings detailed herein and/or variations thereof. Briefly, it is noted that any teaching detailed herein can be combined with a robotic apparatus and/or a robotic system according to the teachings detailed herein and/or variations thereof. In this regard, any method action detailed herein corresponds to a disclosure of a method action executed by a robotic apparatus and/or utilizing a robot to execute that action and/or executing that method action is part of a method where other actions are executed by robot and/or a robotic system etc. Still further, it is noted that any apparatus detailed herein can be utilized in conjunction with a robotic apparatus and/or a robot and/or a system utilizing such. Accordingly, any disclosure herein of an apparatus corresponds to a disclosure of an apparatus that is part of a robotic apparatus and or a robotic system etc. and or a system that includes a robotic apparatus etc.

System 400 includes a robotic insertion apparatus including arm 7510 to which insertion guide 200 or any other insertion guide according to the teachings detailed herein and/or variations thereof is attached (e.g., bolted to arm 7510). In this exemplary embodiment, arm 7510 is depicted as a single structure extending from the insertion guide to mount 7512. However, in an alternate embodiment, arm 7510 can be a multifaceted component which is configured to articulate at various locations thereabout.

In an exemplary embodiment, arm 7510 is releasably connected by way of a releasable connection to mount 7512, which is supported by a support and movement system 420, comprising support arm 422 which is connected to joint 426 which in turn is connected to support arm 424. Support arm 424 is rigidly mounted to a wall, a floor, or some other relatively stationary surface. That said, in an alternative embodiment, support arm 424 is mounted to a frame that is attached to the head of the recipient or otherwise connected to the head of the recipient such that global movement of the head will result in no relative movement of the system 400 in general, and the insertion guide in particular, relative to the cochlea. Joint 426 permits arm 2510, and thus the insertion guide, to be moved in one, two, three, four, five, or six degrees of freedom. (It is noted again that FIG. 75 is but a conceptual FIG.—there can be joints located along the length of arm 7510, so as to enable arm 75102 articulate in the one or more the aforementioned degrees of freedom at those locations. In an exemplary embodiment, joint 426 includes actuators that move mount 7512, and thus the insertion guide, in an automated manner, as will be described below. In an exemplary embodiment, the system is configured to be remotely controlled via communication with a remote control unit via communication lines of cable 430. In an exemplary embodiment, the system is configured to be automatically controlled via a control unit that is part of the system 400. Additional details of this will be described below.

The system 400 further includes by way of example only and not by way of limitation, sensor/sensing unit 432. That said, in some embodiments, sensor 432 is not part of system 400. In some embodiments, it is a separate system. Still further, in some embodiments, it is not utilized at all with system 400. While sensor 432 is depicted as being co-located simultaneously with the insertion guide, etc., as detailed below, sensor 432 may be used relatively much prior to use of the insertion guide. Sensing unit 432 is configured to scan the head of a recipient and obtain data indicative of spatial locations of internal organs (e.g., mastoid bone 221, middle ear cavity 423 and/or ossicles 106, etc.) In an exemplary embodiment, sensing unit 432 is a unit that is also configured to obtain data indicative of spatial locations of at least some components of the insertion guide and/or other components of the robotic apparatus attached thereto. The obtained data may be communicated to remote control unit 440 via communication lines of cable 434. As may be seen, sensor 432 is mounted to a support and movement system 420 that may be similar to or the same as that used by the robotic apparatus supporting the insertion guide.

In an exemplary embodiment, sensing unit 432 is an MRI system, an X-Ray system, an ultrasound system, a CAT scan system, or any other system which will permit the data indicative of the spatial locations to be determined as detailed herein and/or variations thereof. As will be described below, this data may be obtained prior to surgery and/or during surgery. It is noted that in some embodiments, at least some portions of the insertion guide are configured to be better imaged or otherwise detected by sensing unit 432. In an exemplary embodiment, the tip of the insertion guide includes radio-opaque contrast material. The stop of the insertion guide can also include such radio-opaque contrast material. In an exemplary embodiment, at least some portions of insertion guide in general, and the robotic system in particular, or at least the arm 7510, mount 7512, arm 422, etc., are made of non-ferromagnetic material or other materials that are more compatible with an MRI system or another sensing unit utilized with the embodiment of FIG. 75 than ferromagnetic material or the like. As will be described in greater detail below, the data obtained by sensing unit 432 is used to construct a 3D or 4D model of the recipient's head and/or specific organs of the recipient's head (e.g., temporal bone) and/or portions of the robotic apparatus of which the insertion guide is a part.

It is also noted that in some exemplary embodiments of system 400, there are actuators or the like that drive the electrode array through the insertion guide into the cochlea. These actuators can be in signal communication with the control unit. In an exemplary embodiment, the control unit can control the actuators to push the electrode array into and/or out of the cochlea as will be described in greater detail below. Concomitant with the robotic assembly supporting the insertion guide, in an exemplary embodiment, the control unit is configured to automatically control these actuators.

Figure 76:
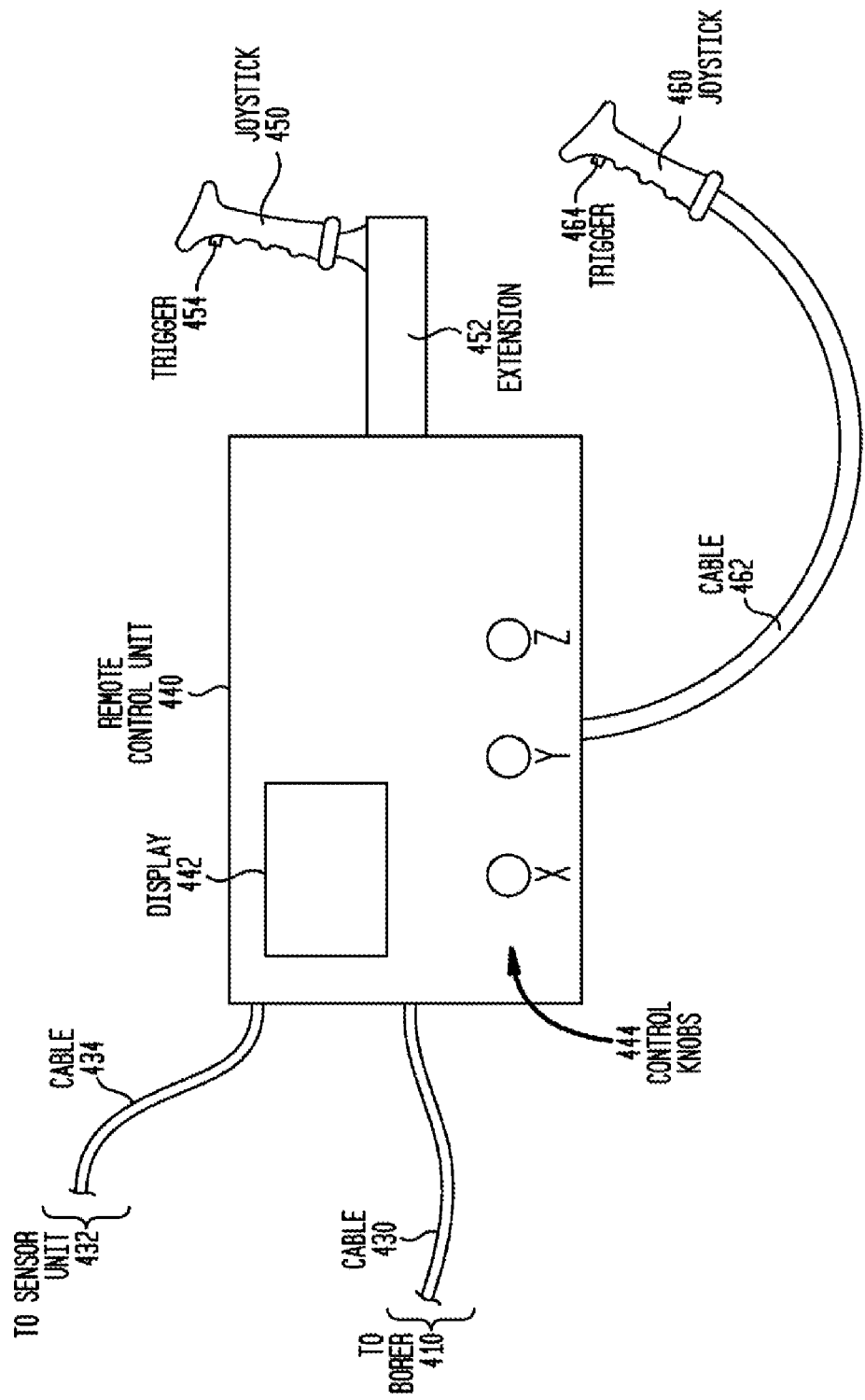
FIG. 76 depicts an exemplary control unit for the robot of FIG. 75 and variations thereof.

FIG. 76 is a simplified block diagram of an exemplary embodiment of a remote control unit 440 for controlling the robotic apparatus supporting the insertion guide and sensing unit 432 via communication lines 430 and 434, respectively. Again, it is noted that in some alternate embodiments, the remote control unit 440 is an entirely automated unit. That said, in some alternate embodiments, the remote control unit can be operated automatically as well as manually, which details will be described below.

Remote control unit 440 includes a display 442 that displays a virtual image of the mastoid bone obtained from sensor 432 and may superimpose a virtual image of the insertion apparatus onto the virtual image indicative of a current position of the drill bit relative to the ear anatomy. An operator (e.g., surgeon, certified healthcare provider, etc) utilizes remote control unit 440 to control some or all aspects of the robotic apparatus and/or sensing unit 432. Exemplary control may include depth of insertion guide insertion, angle of guide insertion, speed of advancement and/or retraction of electrode array, etc. Such control may be exercised via joystick 450 mounted on extension 452 which fixedly mounts joystick 450 to a control unit housing. Such control may be further exercised via joystick 460 which is not rigidly connected to housing of remote control unit 440. Instead, it is freely movable relative thereto and is in communication with the remote control unit via communication lines of cable 462. Joystick 462 may be part of a virtual system in which the remote control unit 440 extrapolates control commands based on how the joystick 462 is moved in space, or joystick may be a device that permits the operator more limited control over the cavity borer 410. Such control may include, for example an emergency stop upon release of trigger 464 and/or directing the robot to drive the insertion guide further into the cochlea by squeezing the trigger 464 (which, in some embodiments, may control a speed at which the insertion guide is advanced by squeezing harder and/or more on the trigger). In the same vein, trigger 454 of joystick 450 may have similar and/or the same functionality.

Control of the robot assembly supporting the insertion guide may also be exercised via knobs 440 which may be used to adjust an angle of the insertion guide in the X, Y and Z axis, respectively. Other controls components may be included in remote control 440.

Figure 77:
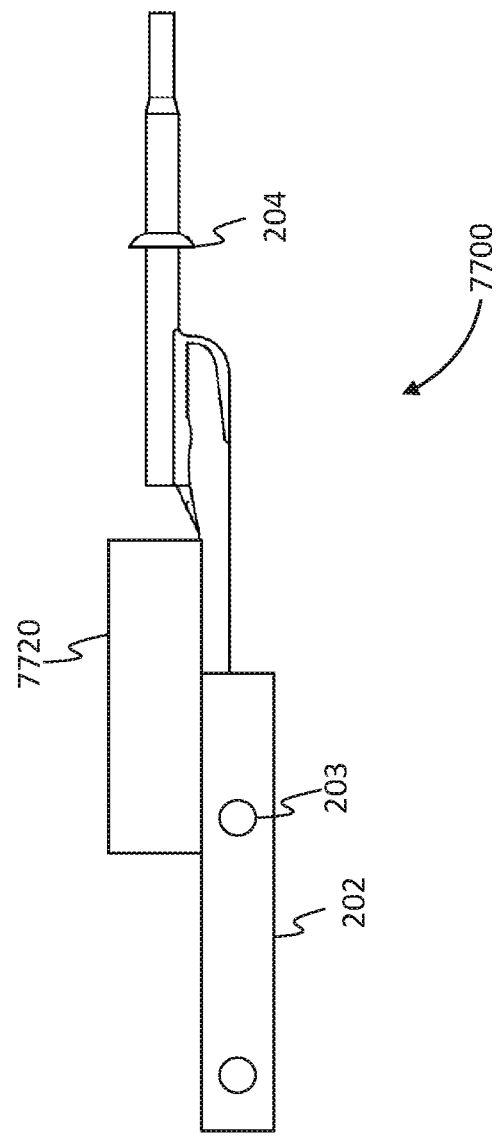
FIG. 77 depicts an exemplary insertion guide according to another exemplary embodiment having an actuator assembly configured to advance and/or retract the electrode array.

FIG. 77 depicts an exemplary insertion guide which can correspond to any of the insertion guide detailed herein and/or variations thereof, or any other insertion guide for that matter, further including an electrode array insertion actuator 7720. In an exemplary embodiment, actuator assembly 7720 includes a passageway therethrough through which the electrode array extends. The actuator assembly drives the electrode array in a manner replicating that by which the surgeon pushes the electrode array forward along the insertion guide and into the insertion tube and thus into the cochlea.

Figure 99:
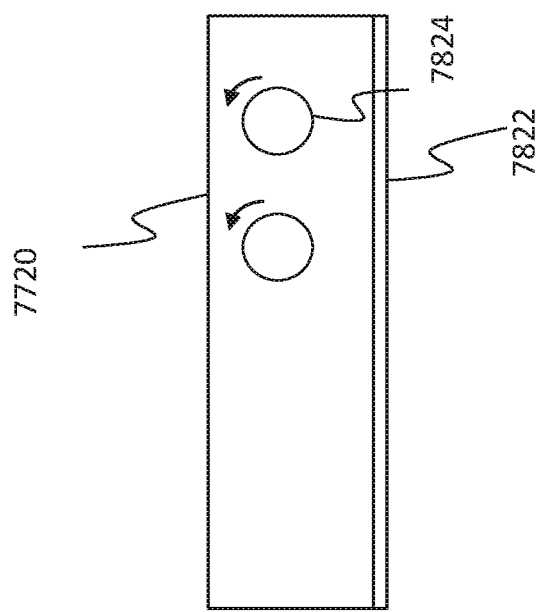

FIG. 99 depicts an exemplary embodiment of the actuator assembly 7720. As can be seen, actuator assembly includes two actuators 7824 in the form of wheels mounted to electric motors that rotate the wheels in a counterclockwise direction so as to advance the electrode array, and in a clockwise direction so as to retract the electrode array. Actuator assembly 7720 further includes a floor 7822. The floor 7822 works in combination with the actuators 7824 so as to "trap" the electrode array there between with a sufficiently compressive force so that the friction forces between the actuators 7824 and the electrode array enable the actuators 7824 to drive the electrode array forward and/or backwards, but not enough so as to damage the electrode array.

Figure 78:
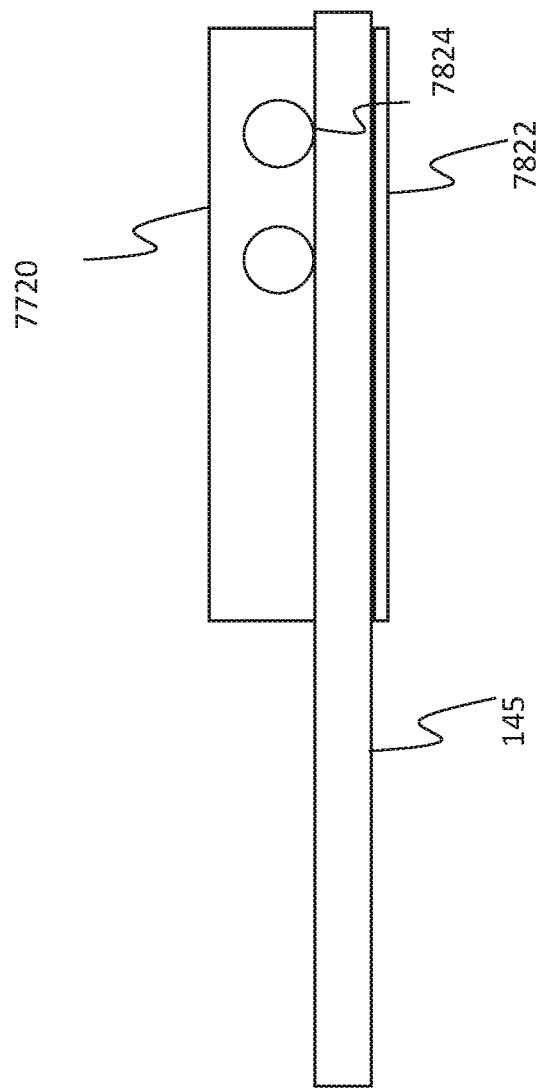
Figure 79:
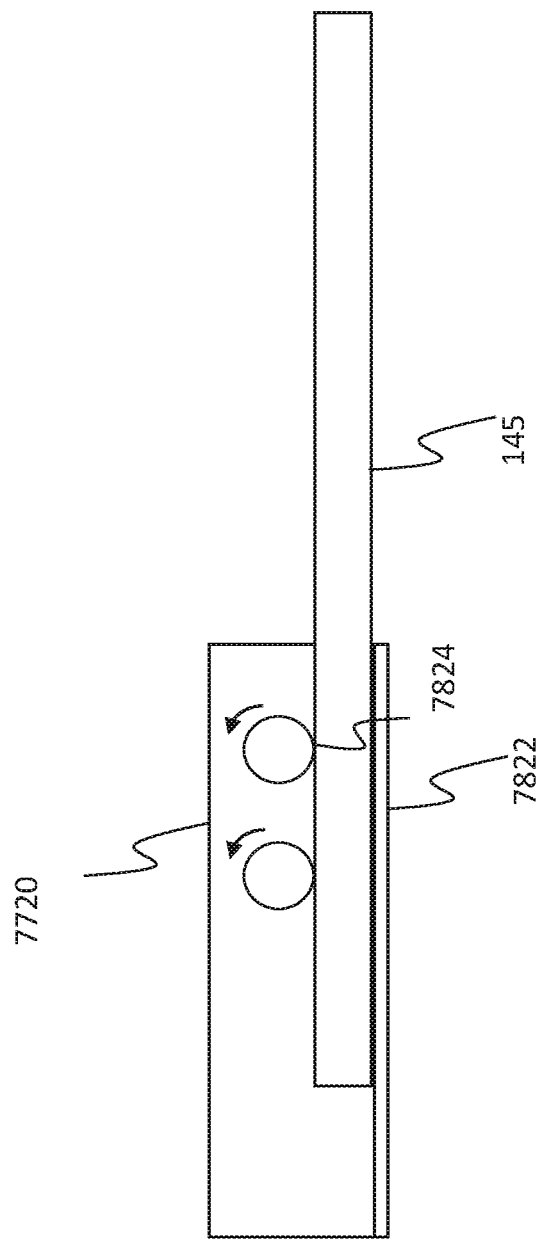

FIG. 78 functionally depicts an electrode array 145 "loaded" in actuator assembly 7720 prior to driving the electrode array into the insertion sheath. FIG. 79 functionally depicts the electrode array being driven forward (FIG. 79 is depicted in a functional manner—in reality, the electrode array 145 would extend up the ramp and then into the insertion sheath), and FIG. 80 functionally depicts the electrode array being retracted from the position seen in FIG. 79.

While the embodiment of the actuator assembly depicted in FIG. 77 includes two top actuators, in an alternate embodiment, only one top actuator is utilized and/or in another embodiment, three or four or five or six or more actuators are utilized. Also, in an exemplary embodiment, one or more bottom actuators can also be utilized. Note also that instead of the actuators being located on the top and the floor 7822 being on the bottom, the actuators can be located on the bottom and the floor can be located on the top.

Figure 81A:
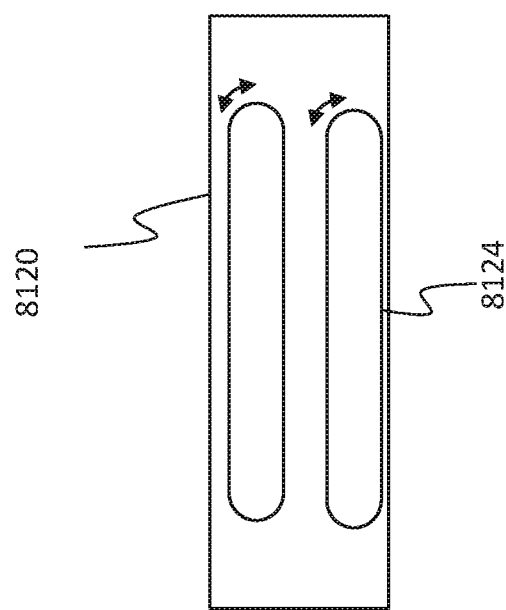
FIG. 81A depicts another exemplary embodiment of an actuator assembly usable with the embodiment of FIG. 77.

It is noted that while the embodiment of FIG. 77 is depicted utilizing actuators having round wheels, in an alternate embodiment, other types of working and of the actuators can be utilized. In this regard, FIG. 81A depicts an exemplary actuator assembly 8120, that includes Caterpillar drives 8124 that operate on a conveyor belt principle, which Caterpillar drives squeeze the electrode array there between ever so slightly to obtain the sufficient friction so as to drive the electrode array forward and/or backwards. Also, while the embodiments depicted herein present the actuators being located one on top of the other, in an alternate embodiment, the actuators can be located side by side. Indeed, while the views depicted in the FIGS. have been presented for purposes of depicting a side view of the actuator (that corresponding to FIG. 76), in alternate embodiment, these views can be considered top use and/or bottom views etc.

Note also that the actuators can be located on the top and the sides and the bottom.

Figure 81B:
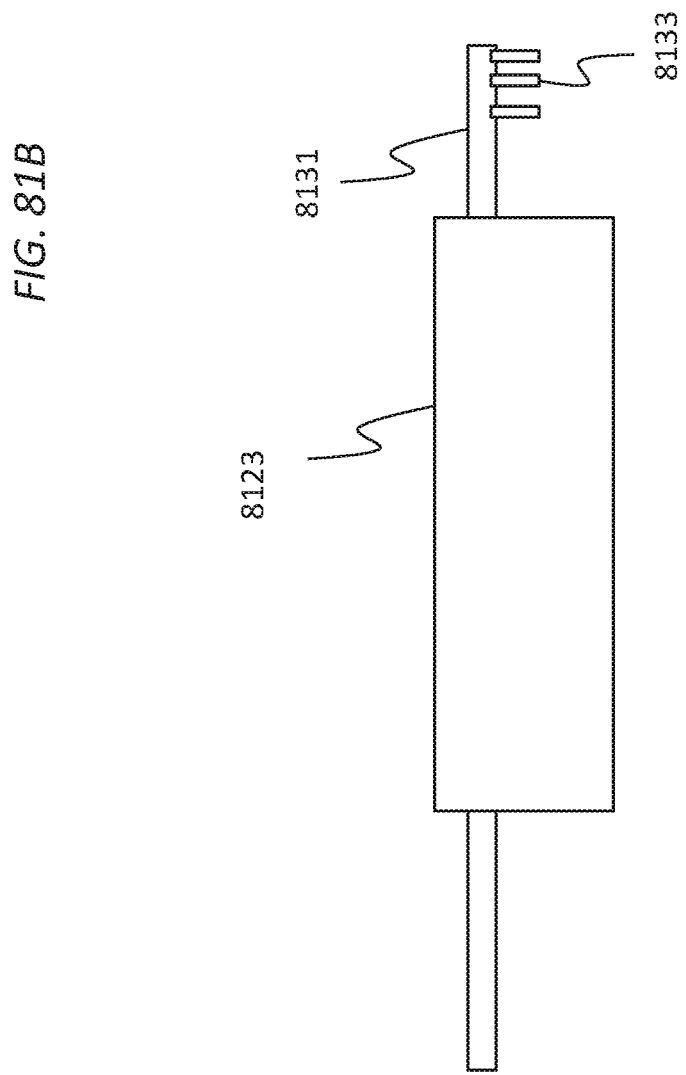
FIGS. 81B-H depict other exemplary embodiments of an actuator assembly usable with the embodiment of FIG. 77.
Figure 81C:
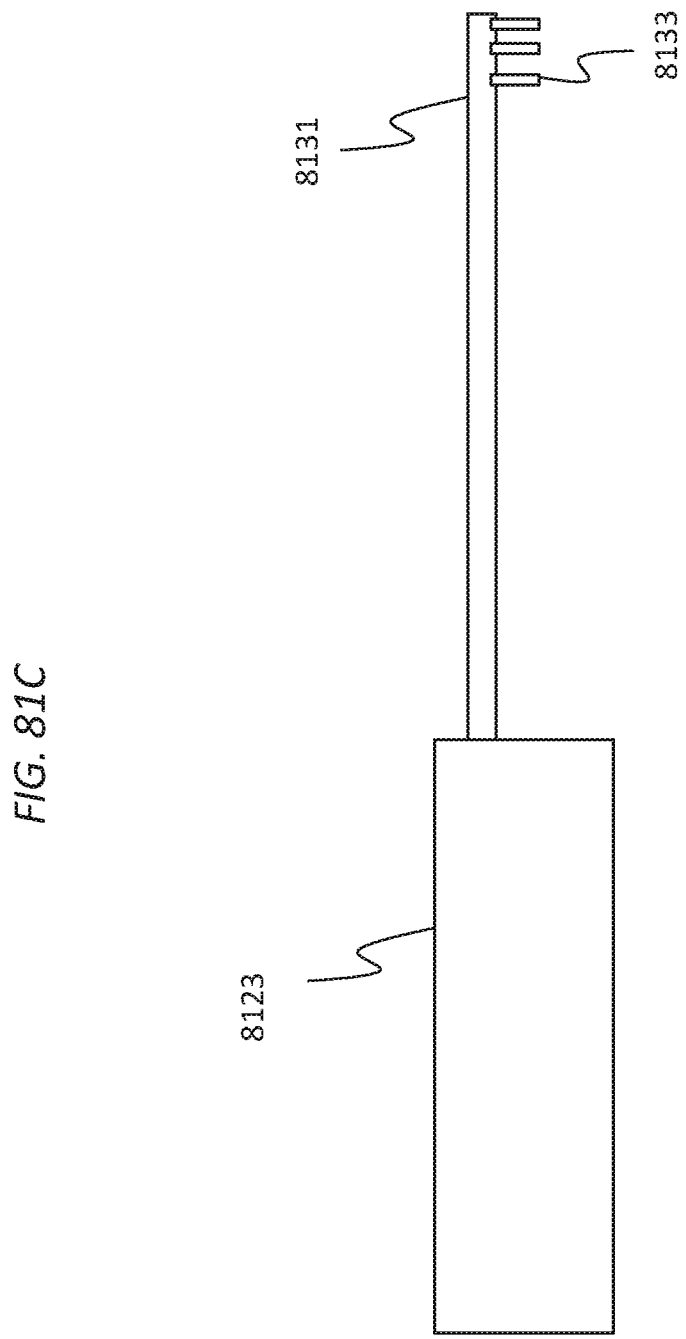

In an alternate embodiment, the actuator can be a linear actuator that drives the electrode array forward and/or backward by extending the working end of the actuator and retracting the working end of the actuator, where the working end is coupled in some form or another to electrode array. In this regard, FIG. 81B depicts an exemplary actuator apparatus 8123 that includes a retractable and extendable boom 8131. The actuator of the actuator apparatus 8123 is a linear actuator. That said, in an alternate embodiment, a rotary actuator can be utilized to extend and/or retract the boom 8131 (e.g., via the use of gears and sprockets or a rack and pinion system, or by the use of frictional rollers that extend and retract the boom 8131 as a result of friction forces between the rollers and the service of the boom 8131). Any actuator that can linearly extend and/or retract the boom 8131 can utilize in at least some exemplary embodiments. Still with reference to FIG. 81B, at the end of the boom, there are grips 8133. In an exemplary embodiment, grips 8133 are semicircular components sized and dimensioned to interface with a portion of the electrode array that is gripped. FIG. 81B depicts the grips on one side of the boom 8131. Not depicted in the figure are the grips on the other side of the boom which work in conjunction with the grips scene in the figure. In an exemplary embodiment, grips 8133 can be configured to open and close about the electrode array so as to releasably grip the electrode array. In an exemplary embodiment, the system of which the actuator assembly 8123 is a part is configured to automatically open and close the grips 8133/grip and release the electrode array via controlled actuation of actuators or other mechanical components and/or other electromechanical components that move the grips 8133 to open and/or close about the electrode array. FIG. 81B depicts the boom 8131 in a retracted state, such as that which exists when the electrode array is first loaded onto the actuator assembly 8123 prior to insertion into the cochlea. FIG. 81C depicts the boom 8131 in an extended state, such as that which occurs when the electrode array has been inserted into the cochlea via the actuator assembly.

Figure 81D:
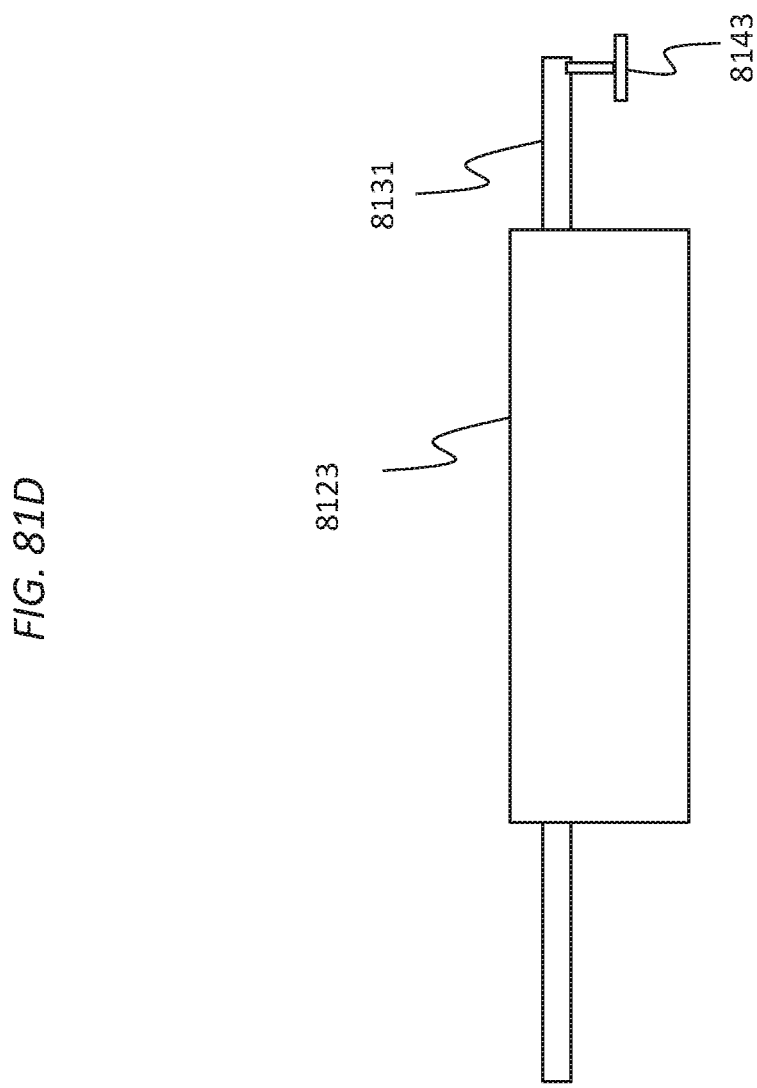

FIG. 81D depicts an alternate embodiment of a grip 8143, where an equal and opposite grip is located on the far side, and is eclipsed by the grip on the near side in the view of FIG. 81D. In an exemplary embodiment, the grip 8143 functions more as a tweezers or the like and grips the so-called "handle portion" of the extra cochlear portion of the electrode array—an area that is wider than the other portions of the electrode array and also flatter so as to enhance gripping by a tweezer like device during insertion. In at least some exemplary embodiments, the "handle portion" is an elongated shallow triangular shape with two legs that extend a length many times that of the third leg, where the third leg is normal to the direction of extension of the electrode array. In this regard, the elongated feature of the grip 8143 seen in FIG. 81D is such that the grips grip the shallow triangular portion of the electrode array so as to support and otherwise insert the electrode array into the cochlea. As with the embodiment detailed above, the grips 8143 are attached to electro mechanical actuators that open and close the grips about the electrode array to releasably grip the electrode array for insertion into the cochlea or otherwise to support the electrode array.

Figure 81E:
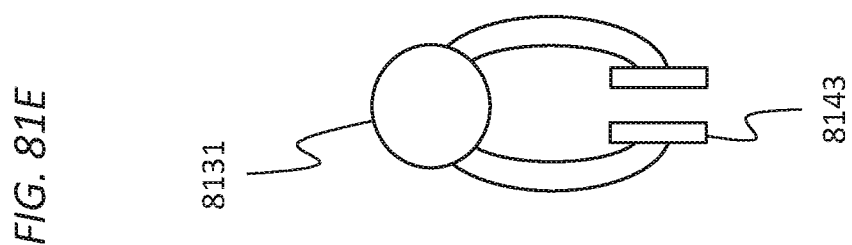
Figure 81F:
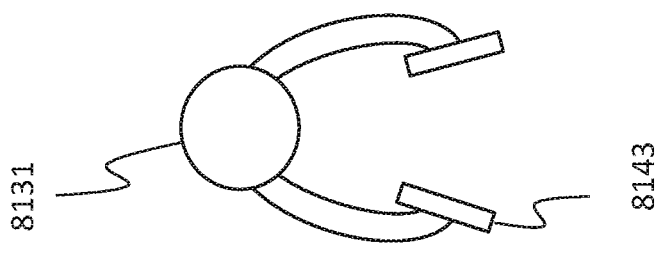

FIG. 81E depicts a view of the boom 8131 and the grips 8143 looking down the axis of the boom 8131 with the grips 8143 in a closed state (e.g., that which would be the case when the grips are gripping electrode array). FIG. 81F depicts a view having an orientation corresponding to that of FIG. 81E, but with the grips 8143 in an open position.

Figure 81G:
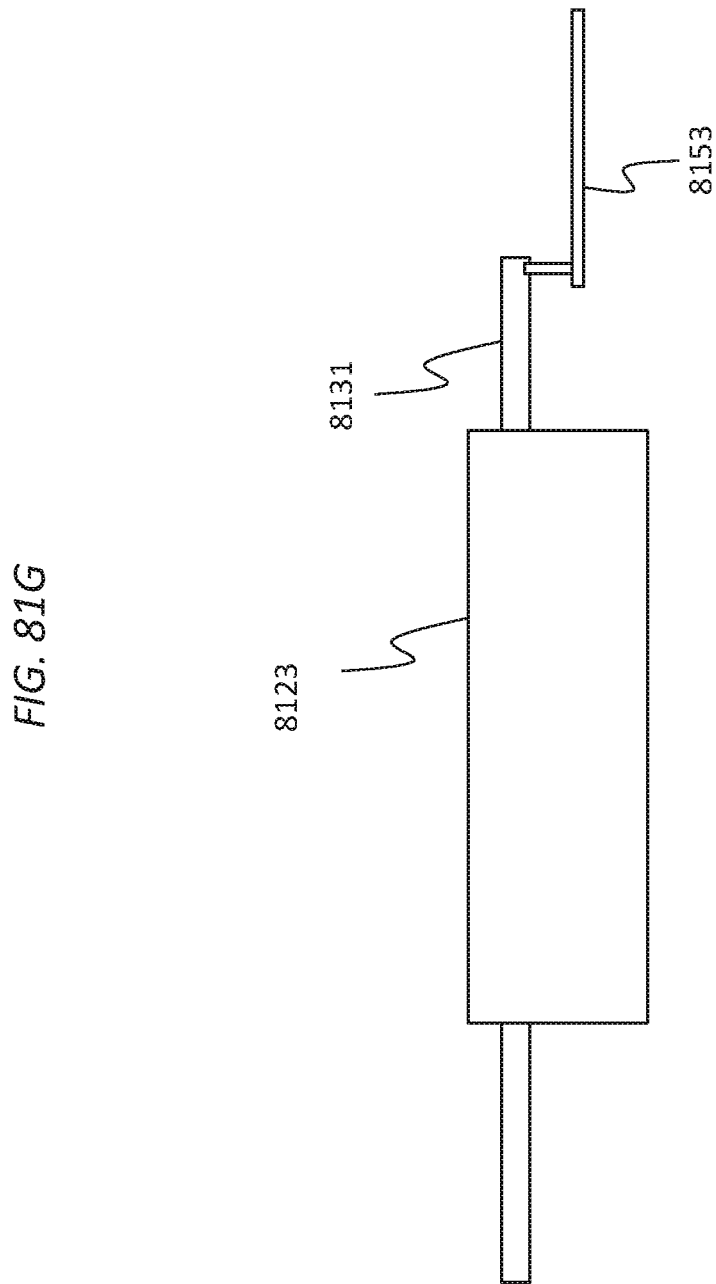
Figure 81H:
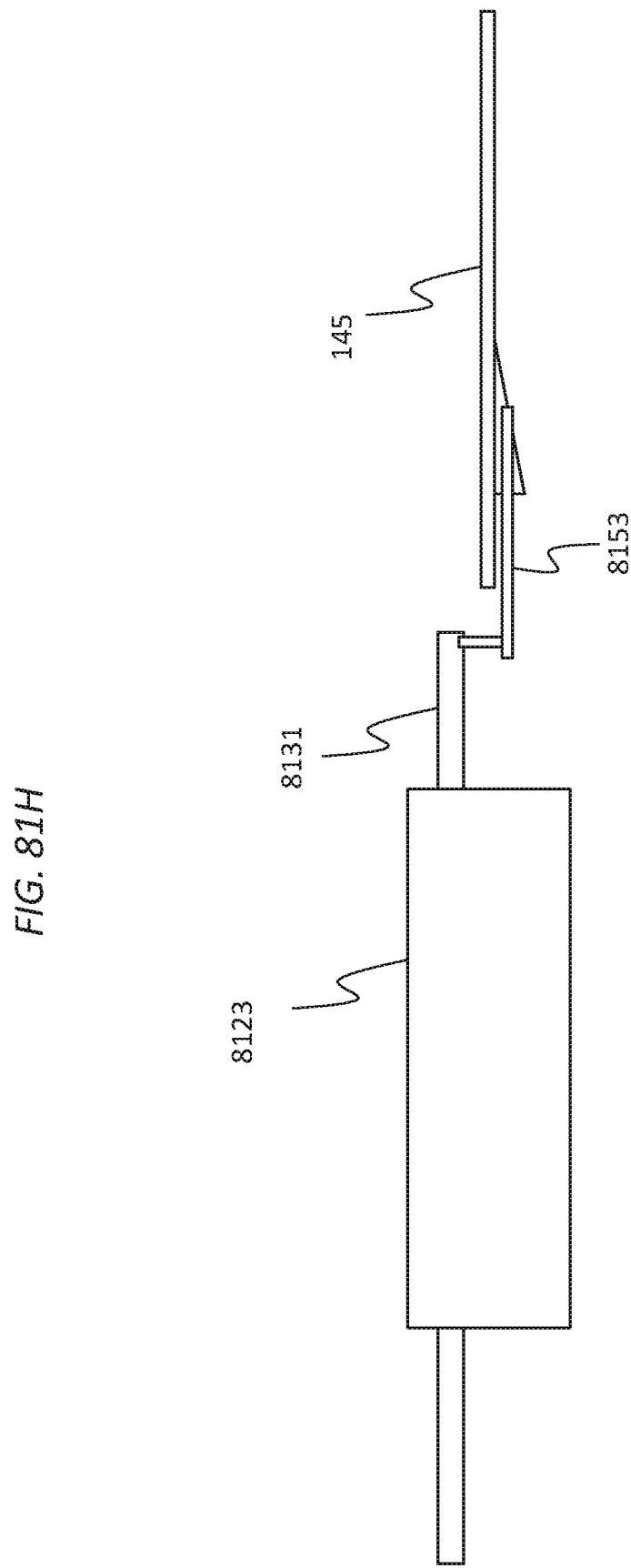

FIG. 81G depicts yet another alternate exemplary embodiment of an exemplary actuator assembly, where the grip 8153 extends and an elongated fashion. As with the embodiments detailed above, the grips 8153 open and close via electromechanical actuators. Here, the grips 8153 are elongated such that the grips extend a considerable way beyond the end of the boom 8131. This can provide additional clearance when inserting the electrode array into the cochlea. In this regard, the grips 8153 are configured so as to be structurally rigid so as to be able to support and grip and insert the electrode array even when the electrode array is held at the tips of the grips 8153 (e.g., the distal tips, as is depicted by way of example in FIG. 81H).

Any arrangement of advancing and/or retracting the actuator assembly can be utilized in at least some exemplary embodiments.

To be clear, the embodiment of FIG. 75 depicted above can also include the actuator assembly's detailed herein and/or variations thereof. That is, insertion guide 7700 can be attached to the arm 7510 of the system 400. Moreover, the actuators of the actuator assembly can be placed into signal communication with the control unit 440 or any other control unit of the system 400 to enable the control unit to advance and/or retract the electrode array. Note also that in some alternate embodiments, the system 400 is such that the only non-manually actuating component is the actuator assembly. That is, in an exemplary embodiment, system 400 can be such that the frame of the like is placed around the recipient's head and secured thereto, and the arm 7510 supporting the insertion guide attached thereto can be moved manually by the surgeon, such that the surgeon can align or otherwise place the insertion guide into the cochlea. In this regard, by way of example only and not by way of limitation, the insertion guide can be configured so as to attached to the arm 7510 on a trolley or the like. In an exemplary embodiment, the surgeon moves arm 7510 into position so that the insertion guide is aligned with the cochlea, at the desired angle, etc., and then be surgeon manually pushes the insertion guide forward into the cochlea (in the case of an intra-cochlear insertion guide) or against the cochlea in the case of a non-intra-cochlea insertion guide). After that, the actuator assembly can be utilized in a remote-controlled and/or automated manner.

That said, in an alternate embodiment, the general positions of the system 400 can be established utilizing manual methods, and then the positions can be refined utilizing automated/remote controlled methods (e.g., the actuators on the arm 7510 and/or the actuator at joint 426 can be actuated so as to finally position the insertion guide.

Note also that in some exemplary embodiments, the actuator assembly's detailed herein and/or variations thereof that are utilized to advance and/or retract the electrode array are configured to be utilized with an insertion tool that is handheld instead of being attached to arm 750 system 400. To this end, FIG. 82 depicts an exemplary insertion tool 8200 that includes actuator apparatus 7720 as seen. Hereinafter, the reference will often be made to actuator apparatus 7720 as utilized in conjunction with other components detailed herein. Any disclosure herein of the utilization of actuator apparatus 7720 in conjunction with other teachings detailed herein corresponds to a disclosure of the utilization of the actuator apparatus 8123 or any of the other actuator apparatuses detailed herein or variations thereof utilized to grip and support and/or insert the electrode array into the cochlea. FIG. 82 depicts a connector 67405 in signal communication with an actuator apparatus 7720, which connector is connected to connector 7407, which in turn is connected to a lead which extends to the control unit. In an exemplary embodiment, the surgeon holds the tool 8200 in the traditional manner of use, but the control unit controls the actuation of the actuator 7720 to advance and/or retract the electrode array. In an exemplary embodiment, the surgeon or other healthcare professional can exercise override control over the insertion of the electrode array and/or the retraction of the electrode array. For example, switching components of the like or other types of input devices can be located on the tool 8200 so that the surgeon or the like can provide input into the system of which the tool 8200 is a part. In an alternate embodiment, the tool 8200 can include an input device that interacts with the surgeon, where the surgeon provides the direction to the system advance and/or retract the electrode array, but the control unit evaluates the inputs from the surgeon and controls the actuation accordingly. By way of example only and not by way of limitation, such a system can be analogous to a fly by wire system on an aircraft, where the pilot moves the controls in a manner correlated to the direction that the pilot wants the aircraft to move, and the flight control system controls everything else to achieve the desired outcome. Note also that any the other actuators detailed herein and/or variations thereof can be part of a system that is operated in a similar manner. By way of example only and not by way of limitation, the system 400 can be configured such that the surgeon pushes on the arm 7510 to move the insertion guide is desired, but the system 400 moves the arm 7510 using actuators. That is, the system 400 is configured to sense or otherwise detect the force is applied on to the structure thereof by the surgeon, and then determine what actuator action should be executed so as to position the insertion guide at the desired location in a manner analogous to fly by wire.

It is noted that the electrical lead assembly and the connectors thereof depicted in FIG. 82 can be applicable to any of the insertion guides detailed herein and/or variations thereof so as to place the insertion guide in general, and the actuator assembly thereof in particular, into signal communication with the control unit or other controllers of the system. Note also that in an exemplary embodiment, the lead apparatus depicted in FIG. 82 can be utilized to also convey the other signals detailed herein and/or variations thereof with respect to the other functionalities associated with the insertion guides. Alternatively, and/or in addition to this, the other lead apparatuses detailed herein and variations thereof can be utilized to convey the signals from the actuator apparatus 7720 to the control unit or the like when the insertion guides detailed above are utilized in conjunction with the actuator assembly so as to provide a machine drive to advance and/or retract the electrode array. Any device, system and/or method of communication between any functional component of any of the insertion guides detailed herein and/or variations thereof with a control unit and/or vice versa and/or the implantable component of the electrode array, etc., can be utilized in at least some exemplary embodiments It is also noted that while the embodiments detailed herein have been directed towards an electrode array guide, it is also noted that in some alternate embodiments, an electrode array support is instead utilized, which support may not necessarily guide the electrode array, but otherwise might simply support the electrode array proximate to the cochlea. Note that in an electrode array support can also be an electrode array guide, and vice versa.

In view of the above, it can be understood that in an exemplary embodiment, there is an apparatus, such as any of the insertion guides detailed herein and/or variations thereof, that includes an electrode array support, and an actuator. In at least some of these exemplary embodiments, the apparatus is configured to inserts an electrode array into cochlea by a controlled actuation of the actuator. In an exemplary embodiment of such an exemplary embodiment, the controlled actuation is at least partially based on electrical phenomenon of the recipient. Some additional details of such will now be described.

As noted above, some exemplary embodiments of the insertion guides can be utilized with or otherwise as a part of an ECoG system. By way of example only and not by way of limitation, the embodiments of FIGS. 19 to 40 can be utilized in part or in whole in conjunction with an ECoG system. Accordingly by way of example only and not by way of limitation, in an exemplary embodiment, those embodiments can be combined with the actuator apparatus of the embodiment of FIG. 76 or the variations thereof. That said, in an alternate embodiment, the embodiment of FIG. 76 and variations thereof can be utilized in conjunction with a separate ECoG system completely separate from the insertion guide, except that a control unit or the like receive signals or other data from the separate ECoG system and evaluates the systems to output a signal to the actuator apparatus of the insertion guide, thus controlling the actuator apparatus to advance and/or retract the electrode array.

Figure 83:
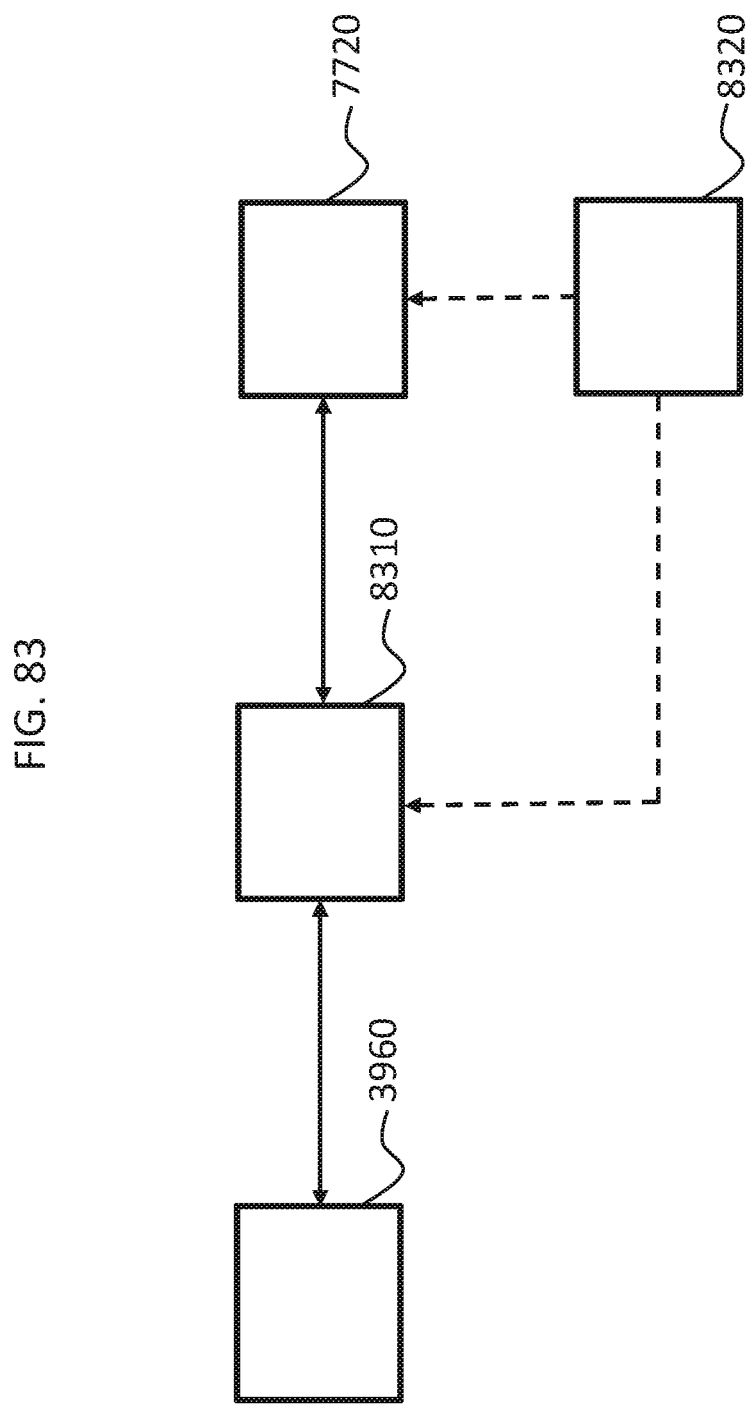
FIG. 83 depicts an exemplary functional diagram of an exemplary embodiment.

FIG. 83 depicts an exemplary functional schematic of an exemplary system that includes the ECoG test unit 3960 detailed above in signal communication with a control unit 8310 which is in turn in signal communication with the actuator assembly 7720.

(Briefly, it is noted that while the following embodiment is described in terms of an ECoG test unit that is integral with the system 400 in general, and utilizes componentry that is a part of the robot assembly (e.g., an ECoG measurement electrode supported by a insertion guide, concomitant with the embodiments detailed above the insertion guides), alternative embodiments utilize an ECoG system that is separate from the system 400 in general, and separate from the robot assembly in particular. By way of example only and not by way of limitation, the measurement electrodes of the ECoG system could be mounted in a traditional manner, and, in fact, could be held by hand, and the acoustic signal generator could also be held by hand, and the ECoG system could provide a signal to the system 400 in general, and the control unit thereof in particular, which control unit evaluates the signal so as to implement the teachings detailed herein.)

Also functionally depicted in FIG. 83 is the optional embodiment where an input device 8320 is included in the system (e.g., which could be on an embodiment where the actuator assembly 7720 is part of a hand tool (e.g., the embodiment of FIG. 82) or where actuator assembly 7720 is part of an insertion guide, where the input device 8320 is located remote from the insertion guide, which could be part of a remote unit 440). In an exemplary embodiment, the input device 8320 could be the trigger for 54 and/or 464 of the remote control unit 440. In an exemplary embodiment, the input device 8320 could be a trigger on the tool 8200. Again, in an exemplary embodiment, the input device 8320 can be utilized to enable advancement and/or withdrawal of the electrode array, and the system 400 could control the advancement and/or withdrawal based on an automated protocol or some other flyby wire type system. In the embodiment of FIG. 83, the input device 8320 can be in signal communication directly to the actuator assembly 7720, and/or in signal communication with the control unit 8310.

In an exemplary embodiment, control unit 8310 can correspond to the remote unit 440. That said, in an alternate embodiment, remote unit 440 can be a device that is in signal communication with control unit 8310. Indeed, in an exemplary embodiment, input device 8320 can correspond to remote control unit 440.

More particularly, control unit 8310 can be a signal processor or the like or a personal computer or the like or a mainframe computer or the like etc., that is configured to receive signals from the ECoG test unit 3960 and analyze those signals to evaluate an insertion status of the electrode array. More particularly, the control unit 83 can be configured with software the like to analyze the signals from test unit 3960 in real time and/or in near real time as the electrode array is being advanced into the cochlea by actuator assembly 7720. The control unit 8310 analyzes the input from test unit 3960 as the electrode array advanced by the actuator assembly 7720 and evaluates the input to determine if there exists an undesirable insertion status of the electrode array and/or evaluates the input to determine if the input indicates that a scenario could occur or otherwise there exists data in the input that indicates that a scenario is more likely to occur relative to other instances where the insertion status of the electrode array will become undesirable if the electrode array is continued to be advanced into the cochlea, all other things remaining the same (e.g., insertion angle/trajectory, etc., which can be automatically changed as well via—more on this below). In an exemplary embodiment, upon such a determination, control unit 8310 could halt the advancement of the array into the cochlea by stopping the actuator(s) of actuator assembly 7720 and/or could slow the actuator(s) so as to slow rate of advancement of the electrode array into the cochlea and/or could reverse the actuator(s) so as to reverse or otherwise retract the electrode array within the cochlea (either partially or fully). In at least some exemplary embodiments, control unit 8310 can be configured to override the input from input unit 8320 input by the surgeon or the user or the like of the system of FIG. 83.

In an exemplary embodiment, the outputs of test unit 3960 corresponds to the output of test unit 560 detailed above. Alternatively and/or in addition to this, input into control unit 8310 can flow from other sources. Any input relating to the measurement of voltage associated with ECoG measurements into control unit 8310 can be utilized in at least some exemplary embodiments.

In an exemplary embodiment, control unit 8310 can be configured to determine, based on the input from test unit 3960, whether the electrode array has come into contact with the basilar membrane of the cochlea and/or whether there exists an increased likelihood that such contact will occur, and automatically control the actuator assembly 7720 accordingly. In an exemplary embodiment, control unit 8310 does not necessarily determine that such an insertion status exists or is more likely to exist, but instead is programmed or otherwise configured so as to control the actuator assembly 7720 according to a predetermined regime based on the input from the test unit 3960. That is, the control unit 8310 need not necessarily "understand" otherwise "know" the actual insertion status or the forecasted insertion status of the electrode array, but instead need only be able to control the actuator assembly 7720 based on the input.

In an exemplary embodiment, control unit 8310 can be configured to determine, based on the input from test unit 3960, the insertion depth of the electrode array and/or a forecasted insertion depth of the electrode array, and automatically control the actuator assembly 7720 accordingly. In an exemplary embodiment, control unit 8310 does not necessarily determine the insertion depth or forecasted insertion depth, but instead is programmed or otherwise configured so as to control the actuator assembly 7720 according to a predetermined regime based on the input from the test unit 3960. That is, the control unit 8310 need not necessarily "understand" otherwise "know" the actual insertion depth or the forecasted insertion depth of the electrode array, but instead need only be able to control the actuator assembly 7720 based on the input.

In an exemplary embodiment, control unit 8310 can be configured to determine, based on the input from test unit 3960, whether the electrode array has buckled and/or bent and/or whether there exists an increased likelihood that such buckling and/or bending will occur, and automatically control the actuator assembly 7720 accordingly. In an exemplary embodiment, control unit 8310 does not necessarily determine that such buckling and/or bending exists or is more likely to exist, but instead is programmed or otherwise configured so as to control the actuator assembly 7720 according to a predetermined regime based on the input from the test unit 3960. That is, the control unit 8310 need not necessarily "understand" otherwise "know" that the electrode array has actually buckled or will buckle in the future, but instead need only be able to control the actuator assembly 7720 based on the input.

Thus, it can be understood that there is an apparatus that is configured to receive input indicative of the electrical phenomenon/phenomena inside the recipient, and develop data indicative of a position of the electrode array within the cochlea based on the input. (It is briefly noted that unless otherwise specified, the singular term phenomenon also includes a disclosure of the plural thereof, and vis-a-versa, as is also the case with the disclosure of data). Still further, such an exemplary embodiment can be configured to adjust the control of the actuation of the actuator based on the develop data indicative of the position of the electrode array.

Figure 84:
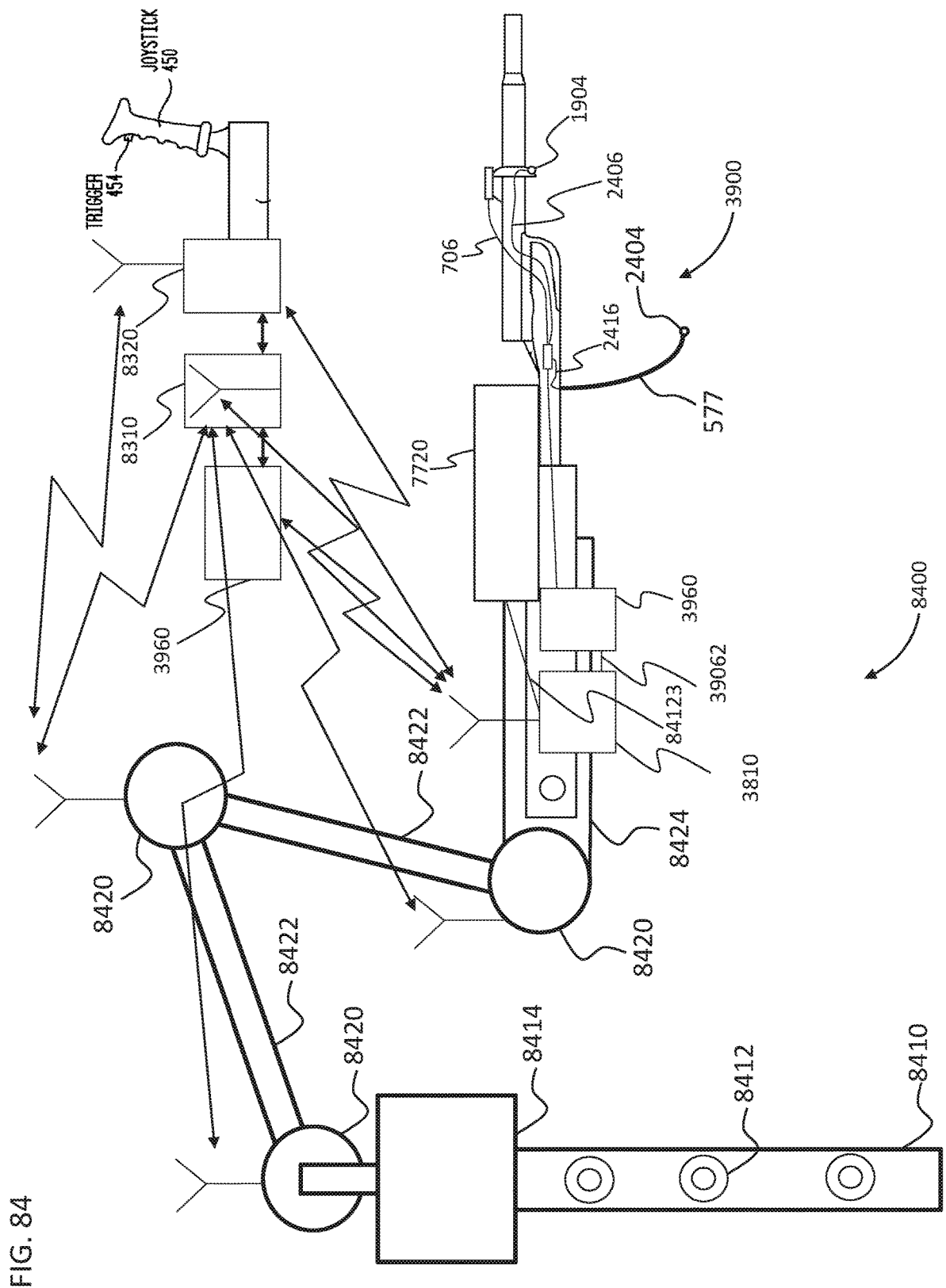
FIG. 84 depicts an exemplary embodiment of an exemplary robot apparatus.

To be clear, while the embodiment detailed above is focused on controlling the actuator assembly 7720 based on data from the ECoG system so as to control the advancement and/or retraction of the electrode array based on electrical phenomenon/phenomena inside the recipient and/or based on electrical characteristics associated with the recipient, in an alternate embodiment, the system 400 controls one or more other actuators of the robot apparatus of system 400. These one or more other actuators can be exclusive from the actuator assembly 7720, or can include the actuator assembly 7720. In this regard, FIG. 84 depicts an exemplary robot apparatus 8400, that includes the insertion guide 3900 detailed above with respect to the integration of an ECoG system therewith, mounted on arm 8424 utilizing bolts in a manner concomitant with that detailed above. In an exemplary embodiment, robot apparatus 8400 has the functionality or otherwise corresponds to that of the embodiment of FIG. 75. In this regard, any functionality associated or otherwise described with respect to the embodiment of FIG. 75 corresponds to that of the embodiment of FIG. 84, and vice versa. In this exemplary embodiment, the actuator apparatus 7720 is in signal communication with unit 3810 via electrical lead 84123. In this regard, signals to and/or from the actuator assembly 7720 can be transmitted to/from the antenna of unit 8310 (in FIG. 84, the "Y" shaped elements are antennas) and thus communicated via lead 84123. It is briefly noted that while the embodiment depicted in FIG. 84 utilizes radiofrequency communication, in alternate embodiments, the communications can be wired. In an exemplary embodiment both can be utilized.

That said, with the addition of the actuator assembly 7720 and the communication components associated there with, insertion guide 3900 corresponds to that of FIG. 39.

The robot apparatus 8400 includes a recipient interface 8410 which entails an arch or halo like structure made out of metal or the like that extends about the recipient's cranium or other parts of the body. The interface 8410 is bolted to the recipient's head via bolts 8412. That said, in alternate embodiments, other regimes of attachment can be utilized, such as by way of example only and not by way of limitation, strapping the robot to the recipient's head. In this regard, the body and interface 8410 can be a flexible strapping can be tightened about the recipient's head.

Housing 8414 is located on top of the interface 8410, as can be seen. In an exemplary embodiment, housing 8414 includes a battery or the like or otherwise provides an interface to a commercial/utility power supply so as to power the robot apparatus. Still further, in an exemplary embodiment, housing 8414 can include hydraulic components/connectors to the extent that the actuators herein utilize hydraulics as opposed to and/or in addition to electrical motors. Mounted on housing 8414 is the first actuator 8420, to which arm 8422 is connected in an exemplary embodiment, actuator 8420 enables the components "downstream" (i.e., the arm connected to the actuator, and the other components to the insertion guide) to articulate in one, two, three, four, five or six degrees of freedom. A second actuator 8420 is attached to the opposite end of the arm 8422, to which is attached a second arm 8422, to which is attached a third actuator 8420, to which is attached to the insertion guide attachment structure 8424. Elements 8422 and 8424 can be metal beams, such as I beams or C beams or box beams, etc. actuators 8420 can be electrical actuators and/or hydraulic actuators.

As can be seen, each actuator 8420 is provided with an antenna, which antenna is in signal communication with the control unit 8310. In an exemplary embodiment, control unit 8310 can control the actuation of those actuators 8420 so as to position the insertion guide 3900 at the desired position relative to the recipient. That said, in an alternate embodiment, a single antenna can be utilized, such as one mounted on housing 8414, which in turn is connected to a decoding device that outputs a control signal, such as a driver signal based on the decoded RF signal, to the actuators 8420 (as opposed to each actuator having such a device), which control signals can be provided via a wired system/electrical leads extending from housing 8414 to the actuators. Note also that in some alternate embodiments, control unit 8310 is in wired communication with the actuators, either directly or indirectly, and/or is in wired communication with the decoding device located in the housing 8414. Any arrangement that can enable control of the robot apparatus in general, and the actuators thereof in particular, via control unit 8310 can be utilized in at least some exemplary embodiments.

Note also that while the embodiment depicted in FIG. 84 is such that the actuators 8420 must actuate so as to extend the intracochlear portion of the insertion guide into the cochlea, in an alternate embodiment, as noted above, the insertion guide can be mounted on a rail system or the like, wherein a cylindrical actuator or the like pushes the insertion guide in a linear manner into the cochlea and withdrawals the insertion guide in the linear manner from the cochlea. In an exemplary embodiment, this actuator apparatus can enable one degree of freedom movements of the insertion guide, while in other embodiments, this actuator apparatus can enable two or three or four or five or six degrees of freedom. Indeed, in an exemplary embodiment, this actuator apparatus can enable movement only in a linear direction, but can enable rotation of the insertion guide about the longitudinal axis thereof. Any arrangement of actuator assemblies that will enable the insertion guide to be positioned relative to the cochlea and/or inserted into the cochlea via robotic positioning thereof can be utilized in at least some exemplary embodiments.

As can be seen, the insertion guide 3900 is in signal communication with the ECoG test unit 3960, which in turn is in signal communication with the control unit 3810. Note that in some alternate embodiments, signals from the insertion guide are only directed to the control unit 3810, which signals are then relayed to the ECoG test unit 3960 for analysis of the like. Any arrangement of signal communication with the ECoG components of the insertion guide can be utilized in at least some exemplary embodiments.

Still further, note that the interface unit 3820 is depicted in signal communication with the antenna of the insertion guide 3900. It is further noted that, even though the link between the interface unit 3820 is not depicted between every actuator of the robot apparatus 8400, in some exemplary embodiments, the interface unit 3820 is in signal communication with all of the actuators of the robot apparatus 8400. Again, the interface unit 8320 can be a unit that provides override or the like of the system, and/or can be a unit that provides the course positioning of the insertion guide 3900, with the control unit 8310 providing the fine positioning of the insertion guide 3900.

It is noted that in an exemplary embodiment, the teachings detailed herein can be utilized in conjunction with the sensing unit 432. Briefly, any of the methods detailed herein and/or variations thereof can be combined with the utilization of the sensing unit 432 and the functionalities thereof. Moreover, control of the insertion of the electrode array via control unit 3810 vis-à-vis the robotic apparatuses detailed herein and/or variations thereof can be performed in conjunction with data from the sensing unit 432. By way of example only and not by way of limitation, the controller 8310 can receive feedback or otherwise data from the sensing unit 432 during the insertion process. Such exemplary feedback could be data indicating a distance of the electrode array from a wall of the cochlea, etc. The control unit 8310 can evaluate this data and make adjustments to the various actuators of the robotic system accordingly. By way of example only and not by way of limitation, if the data from sensing unit 432 indicates that continued advancement of the electrode array along a given trajectory will result in contact of the electrode array with the modiolis wall of the cochlea, control unit 8310 can adjust the angular orientation of the insertion guide to avoid contact with the wall. Alternatively, and/or in addition to this, control unit 8310 can simply halt continued advancement of the electrode array in an automated fashion.

Briefly, as noted above, some exemplary embodiments include an ultrasonic transducer mounted on the insertion guide, which ultrasonic transducer is configured to provide ultrasonic imaging or otherwise provide data with respect to features within the cochlea of the recipient. By way of example only and not by way of limitation, as a matter of functional and conceptual teachings, aforementioned sensing unit 432 can correspond to the ultrasonic transducer. By way of example only and not by way of limitation, the output from the ultrasonic transducer can be provided to the control unit 8310, which control unit can evaluate the output from the ultrasonic transducer and control the robotic assembly accordingly.

As will be understood from FIG. 84, an exemplary embodiment include systems that not only control the insertion and/or retraction of the electrode array 145 into and out of the cochlea, but also control the positioning of that electrode array 145, whether utilizing and insertion guide or an electrode array support, relative to the cochlea. In an exemplary embodiment, such can be done at least partially based on electrical phenomenon of the recipient/based on electrical characteristics associated with the recipient. Indeed, such encompasses a scenario where the insertion angle of the electrode array is changed during the insertion process based on the electrical phenomenon of the recipient/based on electrical characteristics associated with the recipient monitored during the insertion process. In this exemplary embodiment, the electrical phenomenon/electrical characteristics correspond to that sensed or otherwise measured by an ECoG system. Thus, in an exemplary embodiment, there is an apparatus that is configured to insert the electrode array into a cochlea via controlled actuation of an actuator, wherein the controlled actuation is at least partially based on ECoG data, wherein the ECoG data is based on the electrical phenomenon of the recipient/based on electrical characteristics associated with the recipient. Note that such can also include controlling actuation based on other phenomenon such as by way of example only and not by way of limitation, resistance to insertion of the electrode array measured by a sensor or the like one the robot apparatus, as long as the actuation is controlled at least partially based on ECoG data.

It is briefly noted that in at least some exemplary embodiments, the control of the robot and the like or otherwise control the components of the system utilized to insert the electrode array can be based on analysis of the measurements or otherwise data from the measurement electrodes, etc., of the system as follows. By way of example only and not by way of limitation, the system can be configured, such as via the utilization of a processor or the like with a programmed algorithm, where the processor is in electrical communication either directly or indirectly with the measurement electrodes of the like, where if a measured quantity exceeds or is below or is at a predetermined threshold, which threshold can be a generic threshold for all recipients or a specific threshold developed for a specific recipient (the threshold could be a dynamic threshold—other measurements in real time could influence the threshold, thus changing the threshold based on the other measurements), or when a directional rate of change of the quantity exceeds a certain threshold or meets a certain threshold or is below a certain threshold, the algorithm could automatically control one or more of the actuators to adjust the insertion process (or the withdrawal process), which includes halting the insertion process, based on the various thresholds. (It is noted that while the aforementioned thresholds are directed towards the ECoG system, similar thresholds can be utilized for the other measurement/telemetry systems detailed herein and/or variations thereof).

Figure 85:
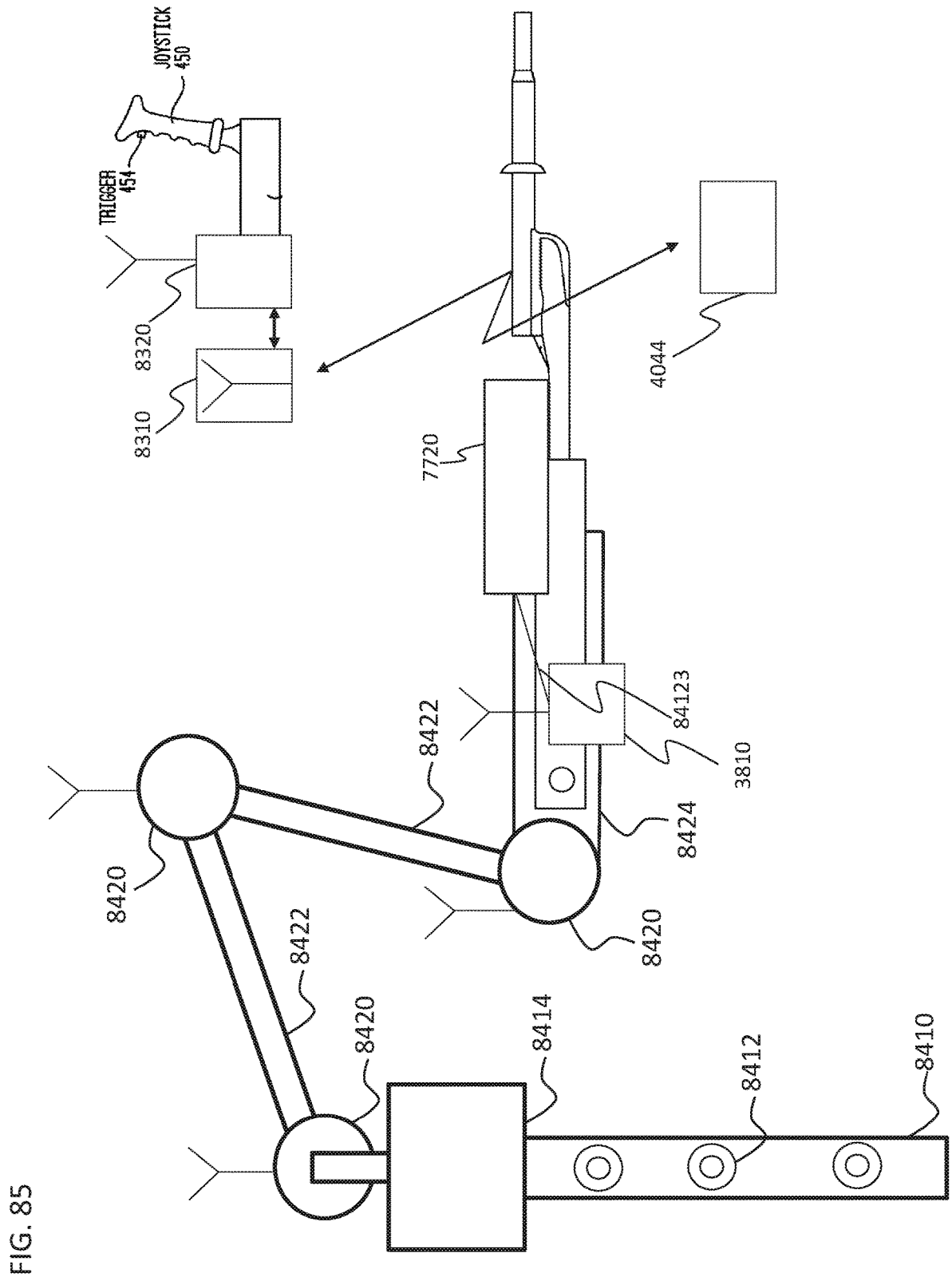
FIG. 85 depicts an exemplary embodiment of an exemplary robot apparatus with some of the details presented in FIG. 84 removed for clarity purposes associated with this embodiment and the embodiment of FIG. 84.

Again, while the embodiment of FIG. 84 is depicted as having components of an ECoG system that is part of the robot apparatus 8400, in an alternative embodiment, the ECoG system is a separate component from the robot apparatus, which is in signal communication with the robot apparatus and/or the control unit thereof of the system of which the robot apparatus is a part. FIG. 85 presents such an exemplary embodiment, with the links between the antennas removed for clarity. ECoG system 4044 detailed above is shown in signal communication with control unit 8310. In this exemplary embodiment, ECoG system 4044 corresponds to that detailed above with the exception that it is entirely divorced from the insertion guide (save for the communication between ECoG system 4044 and the control unit 8310, to the extent such is relevant for the purposes of discussion, where control unit 8310 is in signal communication with one or more of the assemblies of the robot apparatus of FIG. 88, such as the actuator assembly 7720. Here, during insertion, and/or prior to insertion and/or after insertion, the ECoG system 4044 monitors or otherwise measures electrical phenomenon associated with the recipient/electrical characteristics associated with the recipient and communicates those measurements and/or the analysis thereof to control unit 8310, which analyzes those signals and develops a control regime for electrode array insertion and/or electrode array positioning based on those signals. Note also that in some exemplary embodiments, the ECoG system can have multiple measurement electrodes and/or signal generators/sources of acoustic signal generation, some of which are part of the robot apparatus, and some of which are separate from the robot apparatus, all of which are part of system 4044. Alternatively, these various components of ECoG system can communicate with test unit 3960. Such can have utilitarian value with respect to a scenario where ECoG measurements are first taken prior to placing the electrode array near the cochlea and after inserting the electrode array into the cochlea, where it is undesirable to have the insertion guide and/or electrode array support proximate the cochlea. Any device, system, and/or method that will enable controlled movement of the electrode array relative to the cochlea based on electrical phenomenon associated with the recipient/based on electrical characteristics associated with the recipient can be utilized in at least some exemplary embodiments.

In view of the above, it is to be understood that in an exemplary embodiment, the robot apparatus is configured such that the electrode array support is an insertion tool including an electrode mounted their one, wherein the apparatus is configured to utilize the electrode to obtain data indicative of the electrical phenomenon of the recipient/data indicative of electrical characteristics associated with the recipient. Of course, in some alternate embodiments, two or more electrodes are mounted on the insertion tool. Still further, in an exemplary embodiment, the actuator is configured to drive the electrode array relative to the insertion tool to insert the electrode array into the cochlea, which driving by the actuator is controlled based on the electrical phenomenon associated with the recipient/based on electrical characteristics associated with the recipient.

In view of the above, it can be understood that in an exemplary embodiment, there is a system, such as the system of 400 detailed above, including a robotic assembly, such as the assembly of FIGS. 84 and 85 and 75, wherein the robotic assembly is configured to move the electrode array relative to the cochlea. In an exemplary embodiment, this corresponds to advancing the electrode array into the cochlea and/or with drawing at least a portion of the electrode array from the cochlea. In an exemplary embodiment, this entails moving the electrode array from a first location outside the cochlea to a second location outside the cochlea. In an exemplary embodiment, this entails changing the angle of the electrode array relative to the cochlea, whether such be executed prior to the insertion of the electrode array into the cochlea, during insertion of the electrode array into the cochlea (whether such occurs while the electrode array is being advanced or during a pause in advancement in the electrode array, etc.). Still further, the system includes a control unit such as the control unit 8310 detailed above, configured to receive a recipient physiological data and control the robotic assembly based at least in part on the data. Consistent with the embodiments detailed above, in some embodiments, the physiological data corresponds to electrical phenomenon associated the recipient/electrical characteristics associated with the recipient, such as that which is measured by an ECoG system. That said, in other embodiments, other physiological data can be utilized. Any physiological data that can be utilized to control the robotic assembly can be utilized in at least some exemplary embodiments.

Still further, in an exemplary embodiment, this system is configured to evaluate the recipient physiological data to develop data indicative of a position of the electrode array relative to the cochlea. Such position information can include the exact position of the electrode array, as will be described in greater detail below, but can also correspond to that detailed above, such as determining whether the electrode array has come into contact with basilar membrane, which corresponds to data indicative of a position of the electrode array relative to the cochlea. Still further, in an exemplary embodiment, the apparatus is configured to control the robotic assembly while moving the electrode array into the cochlea based on the develop data indicative of the position of the electrode array. As detailed above, such can entail halting the insertion of the electrode array based on the develop data. Such can also entail with drawling at least a portion of the electrode array from the cochlea based on the develop data. Such can entail slowing and/or speeding the insertion of the electrode array based on the develop data (e.g., the speed at which the electrode array travels through the insertion sheath/past the wall of the cochlea at the cochleostomy, etc.). That said, such can entail changing an angle of trajectory of the insertion of the electrode array, which angle of trajectory can be changed before insertion of the electrode array into the cochlea, during the process of inserting the electrode array to the cochlea (whether such occurs while the electrode array is moving into the cochlea or during a pause in the insertion of the electrode array to the cochlea, etc., and/or while the electrode array is being withdrawn from the cochlea or during a pause thereof etc.), or after the election array is inserted into the cochlea.

Still further, as noted above, some exemplary embodiments of the systems detailed herein are utilized in conjunction with systems that can enable the detection of buckling and/or bending of an array, and/or contact of the electrode array with the basilar membrane of the cochlea, etc. as detailed above, exemplary embodiments can be configured so as to control one or more of the actuators of the robotic assembly based on the occurrence of such event (the detection or the indication of the occurrence of such event, such as based on the ECoG data, etc.), or based on a forecast that such event is likely to occur if the electrode array is continued to be inserted into the cochlea according to a current insertion regime. Thus, in an exemplary embodiment, the control unit of the system detailed above can be configured to evaluate the recipient physiological data to determine whether a deleterious array insertion event has occurred or is likely to occur, and the control unit is configured to control the robotic assembly based at least in part on this evaluation (e.g., to stop or otherwise halt advancement of the electrode array into the cochlea, reverse advancement, change the trajectory of the electrode array insertion etc.).

While the embodiments detailed above have focused on ECoG measurements or the like, in some alternate embodiments, controlled actuation of the actuators of the robotic assembly is at least partially based on voltage measurements during electrical stimulation data/voltage measurements during energizement of an electrode inside the recipient (either by an electrode of a cochlear electrode array and/or by the electrode(s) of the insertion guide (sometimes referred to as voltage tomography). In an exemplary embodiment, the voltage measurement during electrical stimulation/relating to energizement of an electrode inside the recipient data is based on the electrical phenomenon of the recipient/based on electrical characteristics associated with the recipient. In this regard, at least some instances are such where the voltage measurements during electrical stimulation/energizement of an electrode inside the recipient is based at least in part on the electrical phenomenon of the recipient/based at least in part on electrical characteristics associated with the recipient. Such can have utilitarian value with respect to identifying a tip fold-over condition, and angular insertion depth of the electrode array, a linear or absolute insertion depth of the electrode array, a relative location of the electrode array to a wall of the cochlea, and occurrence of twisting of the array, and/or a determination of a punctual of the basilar membrane. Other occurrences can also be identified utilizing such data.

Briefly, while the embodiment of FIG. 64 detailed above has been presented in terms of utilizing an electrode on the insertion guide, some exemplary embodiments are such that the voltage measurements are achieved utilizing only the electrodes of the electrode array. In this regard, while some embodiments of the systems detailed herein utilizing the robotic apparatus utilize an electrode of the insertion guide to obtain at least some of the voltage measurements so that the actuators can be controlled based on those measurements, some alternate embodiments include utilizing electrodes of the electrode array to obtain those voltage measurements. Thus, the following is somewhat different from the embodiment detailed above with respect to FIG. 64, although similarities will be seen as well. To be clear, method 300 of the embodiment of FIG. 64 can be utilized in conjunction with a robotic apparatus of the like, where at least some of the results of executing that method can be utilized to control the actuators of the robotic assembly. However, the following will be focused on a different manner of obtaining the voltage measurements, which measurements are utilized at least in part to control the actuators.

Figure 86:
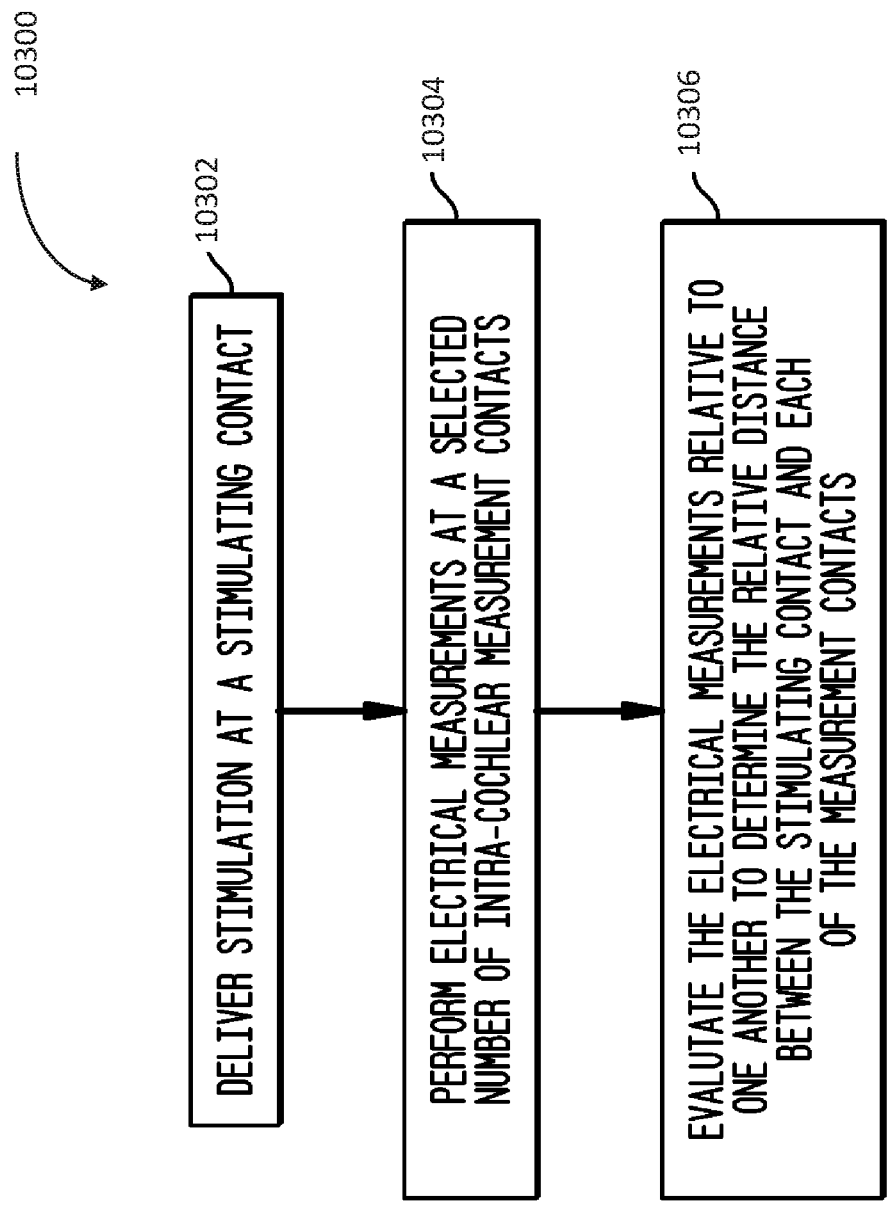
FIG. 86 presents an exemplary flowchart for an exemplary method according to an exemplary embodiment Nicole and FIG. 87 depicts an exemplary system according to an exemplary embodiment that utilizes the robot apparatus according to the teachings detailed herein.

FIG. 86 is a flowchart of a method 10300 for monitoring the physical state of the electrode array (sometimes herein referred to as a stimulating assembly) through the use of localized stimulation, where the data that results from executing that method can be used to control the actuator(s) of the robot assembly. The method 10300 of FIG. 86 is sometimes referred to herein as a localized monitoring method as the method uses the delivery of localized stimulation (i.e., current signals) to induce voltages at a plurality of other contacts.

Method 10300 begins at 10302 where stimulation (i.e., one or more current signals) is delivered/sourced at a selected intra-cochlear electrode (sometimes referred to herein as contact, as noted above). In one specific example, the stimulation is delivered at the most distal/apical electrode/contact and is sunk at the second most distal electrode/contact (i.e., the contact adjacent to contact). The electrode/contact that delivers the current signals is sometimes referred to herein as the "stimulating" or "source" electrode/contact and the electrode/contact that sinks the current signals is sometimes referred to herein as the "return" electrode/contact. Additionally, the two electrodes/contacts between which the stimulation is delivered (i.e., the most distal/apical contacts in the embodiment of FIG. 86) are collectively referred to herein as a "stimulating pair." The remaining electrodes/contacts that are not part of the stimulating pair are disconnected from the system ground (i.e., are electrically "floating").

In general, two intra-cochlear electrodes/contacts are selected for delivery of the stimulation. However, alternative embodiments may use extra-cochlear electrodes/contact to source/sink current. Additionally, it is to be that the use of the most distal electrodes/contacts for sourcing/sinking the current is illustrative and other electrodes/contacts could be used in alternative embodiments.

During insertion of the electrode array into the recipient's cochlea, the scala tympani is typically substantially filled with a conductive fluid known as perilymph. As such, when current signals are delivered at one of the intra-cochlear electrodes/contacts, at least a portion of the current will spread through the perilymph. The flow of the current through the perilymph will cause the generation of voltages at the other intra-cochlear stimulating electrodes/contacts. That is, although the stimulus is localized, due to the conductive perilymph the electric field spreads and induces voltage at the other electrodes/contacts.

At 10304, following the delivery of the current signals at the given contact, voltage measurements are performed at a selected number of other intra-cochlear contacts. That is, the voltage induced at the selected other electrodes/contacts as a result of the delivery of the current signals at the measurement contact are measured. (The contacts at which the voltages are measured are sometimes referred to herein as "measurement" contacts or "measurement electrodes.") In the embodiment of FIG. 86, the measurement contacts may include any of the contacts/electrodes.

In certain circumstances, the cochlear implant associated with the electrode array is configured to make a plurality of voltage measurements at substantially the same time in response to the delivery of stimulation. In such embodiments, a single set of localized current signals is applied and the voltage induced at a selected number of the measurement electrodes/contacts is measured substantially simultaneously at the measurement electrodes/contacts. In other embodiments, the cochlear implant is configured to measure the voltage at a single electrode/contact in response to the delivery of a set of current signals. In such embodiments, a plurality of sets of localized current signals is applied in sequence at a given electrode, and a voltage is measured at a different electrode/contact after each sequential stimulation. As such, in the context of FIG. 86, the delivery of single stimulation pattern may refer to the delivery of one set of current signals (with subsequent substantially simultaneous measurement at each of the selected measurement contacts) or the sequential delivery of plurality of sets of current signals (with subsequent measurement at one of the selected measurement contacts after each set of current signals are delivered).

As noted above, stimulation delivered at a contact will have an effect on the other contacts, and the effect may depend on a number of factors. However, a primary factor that controls the effects of stimulation is the distance between the stimulating contact and the measurement contact. For example, in the embodiment of FIG. 86, when stimulation is delivered at a contact/electrode, the voltage measured at other contacts should be increasingly smaller for contacts positioned farther from the stimulating contact. Therefore, at 10306 of FIG. 86, the induced voltages measured at each of the measurement contacts in response to the single stimulation pattern are evaluated relative to one another to determine the relative distance between the stimulating contact and each of the measurement contacts (i.e., the contacts at which voltages are measured). An evaluation of the voltages relative to one another enables the determination of the physical state of the electrode array within the cochlea. Also as described further below, based on the evaluation of measurements relative to one another, the cochlear implant or a connected device may generate feedback to a surgeon or other user that provides information about the physical state of the electrode array and/or the occurrence of an adverse event. Because the current must past through the perilymph, and the perilymph influences the voltage recorded as the measurement electrode(s), the voltage is thus at least partially based on electrical phenomenon of the recipient/based on electrical characteristics associated with the recipient/electrical phenomenon/characteristics inside the recipient. To be clear, the perilymph is not the only feature that influences voltage. In this regard, the voltage difference is a function of the resistance of the medium between two contacts. In an exemplary embodiment, most of the current will flow through the perilymph, and the conductive the thereof will affect the voltage drop between the two contacts. However, the resistance of alternate current paths, such as through bone and nerve and blood vessels, will also contribute. In this regard, the voltage is also thus at least partially based on electrical phenomenon of the recipient/based on electrical characteristics associated with the recipient/inside the recipient, etc. While it is noted that there are features such as interface impedance, etc., at the service of the stimulating contact, that can impact the voltage, because the voltage drop between the contacts is still at least partially (in most instances, primarily) based on the perilymph and/or tissue, the voltage is thus at least partially based on electrical phenomenon associated with the recipient/based on electrical characteristics associated with the recipient/inside the recipient.

Thus, the robotic apparatuses detailed herein and variations thereof can be utilized in conjunction with the electrode array of the cochlear implant to evaluate or otherwise determine the status of an electrode array within the cochlea as detailed in the '255 patent application. In an exemplary embodiment, this can be done while the electrode array is being inserted into the cochlea. In an exemplary embodiment, the system 400 is configured to receive data from a system configured to implement the teachings of the '255 patent application, such as by way of example only and not by way of limitation, a cochlear implant having the capabilities to do so, as is detailed by way of example in the '255 patent application. Based on this data from the system implementing the teachings of the '255 patent application relating to voltage measurements, data relating to a status of the electrode array within the cochlea can be evaluated, and based on this data, the actuators of the robotic apparatus are controlled during the cochlear electrode array insertion process.

In an exemplary embodiment, voltages measured during execution of the localized monitoring method 10300 during a typical normal insertion (i.e., where no adverse events occur with respect to the electrode array) will have a typical pattern or at least will follow a typical trend (as is detailed in the '255 patent application). Conversely, voltages measured during execution of the localized monitoring method 10300 during insertion of a cochlear electrode array where an adverse event occurs will result in a deviation from this typical pattern typical trend (as is detailed in the '255 patent application). By way of example only and not by way of limitation, the voltages measured can be utilized to determine whether or not a tip fold-over occurrence has occurred, and also in some embodiments, whether a tip fold-over is likely to occur or otherwise forecast that such a scenario will occur or even may occur. Still further by way of example only and not by way of limitation, the voltages measured can be utilized to determine whether or not a deformation (an undesirable deformation) of the electrode array has occurred, and also in some embodiments, whether such deformation is likely to occur or otherwise forecast that such a scenario will occur or even may occur. These exemplary scenarios are specifically detailed in the aforementioned '255 patent application. It is noted that in some alternate embodiments, the voltage measurements achieved by implementing the teachings of the '255 patent application can be utilized to determine other features associated with the status of the electrode array as it is being inserted into the cochlea or after it is inserted into the cochlea. In some exemplary embodiments, any feature of the electrode array relating to a status thereof as it is being inserted into the cochlea or after it is inserted into the cochlea that can be identified or otherwise evaluated or estimated based on measurements of voltage as detailed herein that can enable a status of the electrode array to be determined or otherwise forecasted or estimated, can be utilized in at least some exemplary embodiments.

Figure 87:
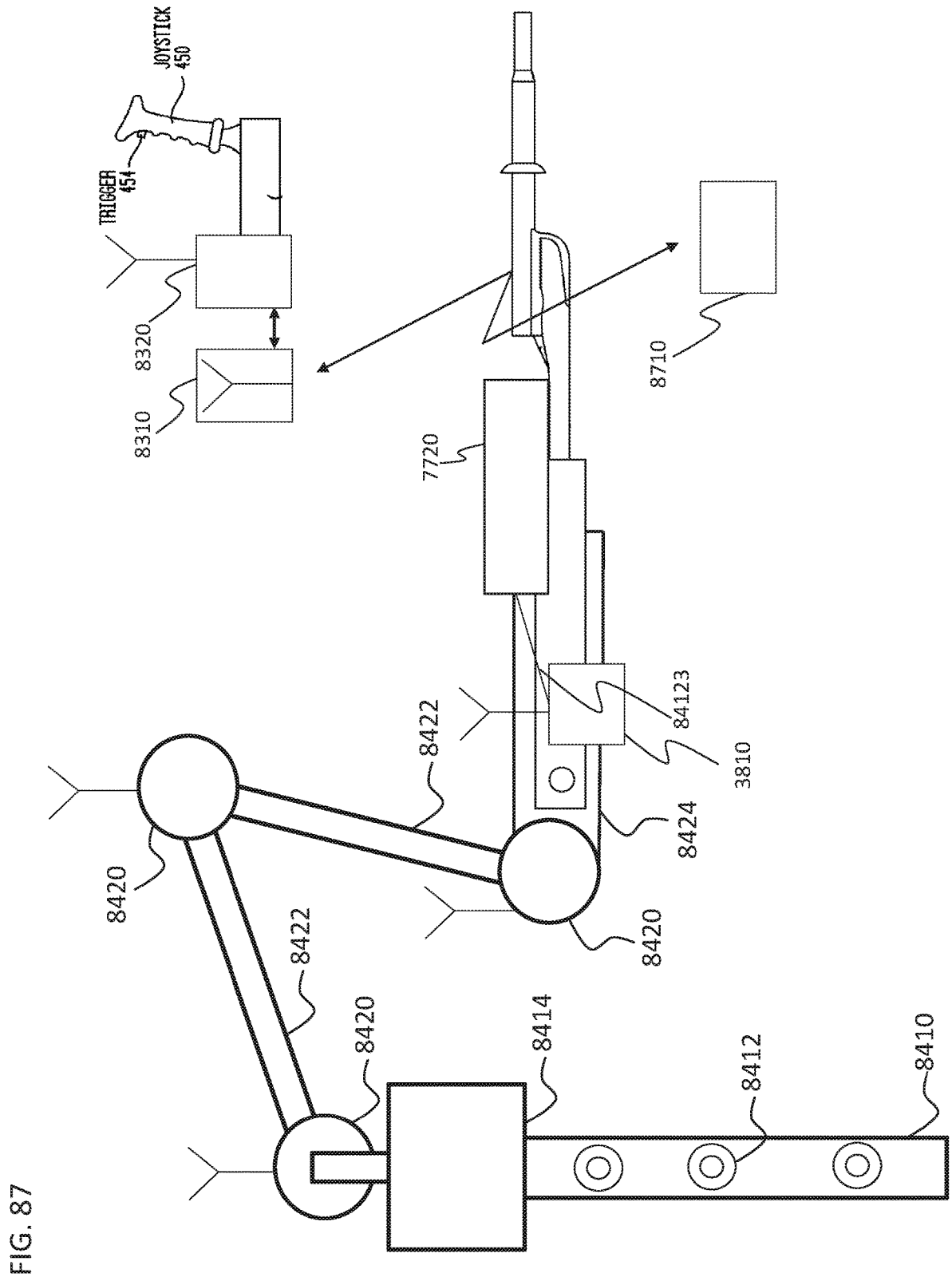

To this end, FIG. 87 depicts an exemplary system including the robot apparatus as shown, along with voltage measurement device 8710 which is in signal communication with the control unit 8310. In an exemplary embodiment, voltage measurement device 8710 corresponds to a cochlear implant configured to execute method 10300 detailed above, and communicate the results of that method to control unit 8310. In this regard, the voltage measurement device can correspond to a receiver/stimulator of a cochlear implant, which has an inductance coil. The inductance coil can be placed into signal communication with another inductance coil that in turn is in signal communication with control unit 8310. Control unit 8310 can be configured to activate the receiver/stimulator of the cochlear implant to execute method 3000. In an alternative embodiment, the receiver/stimulator of the cochlear implant can execute such autonomously. The receiver/stimulator of the cochlear implant, represented by the measurement device 8710 in functional terms as seen in FIG. 87, transmits the data based on or otherwise resulting from the execution of method 10300 to the control unit 8310. Control unit 8310 analyzes the data, and, at least based in part on that data, controls the actuators of the robot assembly.

Figure 88:
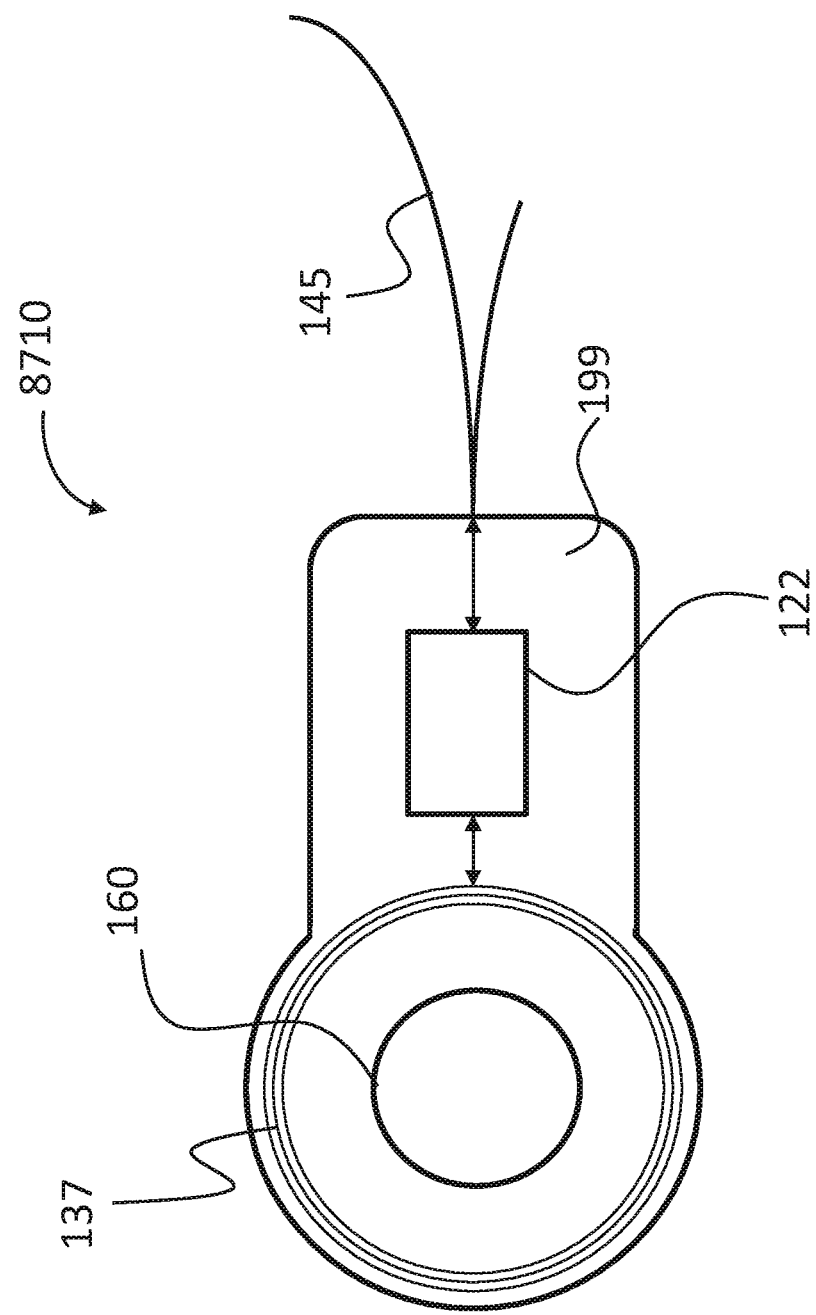
FIG. 88 depicts an exemplary implantable component of a cochlear implant according to an exemplary embodiment.
Figure 89:
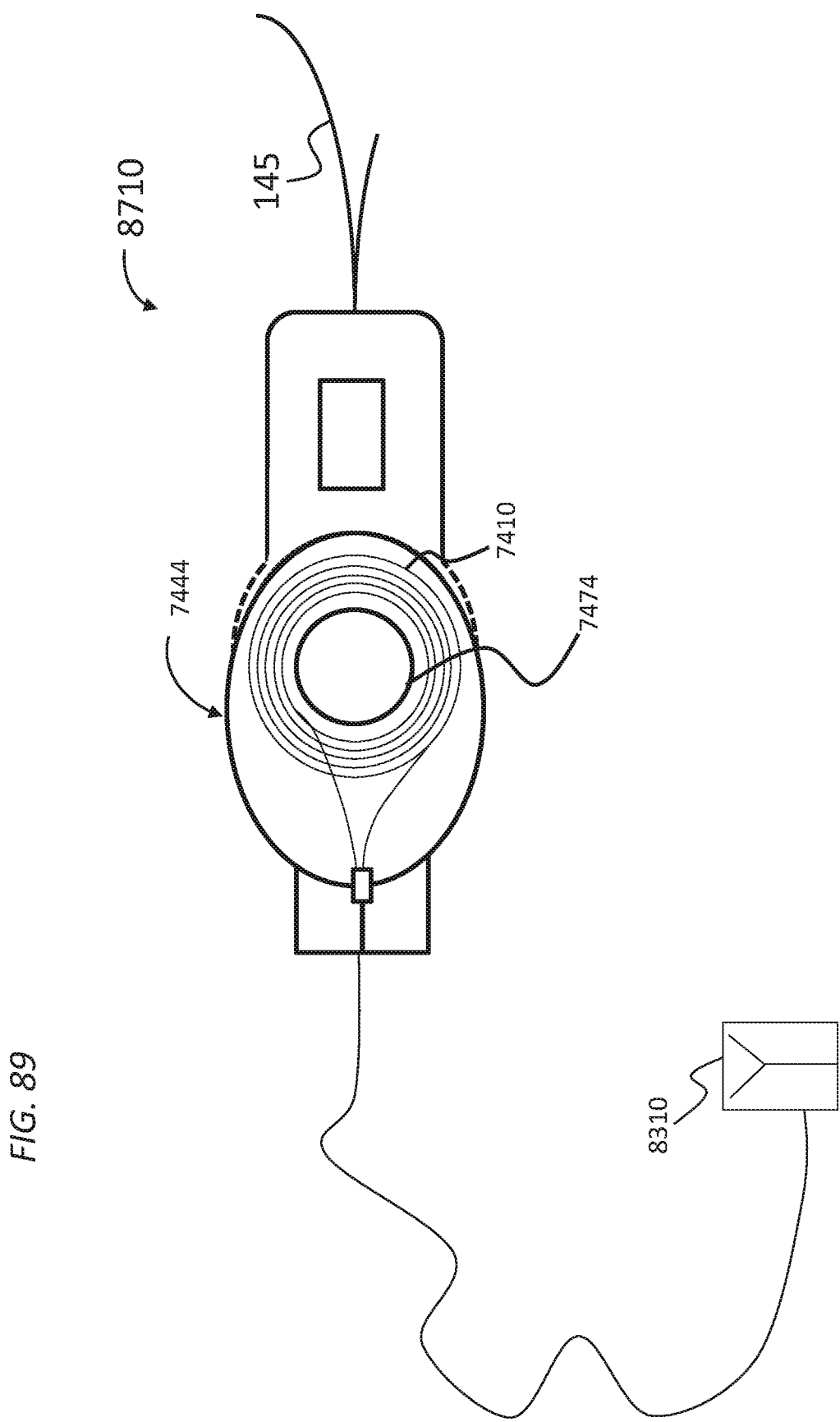
FIG. 89 depicts the cochlear implant of FIG. 88 in signal communication with a communication device that enables communication between the cochlear implant and a control unit according to an exemplary embodiment.

To be clear, FIG. 88 depicts an exemplary high-level diagram of a receiver/stimulator 8710 of a cochlear implant, corresponding to the measurement device 8710 of FIG. 88 in an exemplary embodiment, looking downward. As can be seen, the receiver/stimulator 8710 includes a magnet 160 that is surrounded by a coil 137 that is in two-way communication (although in other embodiments, the communication is one-way) with a stimulator unit 122, which in turn is in communication with the electrode array 145. Receiver/stimulator 8710 further includes a cochlear stimulator unit 122, in signal communication with the coil 137. The coil 137 and the stimulator unit 122 are encased in silicon as represented by element 199. FIG. 89 depicts an exemplary embodiment of the receiver/stimulator 8710 in signal communication with the control unit 8310 via electrical lead that extends from an inductance coil device 7444 having coil 7410 about a magnet 7474 as can be seen. The inductance coil device 7444 communicates via an inductance field with the inductance coil of the receiver/stimulator 8710 so that the data acquired by the implantable component 8710 can be transferred to the control unit 8310.

Note also that in at least some alternate exemplary embodiments, control unit 8310 can communicate with the so-called "hard ball" reference electrode of the implantable component of the cochlear implant so as to enable communication of data from the receiver/stimulator 8710 to control unit 8310 and/or vice versa.

It is noted that in the embodiment of FIG. 89, control unit 8310 is in signal communication with the various other components as detailed herein, which components are not depicted in FIG. 89 for purposes of clarity.

To be clear, the various other methods of the '255 patent application can be executed by the measurement unit 8710, and the results thereof can be used as a basis to control the actuators of the robot assembly. By way of example only and not by way of limitation, the bipolar voltage measurement techniques detailed in that patent application can be utilized in at least some exemplary embodiments. Indeed, the teachings of that patent application are such that those teachings can enable a determination that an adverse event associated with the electrode array has occurred or is about to occur, as is detailed in that patent application. Further, measurement unit 8710 can correspond to the cochlear implant 700 of the '255 patent application, which cochlear implant is configured to monitor the physical state of the electrode array according to the teachings of that patent application.

To be clear, while the just detailed exemplary embodiments have been directed toward utilizing a device that is completely separate from the robotic apparatus in general, and the insertion guide in particular of system 400, in some alternate embodiments, the embodiments associated with method 300 detailed above, where the electrode and/or other components are part of the insertion guide in particular, and the robot apparatus in general, can be utilized to obtain the voltage measurements as well. Any device, system, and/or method that can enable the voltage measurements to implement the teachings detailed herein and/or variations thereof in conjunction with or otherwise based on the teachings of the '255 patent application, can be utilized at least in some exemplary embodiments. Thus, in an exemplary embodiment, method 300 can be executed in conjunction with utilization of a robotic assembly or the other systems detailed herein, so as to obtain data upon which to base the control of the actuators, etc., according to an exemplary embodiment.

Thus, an exemplary embodiment includes a robotic apparatus as detailed herein and/or variations thereof, along with a control unit, such as control unit 8310, which control unit is configured to provide a controlled actuation of the actuator at least partially based on the electrical phenomenon/at least partially based on electrical characteristics associated with the recipient. The system of which the robotic apparatus is a part is configured to place the control unit into signal communication with a cochlear implant (e.g., via the embodiment of FIG. of FIG. 89) of which the electrode array is a part. The cochlear implant is configured to obtain data indicative of the electrical phenomenon of the recipient/electrical characteristics associated with the recipient (e.g., configured to execute method 10300, etc.). The system of which the robotic apparatus is a part is also configured to convey data based on the obtained data to the control unit via the established signal communication with the cochlear implant so that the control unit can provide the controlled actuation of the actuator at least partially based on the electrical phenomenon/electrical characteristics.

Corollary to the above, in an exemplary embodiment, with respect to the system including a control unit configured to receive data based on data related to electrical phenomenon inside the recipient, control unit 8310 is configured to receive telemetry from an implantable system, such as the cochlear implant, of which the electrode array is a part. In such an exemplary embodiment, the data based on the data based on electrical phenomenon inside the recipient is based on the telemetry received by the control unit 8310 from the implantable system (cochlear implant).

Figure 90:
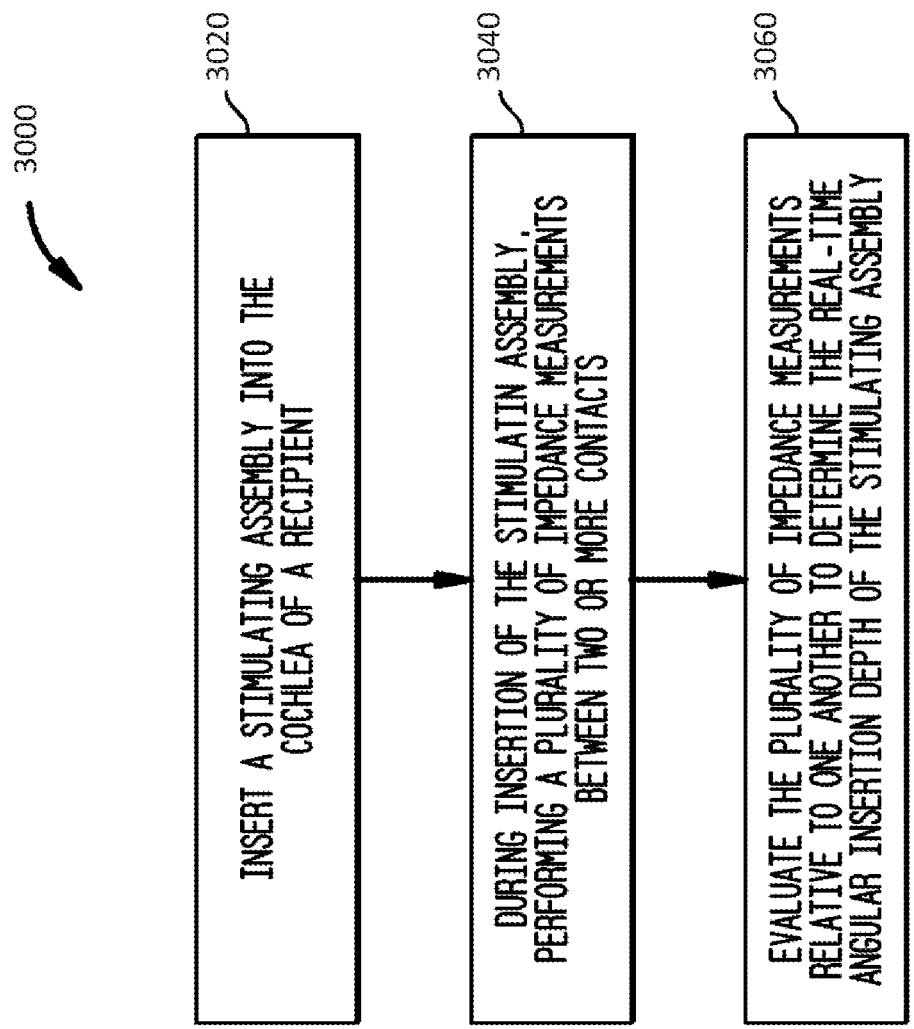
FIGS. 90-95 present exemplary flowcharts for exemplary methods according to some exemplary embodiments.

Still further, it is noted that some alternate embodiments of the robotic apparatuses and systems detailed herein can be utilized with methods and apparatuses associated with obtaining impedance measurements within a recipient, which methods can be used to determine an insertion depth of the electrode array. For example, the methods of U.S. patent application Ser. No. 14/843,259 can be utilized in conjunction with the teachings detailed herein, as noted above. While the teachings detailed above associated with the '259 patent application are directed towards utilizing an electrode or the like that is mounted on the insertion guide or otherwise is part of the robotic apparatus, in some other embodiments, as is the case with the '255 patent application, the teachings detailed herein can be utilized such that the components that are utilized to execute the teachings of the '259 patent are completely separate from the robotic apparatus save for the communication with such components and the control unit of the system 400. In this regard, FIG. 90 is a flowchart of a first intra-operative method 3000 for setting and/or determining an angular insertion depth of the cochlear electrode array. FIG. 90 illustrates a real-time method that enables the determination of the current/present (i.e., actual) angular insertion depth of the electrode array within the cochlea. Method 3000 begins at 3020 where the electrode array is at least partially inserted into the cochlea. At 3040, during insertion of the electrode array into the cochlea, the impedance between different pairs of intra-cochlear contacts of the electrode array is measured and used to determine the angular insertion depth of the stimulating assembly. In one embodiment, to measure the impedance between two intra-cochlear contacts, bipolar electrical stimulation (i.e., one or more bipolar current signals) is repeatedly delivered between a first intra-cochlear contact and a second intra-cochlear contact. After the delivery of each set of bipolar stimulation between the first and second intra-cochlear contacts, the impedance between the first and second contacts is measured (e.g., at the second intra-cochlear contact). It is to be appreciated that impedance measurements are made between two points, thus the impedance may be "measured" at either of the two points (i.e., it is a relative measurement between those two points). However, merely for ease of illustration of certain embodiments presented herein, the return contact of the stimulating pair is sometimes referred to herein as a "measurement" contact.

In general, the impedance between two intra-cochlear contacts in a stimulating pair can be correlated to their physical proximity with one another and their location in the cochlea. The physically closer the contacts of the stimulating pair are to one another, the lower the impedance that will be measured between the contacts. At 3060, again while inserting the electrode array, the impedance-to-proximity relationship is used to evaluate the plurality of impedance measurements relative to one another to determine the relative proximity between the two or more intra-cochlear contacts and thus determine the real-time (current/present) angular insertion depth of the electrode array. As described further below, the method includes the selection one or more sets/pairs of intra-cochlear contacts for impedance measurement that have a relationship to one another that enables the angular insertion depth of the electrode array to be determined from the relative proximity of the one or more pairs of intra-cochlear contacts. In certain embodiments of FIG. 90, the two or more intra-cochlear contacts selected for impedance measurement comprise two specific (static contacts) that have a maximum physical separation when the angular insertion depth of the electrode array is 180° (i.e., the distal end of the electrode array is inserted to 180°), and a minimum physical separation when the angular insertion depth of the electrode array is 360° (i.e., the distal end of the electrode array is inserted to 360°). This relationship between contacts having a maximum and minimum separation arrangement at the specific 180° and 360° points is referred to herein as an angular proximity relationship.

Depending on, for example, the shape, size, length, etc. of a stimulating assembly, different contacts may have an angular proximity relationship. As such, different stimulating pairs of contacts may be used in accordance with different embodiments to determine the angular insertion depth of the electrode array. Therefore, in certain embodiments, the method includes determining and selecting the one or more pairs of intra-cochlea contacts that are believed to have a correct angular proximity relationship.

For example, as is detailed in the '259 patent application, in one illustrative embodiment, the most distal/apical contact and the most proximal/basal contact have an angular proximity relationship that enables the use of impedance measurements between these two contacts to determine the angular insertion of the electrode array. Bipolar stimulation is delivered between various contacts (e.g., the most proximal and the most distal) and the impedance between the contacts is measured. This process is repeated over a period of time to produce a plurality of impedance measurements. These impedance measurements are plotted as an impedance curve. The measurement of the impedance between the various contacts begins at a point along the impedance curve that is created. The measurement of the impedance between contacts may begin, for example, when a first contact enters the cochlea through a cochleostomy, and may continue while the electrode array is inserted into the cochlea. In general, the contacts experience a significant impedance change after entering into the cochlea (e.g., due to immersion in the conductive perilymph). As such, the system can monitor the impedance at a given contact to determine when the contact enters the cochlea 130.

Utilizing the measured impedance plotted against the angular insertion depth of the electrode array, it will typically be seen that the impedance rises from a starting point to a first peak/maximum at a second point. The impedance subsequently falls to a minimum at a third point, then again rises to second peak/maximum at a fourth point. Because the impedance between the pertinent contacts is a maximum at the second point, the second point indicates that the electrode array has been inserted 180 degrees (e.g., the distal most and proximal most contacts are at the maximum possible distance from one another within cochlea). Stated differently, this first maximum point indicates that the distal end of the electrode array has reached 180° point, while the most proximate contact is relatively close to 0° point.

Similarly, because the impedance between the most distal and the most proximal contacts is a minimum at the third point, the third point indicates that the electrode array has been inserted 360 degrees (i.e., the distal most and proximal most contacts are at the minimum possible distance from one another within cochlea). Stated differently, this minimum point indicates that the distal end of electrode array has reached 360° point, while the most proximal contact is located within the basal region of cochlea substantially close to 360° point (i.e., the distal most and proximal most contacts are physically close together, but separated by a section of the modiolus). Continuing with reference to the '259 patent application, the second maximum of the impedance curve indicates a location of distal end of the electrode array at which the impedance between the distal most contact and the proximal most contact is a second maximum. That is, the electrode array has been inserted another 180 degrees from the minimum point such that the electrode array is at an angular insertion depth of 540 degrees.

In summary, by monitoring impedance between two selected contacts and evaluating the impedance curve or other data associated therewith or other data, the relative positions of the electrodes can be determined, which can provide information indicative of the relative positions of the electrodes within the cochlea, and thus the insertion angle depth. In further embodiments of FIG. 90, the impedances between different pairs of contacts may be monitored and simultaneously evaluated to determine the angular insertion depth of the electrode array. For example, a plaque can be created with respect to a curve of impedance measured between a distal end or a proximal contact and a middle contact (e.g., contact 12 of 24 contacts) during insertion the electrode array. The plot can have a vertical (Y) axis that represents the measured impedance and a horizontal (X) axis that represents contacts.

It is noted that in some exemplary embodiments, plots can be made that illustrate measured impedance values between two specific contacts over a period of time, and thus the positions of the various electrodes can be determined on a temporal basis. However, the data can also be presented in terms of illustrating the impedance values measured between a distal most and/or a proximal most electrode array and the contacts between such electrode and the middle electrode thereof (e.g., electrode 12) at a particular instant while the electrode array is at a specific location. The impedance curve may be generated by sequentially delivering bipolar stimulation between a stimulating contact at the distal most location of the proximal most location and each of the return contacts, and measuring the impedance at each contact (i.e., sequentially changing the return contact for the bipolar stimulation measuring the impedance between the present return contact and the stimulating contact). Some exemplary embodiments include utilization of any of the teachings detailed in the '259 patent application with respect to obtaining data indicative of the angular insertion depth of the electrode array. Thus, the bipolar stimulation features associated with that patent application can be utilized in at least some exemplary embodiments.

It is noted that in some alternate embodiments, the impedance measurements achieved by implementing the teachings of the '259 patent application can be utilized to determine other features associated with the status of the electrode array as it is being inserted into the cochlea or after it is inserted into the cochlea. In some exemplary embodiments, any feature of the electrode array relating to a status thereof as it is being inserted into the cochlea or after it is inserted into the cochlea that can be identified or otherwise evaluated or estimated based on measurements of impedance as detailed herein that can enable a status of the electrode array to be determined or otherwise forecasted or estimated, can be utilized in at least some exemplary embodiments.

To this end, with respect to FIG. 87, which as noted above, depicts an exemplary system including the robot apparatus as shown, along with voltage measurement device 8710 which is in signal communication with the control unit 8310. It is noted that in an alternate embodiment, device 8710 is an impedance measurement device. In an exemplary embodiment, device 8710 can be both a voltage measurement device and an impedance measurement device. In an exemplary embodiment, device 8710 in the form of an impedance measurement device (or a voltage and impedance measurement device) corresponds to a cochlear implant configured to execute method 3000 detailed above, and communicate the results of that method to control unit 8310. In this regard, the impedance measurement device can correspond to a receiver/stimulator of a cochlear implant, which has an inductance coil and can be utilized as detailed above, albeit with respect to measuring impedance and conveying such measurements to the control unit 8310. Corollary to this is that control unit 8310 can be configured to activate the receiver/stimulator of the cochlear implant to execute method 3000. In an alternative embodiment, the receiver/stimulator of the cochlear implant can execute such autonomously. The receiver/stimulator of the cochlear implant, represented by the measurement device 8710 in functional terms as seen in FIG. 87, transmits the data based on one or otherwise resulting from the execution of method 3000 to the control unit 8310. Control unit 8310 analyzes the data, and at least based in part on that data, controls the actuators of the robot assembly.

To be clear, the various other methods of the '259 patent application can be executed by the measurement unit 8710, and the results thereof can be used as a basis to control the actuators of the robot assembly. By way of example only and not by way of limitation, the bipolar stimulation techniques detailed in that patent application can be utilized in at least some exemplary embodiments. Further, measurement unit 8710 can correspond to the cochlear implant of the '259 patent application, which cochlear implant is configured to monitor the location of the electrode array according to the teachings of that patent application.

To be clear, while the just detailed exemplary embodiments have been directed toward utilizing a device that is completely separate from the robotic apparatus in general, and the insertion guide in particular of system 400, in some alternate embodiments, the embodiments associated with method 1300 detailed above, where the electrode and/or other components are part of the insertion guide in particular, and the robot apparatus in general, can be utilized to obtain the impedance measurements as well. Any device, system, and/or method that can enable the impedance measurements to implement the teachings detailed herein and/or variations thereof in conjunction with or otherwise based on the teachings of the '259 patent application can be utilized in at least some exemplary embodiments. Thus, in an exemplary embodiment, method 1300 can be executed in conjunction with utilization of a robotic assembly or the other systems detailed herein, so as to obtain data upon which to base the control of the actuators etc., according to an exemplary embodiment.

Thus, an exemplary embodiment includes a robotic apparatus as detailed herein and/or variations thereof, along with a control unit, such as control unit 8310, which control unit is configured to provide a controlled actuation of the actuator at least partially based on the electrical phenomenon/based on the electrical characteristics. The system of which the robotic apparatus is a part is configured to place the control unit into signal communication with a cochlear implant (e.g., via the embodiment of FIG. 89) of which the electrode array is a part. The cochlear implant is configured to obtain data indicative of the electrical phenomenon of the recipient the electrical characteristics of the recipient (e.g., configured to execute method 3000, etc.). The system of which the robotic apparatus is a part is also configured to convey data based on the obtained data to the control unit via the established signal communication with the cochlear implant so that the control unit can provide the controlled actuation of the actuator at least partially based on the electrical phenomenon/electrical characteristics.

Still further with respect to the embodiments detailed above associated with an apparatus configured to control actuation of actuators at least partially based on electrical phenomenon of the recipient/electrical characteristics of the recipient, in an exemplary embodiment, the controlled actuation is at least partially based on evoked compound action potentials (ECAP)—sometimes referred to in the art as NRT—data. In an exemplary embodiment, this ECAP data is based at least in part on the electrical phenomenon of the recipient/electrical characteristics of the recipient. In an exemplary embodiment, the ECAP data is utilized to determine one or more of the conditions of the electrode array detailed herein and/or variations thereof (tip fold over, insertion angle depth, distance of the electrode array from the modiolis wall, etc.). To this end, with respect to FIG. 87, which as noted above, depicts an exemplary system including the robot apparatus as shown, along with voltage measurement device 8710 which is in signal communication with the control unit 8310. It is noted that in an alternate embodiment, device 8710 is an ECAP device. In an exemplary embodiment, device 8710 can be a voltage measurement device and an impedance measurement device (generically speaking) and an ECAP device. In an exemplary embodiment, device 8710 is in the form of a cochlear implant configured to execute ECAP measurements to obtain the ECAP data, which cochlear implant is configured to communicate the results of such measurements to control unit 8310. In this regard, the ECAP measurement device/ECAP data collection device can correspond to a receiver/stimulator of a cochlear implant, which has an inductance coil and can be utilized as detailed above, albeit with respect to measuring ECAP or otherwise developing or collecting ECAP data and conveying such measurements to the control unit 8310. Corollary to this is that control unit 8310 can be configured to activate the receiver/stimulator of the cochlear implant to execute the measurements/the collection of the data. In an alternative embodiment, the receiver/stimulator of the cochlear implant can execute such autonomously. The receiver/stimulator of the cochlear implant, represented by the ECAP measurement device 8710 in functional terms as seen in FIG. 87, transmits the data based on or otherwise resulting from the execution of ECAP measurements to the control unit 8310. Control unit 8310 analyzes the data, and at least based in part on that data, controls the actuators of the robot assembly.

To be clear, while the just-detailed exemplary embodiments have been directed toward utilizing a device that is completely separate from the robotic apparatus in general, and the insertion guide in particular of system 400, in some alternate embodiments, the ECAP data is collected or otherwise measured with components part of the insertion guide in particular, and the robot apparatus in general. Any device, system and/or method that can enable ECAP measurements and/or the collection of ECAP data to implement the teachings detailed herein and/or variations thereof can be utilized in at least some exemplary embodiments so as to obtain data associated with a condition or otherwise location of the electrode array or otherwise control the actuators of the robot apparatus.

Figure 91:
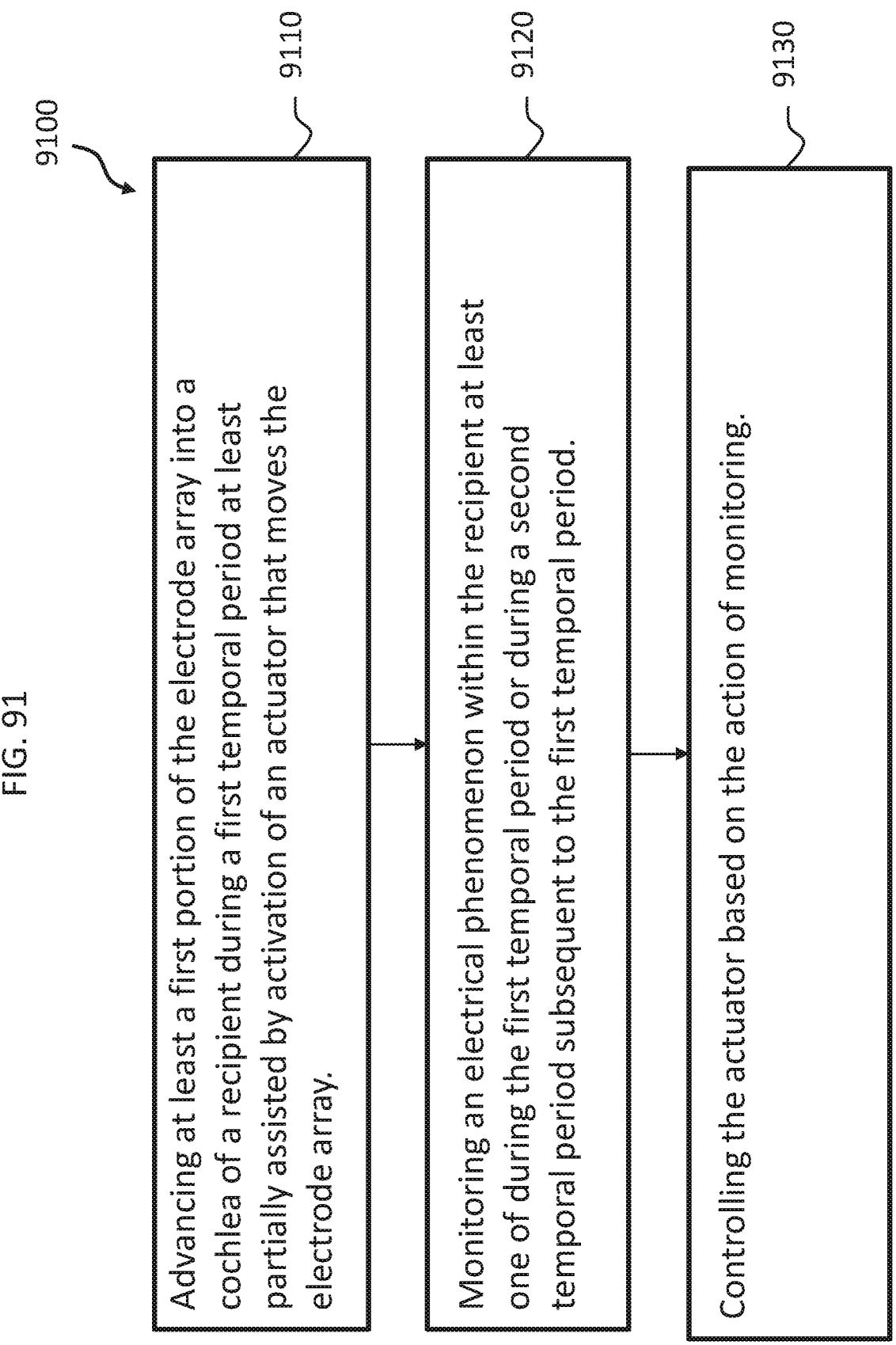

Concomitant with the teachings detailed above, FIG. 91 depicts an exemplary flowchart for an exemplary method 9100. Method 9100 includes method action 9110, which entails advancing at least a first portion of an electrode array into a cochlea of a recipient during a first temporal period at least partially assisted by activation of an actuator that moves the electrode array. In an exemplary embodiment, the actuator can correspond to the actuator of the actuator assembly 7720 detailed above where actuators of the other embodiments of the actuator assembly's detailed herein and/or variations thereof. Method 9100 further includes method action 9120, which entails monitoring and electrical phenomenon/electrical characteristics within the recipient at least one of during the first temporal period or during a second temporal period subsequent to the first temporal period. In an exemplary embodiment, the electrical phenomenon/electrical characteristics monitored can correspond to any of the electrical phenomenon/characteristics detailed herein. It is noted that in at least some exemplary embodiments, the electrical phenomenon/characteristics is monitored while the electrode array is being advanced during the first temporal period, in some alternate embodiments, the electrical phenomenon/characteristics is monitored after the electrode array has been advanced during the first temporal period. In an exemplary embodiment, the second temporal period can correspond to a temporal period where the electrode array is not being advanced and/or not being retracted. By way of example only and not by way of limitation, method action 9100 can be executed in a manner having discrete advancement steps. For example, the electrode array can be advanced, then stopped, then the electrical phenomenon/characteristics could be monitored, then the electrode array can begin to be advanced again, then stopped, then the electrical phenomenon/characteristics can be monitored again, then the electrode array can begin to be advanced again, then stopped, then the electrical phenomenon/characteristics can be monitored yet again, and so on. Note also that the electrical phenomenon characteristics can be monitored during the entire period (i.e., while the electrode array is being advanced and while the electrode array is stationary). In an exemplary embodiment, the method 9100 is executed in a manner analogous to the look-shoot-look way of air to air combat.

Note also that in some alternate exemplary embodiments, the electrode array can be advanced all the time, but the phenomenon is monitored only some of the time. Note also that depending on the system, different electrical phenomenon/characteristics can be monitored at different times. By way of example only and not by way of limitation, a scenario can exist where during a first temporal period, the ECoG measurements are being taken, during a second temporal period, the voltage measurements are being taken, and during a third temporal period, the ECAP measurements are being taken. Those three periods could be proceeded or proceeded by advancement of the electrode array. Thus, in an exemplary embodiment, method 9100 is executed by advancing the electrode array by a first amount, then stopping, then taking the ECOP measurements, the voltage measurements, and then the ECAP measurements (in any order), and then advancing the electrode array beyond the first amount by another amount, and then taking the measurements again, and so on. Again, the measurements can be taken in any order, and those measurements can be taken while the electrode array is being advanced and/or retracted.

Still with reference to method 9100 of FIG. 91, method 9100 further includes method action 9130, which entails controlling the actuator based on the action of monitoring in method action 9120. As detailed above, in an exemplary embodiment, the actuator can be halted and/or reversed in a scenario where the measurements indicate that a deleterious result will occur by continuing advancements of the electrode array into the cochlea. Alternatively, and/or in addition to this, the rate of advancement can be increased and/or decreased based on the measurements.

Note that in an exemplary embodiment of method 9100, the action of controlling the actuator based in the action of monitoring can be executed by a human. By way of example only and not by way of limitation, as a result of method action 9120, an indicator or the like can be provided to the surgeon or the like or the healthcare professional operating the user input device of the system 400. In an exemplary embodiment, the surgeon or the like executes method action 9130. That said, in an alternate embodiment, method action 9130 can be executed by the control unit 8310 detailed above, or variations thereof.

Figure 92:
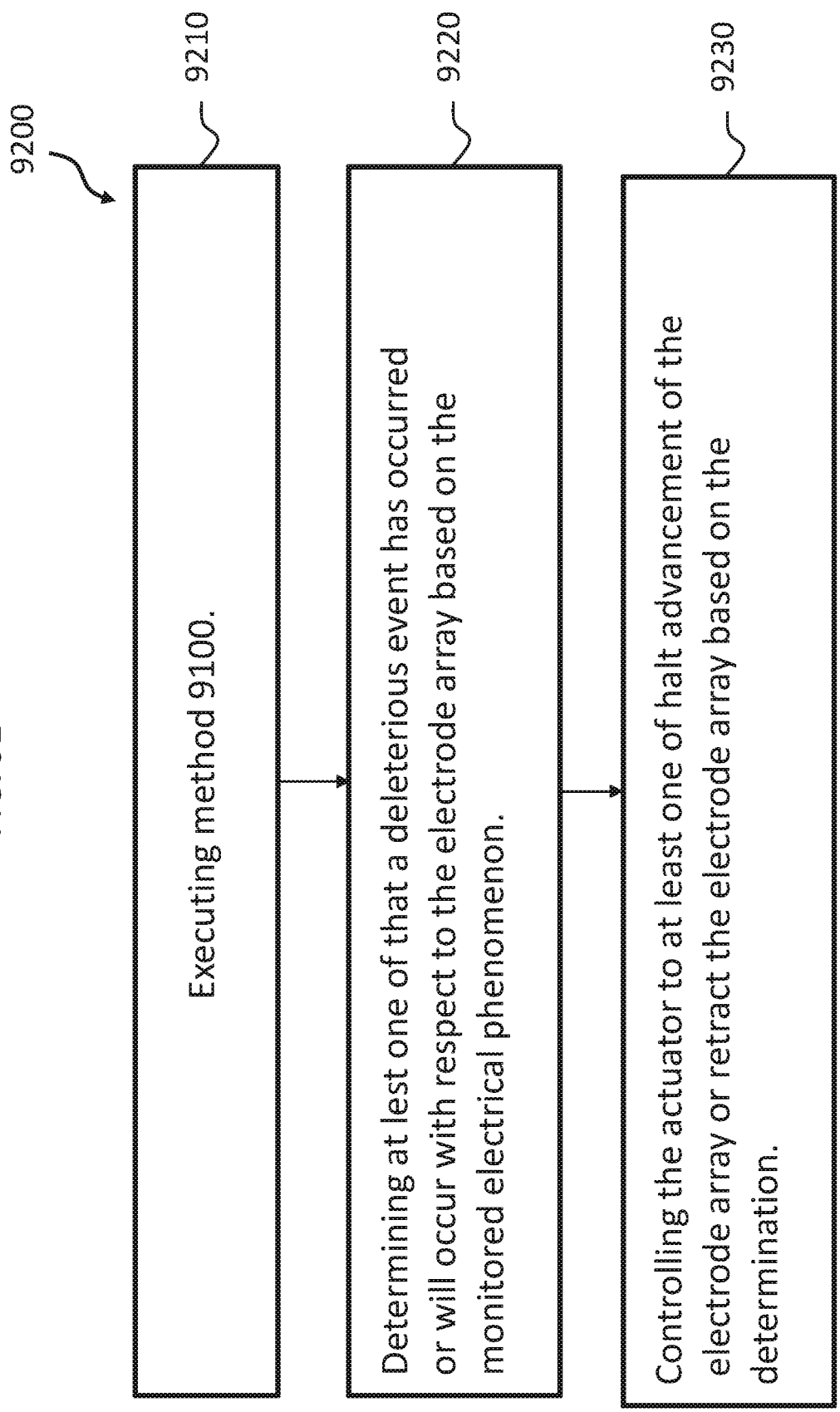

As noted above, the status of the electrode array can be evaluated utilizing the monitored electrical phenomenon. By way of example only and not by way of limitation, there is an exemplary method as represented by the flowchart of FIG. 92. Specifically, FIG. 92 presents a flowchart for method 9200. Method 9200 includes method action 9210, which entails executing method 9100. Method 9120 further includes method action 9220, which entails determining that a deleterious event has occurred with respect to the electrode array based on the monitored electrical phenomenon/characteristics. Method 9200 further includes method action 9230, which entails controlling the actuator to at least one of halt advancement of the electrode array or retracted the electrode array based on the determined deleterious event. In this regard, in an exemplary embodiment, a species of method action 9220 can entail determining that an electrode array tip fold-over has occurred based on the monitored electrical phenomenon characteristics. Also, an exemplary species of method action 9220 can entail determining that the electrode array has buckled. Alternatively, and/or in addition to this, an exemplary species of method action 9220 can entail determining that the electrode array has come into contact with a wall of the cochlea that is not desired to contact. By way of example only and not by way of limitation, in an exemplary embodiment, the deleterious event can correspond to the electrode array coming into contact with the modiolus wall during advancement of the electrode array. Note also that in some alternate exemplary embodiments, method action 9220 can alternatively correspond to determining that the deleterious event will occur instead of determining that the event has occurred. That said, in an alternate embodiment, method action 920 can entail determining both.

Also, in an exemplary species of method action 9220, method action 920 can entail determining at least one of whether the electrode array has twisted or will twist based on the monitored electrical phenomenon/characteristics.

As is to be understood in view of the above, in an exemplary embodiment, method 9100 further includes utilizing at least one of ECoG, ECAP measurement or voltage measurements during the first temporal period and/or the second temporal period to monitor the electrical phenomenon/characteristics. In an exemplary embodiment, any of the devices and/or systems detailed herein and/or variations thereof can be utilized in at least some exemplary embodiments.

Figure 93:
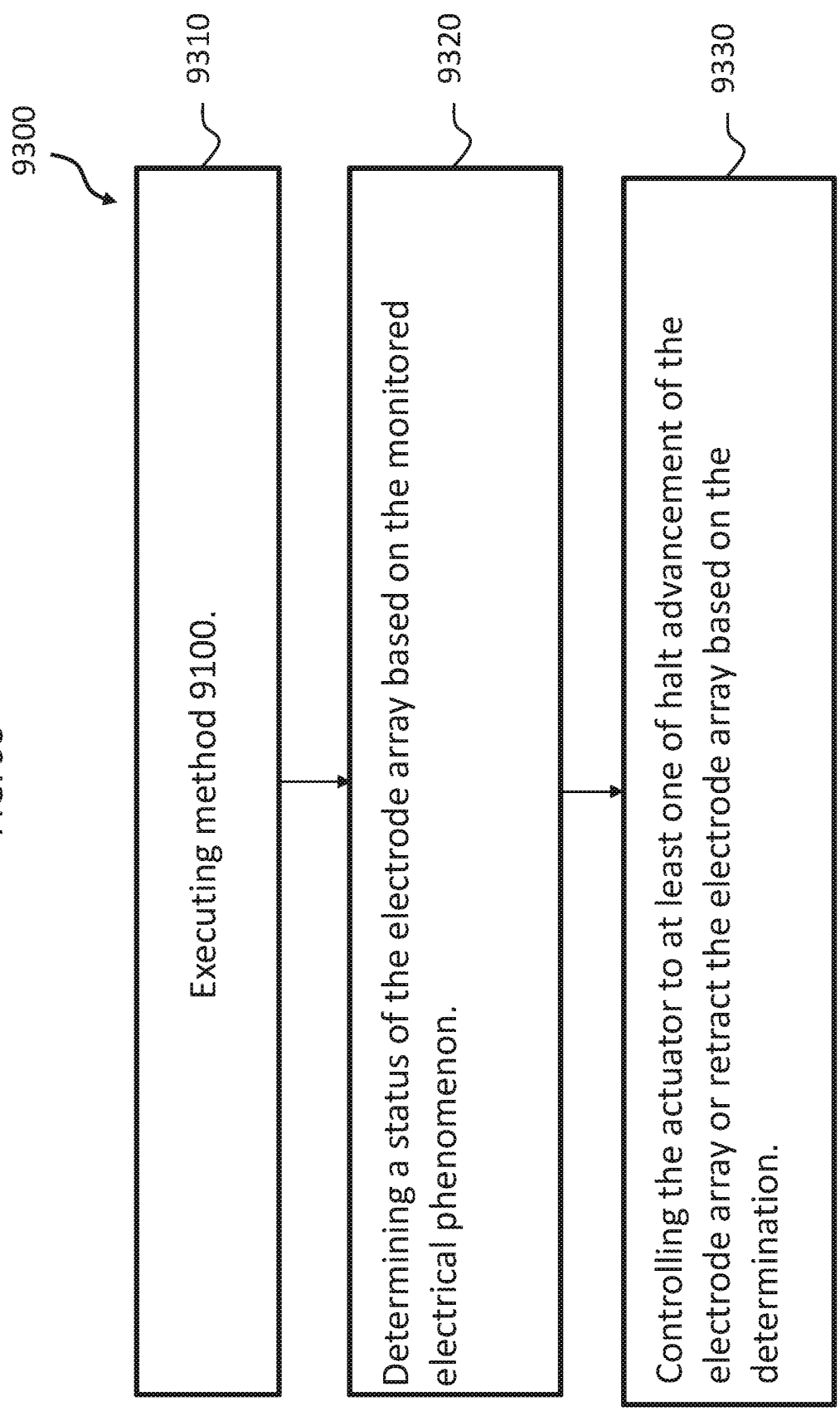

FIG. 93 depicts an exemplary flowchart for an exemplary method 9300. Method 9300 includes method action 9310, which entails executing method 9100. Method 9300 further includes method action 9320, which entails determining a status of the electrode array based on the monitored electrical phenomenon/characteristics. Method action 9330 entails controlling the actuator to at least one of halt advancement of the electrode array or retract the electrode array based on the determination of method action 9320. In an exemplary species of method action 9320, the status that is determined is an angular insertion depth of the electrode array. In an exemplary species of method action 9320, the status that is determined is a proximity of the electrode array to a wall of the cochlea.

Figure 94:
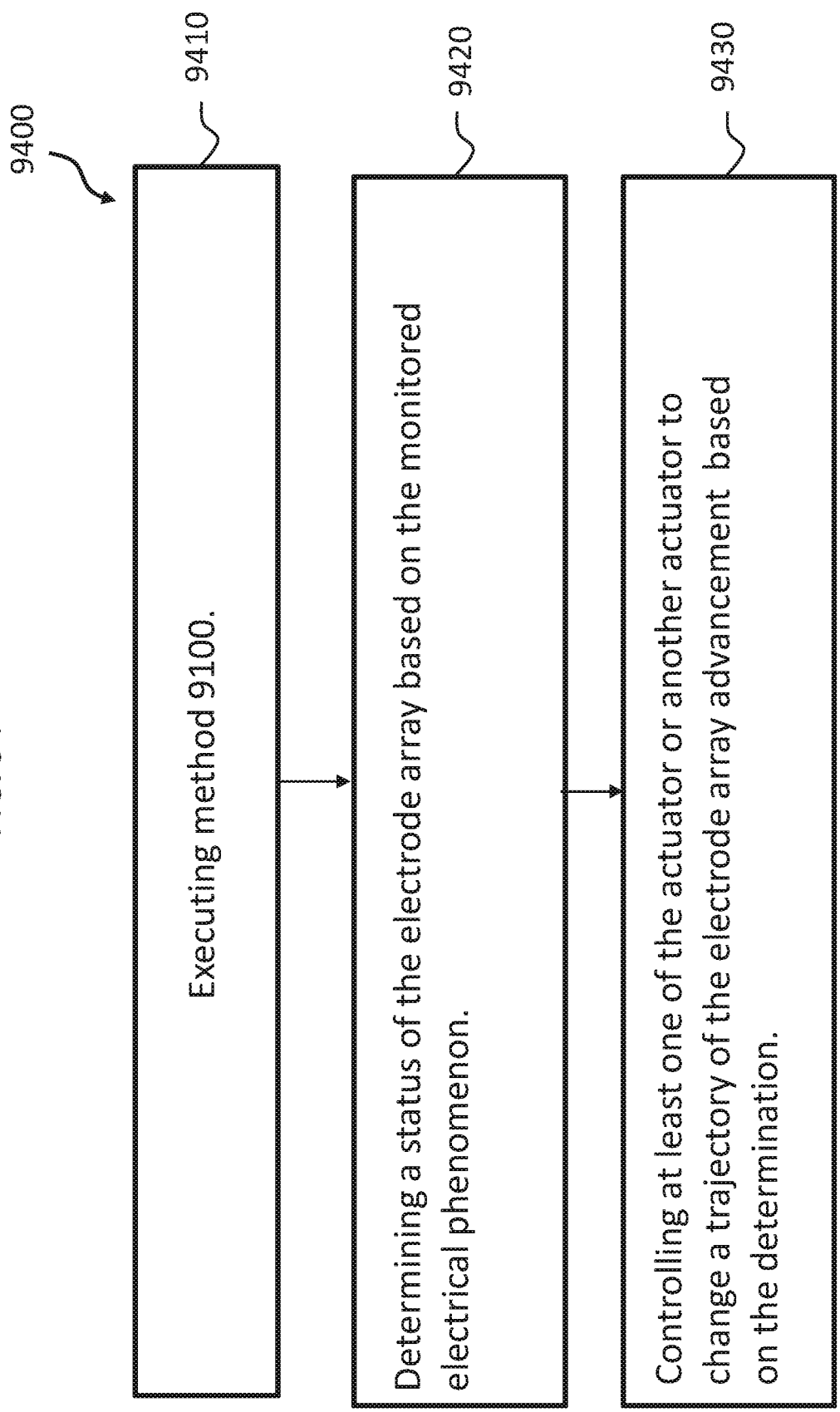
Figure 95:
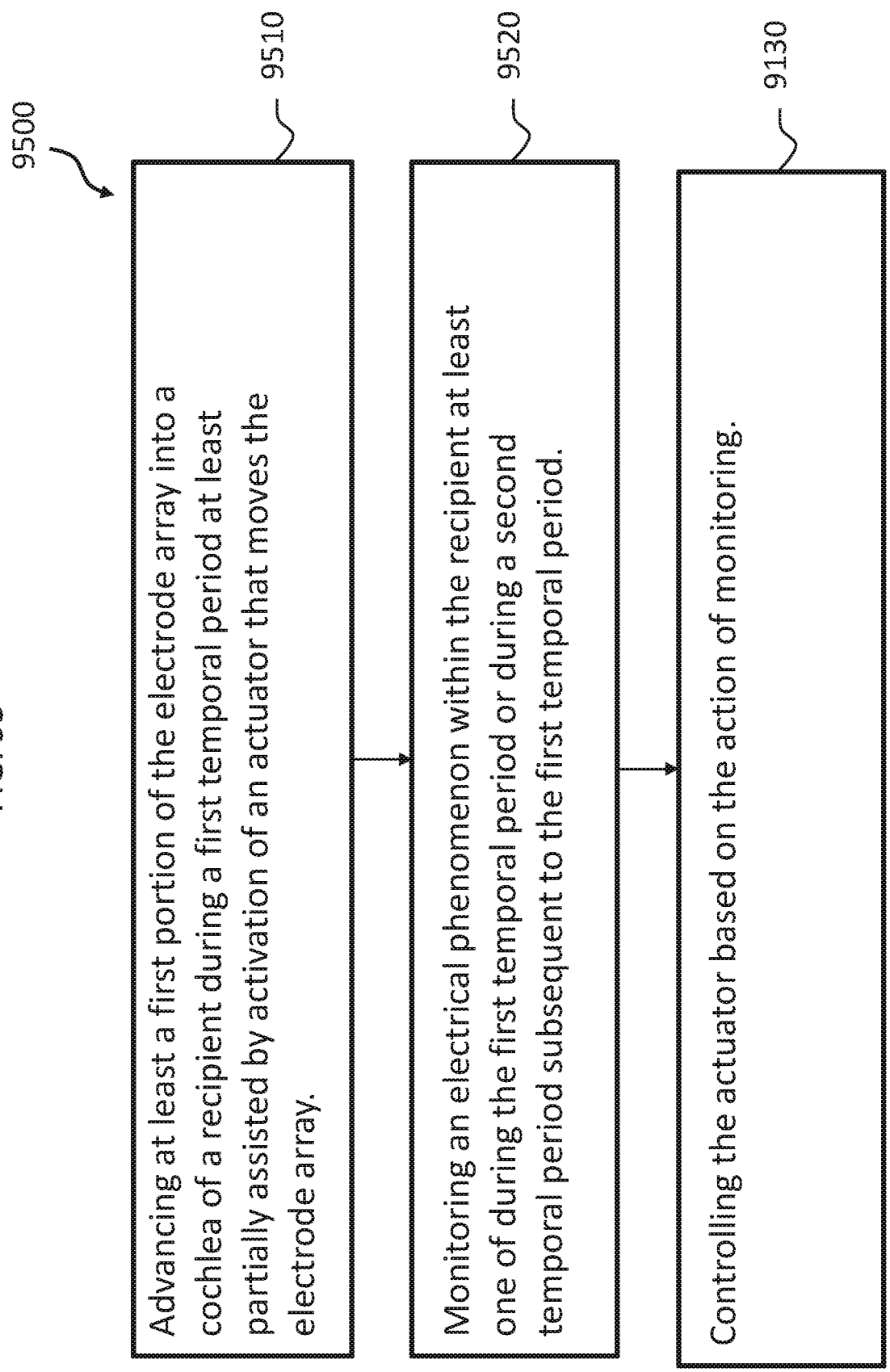

FIG. 94 depicts an exemplary flowchart for another exemplary method, method 9400. Method 9400 includes method action 9410, which entails executing method 9100. Method 9400 includes method action 9420, which entails determining a status of the electrode array based on the monitored electrical phenomenon/characteristics. Method 9400 further includes method action 9430, which entails controlling at least one of the actuator or another actuator to change a trajectory of the electrode array insertion based on the determination. As noted above, some exemplary scenarios can exist where the deleterious result of an electrode array piercing a wall of the cochlea (other than where the cochleostomy is present) can occur as a result of the advancement process of the electrode array. Accordingly, an exemplary embodiment of method action 9320 can entail that the electrode array is continued to be advanced along at given trajectory, it is on a trajectory that could result in the electrode array piercing the wall, that being the status of the electrode array. Accordingly, the actuator that is utilized to advance the electrode array can be an actuator that operates on more than one degree of freedom, and thus the method 9400 entails controlling that actuator to change the trajectory of the electrode array insertion based on the determination. That said, in an alternate embodiment, another actuator can be controlled, such as one of the actuators on or otherwise connected to one of the arms, etc., of the robot assembly, to change the trajectory of electrode array advancement based on the determination.

Note also that in an exemplary embodiment of method 9420, the status of the electrode array can be that which corresponds to the electrode array having pierced the wall of the cochlea. Thus, in an exemplary embodiment of method 9400, the method can include the action of utilizing the actuator utilized in method 91002 retract the electrode array so that it is no longer piercing the wall of the cochlea. Then (or simultaneously therewith), method action 9430 is executed to change the trajectory of the electrode array advancement so that it is less likely to again pierced the wall of the cochlea. Thus, in an exemplary embodiment, the various methods detailed herein can include the action of determining at least one of whether the electrode array has dislocated from one scale of the cochlea to another scale of the cochlea or whether such will happen based on the monitored electrical phenomenon/characteristics.

Note also that the status of the electrode array determined in action 9420 could be that of a tip fold over or a buckling or a twisting of the electrode array, etc.

In an exemplary method of executing method 9100, there is further an action of guiding advancement of the first portion of the electrode array into the cochlea using an insertion guide mounted on a support arm, such as the support arm of the robotic assembly. Note that while the embodiments described up to now have tended to be directed towards an embodiment where there is an actuator that controls the orientation of the insertion guide, in some alternate embodiments, the support arm can be that of a generic rig that is manually moved by the recipient. In this regard, by way of example only and not by way of limitation, with respect to the embodiment of FIG. 85, components 8420 can instead be damping devices or the like that provide resistance against movement of one arm relative to another arm, etc., in a manner analogous to the contraption that is utilized by dentist or the like. That is, in an exemplary embodiment, the surgeon or other healthcare professional moves the insertion guide manually by applying a force on to the insertion guide to position the insertion guide to a desirable location. This force is sufficient enough to overcome the resistance provided by components 8420 to the overall movement however, the resistance provided by components 8420 is sufficient enough that the guide tool generally stays in the location desired by the surgeon.

In any event, in at least some exemplary embodiments, the angular orientation of the insertion tool is adjustable relative to the cochlea via at least one of the actuator another actuator (if such actuators are used). In an exemplary embodiment, the electrical phenomenon/characteristics that is monitored is a phenomenon indicative of an orientation of the electrode array inside the cochlea. In this regard, the orientation can be the insertion angle. In an exemplary embodiment, the orientation can be the location of one or more portions of the electrode array relative to one of the walls of the cochlea. Any orientation that has utilitarian value can be utilized in this exemplary method.

Continuing with this method, in an exemplary embodiment, this method further includes the action of controlling at least one of the actuator or another actuator based on the action of monitoring the electrical phenomenon/characteristics to adjust an orientation of at least a portion of the insertion guide relative to the cochlea, thereby changing the orientation of the electrode array inside the cochlea relative to that which was the case when the electrical phenomenon/characteristics was monitored. In this regard, in an exemplary embodiment, the guide tube of the insertion guide can potentially gimbal or the like or otherwise can be moved by one of the actuators so as to change the orientation of the guide tube. That said, in an alternative embodiment, the entire insertion guide is moved so as to change the orientation thereof. It is noted that orientation can be any orientation about any axis of the electrode array. This can correspond to rotation of the electrode array about any one of its three axes. To be clear, in an exemplary embodiment, the guide tube of the insertion guide can be moved so as to change an approach direction of the electrode array during the insertion process. In this regard, the guide tube can be adjusted to change in approach of the electrode array towards a given wall of the cochlea. Indeed, with respect to actions prior to insertion of the electrode array into the cochlea, the guide tube can be adjusted to change the approach direction of the guide tube as it is moved towards the cochlea prior to contact with the cochlea.

As noted above, some exemplary embodiments of the insertion guide's detailed herein have components that are part of a system that enables the electrical phenomenon/characteristics to be monitored. In this regard, in an exemplary embodiment, at least some of the methods detailed herein are such that the insertion guide includes an electrode, and the electrical phenomenon/characteristics monitored during the methods is monitored utilizing the electrode.

In some alternate embodiments, some exemplary methods entail inserting an electrode array into a cochlea of the recipient utilizing a robotic apparatus by controlling the robotic apparatus at least partially based on electrical phenomenon associated with the recipient. As detailed above, the ECoG measurements, or the voltage, or impedance measurements, etc. correspond to electrical phenomenon associated with the recipient (and in this instance, the electrical phenomenon inside the recipient). Here, the recipient's body influences these measurements. For example, the conductivity of the perilymph in the cochlea corresponds to an electrical phenomenon of the recipient. This is as contrasted to measurements taken by sensor or the like on the robotic assembly, etc., indicating features associated with the robotic apparatus (e.g., a force applied by an actuator with respect to inserting the electrode array, measuring a voltage or a current spike at the actuators, etc.). Indeed, such measurements can be influenced by the recipient's body (e.g., because the electrode array is wedged against a wall of the cochlea), but those are not electrical phenomenon associated with the recipient. These are physiological phenomenon associated with the insertion of the electrode array into the recipient, but not physiological phenomenon associated with the recipient.

Consistent with the teachings above, in an exemplary method, the action of inserting the electrode array into the cochlea entails making adjustments to an operation of the robotic apparatus to maintain measurements of the physiological phenomenon and/or electrical phenomenon within predetermined parameters. By way of example only and not by way of limitation, if the impedance and/or voltages are being measured during the insertion of the electrode array into the cochlea (whether such measurements are made during a pause in the advancement of the electrode array or whether such measurements are made while the electrode array is being advanced), the method is executed such that the these measurements are maintained within the predetermined parameters. Note that in an exemplary embodiment, such as automatically done. By way of example only and not by way of limitation, the aforementioned control unit 3810 can be programmed or otherwise can have a script therein that controls the robotic assembly and makes adjustments to the operation thereof so that the measurements are maintained within the predetermined parameters during the insertion process. Note that in some exemplary embodiments, these parameters can change as the electrode array is inserted into the cochlea. For example, as noted above, as the electrode array curls backwards towards the cochleostomy as a result of the spiral shape of the cochlea, the measurements associated with the impedance between the various electrodes will change. Thus, in an exemplary embodiment, the predetermined parameters can be based on insertion depth of the like, and thus these predetermined parameters can be different and otherwise change during the electrode array insertion process.

In an exemplary embodiment, the action of inserting the electrode array into the cochlea entails making adjustments to the operation of the robotic apparatus to address perturbations of the electrode array in the insertion process based on the physiological phenomenon/electrical phenomenon. By way of example only and not by way of limitation, perturbations can create an undesirable trajectory of the electrode array. In an exemplary embodiment, the physical phenomenon can be used as a basis to make adjustments to the operation of one or more actuators of the electrode array.

It is noted that in an exemplary embodiment, the action of inserting the electrode array into the cochlea of the recipient, utilizing the robotic apparatus, entails utilizing a robotic apparatus by controlling the robotic apparatus at least partially based on a plurality of different physiological phenomenon/electrical phenomenon associated with a recipient. By way of example only and not by way of limitation, as noted above, the voltage measurements can be utilized to determine that occurrence of electrode array to fold over has happened or otherwise that such may be about to occur. Also, the ECoG data can be utilized to determine the relative location of the electrode array to one of the walls of the cochlea. In an exemplary embodiment, the method entails controlling the robotic apparatus based on a control regime that weights data based on the respective electrical phenomenon differently. By way of example only and not by way of limitation, in an exemplary embodiment, the control regime that controls the robotic assembly can be such that the insertion process is controlled such that actions will be taken to reduce the occurrence or otherwise the likelihood of tip fold over at the expense of increasing the likelihood of some other deleterious results or otherwise less than utilitarian result occurs. For example, the control regime can be configured such that in a scenario where, for example, the electrode array is intended to be located at the mid-scala position, during the insertion process, electrical phenomenon indicative of tip fold over or the likely occurrence thereof will drive the insertion process such that tip fold over can be avoided, but the electrode array may not be located exactly at the mid-scala position. Of course, in some alternate embodiments, the reverse can be true—tip fold over can be deemed more acceptable than a deviation from the mid-scala position. The point is that the data related to the plurality of physical phenomenon can be weighted by the control regime, such as the control regime of the control unit 8310, in at least some exemplary embodiments.

In some exemplary embodiments, the control unit that controls the robotic apparatus in general, and one or more of the actuators in particular, is configured to receive input indicative of an insertion regime of the electrode array. In this regard, in at least some exemplary embodiments, a given electrode array may not necessarily be inserted or otherwise positioned in a given cochlea the same as that which would be the case for another recipient. By way of example, some electrodes are inserted further into the cochlea than others (absolute distance (relative to the length of the electrode array), angular insertion depth, etc.). Accordingly, a given insertion regime can correspond to that which results in a given absolute distance and/or a given angular insertion depth. Still further, some insertion regimes correspond to that which results in the electrode array being in a mid-scala position (no contact with the cochlea walls that extend along the longitudinal axis of the electrode array, or at least relatively minimal contact). Accordingly, a given insertion regime can correspond to that which results in the electrode array being in a mid-scala position at the end of the insertion thereof. Note that in some exemplary embodiments, such an insertion regime can result in the electrode array contacting the walls of the cochlea during insertion. That said, in some alternate embodiments, there is an insertion regime that is such that the electrode array does not contact the walls along the longitudinal axis of the electrode array, or at least has minimal contact therewith. Also, some insertion regimes correspond to that which results in the electrode array being positioned against the modiolus wall of the cochlea. Thus, a given insertion regime can correspond to that which results in the electrode array being positioned against the modiolus wall. That said, in some alternate embodiments, there exists an insertion regime that is such that during insertion of the electrode array, the electrode array does not come into contact with the modiolus wall of the cochlea. In an exemplary embodiment of this insertion regime, the electrode array comes into contact after the electrode array is inserted into the cochlea (or at least the desired length of the electrode array has been placed into the cochlea). Also, in some exemplary embodiments, the insertion regime is such that the electrode array never comes into contact with the modiolus wall. Still further, in some exemplary insertion regimes, the electrode array is inserted such that it slides along the lateral wall of the cochlea during insertion. Thus, an exemplary insertion regime entails that which maintains the electrode array in contact with the lateral wall of the cochlea during advancement of the electrode array. Note that this can be such even though the electrode array ultimately moves away from the lateral wall, at least in part, after advancement, or at least after advancement commences. The point is, for a given electrode array, there are many insertion regimes.

Thus, as noted above, in an exemplary embodiment, the control unit that controls the robotic apparatus is configured to receive input indicative of an insertion regime of the electrode array. By way of example only and not by way of limitation, the control unit can correspond to a personal computer or the like with a program thereon that asks the surgeon or other user of the robotic apparatus what insertion regime the user would like. Such can provide a list of various insertion regimes. The control unit can be configured to enable the user to input data indicative of the desired insertion regime. Based on this input, the control unit can automatically coordinate the insertion regime with data based on the electrical phenomenon/characteristics of the recipient to control the actuation of the actuator(s) of the robot apparatus to achieve controlled actuation of the actuator based on electrical phenomenon/characteristics of the recipient. For example, with respect to an insertion regime where the electrode array will be inserted to have a specific insertion angle, impedance between the pertinent electrodes can be monitored and when an impedance is measured that is indicative of the electrode array reaching the desired insertion angle, further advancement electrode array is halted by halting actuation of actuator 7720 for example. Still further by way of example, an insertion regime can be a mid-scala insertion regime, and the pertinent electrical phenomenon/characteristics detailed herein can be measured or otherwise evaluated so as to control the robot apparatus to angle the insertion guide relative to the cochlea such that the electrode array is inserted in a manner that should result in a mid-scala position.

Corollary to the above, in an exemplary embodiment, with respect to the control unit 8310, in an exemplary embodiment, the control unit is configured to control the robotic assembly to move the electrode array into the cochlea according to a general insertion regime, and make micro adjustments to at least one of (i) the general insertion regime or (ii) control output to the robotic assembly from the control unit that is based on the general insertion regime, wherein the adjustments are based on the received recipient electrical data. For example, in an exemplary scenario where the insertion regime corresponds to advancing the electrode array such that it is generally in constant contact with the lateral wall of the cochlea, the control unit 8310 will have control data therein supporting such a general insertion regime, which data is used by the control unit 8310 to control the actuators of the robot apparatus to achieve the desired results of that general insertion regime. For example, the general insertion regime can include control data that causes the robot apparatus to adjust the angular orientation of the insertion guide at different insertion depths of the electrode array. Because the control data of the general insertion regime is developed based on an ideal situation, and during the process of advancing the electrode array into the cochlea, deviations from that ideal situation will result, the control unit is configured to make micro-adjustments to the general insertion regime, or more specifically, to the control data of the general insertion regime. In this regard, in an exemplary scenario where the original insertion regime was such that after the electrode array was inserted a length of X millimeters, the angle of the insertion guide was to be changed Y degrees. However, based on the received recipient electrical data, the control unit can be configured so as to adjust the insertion regime such that when the electrode array is inserted a length of X millimeters, the angle of the insertion guide is instead changed by Z degrees.

That said, in some alternate embodiments, the micro-adjustments are made to the control output from the control unit to the robotic assembly. That is, the underlying general insertion regime is not changed, but the output to the actuators of the robotic assembly is changed or otherwise adjusted from that which would otherwise be the case so as to take into account the received recipient electrical data. That is, instead of changing the general insertion regime, or more specifically, the control data, the adjustments are made to the output. This is analogous to applying a correction factor to the output.

Any device, system, and/or method that will enable adjustments during insertion of the electrode array by the robot apparatus based on received recipient electrical data or the like can be utilized in at least some exemplary embodiments.

As will be understood, there are a plurality of different insertion regimes that can be selected for a given electrode array. In an exemplary embodiment, the control unit 8310 is configured to control the robotic assembly to move the electrode into the cochlea according to a respective insertion regime that is a member of a plurality of different insertion regimes. Again, with reference to the above scenario where the control unit includes a display that displays an insertion regime corresponding to a mid-scala insertion regime, and an insertion regime that corresponds to a lateral wall insertion regime, etc., such can correspond to the plurality of different insertion regimes. Other insertion regimes can also be included within the plurality of different insertion regimes. In an exemplary embodiment, these different insertion regimes are predetermined insertion regimes, and the user can select one of the insertion regimes from the various insertion regimes. The control unit 8310 is configured to automatically control the robotic apparatus in general, and the actuators thereof in particular, to achieve electrode array insertion according to that insertion regime.

In an exemplary embodiment, the control unit is configured to weight different electrical features of the electrical data based on the respective insertion regime and control the robotic assembly differently based on the different weights. In this regard, some electrical features will be more prominent with respect to a given insertion regime. For example, with respect to a mid-scala insertion regime, electrical features that enable the distance of the electrode array to a given wall of the cochlea will be weighted more heavily than other electrical features. Conversely, with respect to a lateral wall insertion regime, electrical features indicative of tip fold over may be weighted lower in such a regime with respect to other regimes because it is less likely that tip fold over may occur while the electrode array is being driven along the lateral wall (at least with respect to a curved electrode).

It is noted that while the various teachings detailed herein are sometimes described in terms of electrical features/electrical phenomenon associated with a recipient and/or electrical phenomenon/characteristics of the recipient, it is also noted that these features/phenomenon need not necessarily be identified. That is, the various measurements associated with the methods and/or devices detailed herein can be used as a proxy for these features/phenomena. Accordingly, any disclosure herein of an electrical feature and/or an electrical phenomenon and/or an electrical feature phenomenon associated with the recipient corresponds to a disclosure of measurements relating thereto, they can be used by the control unit or other system to achieve the teachings detailed herein. Thus, a disclosure of an electrical phenomenon that is indicative of tip fold over corresponds to a disclosure of measurements from measurement devices of the apparatuses detailed herein and/or variations thereof resulting from such electrical phenomenon (and vice versa).

Also in view of the above, it is to be understood that in an exemplary embodiment, the systems and devices disclosed herein and/or variations thereof can be configured to receive user input and establish an automated insertion regime for the electrode array into the cochlea based on the received user input. In this regard, the user can be a surgeon or other healthcare professional. That said, in an extreme example, the user can be the recipient himself or herself, such as might result in an exemplary scenario associated with a long-term deep space mission. With respect to this exemplary embodiment, the system or device, etc. is configured to automatically determine if the insertion regime is being followed based on recipient physiological data/electrical data.

It is noted that an exemplary insertion regime can correspond to that for a straight electrode. Corollary to this is that an exemplary insertion regime can correspond to that for a curved electrode. In an exemplary embodiment, the control unit 8310 can be configured to evaluate data based on the electrical data and determine if the insertion regime is being followed. This can be done during the insertion process of the electrode array. That said, in an alternate embodiment, this can be done after the electrode array is inserted as a check to determine whether or not the electrode array has been properly placed.

Another way of considering the application of at least some of the teachings detailed herein is in view of an exemplary method that includes the action of determining an electrode array surgery results species from a genus of electrode array surgery results. Again, the genus of such results could be that of a mid-scala electrode array location or a modiolus wall electrode array location, etc. In an exemplary embodiment, a surgeon or other healthcare professional chooses an exemplary species from the genus of surgery results. This method further includes establishing a control regime based on the determined electrode array surgery result species. In this exemplary method, the insertion of the electrode array into the cochlea is based at least in part on the established control regime. For example, control unit 8310 can be configured to receive input indicative of how the surgeon wants the electrode array to ultimately be placed in the cochlea at the results of the surgery. The control unit 8310 is configured to develop a control regime based on that input. That is, the control unit can evaluate how it should control the actuators etc. of the robotic apparatus or the like so as to achieve that result. The control unit can be configured to develop a control regime or otherwise select a control regime to achieve that result. The control unit can thus control the robotic apparatus of the like during insertion of the electrode array into the cochlea based on the control regime, the idea being is that the control regime will result in the selected electrode array surgery result.

Note also that in an exemplary method there includes method actions that entail inputting at least one of a plurality of inputs into a controller of a robotic electrode array insertion system. In an exemplary embodiment, this robotic electrode array insertion system can correspond to any of the pertinent apparatuses detailed herein and/or variations thereof. The one or more of the plurality of inputs can be indicative of respective parameters associated with the electrode array. By way of example only and not by way of limitation, the input can correspond to whether or not the electrode array is a straight electrode array or a curved electrode array. Still further by way of example only and not by way of limitation, the input can correspond to whether or not the electrode array includes a stylet. The input can correspond to whether or not the electrode array has the aforementioned square cross-section/rectangle across the skin detailed above, or whether that electrode array has more than oval or circular shaped. The input can correspond to the number of electrodes in the electrode array. The input can correspond to whether or not the electrode array is a so called short electrode array. Any type of input relating to the electrode array can be the input in at least some exemplary embodiments. Still further, in this exemplary method, control of the robotic apparatus is executed at least in part based on this input. That is, in an exemplary embodiment, the control unit 8310 can be configured to develop a control regime or otherwise select a control regime based on the input related to the electrode array. By way of example only and not by way of limitation, actions associated with controlling the robotic apparatus during the insertion process could be different if the electrode array includes a straightening stylet as opposed to an electrode array that does not include a straightening stylet. Still further, actions associated with controlling the robotic apparatus during the insertion process can be different if the electrode array is a curled electrode array as opposed to a straight electrode array.

It is noted that some exemplary embodiments further include inputting data into a controller of a robotic electrode array insertion system indicative of a status of an electrode array. In this regard, according to an exemplary embodiment, as noted above, some exemplary insertion guides enable automatic determination of the length of the electrode array that has been inserted into the cochlea (e.g., by monitoring passage of the electrodes as they pass a sensor). In this regard, in an exemplary embodiment, the sensors or the like of the insertion guide are not signal communication in one way or another with the control unit 8310, such as by way of example only and not by way of limitation, the signal communication system between the communication unit of the insertion guide and the control unit as detailed above. During the insertion process, the insertion guide can communicate data indicative of the distance that the electrode array has been inserted into the cochlea, or at least the distance inserted relative to a set point with respect to the insertion guide, which set point is known in the greater scheme of things in a manner that can have utilitarian value with respect to controlling the insertion process of the electrode array. Accordingly, in an exemplary embodiment, the action of inputting data into the controller of a robotic electrode array can correspond to the automatic transmission of the data relating to the insertion depth to the controller 8310.

Still further, in an exemplary embodiment, control of the robotic apparatus is executed based at least in part by comparing data related to the input (e.g., insertion depth measured by the insertion guide sensors) to data related to the electrical phenomenon upon which the robotic apparatus is controlled. In this regard, in an exemplary embodiment, there can be a predetermined set of ideal electrical phenomenon that should be seen or otherwise exists, which electrical phenomenon change with distance that the electrode array is inserted into the cochlea. By comparing the input indicative of a given distance to which the electrode array has been inserted to the data relating to the p electrical phenomenon, a "sanity check" can be performed to determine or otherwise estimate whether or not the insertion process is going as planned. Alternatively, and/or in addition to this, such input can be utilized to discount or otherwise change the weightings of certain electrical phenomena as compared to other certain electrical phenomena. For example, electrical phenomena associated with the fold-over could be weighted more heavily when only a small portion or a minimal portion of the electrode array is inserted into the cochlea, and weighted less heavily when 90% or 95% of the electrode array is inserted in the cochlea, etc. It is noted that this is just one exemplary embodiment. Another exemplary embodiment could entail avoiding contact with the modiolis wall. In an exemplary embodiment, contact with the modiolis wall when only a small portion or a small length of the electrode array is inserted to the cochlea could correspond to a scenario where continued insertion of the electrode array to the cochlea is immediately halted. Conversely, an electrical phenomenon indicative of contact with that wall when 90 or 95% of the electrode array is inserted in the cochlea might not necessarily result in halting further insertion into the cochlea.

While the above embodiments have been directed towards automatic communication between the insertion guide and the control unit, in some embodiments, the surgeon or the like can input data directly into the controller of the robotic electrode array insertion system indicative of a status of an electrode array within the cochlea. In this regard, it could be that some exemplary systems are not as sophisticated as other exemplary systems. By way of example only and not by way of limitation, a scenario can exist where the surgeon quasi-dictates the insertion depth of the electrode array into the control unit of the robotic apparatus. By way of example only and not by way of limitation, a scenario can exist where the robotic apparatus does not have the ability to determine the distance or the insertion amount of the electrode array, for whatever reason. Instead, the surgeon can talk, and the system, utilizing a voice recognition system or the like, can receive the input.

Note further that in some exemplary embodiments, there exist methods that include a method action of outputting data relating to the electrode array during the action of insertion, which output comes from a robotic electrode array insertion system. In an exemplary embodiment, there exists a method action that entails manually adjusting operation of the robotic apparatus based on the output. Such an exemplary embodiment can have utilitarian value with respect to combining the automatic insertion techniques with manual insertion techniques. As noted above, some exemplary embodiments can utilize a quasi-fly by wire system where the surgeon controls the overall insertion process, but the control unit 8310 controls the finer points of the insertion process. In such an exemplary embodiment, there can be utilitarian value with respect to the surgeon or other healthcare professional receiving output relating to the electrode array during the action of insertion with the robotic system. This output can be utilized by the surgeon to allow him or her to make adjustments to his or her actions insertion process. Note also that in an exemplary embodiment, such exemplary methods can serve as an override or the like to the automatic insertion process.

Note that the teachings detailed herein utilizing machines to move the electrode array relative to the cochlea can have utilitarian value with respect to providing controlled insertion of the electrode array into the cochlea. For example, utilizing an actuator to drive the electrode array into the cochlea can have utilitarian value with respect to enabling a relatively slow insertion speed of the electrode array into the cochlea. As with many tasks performed by a human being, a human being will become fatigued the longer that the task is executed. A human being could hold a bucket of water in an outstretched arm for a number of seconds, but such may not necessarily be possible for a temporal period lasting a number of minutes. The same is also the case with respect to the surgeon. There is only so long that the surgeon can hold the electrode array in place against the cochlea during the insertion process before fatigue takes over and the likelihood of a fatigue related injury to the recipient or otherwise a deleterious effect associated with the insertion of the electrode array occurs. Utilizing the machines detailed herein, such is not necessarily the case. For example, the actuators detailed herein can be utilized to drive the electrode array into the cochlea at a speed of no more than 2 mm/s or no more than 1.5 mm/s 1 mm/s, or no more than 0.5 mm/s, or not more than 0.25 mm/s, or no more than 0.2 or 0.15 or 0.1 or 0.075 or 0.05 or 0.025 or 0.02 or 0.01 or 0.005 mm/s or less (or any value or range of values therebetween in 0.001 mm/s).

Note also that such exemplary micro-movement capabilities are also applicable to the other actuators of the robotic apparatus. In this regard, such micro-movement can be applied to insertion of the intracochlear portion of the insertion guide utilizing the robotic apparatus. In this regard, the aforementioned speeds associated with electrode array insertion are also applicable to movements of the insertion guide into the cochlea or towards the cochlea.

It is noted that any of the method actions detailed herein and/or the functionalities of the given tools and/or systems detailed herein exist or can exist while the surgeon is inserting the electrode array into the recipient. This means that the surgeon is actually moving the electrode array into the recipient, not just during the procedure spanning a first temporal period where only a subset of that first temporal period involves actually moving the electrode array into the cochlea.

While various embodiments detailed herein have been in some instances directed to correlating various phenomenon with other data, in an exemplary embodiment, the method actions detailed herein associated with insertion of the electrode array can be executed until data is received indicating that such should be stopped. For example, in an exemplary embodiment, the robotic apparatuses detailed herein can machine advance the electrode array into the cochlea utilizing the actuators detailed herein and/or variations thereof until data is received indicating that advancement should be stopped. Such can have utilitarian value, by way of example only and not by way of limitation, with respect to the exemplary handheld tool 8200 of FIG. 82. In an exemplary embodiment, the hand tool 8200 can be utilized to machine dry the electrode array into the cochlea until certain types of data are received, at which point a signal from a control unit or the like is sent to the actuator 7720, such as via the electrical lead connected to connector 67405, to shut down the actuator. In this regard, this can be the opposite of the exemplary scenario detailed above where the surgeon exercises override capabilities over the robotic system. Here, it is the control unit that can exercise override over what the surgeon is doing. Indeed, in an exemplary embodiment, both the surgeon and the control unit can exercise override. Note while this exemplary scenario has been directed towards the embodiment of FIG. 82, in some alternate embodiments, such scenarios can be directed towards the other apparatuses detailed herein and/or variations thereof.

Figure 96:
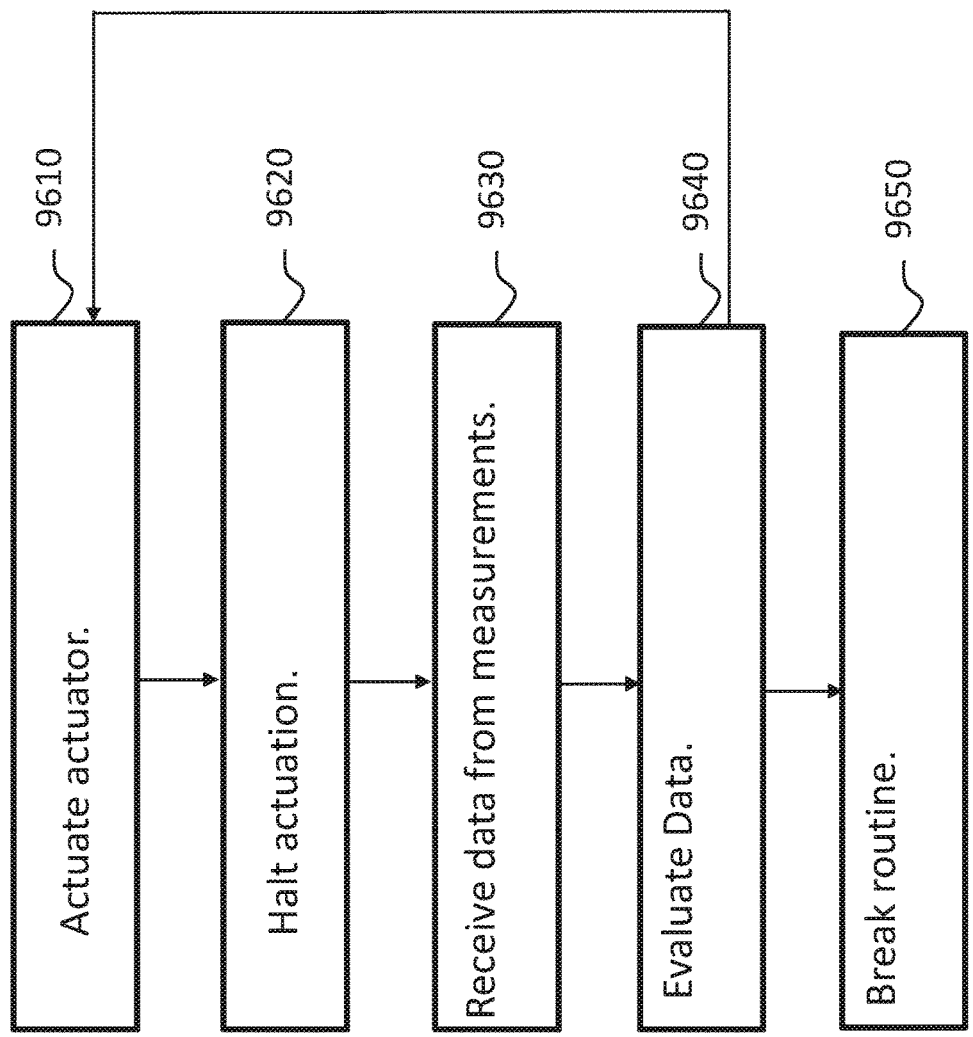
FIGS. 96-98 depict exemplary flowcharts for feedback regimes according to exemplary embodiments.

FIG. 96 depicts an exemplary flowchart representing a regime that utilizes feedback in the form of data from any of the various sensors/measurement techniques detailed herein, etc. Specifically, FIG. 96 includes action 9610, which entails actuating the actuator. In this exemplary embodiment, there is action 9620, which entails halting the actuator. Action 9630 entails receiving data from measurements (e.g., ECoG measurements, etc.—Action 9630 can instead be data relating to any of the electrical properties detailed herein and/or variations thereof of the recipient, etc.) Action 9640 entails evaluating the data. With respect to this regime, if the evaluation of the data at action 9640 indicates acceptable data, the routine goes back to action 9610. This is continued until an event occurs that breaks the routine at action 9650. This could be a result of the evaluation at action 9640 indicating that the data is not acceptable.

Figure 97:
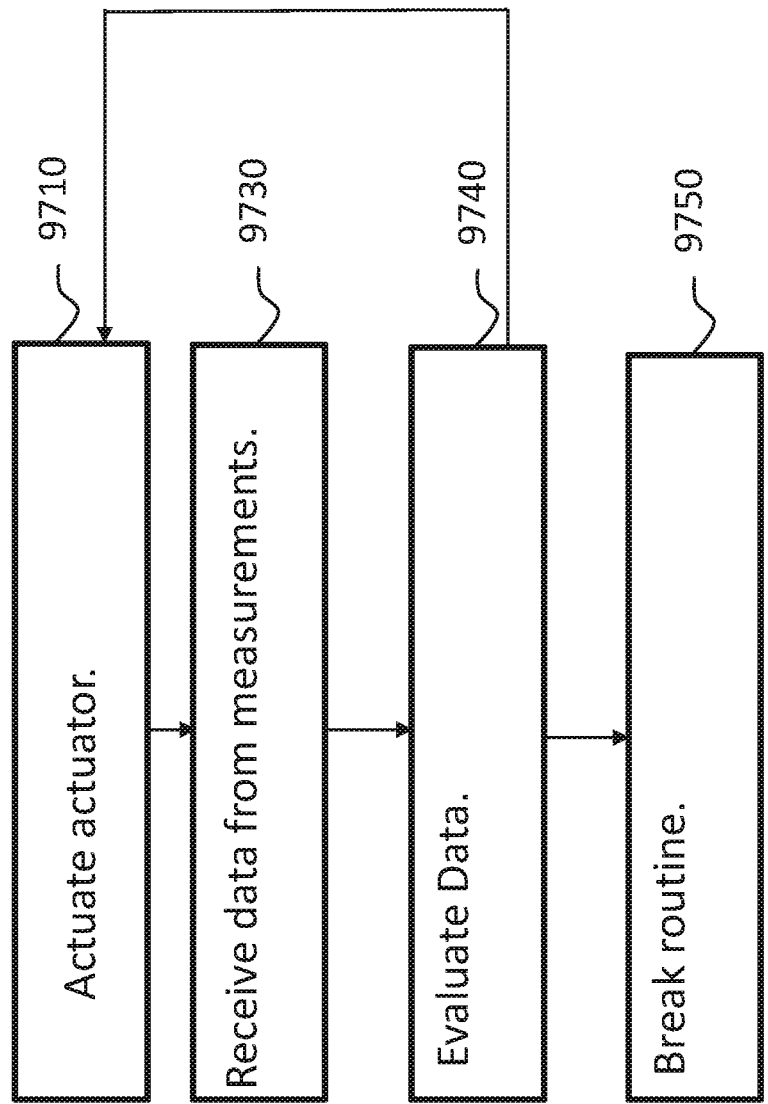

FIG. 97 depicts another exemplary flowchart representing a regime that utilizes feedback in the form of data from any of the various sensors/measurement techniques detailed herein, etc. Specifically, FIG. 97 includes action 9610, which entails actuating the actuator. In this exemplary embodiment, the actuator is not halted unlike the embodiment of FIG. 96. Action 9630 entails receiving data from measurement. Action 9640 entails evaluating the data. With respect to this regime, if the evaluation of the data at action 9640 indicates acceptable data, the routine goes back to action 9610. This is continued until an event occurs that breaks the routine at action 9650. This could be a result of the evaluation at action 9640 indicating that the data is not acceptable.

Figure 98:
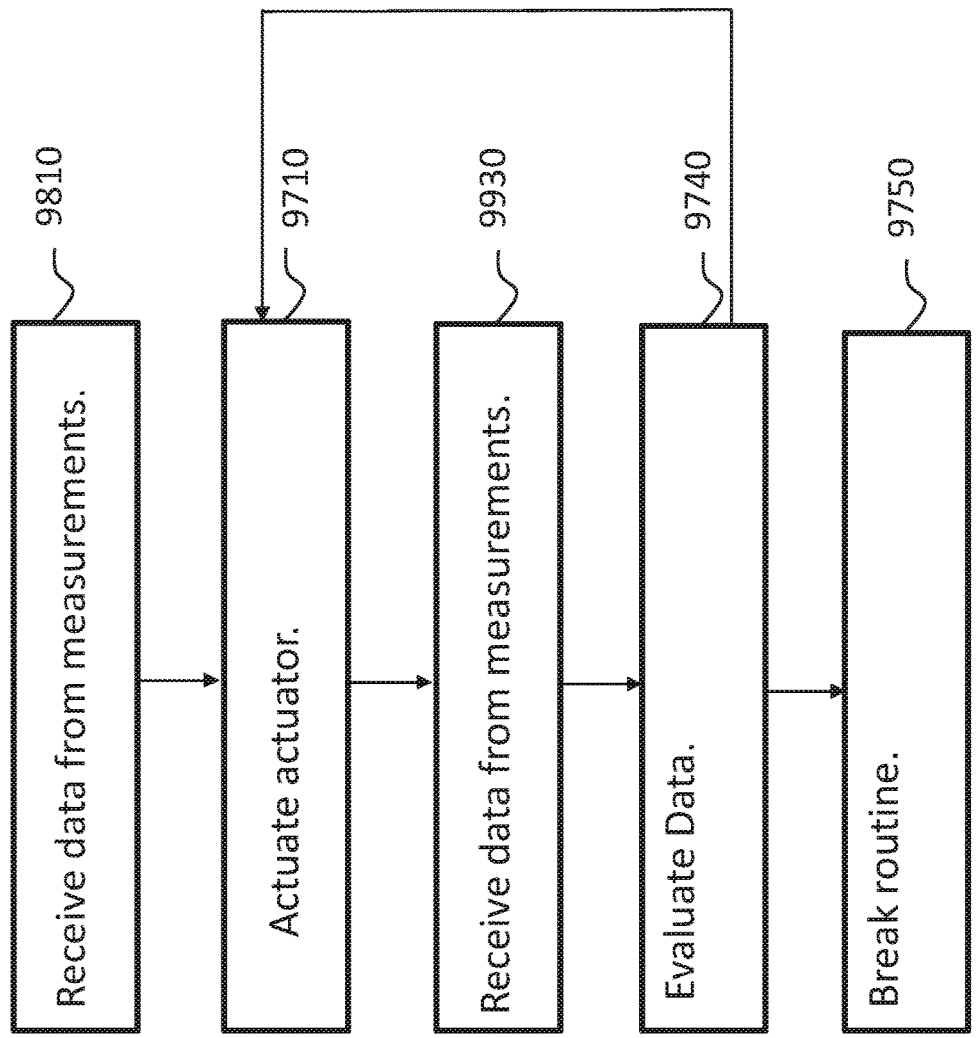

FIG. 98 depicts yet another exemplary flowchart representing a regime that utilizes feedback in the form of data from any of the various sensors/measurement techniques detailed herein, etc. This routine generally follows that of FIG. 97, except that the routine begins with the action 9810, which entails receiving data from measurements. In this regard, it is noted that at least some exemplary embodiments can utilize the measurements detailed herein to evaluate whether or not the actuator should begin to be actuated in the first instance.

In view of the above, it can be seen that in an exemplary embodiment, there is an apparatus, comprising, an actuator, an electrode array support, wherein the apparatus is configured to insert an electrode array into a cochlea via controlled actuation of the actuator, wherein the controlled actuation is at least partially based on data that is at least partially based on electrical characteristics associated with the recipient. In view of the above, it can be seen that in an exemplary embodiment, there is an apparatus, as described above and/or below, wherein the controlled actuation is at least partially based on ECoG data, wherein the ECoG data is based on the electrical characteristics of the recipient. In view of the above, it can be seen that in an exemplary embodiment, there is an apparatus, as described above and/or below, wherein the controlled actuation is at least partially based on voltage measurements relating to energization of an electrode inside the recipient data, wherein the voltage measurements are based at least in part on the electrical characteristics associated with the recipient. In view of the above, it can be seen that in an exemplary embodiment, there is an apparatus, as described above and/or below, wherein the controlled actuation is at least partially based on evoked compound action potentials data, wherein the neural response data is based at least in part on the electrical characteristics associated with the recipient. In view of the above, it can be seen that in an exemplary embodiment, there is an apparatus, as described above and/or below, wherein the apparatus has a control unit configured to receive input indicative of an insertion regime of the electrode array, and the apparatus is configured to automatically coordinate the insertion regime with data based on the electrical characteristics associated with the recipient to control the actuation of the actuator to achieve the controlled actuation of the actuator.

In view of the above, it can be seen that in an exemplary embodiment, there is an apparatus, as described above and/or below, wherein the apparatus is configured to receive input indicative of the electrical characteristics associated with the recipient, develop data indicative of a position of the electrode array within the cochlea based on the input, and adjust the control of the actuation of the actuator based on the developed data indicative of the position of the electrode array. In view of the above, it can be seen that in an exemplary embodiment, there is an apparatus, as described above and/or below, wherein the electrode array support is an insertion tool including an electrode mounted thereon, wherein the apparatus is configured to utilize the electrode to obtain data indicative of the electrical characteristics associated with the recipient, and the actuator is configured to drive the electrode array relative to the insertion tool to insert the electrode array into the cochlea.

In view of the above, it can be see that in an exemplary embodiment, there is a system, such as any of the systems detailed above, comprising a robotic assembly configured to move an implantable medical device relative to an anatomical structure of a recipient, and a control unit configured to receive data from the implantable medical device and control the robotic assembly based at least in part on the received data. In an exemplary embodiment, the data includes measurements of electrical phenomenon inside the recipient. In an exemplary embodiment, the implantable medical device is a component of a cochlear implant, the system is a cochlear implant electrode array insertion system, the robotic system includes an actuator configured to advance and retract the electrode array, and the control unit controls actuation of the actuator to advance and retract the electrode array into and out of the cochlea based on the data from the implantable medical device.

In an exemplary embodiment, there is an apparatus as described above and/or below, wherein, the apparatus includes a control unit configured to provide the controlled actuation of the actuator at least partially based on the electrical characteristics associated with the recipient, the the apparatus is configured to place the control unit into signal communication with a cochlear implant of which the electrode array is a part, the cochlear implant being configured to obtain data indicative of the electrical characteristics associated with the recipient, and the apparatus is configured to convey data based on the obtained data to the control unit via the established signal communication with the cochlear implant so that the control unit can provide the controlled actuation of the actuator at least partially based on the electrical characteristics associated with the recipient. In an exemplary embodiment, there is a system as described above and/or below, wherein the control unit is configured to control the robotic assembly to move the electrode into the cochlea according to a respective insertion regime that is a member of a plurality of different predetermined insertion regimes, and the control unit is configured to weight different features of the data based on electrical phenomenon inside the recipient based on the respective insertion regime and control the robotic assembly differently based on the different weights. In an exemplary embodiment, there is a system as described above and/or below, wherein the system is configured to receive user input and establish an automated insertion regime for the electrode array into the cochlea based on the received user input, and the system is configured to automatically determine if the insertion regime is being followed based on the electrical phenomenon inside the recipient.

In an exemplary embodiment, there is a method as described above and/or below, further comprising determining at least one of whether the electrode array has twisted or will twist based on the monitored electrical phenomenon, and controlling the actuator to at least one of retract the electrode array or halt advancement of the electrode array upon the determination. In an exemplary embodiment, there is a method as described above and/or below, further comprising utilizing at least one of ECoG, voltage measurements relating to energizement of an electrode inside the recipient or measurements of evoked compound action potentials during the first temporal period to monitor the electrical phenomenon. In an exemplary embodiment, there is a method as described above and/or below, further comprising guiding advancement of the first portion of the electrode array into the cochlea using an insertion guide mounted on a support arm, wherein an angular orientation of the insertion tool is adjustable relative to the cochlea via at least one of the actuator or another actuator, wherein the electrical phenomenon monitored is phenomenon indicative of an orientation of the electrode array inside the cochlea, and the method further comprises controlling at least one of the actuator or the another actuator based on the action of monitoring the electrical phenomenon to adjust an orientation of at least a portion of the insertion guide relative to the cochlea, thereby changing at least one of the orientation of the electrode array or a direction of approach of the electrode array inside the cochlea relative to that which was the case when the electrical phenomenon was monitored.

In an exemplary embodiment, there is a method as described above and/or below, wherein the insertion guide includes an electrode, and the electrical phenomenon is monitored using the electrode. In an exemplary embodiment, there is a method as described above and/or below, further comprising determining at least one of whether the electrode array has dislocated from one scala of the cochlea to another scala of the cochlea or that such will happen based on the monitored electrical phenomenon, and controlling the actuator to at least one of retract the electrode array or halt advancement of the electrode array upon the determination.

In an exemplary embodiment, there is a method as described above and/or below, further comprising inputting data into a controller of a robotic electrode array insertion system indicative of a status of an electrode array, wherein control of the robotic apparatus is executed based at least in part by comparing data related to the input to data related to the electrical phenomenon associated with the upon which the robotic apparatus is controlled. In an exemplary embodiment, there is a method as described above and/or below, further comprising outputting data relating to the electrode array during the action of insertion from a robotic electrode array insertion system, wherein the robotic apparatus is part of the robotic electrode array insertion system, and manually adjusting operation of the robotic apparatus based on the output. In an exemplary embodiment, there is a method as described above and/or below, further comprising determining that the electrode array has buckled based on the phenomenon associated with the recipient, automatically halting insertion of the electrode array upon the determination that the electrode array has buckled.

Any disclosure of any method action detailed herein corresponds to a disclosure of a device and/or a system for executing that method action. Any disclosure of any method of making an apparatus detailed herein corresponds to a resulting apparatus made by that method. Any functionality of any apparatus detailed herein corresponds to a method having a method action associated with that functionality. Any disclosure of any apparatus and/or system detailed herein corresponds to a method of utilizing that apparatus and/or system. Any feature of any embodiment detailed herein can be combined with any other feature of any other embodiment detailed herein providing that the art enables such, unless such is otherwise noted.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. A system, comprising:
a robotic assembly configured to move an implantable medical device relative to an anatomical structure of a recipient; and
a control unit configured to receive data from the implantable medical device and control the robotic assembly based at least in part on the received data, wherein
the control unit is configured to control the robotic assembly to move the implantable medical device relative to the anatomical structure according to a respective insertion regime that is a member of a plurality of different predetermined insertion regimes; and
the control unit is configured to weight different features of data based on the data from the implantable medical device based on the respective insertion regime and control the robotic assembly differently based on the different weights.

2. The system of claim 1, wherein:
the implantable medical device is a component of a sensory supplement implant;
the system is a sensory supplement implant electrode array insertion system;
the robotic assembly includes an actuator configured to advance and retract an electrode array; and
the control unit controls actuation of the actuator to advance and retract the electrode array into and out of an anatomical area based on the data from the implantable medical device.

3. The system of claim 1, wherein:
the robotic assembly includes an actuator that moves the implantable medical device and an electrode array support, wherein
the system is configured to insert an electrode array into a cochlea via controlled actuation of the actuator, wherein the controlled actuation is at least partially based on data that is at least partially based on electrical characteristics associated with the recipient, the electrical characteristics corresponding to the received data.

4. The system of claim 3, wherein:
the controlled actuation is at least partially based on voltage measurements relating to energizement of an electrode inside the recipient, wherein the voltage measurements are based at least in part on the electrical characteristics associated with the recipient.

5. The system of claim 4, wherein:
the implantable medical device is an implantable electrode assembly;
the electrode is part of the implantable electrode assembly;
the system is a sensory supplement implant electrode assembly insertion system; and
the implantable electrode assembly is configured to stimulate tissue of the recipient using at least the electrode.

6. The system of claim 3, wherein:
the controlled actuation is at least partially based on evoked compound action potentials data, wherein the evoked compound action potentials data is based at least in part on the electrical characteristics associated with the recipient.

7. The system of claim 1, wherein:
the system includes the implantable medical device; and
the data from the implantable medical device is data from only stimulating electrodes or stimulating and return electrodes utilized to stimulate the recipient during normal use.

8. The system of claim 1, wherein:
the medical device is an electrode array;
the system is configured to determine an angular insertion depth of the electrode array into a cochlea of the recipient based on the received data from the implantable medical device; and
the system is configured to control the robotic assembly to at least one of halt advancement of the electrode array or retract the electrode array based on the determined angular insertion depth.

9. A system, comprising:
a robotic assembly configured to move an assembly including an electrode relative to an anatomical body part of a human; and
a control unit configured to receive data based on electrical phenomenon inside the human and control the robotic assembly based at least in part on the received data, wherein
the control unit is configured to control the robotic assembly to move the assembly including the electrode relative to the anatomical body part according to a respective insertion regime that is a member of a plurality of different predetermined insertion regimes, and
the control unit is configured to weight different features of the data based on electrical phenomenon inside the human based on the respective insertion regime and control the robotic assembly differently based on the different weights.

10. The system of claim 9, wherein:
the system is configured to evaluate the data based on electrical phenomenon inside the human to develop data indicative of a position of the assembly including the electrode relative to the anatomical body part of the human; and
the system is configured to control the robotic assembly while moving the assembly including the electrode into the anatomical body part of the human based on the developed data indicative of the position of the assembly including the electrode.

11. The system of claim 9, wherein:
the control unit is configured to control the robotic assembly to move the assembly including the electrode into the anatomical body part of the human according to a general insertion regime and make micro adjustments to at least one of (i) the general insertion regime or (ii) control output to the robotic assembly from the control unit that is based on the general insertion regime, wherein the adjustments are based on the received data based on electrical phenomenon inside the human.

12. The system of claim 9, wherein:
the control unit is configured to evaluate the data based on electrical phenomenon inside the human to determine at least one of whether a deleterious assembly including the electrode insertion event has occurred or is likely to occur; and
the control unit is configured to control the robotic assembly based at least in part on the evaluation.

13. The system of claim 12, wherein:
the control of the robotic assembly comprises halting movement of the assembly including the electrode upon a determination of at least one of that the deleterious assembly including the electrode insertion event has occurred or is likely to occur.

14. The system of claim 9, wherein:
the system is configured to monitor evoked compound action potentials.

15. The system of claim 9, wherein:
the electrical phenomenon is based on electrical characteristics associated with the human.

16. The system of claim 9, wherein:
the data is not based on force related data related to force(s) applied to the assembly during movement of the assembly relative to the anatomical body part.

17. The system of claim 9, wherein:
the robotic assembly is configured to move the assembly including the electrode relative to the anatomical body part of the human at a speed of more than 0.1 mm per second.

18. The system of claim 9, wherein:
the robotic assembly is configured to move the assembly including the electrode relative to the anatomical body part of the human at a speed of no more than 2 mm per second.

19. A method, comprising:
advancing at least a first portion of an assembly including an electrode into an anatomical body part of a human during a first temporal period at least partially assisted by activation of an actuator that moves the assembly including the electrode;
monitoring an electrical phenomenon within the human at least one of during the first temporal period or during a second temporal period subsequent to the first temporal period; and
controlling the actuator based on the action of monitoring, wherein
the action of advancing at least the first portion of the assembly including the electrode into the anatomical body part of the human includes controlling the actuator at least partially based on respective data based on a plurality of different physiological phenomenon associated with the human based on the monitored electrical phenomenon; and control of the actuator is based on a control regime that weights the respective data based on the physiological phenomenon differently.

20. The method of claim 19, further comprising:
determining at least one of that a deleterious event has occurred or will occur with respect to the assembly including the electrode based on the monitored electrical phenomenon; and
controlling the actuator to at least one of halt advancement of the assembly including the electrode or retract the assembly including the electrode based on the determination.

21. The method of claim 19, wherein:
the assembly further includes a receiver-stimulator of a sensory implant; and
the action of monitoring the electrical phenomenon is executed using the receiver-stimulator.

22. The method of claim 19, wherein the assembly including the electrode is an electrode array, the method further comprising:
determining an angular insertion depth of the electrode array based on the monitored electrical phenomenon; and
controlling the actuator to at least one of halt advancement of the electrode array or retract the electrode array based on the determined angular insertion depth.

23. He method of claim 19, further comprising:
inserting the first portion of the assembly including the electrode into the anatomical body part of the human at a speed of no more than 0.25 mm per second.

24. The method of claim 19, further comprising:
determining at least one of that the assembly including the electrode buckling has occurred or will occur based on the monitored electrical phenomenon; and
controlling the actuator to at least one of halt advancement of the assembly including the electrode or retract the assembly including the electrode based on the determination.

25. The method of claim 19, wherein:
the electrical phenomenon that is monitored is induced by a stimulation generator, wherein the stimulation generator is completely outside a cochlea of the human.

26. The method of claim 19, wherein:
the action of monitoring the electrical phenomenon is executed using a sensor that is completely outside a cochlea of the human.

27. The method of claim 19, further comprising:
weighting data based on the electrical phenomenon within the human and controlling the actuator based on the weighted data.

28. The method of claim 19, wherein:
the monitored electrical phenomenon is based on electrical characteristics associated with the human.

29. The method of claim 19, further comprising:
inserting the first portion of the assembly including the electrode into the anatomical body part of the human at a speed of more than or equal to 0.25 mm per second.

\* \* \* \* \*